United States Patent
Embree et al.

(10) Patent No.: US 10,632,157 B2
(45) Date of Patent: *Apr. 28, 2020

(54) MICROBIAL COMPOSITIONS AND METHODS OF USE FOR IMPROVING FOWL PRODUCTION

(71) Applicant: ASCUS BIOSCIENCES, INC., San Diego, CA (US)

(72) Inventors: Mallory Embree, San Diego, CA (US); Grant Gogul, Cardiff, CA (US); Cameron Martino, San Diego, CA (US); Norm Pitt, San Diego, CA (US)

(73) Assignee: Ascus Biosciences, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/042,369

(22) Filed: Jul. 23, 2018

(65) Prior Publication Data

US 2018/0333443 A1 Nov. 22, 2018

Related U.S. Application Data

(63) Continuation-in-part of application No. PCT/US2017/028015, filed on Apr. 17, 2017.

(60) Provisional application No. 62/323,305, filed on Apr. 15, 2016, provisional application No. 62/335,559, filed on May 12, 2016, provisional application No. 62/425,480, filed on Nov. 22, 2016, provisional application No. 62/574,031, filed on Oct. 18, 2017.

(51) Int. Cl.
| | |
|---|---|
| *A61K 35/00* | (2006.01) |
| *A61K 35/747* | (2015.01) |
| *A61K 35/741* | (2015.01) |
| *A61K 9/00* | (2006.01) |
| *A61K 35/742* | (2015.01) |
| *A23K 10/18* | (2016.01) |
| *A23K 50/75* | (2016.01) |

(52) U.S. Cl.
CPC .......... *A61K 35/742* (2013.01); *A23K 10/18* (2016.05); *A23K 50/75* (2016.05); *A61K 9/0053* (2013.01); *A61K 9/0056* (2013.01); *A61K 35/741* (2013.01); *A61K 35/747* (2013.01); *A61K 2035/115* (2013.01)

(58) Field of Classification Search
CPC ........ A23K 10/12; A23K 10/18; A23K 50/30; A23K 50/75; B01D 2251/95; B01D 2257/90; B01D 53/77; C12R 1/125
See application file for complete search history.

(56) References Cited

U.S. PATENT DOCUMENTS

| | | |
|---|---|---|
| 3,484,243 A | 12/1969 | Anderson et al. |
| 4,647,536 A | 3/1987 | Mosbach et al. |
| 5,104,662 A | 4/1992 | Kalsta et al. |
| 5,605,793 A | 2/1997 | Stemmer |
| 5,733,568 A | 3/1998 | Ford |
| 5,741,508 A | 4/1998 | Katsumi et al. |
| 5,837,458 A | 11/1998 | Minshull et al. |
| 6,090,416 A | 7/2000 | Iritani et al. |
| 6,210,891 B1 | 4/2001 | Nyren et al. |
| 6,258,568 B1 | 7/2001 | Nyren |
| 6,274,320 B1 | 8/2001 | Rothberg et al. |
| 7,427,408 B2 | 9/2008 | Merritt et al. |
| 7,998,502 B2 | 8/2011 | Harel |
| 8,097,245 B2 | 1/2012 | Harel et al. |
| 8,460,726 B2 | 6/2013 | Harel et al. |
| 9,540,676 B1 | 1/2017 | Zengler et al. |
| 2006/0127530 A1 | 6/2006 | Axelrod |
| 2008/0299098 A1 | 12/2008 | Se et al. |
| 2010/0092428 A1 | 4/2010 | Schmidt et al. |
| 2011/0280840 A1 | 11/2011 | Blaser et al. |
| 2012/0282675 A1 | 11/2012 | Kim et al. |
| 2013/0330307 A1 | 12/2013 | Millan |
| 2014/0147425 A1 | 5/2014 | Henn et al. |
| 2015/0093360 A1 | 4/2015 | McKenzie et al. |
| 2015/0267163 A1 | 9/2015 | Liao et al. |
| 2016/0029666 A1* | 2/2016 | Carpenter .............. A23K 40/20 424/442 |

FOREIGN PATENT DOCUMENTS

| | | |
|---|---|---|
| CN | 101717746 A | 6/2010 |
| KR | 10-0949670 B1 * | 3/2010 |
| WO | WO 2008/076975 A1 | 6/2008 |
| WO | WO 2010/111347 A2 | 9/2010 |
| WO | WO 2010/111565 A2 | 9/2010 |

(Continued)

OTHER PUBLICATIONS

English Translation of KR 10-0949670 B1, pp. 1-27, 2010.*
International Search Report for International Application No. PCT/US2017/028015 dated Sep. 5, 2017, 7 pages.
International Search Report and Written Opinion of the International Searching Authority for International Application No. PCT/US2018/056563 dated Feb. 5, 2019, 12 pages.
Office Action for U.S. Appl. No. 16/214,546 dated Feb. 28, 2019 12 pages.

(Continued)

*Primary Examiner* — Sarvamangala Devi
(74) *Attorney, Agent, or Firm* — Cooley LLP

(57) ABSTRACT

The disclosure relates to isolated microorganisms—including novel strains of the microorganisms—microbial ensembles, and compositions comprising the same. Furthermore, the disclosure teaches methods of utilizing the described microorganisms, microbial ensembles, and compositions comprising the same, in methods for modulating the production of poultry, disease resistance, and egg yield. In particular aspects, the disclosure provides methods of increasing feed efficiency, and methods of preventing colonization of pathogenic microbes.

7 Claims, 17 Drawing Sheets

Specification includes a Sequence Listing.

(56) References Cited

FOREIGN PATENT DOCUMENTS

| WO | WO 2010/138522 A2 | 12/2010 |
|----|-------------------|---------|
| WO | WO 2016/019017 A  | 2/2016  |

OTHER PUBLICATIONS

Blondel et al., "Fast unfolding of communities in large networks," Journal of Statistical Mechanics: Theory and Experiment, vol. 2008, Oct. 2008.
Bennett et al., "Toward the $1000 human genome," Pharmacogenomics (2005); 6:373-382.
Bentley et al., "Accurate whole genome sequencing using reversible terminator chemistry," Nature (2008); 456: 53-59.
Bretonnière et al. "MIC score, a new tool to compare bacterial susceptibility to antibiotics application to the comparison of susceptibility to different penems of clinical strains of Pseudomonas aeruginosa." The Journal of Antibiotics 6911 (2016): 806-810. Published online Mar. 30, 2016.
Burgain et al., "Encapsulation of probiotic living cells: From laboratory scale to industrial applications," Journal of Food Engineering (2011); 104: 467-483.
Caporaso et al., "Ultra-high-throughput microbial community analysis on the Illumina HiSeq and MiSeq platforms," The ISME Journal (2012); 6: 1621-1624.
Chamba et al., "Effect of Partially Protected Sodium Butyrate on Performance, Digestive Organs, Intestinal Villi and $E.\ coli$ Development in Broilers Chickens," International Journal of Poultry Science 13 (7): 390-396, 2014.
Chen et al., "Effects of prebiotic oligosaccharides and trehalose on growth and production of bacteriocins by lactic acid bacteria," Letters in Applied Microbiology 45 (2007) 190-193.
Chichlowski et al., "Metabolic and Physiological Impact of Probiotics or Direct-Fed-Microbials on Poultry: A Brief Review of Current Knowledge," International Journal of Poultry Science 6 (10): 694-704, 2007.
Colby, "Calculating synergistic and antagonistic responses of herbicide combinations," Weeds (1967); 15: 20-22.
Crameri et al., "DNA shuffling of a family of genes from diverse species accelerates directed evolution," Nature (1998); 391: 288-291.
Crameri et al., "Molecular evolution of an arsenate detoxification pathway by DNA shuffling," Nature Biotechnology (1997); 15: 436-438.
De Almeida et al., "Transgenic expression of two marker genes under the control of an *Arabidopsis* rbcS promoter: Sequences encoding the Rubisco transit peptide increase expression levels," Molecular and General Genetics MGG (1989); 218: 78-86.
De Menezes et al., "Microbiome analysis of dairy cows fed pasture or total mixed ration diets," FEMS Microbiology Ecology (2011); 78: 256-265.
Fadrosh et al., "An improved dual-indexing approach for multiplexed 16S rRNA gene sequencing on the Illumina MiSeq platform," Microbiome (2014); 2:6.
Feng et al., "Using In Vitro Immunomodulatory Properties of Lactic Acid Bacteria for Selection of Probiotics against *Salmonella* Infection in Broiler Chicks," PLoS One (2016) 11(1): e0147630, 14 pages.
Gantois et al., "Butyrate Specifically Down-Regulates *Salmonella* Pathogenicity Island 1 Gene Expression," Applied and Environmental Microbiology, Jan. 2006, 72(1):946-949.
Gasaway, "Seasonal variation in diet, volatile fatty acid production and size of the cecum of rock ptarmigan," Comparative Biochemistry and Physiology Part A: Physiology, vol. 53, Issue 1, 1976, pp. 109-114.
Gasaway, "Volatile fatty acids and metabolizable energy derived from cecal fermentation in the willow ptarmigan," Comparative Biochemistry and Physiology Part A: Physiology, vol. 53, Issue 1, 1976, pp. 115-121.
Immerseel et al., "Invasion of *Salmonella enteritidis* in avian intestinal epithelial cells in vitro is influenced by short-chain fatty acids," International Journal of Food Microbiology, vol. 85, 2003, pp. 237-248.
Jones et al., "High level expression of introduced chimaeric genes in regenerated transformed plants," The EMBO Journal (1985); 4 : 2411-2418.
Juven et al., "Antagonistic effects of lactobacilli and pediococci to control intestinal colonization by human enteropathogens in live poultry," J Appl Bacteriol. 1991; 70:95-103.
Kõljalg et al., "UNITE: a database providing web-based methods for the molecular identification of ectomycorrhizal fungi," New Phytologist (2005); 166(3): 1063-1068.
Lan et al., "Using the RDP classifier to predict taxonomic novelty and reduce the search space for finding novel organisms," PLoS One (2012); 7(3): e32491, 15 pages.
Lange et al., "Cost-efficient high-throughput HLA typing by MiSeq amplicon sequencing," BMC Genomics (2014); 15:63, 11 pages.
Lee et al., "Nonradioactive method to study genetic profiles of natural bacterial communities by PCR-single-strand-conformation polymorphism," Applied and Environmental Microbiology (1996); 62: 3112-3120.
Levy et al., "Effect of feeding an encapsulated source of butyric acid (ButiPEARL) on the performance of male Cobb broilers reared to 42 d of age," Poultry Science 2015 94:1864-1870.
Lowe et al., "Growth of anaerobic rumen fungi on defined and semi-defined media lacking rumen fluid." Journal of General Microbiology (1985); 131.9: 2225-2229.
M'Sadeq et al., "Towards the control of necrotic enteritis in broiler chickens with in-feed antibiotics phasing-out worldwide," Animal Nutrition (2015) 1 1-11.
Marounek et al., "Effect of substrate and feed antibiotics on in vitro production of volatile fatty acids and methane in caecal contents of chickens," Animal Feed Science and Technology, vol. 80, 1999, pp. 223-230.
Mardis, "Next Generation DNA Sequencing Methods," Annu. Rev. Genomics Hum. Genet. (2008); 9: 387-402.
Margulies et al., "Genome sequencing in microfabricated high-density picolitre reactors," Nature (2005); 437: 376-380.
Mitra et al., "Analysis of the intestinal microbiota using SOLiD 16S rRNA gene sequencing and SOLiD shotgun sequencing," BMC Genomics (2013); 14(Suppl 5):516, 11 pages.
Moore et al. "Strategies for the in vitro evolution of protein function: enzyme evolution by random recombination of improved sequences," Journal of Molecular Biology (1997); 272: 336-347.
Neal-McKinney et al., "Production of Organic Acids by Probiotic Lactobacilli Can Be Used to Reduce Pathogen Load in Poultry," PLoS One (2012) 7(9): e43928, 11 pages.
Oakley et al., "The chicken gastrointestinal microbiome," FEMS Microbiol Lett (2014) 360:100-112.
Peckham et al. ,"SOLiD™ Sequencing and 2-Base Encoding," San Diego, CA: American Society of Human Genetics, 2007.
Petri et al., "Characterization of the core rumen microbiome in cattle during transition from forage to concentrate as well as during and after an acidotic challenge," PLoS One (2013); 8(12): e83424, 15 pages.
Pool-Zobel et al., "Overview of Experimental Data on Reduction of Colorectal Cancer Risk by Inulin-Type Fructans," J. Nutr. (2007); 137: 2580S-2584S.
Pourabedin et al., "Prebiotics and gut microbiota in chickens," FEMS Microbiol. Lett. (2015); 362:fnv122, 8 pages.
Ramirez-Farias et al., "Effect of inulin on the human gut microbiota: stimulation of Bifidobacterium adolescentis and Faecalibacterium prausnitzii," British Journal of Nutrition (2009); 101(4): 541-550.
Rinttilä et al., "Intestinal microbiota and metabolites—Implications for broiler chicken health and performance," J. Appl. Poult. Res., 2013 22 :647-658.
Roberts et al., "New issues and science in broiler chicken intestinal health: intestinal microbial composition, shifts, and impacts," World's Poultry Science Journal, Jun. 2015, vol. 71, 259-270.
Sanger et al., "DNA sequencing with chain-terminating inhibitors," PNAS USA (1977); 74: 5463-5467.

(56) References Cited

OTHER PUBLICATIONS

Scheinert et al., "Molecular differentiation of bacteria by PCR amplification of the 16-23S rRNA spacer," J Microbiol Meth (1996); 26: 103-117.

Schloss et al., "Assessing and improving methods used in operational taxonomic unit-based approaches for 16S rRNA gene sequence analysis," Applied and Environmental Microbiology (2011); 77(10): 3219-3226.

Schwieger et al., "A New Approach to Utilize PCR-Single-Strand-Conformation Polymorphism for the 16S rRNA Gene-Based Microbial Community Analysis," Applied and Environmental Microbiology (1998); 64: 4870-4876.

Shanks et al., "Community structures of fecal bacteria in cattle from different animal feeding operations," Applied and Environmental Microbiology (2011); 77(9); 2992-3001.

Stemmer, "DNA shuffling by random fragmentation and reassembly: in vitro recombination for molecular evolution," PNAS USA Oct. 1994; vol. 91, pp. 10747-10751.

Stemmer, "Rapid evolution of a protein in vitro by DNA shuffling," Nature, Aug. 4, 1994; vol. 370, pp. 389-391.

Vandamme et al., "Polyphasic taxonomy, a consensus approach to bacterial systematics," Microbiological Reviews (1996); 60: 407-438.

Van der Wielen et al., "Role of Volatile Fatty Acids in Development of the Cecal Microflora in Broiler Chickens during Growth," Applied and Enviromental Microbiology, Jun. 2000, 66(6):2536-2540.

Vineetha et al., "Screening of Lactobacillus isolates from gastrointestinal tract of guinea fowl for probiotic qualities using in vitro tests to select species-specific probiotic candidates." British poultry science 57.4 (2016): 474-482.

Yarza et al., "Uniting the classification of cultured and uncultured bacteria and archaea using 16S rRNA gene sequences." Nature Reviews Microbiology (2014); 12.9: 635-645.

Yeoman et al., "The microbiome of the chicken gastrointestinal tract," Anim Health Res Rev. Jun. 2012;13(1):89-99.

Zhang et al., "Directed evolution of a fucosidase from a galactosidase by DNA shuffling and screening," PNAS USA (1997); 94: 4504-4509.

Office Action for U.S. Appl. No. 16/218,074 dated Mar. 21, 2019, 8 pages.

Blair et al., "Effects of Calsporin® on Turkey Performance, Carcass Yield and Nitrogen Reduction," International Journal of Poultry Science 3 (1): 75-79, 2004.

European Food Safety Authority, "Safety and efficacy of Calsporin®, a preparation of Bacillus subtilis, as a feed additive for chickens for fattening in accordance with Regulation (EC) No. 1831/20031," The EFSA Journal (2007) 543, pp. 1-8.

Jeong et al., "Effect of Bacillus subtilis C-3102 spores as a probiotic feed supplement on growth performance, noxious gas emission, and intestinal microflora in broilers," Poultry Science 2014, 93:3097-3103.

Dahiya et al., "Potential strategies for controlling necrotic enteritis in broiler chickens in post-antibiotic era," Animal Feed Science and Technology (2006) 129:60-88.

Partial Supplementary European Search Report for European Application No. 17783378.7 dated Nov. 12, 2019.

\* cited by examiner

FIG. 3

| Study Day | Event (Phase I Cobb 500) |
|---|---|
| 0 | Place and tag 120 Cobb 500 broilers into floor pens |
| 14 | Place and weigh 96 Cobb 500 broilers into individual cages, weigh feed |
| 15 | Collect excreta samples (24 hour collection), weigh birds individually, feed weigh back |
| 16 | Weigh birds individually, feed weigh back |
| 17 | Weigh birds individually, feed weigh back |
| 18 | Collect excreta samples (24 hour collection), weigh birds individually, feed weigh back |
| 19 | Weigh birds individually, feed weigh back |
| 20 | Weigh birds individually, feed weigh back |
| 21 | Collect excreta samples (24 hour collection), weigh birds individually, feed weigh back, intestinal sample collection, study end |

FIG. 4

| Study Day | Event (Phase I Ross 708) |
|---|---|
| 0 | Place and tag 120 Ross 708 broilers into floor pens |
| 14 | Place and weigh 96 Ross 708 broilers into individual cages, weigh feed |
| 15 | Collect excreta samples (24 hour collection), weigh birds individually, feed weigh back |
| 16 | Weigh birds individually, feed weigh back |
| 17 | Weigh birds individually, feed weigh back |
| 18 | Collect excreta samples (24 hour collection), weigh birds individually, feed weigh back |
| 19 | Weigh birds individually, feed weigh back |
| 20 | Weigh birds individually, feed weigh back |
| 21 | Collect excreta samples (24 hour collection), weigh birds individually, feed weigh back, intestinal sample collection, study end |

FIG. 10
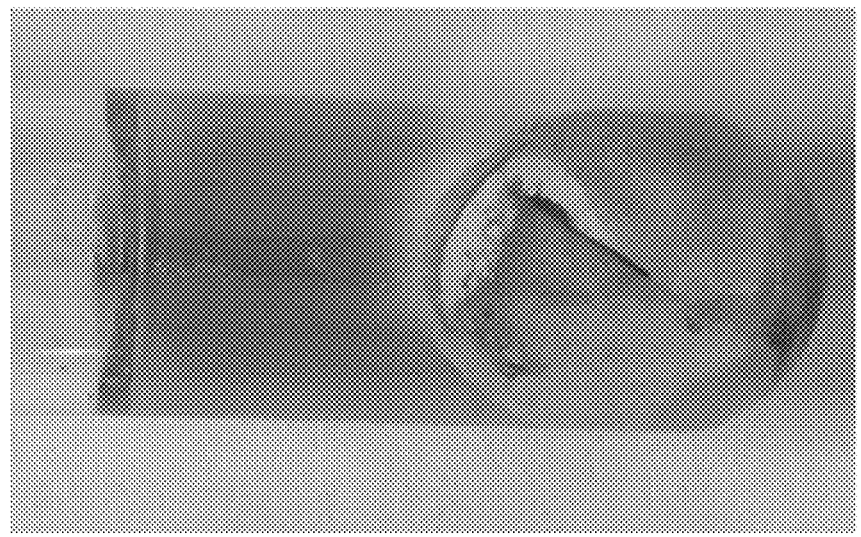
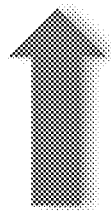
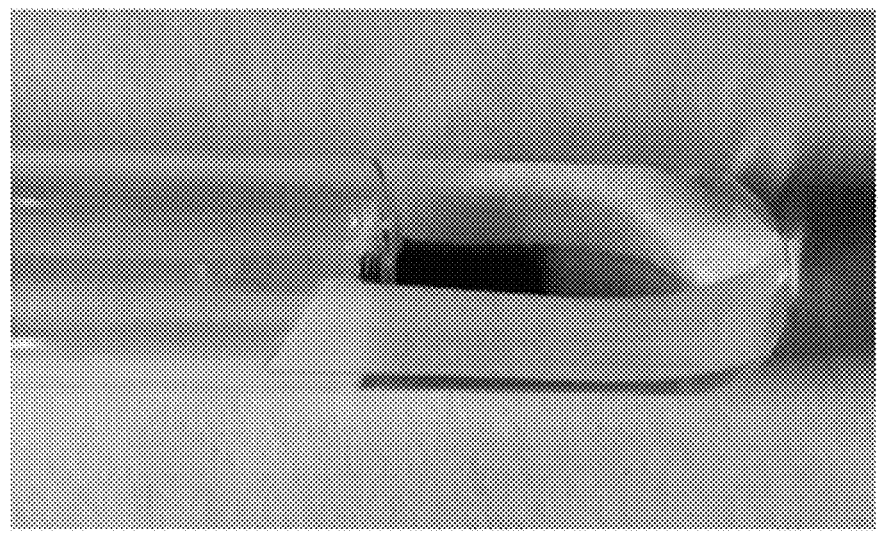

SEQUENCE LISTING

```
<160> NUMBER OF SEQ ID NOS: 387

<210> SEQ ID NO 1
<211> LENGTH: 224
<212> TYPE: DNA
<213> ORGANISM: Unknown
<220> FEATURE:
<223> OTHER INFORMATION: Encodes 16S rRNA from Lactobacillus

<400> SEQUENCE: 1
agatttgatc tggctcagca cgaacgctgg cggcgtacct aatacatgca agtcgagcga       60
gcggaactaa cagatttact tcggtaatga cgttaggaaa gcgagcggcg gatgggtgag      120
taacacgtgg ggaacctgcc ccatagtctg ggataccact tggaaacagg tgctaatacc      180
ggataagaaa gcagatcgca tgatcagctt ttaaaaggcc gcgt                       224

<210> SEQ ID NO 2
<211> LENGTH: 224
<212> TYPE: DNA
<213> ORGANISM: Unknown
<220> FEATURE:
<223> OTHER INFORMATION: Encodes rRNA from Lachnospiraceae (Clostridium
      Cluster XIVa)

<400> SEQUENCE: 2
agatttgatc ctggctcagg atgaacgctg gcggcgtgct taacacatgc aagtcgagcg       60
aagcgctttt gcggatttct tcggattgaa gcaattgtga ctgagcggcg gacgggtgag      120
taacgcgtgg ggaacctggc ccatacaggg ggataacagt tagaaatgac tgctaatacc      180
gcataagcgc acggaaccgc atggttttgt gtgaaaaact ccgg                       224

<210> SEQ ID NO 3
<211> LENGTH: 224
<212> TYPE: DNA
<213> ORGANISM: Unknown
<220> FEATURE:
<223> OTHER INFORMATION: Encodes 16S rRNA from Lactobacillus

<400> SEQUENCE: 3
agatttgctc ctggctcagg acgaacgctg gcggcgtgcc taatacatgc aagtcgagcg       60
agcggaacta acagatttac ttcggtaatg acgttaggaa agcgagcggc ggatgggtga      120
gtaacacgtg gggaacctgc cccatagtct gggataccac ttggaaacag gtgctaatac      180
```

```
cggataagaa agcagatcgc atgatcagct tttaaaaggc ggcg              224
```

<210> SEQ ID NO 4
<211> LENGTH: 224
<212> TYPE: DNA
<213> ORGANISM: Unknown
<220> FEATURE:
<223> OTHER INFORMATION: Encodes 16S rRNA from Lactobacillus

<400> SEQUENCE: 4

```
agagtttgat catggctcag gatgaacgcc ggcggtgtgc ctaatacatg caagtcgagc    60
gcactggccc aactgatatg acgtgcttgc actgaattga cgttggatta ccagtgagcg   120
gcggacgggt gagtaacacg tgggcaacct gccctggagc ggggdataac atctggaaac   180
aggtgctaat accgcataac aacgaaaacc acatggtttt cgtt                    224
```

<210> SEQ ID NO 5
<211> LENGTH: 224
<212> TYPE: DNA
<213> ORGANISM: Unknown
<220> FEATURE:
<223> OTHER INFORMATION: Encodes 16S rRNA from Lactobacillus

<400> SEQUENCE: 5

```
agatttgatc ctggctcagg atgaacgccg gcggtgtgcc taatacatgc aagtcgagcg    60
cactggccca actgatatga cgtgcttgca ctgaattgac gttggattac cagtgagcgg   120
cggacgggtg agtaacacgt gggcaacctg ccctggagcg ggggataaca tctggaaaca   180
ggtgctaata ccgcataaca acgaaaacca catggttttc gttt                    224
```

<210> SEQ ID NO 6
<211> LENGTH: 224
<212> TYPE: DNA
<213> ORGANISM: Unknown
<220> FEATURE:
<223> OTHER INFORMATION: Encodes 16S rRNA from Lactobacillus

<400> SEQUENCE: 6

```
agagtttgat cctggctcag gacgaacgct ggcggcgtgc ctaatacatg caagtcgagc    60
gagcttgcct agatgatttt agtgcttgca ctaaatgaaa ctagatacaa gcgagcggcg   120
gacgggtgag taacacgtgg gtaacctgcc aagagactg gataacacc tggaaacaga    180
tgctaatacc agataacaac actagacgca tgtctaaagt atga                    224
```

<210> SEQ ID NO 7
<211> LENGTH: 224
<212> TYPE: DNA
<213> ORGANISM: Unknown
<220> FEATURE:
<223> OTHER INFORMATION: Encodes 16S rRNA from Faecalibacterium

<400> SEQUENCE: 7

```
agatttgatc atggctcagg acgaacgctg gcggcgcgcc taacacatgc aagtcgaacg    60
gaatacggag aggatttatc ttttctgtgt ttagtggcga acgggtgagt aacgcgtgag   120
gaacctgcct caaagagggg gacaacagtt ggaaacgact gctaataccg cataagccca   180
cggggccgca tggccctgag ggaaaaggag aaatccgctt tgag                    224
```

<210> SEQ ID NO 8
<211> LENGTH: 224
<212> TYPE: DNA

<213> ORGANISM: Unknown
<220> FEATURE:
<223> OTHER INFORMATION: Encodes 16S rRNA from Lactobacillus

<400> SEQUENCE: 8
agatttgatc ctggctcagg acgaacgctg gcggcgtgcc taatacatgc aagtcgagcg    60
agcttgccta gatgatttta gtgcttgcac taaatgaaac tagatacaag cgagcggcgg   120
acgggtgagt aacacgtggg taacctgccc aagagactgg gataacacct ggaaacagat   180
gctaataccg gataccaaca ctagacgcat gtctatagtt tgaa                    224

<210> SEQ ID NO 9
<211> LENGTH: 224
<212> TYPE: DNA
<213> ORGANISM: Unknown
<220> FEATURE:
<223> OTHER INFORMATION: Encodes 16S rRNA from Hydrogenoanaerobacterium

<400> SEQUENCE: 9
agatttgatc atggctcagg acgaacgctg gcggcgtgcc taacacatgc aagtcgaacg    60
gagataagcg ctgatgattt agcttgctag agattcttgc ttatcttagt ggcggacggg   120
tgagtaacgc gtgagcaacc tgcctttcag aggggaataa cgtcttgaaa aggacgctaa   180
taccgcatga tattatggag ccacatggct ctataatcaa agga                    224

<210> SEQ ID NO 10
<211> LENGTH: 224
<212> TYPE: DNA
<213> ORGANISM: Unknown
<220> FEATURE:
<223> OTHER INFORMATION: Encodes 16S rRNA from Peptostreptococcaceae
      (Clostridium Cluster XI)

<400> SEQUENCE: 10
agatttgatc ctggctcagg atgaacgctg gcggcgtgcc taacacatgc aagtcgagcg    60
aactcttcgg agtgagcggc ggacgggtga gtaacgcgtg gtaacctgcc cctgtacaca   120
tggataacat accgaaaggt atgctaatat aagataaaat atatttatcg catgatagct   180
atatcaaagc gttagcggta catgatggac ccgcgtctga ttag                    224

<210> SEQ ID NO 11
<211> LENGTH: 224
<212> TYPE: DNA
<213> ORGANISM: Unknown
<220> FEATURE:
<223> OTHER INFORMATION: Encodes 16S rRNA from Acrocarpospora

<400> SEQUENCE: 11
agatttgatc atggctcagg acgaacgctg gcggcgtgct taacacatgc aagtcgagcg    60
gaaaggccct tcggggtact cgagcggcga acgggtgagt aacacgtgag taacctgccc   120
ctgactctgg gataagcctg ggaaaccggg tctaataccg gatacgacca ccggccgcat   180
ggcctggtgg tggaaagatt catcggttgg ggatgggctc gcgg                    224

<210> SEQ ID NO 12
<211> LENGTH: 224
<212> TYPE: DNA
<213> ORGANISM: Unknown
<220> FEATURE:
<223> OTHER INFORMATION: Encodes 16S rRNA from Lactobacillus

<400> SEQUENCE: 12

```
agatttgatc atggctcagg acgaacgctg gcggcgtgcc taatacatgc aagtcgagcg    60
agcggaacta acagatttac ttcggtaatg acgctgggga cgcgagcggc ggatgggtga   120
gtaacacgtg gggaacctgc cccatagtct gggataccac ttggaaacag gtgctaatac   180
cggataagaa agcagatcgc atgatcagct tataaaaggc ggcg                    224
```

```
<210> SEQ ID NO 13
<211> LENGTH: 224
<212> TYPE: DNA
<213> ORGANISM: Unknown
<220> FEATURE:
<223> OTHER INFORMATION: Encodes 16S rRNA from Bacillus

<400> SEQUENCE: 13
```

```
agatttgatc atggctcagg acgaacgctg gcggcgtgcc taatacatgc aagtcgagcg    60
gacagatggg agcttgctcc ctgatgttag cggcggacgg gtgagtaaca cgtgggtaac   120
ctgcctgtaa gactgggata actccgggaa accgggcta ataccggatg gttgtctgaa    180
ccgcatggtt cagacataaa aggtggcttc ggctaccact taca                    224
```

```
<210> SEQ ID NO 14
<211> LENGTH: 224
<212> TYPE: DNA
<213> ORGANISM: Unknown
<220> FEATURE:
<223> OTHER INFORMATION: Encodes 16S rRNA from Lactobacillus

<400> SEQUENCE: 14
```

```
agatttgatc ctggctcagg atgaacgccg gcggtgtgcc taatacatgc aagtcgaacg    60
cgttggtccg actgattgat gatgcttgca tctgattgac gacggtttac caacgagtgg   120
cggacgggtg agtaacacgt aggcaacctg cccagaagcg ggggacaaca tttggaaaca   180
agtgctaata ccgcataaca acgaaaacca catggttttc gttt                    224
```

```
<210> SEQ ID NO 15
<211> LENGTH: 224
<212> TYPE: DNA
<213> ORGANISM: Unknown
<220> FEATURE:
<223> OTHER INFORMATION: Encodes 16S rRNA from Subdoligranulum

<400> SEQUENCE: 15
```

```
agatttgatc atggctcagg acgaacgctg gcggcgcgcc taacacatgc aagtcgaacg    60
gagttaattt tgttgaagtt ttcggatgga tacgaaatta acttagtggc gaacgggtga   120
gtaacgcgtg agtaacctgc cccgaagtgg gggacaacag ttggaaacga ctgctaatac   180
cgcataagcc cacggcaccg catggtgctg agggaaaagg gctt                    224
```

```
<210> SEQ ID NO 16
<211> LENGTH: 224
<212> TYPE: DNA
<213> ORGANISM: Unknown
<220> FEATURE:
<223> OTHER INFORMATION: Encodes 16S rRNA from Subdoligranulum

<400> SEQUENCE: 16
```

```
agatttgatc atggctcagg acgaacgctg gcggcgcgcc taacacatgc aagtcgaacg    60
gaacttgaga gagcttgctt tttcaagttt agtggcgaac gggtgagtaa cgcgtgagta   120
acctgccctg gagtggggga caacagttgg aaacgactgc taataccgca taagcccacg   180
gtaccgcatg gtactgaggg aaaaggattt attcgcttca ggat                    224
```

```
<210> SEQ ID NO 17
<211> LENGTH: 224
<212> TYPE: DNA
<213> ORGANISM: Unknown
<220> FEATURE:
<223> OTHER INFORMATION: Encodes 16S rRNA from Lachnospiraceae
      (Clostridium Cluster XIVa)

<400> SEQUENCE: 17
agatttgatc atggctcagg atgaacgctg gcggcgtgcc taacacatgc aagtcgaacg      60
aagcgcttta ctttgatttc ttcgggatga agattttgtg actgagtggc ggacgggtga    120
gtaacgcgtg gtaacctgc ctcatacagg gggataacag ttagaaatga ctgctaatac     180
cgcataagac cacagcttcg catggagcag tggtaaaaac tccg                      224

<210> SEQ ID NO 18
<211> LENGTH: 224
<212> TYPE: DNA
<213> ORGANISM: Unknown
<220> FEATURE:
<223> OTHER INFORMATION: Encodes 16S rRNA from Lactobacillus

<400> SEQUENCE: 18
agatttgatc atggctcagg atgaacgccg gcggtgtgcc taatacatgc aagtcgaacg      60
cgttggcccg actgattgat gatgcttgca tctgattgac gacggtttac caacgagtgg    120
cggacgggtg agtaacacgt aggcaacctg cccagaagcg ggggacaaca tttggaaaca    180
agtgctaata ccgcataaca acgaaaacca catggttttc gttt                      224

<210> SEQ ID NO 19
<211> LENGTH: 224
<212> TYPE: DNA
<213> ORGANISM: Unknown
<220> FEATURE:
<223> OTHER INFORMATION: Encodes 16S rRNA from Lactobacillus

<400> SEQUENCE: 19
agatttgatc atggctcagg acgaacgctg gcggtgtgcc taatacatgc aagtcgtacg      60
cactggccca actgattgat ggtgcttgca cctgattgac gatggattac cagtgagtgg    120
cggacgggtg agtaacacgt aggtaacctg ccccggagcg ggggataaca tttggaaaca    180
gatgctaata ccgcataaca acaaaagcca catggctttt gttt                      224

<210> SEQ ID NO 20
<211> LENGTH: 224
<212> TYPE: DNA
<213> ORGANISM: Unknown
<220> FEATURE:
<223> OTHER INFORMATION: Encodes 16S rRNA from Leuconostoc

<400> SEQUENCE: 20
agatttgatc atggctcagg atgaacgctg gcggcgtgcc taatacatgc aagtcgaacg      60
cacagcgaaa ggtgcttgca cctttcaagt gagtggcgaa cgggtgagta acacgtggac    120
aacctgcctc aaggctgggg ataacatttg gaaacagatg ctaataccga ataaaactta    180
gtgtcgcatg acacaaagtt aaaaggcgct tcggcgtcac ctag                      224

<210> SEQ ID NO 21
<211> LENGTH: 224
<212> TYPE: DNA
<213> ORGANISM: Unknown
```

```
<220> FEATURE:
<223> OTHER INFORMATION: Encodes 16S rRNA from Lachnospiracea incertae
      sedis

<400> SEQUENCE: 21
agagtttgat cctggctcag gatgaacgct ggcggcgtgc ctaacacatg caagtcgaac       60
gaagcacttt ctttagattc ttcggatgaa gaagactgtg actgagtggc ggacgggtga      120
gtaacgcgtg ggcaacctgc cctgtacagg gggataacag ttagaaatga ctgctaatac      180
cgcataagcg cacgaggacg catgttcttg tgtgaaaaac tccg                       224

<210> SEQ ID NO 22
<211> LENGTH: 224
<212> TYPE: DNA
<213> ORGANISM: Unknown
<220> FEATURE:
<223> OTHER INFORMATION: Encodes 16S rRNA from Lactobacillus

<400> SEQUENCE: 22
agatttgatc atggctcagg atgaacgccg gcggtgtgcc taatacatgc aagtcgtacg       60
cactggccca actgattgat ggtgcttgca ccggattgac gatggatcac cagtgagtgg      120
cggacgggtg agtaacacgt aggtaacctg ccccggagcg ggggataaca tttgaaaaca      180
gatgctaata ccgcataaca acaaaagtcg catggctttt gttt                       224

<210> SEQ ID NO 23
<211> LENGTH: 224
<212> TYPE: DNA
<213> ORGANISM: Unknown
<220> FEATURE:
<223> OTHER INFORMATION: Encodes 16S rRNA from Anaerofilum

<400> SEQUENCE: 23
agatttgatc atggctcagg acgaacgctg gcggcgcgcc taacacatgc aagtcgaacg       60
gagctgcttt gacagattcc ttcgggatga cgttgattta gcttagtggc gaacgggtga      120
gtaacacgtg agcaacctac ctttcagagg gggacaacag ttggaaacga ctgctaatac      180
cgcataagac cacgctatgg catcgtagag gggtcaaagg agaa                       224

<210> SEQ ID NO 24
<211> LENGTH: 224
<212> TYPE: DNA
<213> ORGANISM: Unknown
<220> FEATURE:
<223> OTHER INFORMATION: Encodes 16S rRNA from Lachnospiracea invertae
      sedis

<400> SEQUENCE: 24
agatttgacc tggctcagga tgaacgctgg cggcgtgctt aacacatgca agtcgaacga       60
agcattggag aacggagatt tcggttgaag ttttcctttg actgagtggc ggacgggtga      120
gtaacgcgtg ggtaacctgc cctgtacagg gggataacag ttagaaatga ctgctaatac      180
cgcataagcg cacagcttcg catggagcgg tgtgaaaaac tgag                       224

<210> SEQ ID NO 25
<211> LENGTH: 224
<212> TYPE: DNA
<213> ORGANISM: Unknown
<220> FEATURE:
<223> OTHER INFORMATION: Encodes 16S rRNA from Lachnospiraceae
      (Clostridium Cluster XIVa)

<400> SEQUENCE: 25
```

```
agatttgatc atggctcagg atgaacgctg gcggcgtgcc taacacatgc aagtcgaacg      60
aagcgatttg aagaagtttt tcggatggaa tccaaattga ctgagtggcg gacgggtgag     120
taacgcgtgg gtaacctgcc tcacactggg ggacaacagc tggaaacggc tgctaatacc    180
gcataagcgc acagcttcgc atgaagcagt gtgaaaaact ccgg                     224
```

```
<210> SEQ ID NO 26
<211> LENGTH: 224
<212> TYPE: DNA
<213> ORGANISM: Unknown
<220> FEATURE:
<223> OTHER INFORMATION: Encodes 16S rRNA from Microbacterium

<400> SEQUENCE: 26
agatttgatc atggctcagg acgaacgctg gcggcgtgct taacacatgc aagtcgaacg      60
atgaagctgg tgcttgcact ggtggattag tggcgaacgg gtgagtaaca cgtgagtaac    120
ctgcccctga ctctgggata actgctgaaa acggtagcta atactggata tgaaccgtac    180
gggcatctgt tgcggttgga aagtttttc ggttgggat gggc                       224
```

```
<210> SEQ ID NO 27
<211> LENGTH: 224
<212> TYPE: DNA
<213> ORGANISM: Unknown
<220> FEATURE:
<223> OTHER INFORMATION: Encodes 16S rRNA from Verrucosispora

<400> SEQUENCE: 27
agatttgatc ctggctcagg acgaacgctg gcggcgtgct taacacatgc aagtcgagcg      60
gaaaggccct tcggggtact cgagcggcga acgggtgagt aacacgtgag caacctgccc   120
taggctttgg gataaccctc ggaaacgggg gctaataccg gatattcact tgctgccgca   180
tggtggtggg tggaaagatt tttcggcttg ggatgggctc gcgg                     224
```

```
<210> SEQ ID NO 28
<211> LENGTH: 224
<212> TYPE: DNA
<213> ORGANISM: Unknown
<220> FEATURE:
<223> OTHER INFORMATION: Encodes 16S rRNA from Anaerofilum

<400> SEQUENCE: 28
agatttgatc atggctcagg acgaacgctg gcggcgcgcc taacacatgc aagtcgaacg      60
gagcattgag agcttgcttt taatgcttag tggcgaacgg gtgagtaacg cgtgagtaac    120
ctgcccttga gtgggggaca acagttggaa acgactgcta ataccgcata agaccacaga   180
gccgcatggc tcggaggtaa aaggatttat tcgctcaagg atgg                     224
```

```
<210> SEQ ID NO 29
<211> LENGTH: 224
<212> TYPE: DNA
<213> ORGANISM: Unknown
<220> FEATURE:
<223> OTHER INFORMATION: Encodes 16S rRNA from Clostridium sensu stricto

<400> SEQUENCE: 29
agatttgatc atggctcagg acgaacgctg gcggcgtgcc taacacatgc aagttgagcg      60
gagatatgag aagcttgctc tttctatttt agcagcgaac gggtgagtaa cacgtagata   120
atttgtccta tactggggga taggccgatg aaaattggat taataccgca tacagctatt    180
```
taaccgcatg gatagatagt gaaaggggaa acttgatata ggag       224

<210> SEQ ID NO 30
<211> LENGTH: 224
<212> TYPE: DNA
<213> ORGANISM: Unknown
<220> FEATURE:
<223> OTHER INFORMATION: Encodes 16S rRNA from Lactobacillus

<400> SEQUENCE: 30
agatttgatc ctggctcaga ttgaacgctg gcggcaggcc taacacatgc aagtcgagcg       60
agcagaacta gcagatttac ttcggtaatg acgctgggga cgcgagcggc ggatgggtga      120
gtaacacgtg gggaacctgc cccatagtct gggataccac ttggaaacag gtgctaatac      180
cggataagaa agcagatcgc atgatcagct tataaaaggc ggcg                       224

<210> SEQ ID NO 31
<211> LENGTH: 224
<212> TYPE: DNA
<213> ORGANISM: Unknown
<220> FEATURE:
<223> OTHER INFORMATION: Encodes 16S rRNA from Lactobacillus

<400> SEQUENCE: 31
agatttgatc atggctcagg acgaacgctg gcggcgtgcc taatacatgc aagtcgaacg       60
aaactttctt acaccgaatg cttgcattca ccgtaagaag ttgagtggcg acgggtgag      120 taacacgtgg gtaacctgcc taaagaagg ggataacact tggaaacagg tgctaatacc      180
gtatatcttt aaggatcgca tgatccttag atgaaagatg gttc                       224

<210> SEQ ID NO 32
<211> LENGTH: 224
<212> TYPE: DNA
<213> ORGANISM: Unknown
<220> FEATURE:
<223> OTHER INFORMATION: Encodes 16S rRNA from Lachnospiraceae
    (Clostridium Cluster XIVa)

<400> SEQUENCE: 32
agatttgatc ctggctcagg atgaacgctg gcggcgtgct taacacatgc aagtcgagcg       60
aagcgcttaa acagatttct tcggaatgaa gttttttgcga ctgagcggcg gacgggtgag     120
taacgcgtgg gcaacctgcc ccataccggg ggataacagc tggaaacggc tgctaatacc      180
gcataagcgc acagtgccgc atggcacggt gtgaaaaact ccgg                       224

<210> SEQ ID NO 33
<211> LENGTH: 224
<212> TYPE: DNA
<213> ORGANISM: Unknown
<220> FEATURE:
<223> OTHER INFORMATION: Encodes 16S rRNA from Blautia

<400> SEQUENCE: 33
agatttgatc atggctcagg atgaacgctg gcggcgtgct taacacatgc aagtcgaacg       60
ggaaacattt tattgaagct tcggcagatt tagcttgttt ctagtggcgg acgggtgagt     120
aacgcgtggg taacctgccc cacacggggg gataacaacc agaaatggct gctaataccg      180
cataagcgca cggggccgca tggccatgtg tgaaaaactc cggt                       224

<210> SEQ ID NO 34
<211> LENGTH: 224
<212> TYPE: DNA

```
<213> ORGANISM: Unknown
<220> FEATURE:
<223> OTHER INFORMATION: Encodes 16S rRNA from Lactobacillus

<400> SEQUENCE: 34
agatttgatc ctggctcagg atgaacgccg gcggtgtgcc taatacatgc aagtcgagcg      60
cactggccca actgatatga cgtgcttgca ctgaattgac gttggattcc cagtgagcgg     120
cggacgggtg agtaacacgt gggcaacctg ccccaaagcg gggataaca tttggaaaca      180 ggtgctaata ccgcataact tggaaaacca catggttttc caat                      224

<210> SEQ ID NO 35
<211> LENGTH: 224
<212> TYPE: DNA
<213> ORGANISM: Unknown
<220> FEATURE:
<223> OTHER INFORMATION: Encodes 16S rRNA from Lactobacillus

<400> SEQUENCE: 35
agatttgatc ctggctcagg acgaacgctg gcggcgtgcc taatacatgc aagtcgagcg      60
agcggaacta acagatttac ttcggtaatg acgttaggaa agcgagcggc ggatgggtga     120
gtaacacgtg gggaacctgc cccatagtct gggataccac ttggaaacag gtgctaatac     180
cgcataacaa caaaagccac atggcttttg tttgaaagat ggct                      224

<210> SEQ ID NO 36
<211> LENGTH: 224
<212> TYPE: DNA
<213> ORGANISM: Unknown
<220> FEATURE:
<223> OTHER INFORMATION: Encodes 16S rRNA from Lactobacillus

<400> SEQUENCE: 36
agatttgatc atggctcagg atgaacgccg gcggtgtgcc taatacatgc aagtcgtacg      60
cactggccca actgattgat ggtgcttgca cctgattgac gatggattac cagtgagtgg     120
cggacgggtg agtaacacgt gggtaacctg cctaaaagaa ggggataaca cttggaaaca     180
ggtgctaata ccggataaga aagcagatcg catgatcagc tttt                      224

<210> SEQ ID NO 37
<211> LENGTH: 224
<212> TYPE: DNA
<213> ORGANISM: Unknown
<220> FEATURE:
<223> OTHER INFORMATION: Encodes 16S rRNA from Pseudomonas

<400> SEQUENCE: 37
agatttgatc ctggctcaga ttgaacgctg gcgacaggcc taacacatgc aagtcgagcg      60
gatgagagga gcttgctcct tgatttagcg gcggacgggt gggtaatgcc taggaatctg     120
cctggtagtg ggggataacg ttccgaaagg aacgctaata ccgcatacgt cctacgggag     180
aaagcagggg accttcgggc cttgcgctat cagatgagcc tagg                      224

<210> SEQ ID NO 38
<211> LENGTH: 224
<212> TYPE: DNA
<213> ORGANISM: Unknown
<220> FEATURE:
<223> OTHER INFORMATION: Encodes 16S rRNA from Lachnospiraceae
      (Clostridium Cluster XIVb); Potential human pathogen (currently
      unconfirmed pathogen status)

<400> SEQUENCE: 38
```

```
agagtttgat cctggctcag gatgaacgct ggcggcgtgc ctaacacatg caagtcgagc    60
ggagttttac gagagcttgc ttttgtaaaa cttagcggcg gacgggtgag taacgcgtgg   120
gtaacctgcc ctatacacag gataacatt gagaaattga tgctaatacc tgataagcta   180
acagctaggc atctagcagt tagaaaaact gaggtggtat agga                   224
```

<210> SEQ ID NO 39
<211> LENGTH: 224
<212> TYPE: DNA
<213> ORGANISM: Unknown
<220> FEATURE:
<223> OTHER INFORMATION: Encodes 16S rRNA from Sporobacter

<400> SEQUENCE: 39

```
agatttgatc atggctcagg acgaacgctg gcggcgtgcc taacacatgc aagtcgaacg    60
gagccaatcg aatgaatttt tcggaaggat tttgaggaag cttagtggcg gacgggcgag   120
taacgcgtga ataacctgcc cataagaggg ggataatcca tggaaacgtg gactaatacc   180
gcatattgag cattaaccgc atggttgatg gttgaaagat ttat                   224
```

<210> SEQ ID NO 40
<211> LENGTH: 224
<212> TYPE: DNA
<213> ORGANISM: Unknown
<220> FEATURE:
<223> OTHER INFORMATION: Encodes 16S rRNA from Lactobacillus

<400> SEQUENCE: 40

```
agatttgatc atggctcagg acgaacgctg gcggcgtgcc taatacatgc aagtcgagcg    60
agcggaacta acagatttac ttcggtaatg acgttaggaa agcgagcggc ggatgggtga   120
gtaacacgtg gggaacctgc cccatagtct gggataccac ttggaaacag gtgctaatac   180
cgcataacaa cgaaaaccac atggttttcg tttaaaagat ggtt                   224
```

<210> SEQ ID NO 41
<211> LENGTH: 224
<212> TYPE: DNA
<213> ORGANISM: Unknown
<220> FEATURE:
<223> OTHER INFORMATION: Encodes 16S rRNA from Lactobacillus

<400> SEQUENCE: 41

```
agatttgatc atggctcagg acgaacgctg gcggcgtgcc taatacatgc aagtcgaacg    60
aaactttctt acaccgaatg cttgcattca ccgtaagaag ttgagtggcg gacgggtgag   120
taacacgtgg gtaacctgcc taaagaagg ggataacatt tggaaacaga tgctaatacc   180
gcataacaac aaaagccaca tggcttttgt ttgaaagatg gctt                   224
```

<210> SEQ ID NO 42
<211> LENGTH: 224
<212> TYPE: DNA
<213> ORGANISM: Unknown
<220> FEATURE:
<223> OTHER INFORMATION: Encodes 16S rRNA from Lactobacillus

<400> SEQUENCE: 42

```
agatttgatc atggctcagg acgaacgctg gcggcgtgcc taatacatgc aagtcgagcg    60
agcagaacca gcagatttac ttcggtaatg acgctgggga cgcgagcggc ggatgggtga   120
gtaacacgtg gggaacctgc cccatagtct gggataccac ttggaaacag atactaatac   180
```

```
cgcataacaa caaaagccac atggcttttg tttgaaagat ggct                      224
```

<210> SEQ ID NO 43
<211> LENGTH: 224
<212> TYPE: DNA
<213> ORGANISM: Unknown
<220> FEATURE:
<223> OTHER INFORMATION: Encodes 16S rRNA from Lachnospiracea incertae
      sedis

<400> SEQUENCE: 43

```
agatttgatc atggctcagg atgaacgctg gcggcgtgct taacacatgc aagtcgaacg      60
aagcactggg aacggagat ttcggttgaa gttttcctttt gactgagtgg cggacgggtg     120
agtaacgcgt gggtaaccctg ccctgtacag ggggataaca gttagaaatg actgctaata   180
ccgcataagc gcacagcttc gcatggagcg gtgtgaaaaa ctga                     224
```

<210> SEQ ID NO 44
<211> LENGTH: 224
<212> TYPE: DNA
<213> ORGANISM: Unknown
<220> FEATURE:
<223> OTHER INFORMATION: Encodes 16S rRNA from Lactobacillus

<400> SEQUENCE: 44

```
agatttgatc atggctcagg acgaacgctg gcggcgtgcc taatacatgc aagtcgagcg     60
agcggaacta acagatttac ttcggtaatg acgttaggaa agcgagcggc ggatgggtga   120
gtaacacgtg gggaacctgc cccatagtct gggataacat ttggaaacag atgctaatac   180
cgcataacaa caaaagccac atggcttttg tttgaaagat ggct                     224
```

<210> SEQ ID NO 45
<211> LENGTH: 224
<212> TYPE: DNA
<213> ORGANISM: Unknown
<220> FEATURE:
<223> OTHER INFORMATION: Encodes 16S rRNA from Lactobacillus

<400> SEQUENCE: 45

```
agatttgatc atggctcagg atgaacgccg gcggtgtgcc taatacatgc aagtcgagcg     60
cattggccca actgatatga cgtgcttgca ctgaattgac gttggattac cagtgagcgg   120
cggacgggtg agtaacacgt gggcaacctg ccctgaagcg ggggataaca tctggaaaca   180
gatgctaata ccgcataaca acaaaagcca catggctttt gttt                     224
```

<210> SEQ ID NO 46
<211> LENGTH: 224
<212> TYPE: DNA
<213> ORGANISM: Unknown
<220> FEATURE:
<223> OTHER INFORMATION: Encodes 16S rRNA from Peptostreptococcaceae
      (Clostridum Cluster XI)

<400> SEQUENCE: 46

```
agatttgatc atggctcagg atgaacgctg gcggcgtgcc taacacatgc aagtcgagcg     60
aactcttcgg agtgagcggc ggacgggtga gtaacgcgtg ggtaacctgc cctgtacaca   120
tggataacat accgaaaggt atgctaatac aagataaaat atatttatcg catgatagat   180
atatcaaagc gttagcggta caggatggac ccgcgtctga ttag                     224
```

<210> SEQ ID NO 47
<211> LENGTH: 224

```
<212> TYPE: DNA
<213> ORGANISM: Unknown
<220> FEATURE:
<223> OTHER INFORMATION: Encodes 16S rRNA of Lactobacillus

<400> SEQUENCE: 47
agatttgatc atggctcagg acgaacgctg gcggcgtgcc taatacatgc aagtcgagcg      60
agcggaacta acagatttac ttcggtaatg acgttaggaa agcgagcggc ggacgggtga     120
gtaacacgtg gtaacctgcc caagagact gggataacac ctggaaacag gtgctaatac     180
cggataagaa agcagatcgc atgatcagct tttaaaaggc ggcg                      224

<210> SEQ ID NO 48
<211> LENGTH: 224
<212> TYPE: DNA
<213> ORGANISM: Unknown
<220> FEATURE:
<223> OTHER INFORMATION: Encodes 16S rRNA of Lactobacillus

<400> SEQUENCE: 48
agatttgatc ctggctcagg acgaacgctg gcggcgtgcc taatacatgc aagtcgagcg      60
agcttgccta gatgattta gtgcttgcac taaatgaaac tagatacaag cgagcggcgg     120
acgggtgagt aacacgtggg taacctgccc aagagactgg gataacacct ggaaacagat     180
gctaataccg cataacaaca aaagccacat ggcttttgtt tgaa                      224

<210> SEQ ID NO 49
<211> LENGTH: 224
<212> TYPE: DNA
<213> ORGANISM: Unknown
<220> FEATURE:
<223> OTHER INFORMATION: Encodes 16S rRNA from Lactobacillus

<400> SEQUENCE: 49
agatttgatc atggctcagg atgaacgccg gcggtgtgcc taatacatgc aagtcgtacg      60
cactggccca actgattgat ggtgcttgca cctgattgat gatggatcac cagtgagtgg     120
cgaacgggtg agtaacacgt aggtaacctg ccccggagcg ggggataaca tttggaaaca     180
ggtgctaata ccgcataaca acgaaaaacca catggttttc gttt                     224

<210> SEQ ID NO 50
<211> LENGTH: 224
<212> TYPE: DNA
<213> ORGANISM: Unknown
<220> FEATURE:
<223> OTHER INFORMATION: Encodes 16S rRNA from Lactobacillus

<400> SEQUENCE: 50
agatttgatc atggctcagg acgaacgctg gcggcgtgcc taatacatgc aagtcgagcg      60
agcggaacta acagatttac ttcggtaatg acgttaggaa agcgagcggc ggacgggtga     120
gtaacacgtg gtaacctgcc cctgaagcgg gggataacat ctggaaacag gtgctaatac     180
cgcataacaa caaaagccac atggcttttg tttgaaagat ggct                      224

<210> SEQ ID NO 51
<211> LENGTH: 225
<212> TYPE: DNA
<213> ORGANISM: Unknown
<220> FEATURE:
<223> OTHER INFORMATION: Encodes ITS region from Nectriaceae

<400> SEQUENCE: 51
```

```
tccgtaggtg aacctgcgga gggatcatta ccgagtttac aactcccaaa ccctgtgaa      60 cataccaatt gttgcctcgg cggatcagcc cgctcccgt aaaacgggac ggcccgccag     120 aggacccta aactctgttt ctatatgtaa cttctgagta aaaccataaa taaatcaaaa     180
ctttcaacaa cggatctctt ggttctggca tcgatgaaga acgca                    225
```

<210> SEQ ID NO 52
<211> LENGTH: 225
<212> TYPE: DNA
<213> ORGANISM: Unknown
<220> FEATURE:
<223> OTHER INFORMATION: Encodes ITS region from Filobasidium floriforme

<400> SEQUENCE: 52

```
tccgtaggtg aacctgcgga aggatcatta atgaatttag attgaaccat aggcgaaagc     60
cagtggttct tctttcatat ccataacacc tgtgcactgt tggatgcttg catccacttt    120
taaactaaac attattgtaa caaatgtagt cttattataa cataataaaa ctttcaacaa    180
cggatctctt ggctctcgca tcgatgaaga acgcagcgaa atgcg                    225
```

<210> SEQ ID NO 53
<211> LENGTH: 225
<212> TYPE: DNA
<213> ORGANISM: Unknown
<220> FEATURE:
<223> OTHER INFORMATION: Encodes ITS region from Gibberella zeae

<400> SEQUENCE: 53

```
tccgtaggtg aacctgcgga gggatcatta ccgagtttac aactcccaaa ccctgtgaa      60 cataccttat gttgcctcgg cggatcagcc cgcgccccgt aaaagggac ggcccgccgc     120 aggaaccctg aactctgttt ttagtggaac ttctgagtat aaaaaacaaa taaatcaaaa    180
ctttcaacaa cggatctctt ggttctggca tcgatgaaga acgca                    225
```

<210> SEQ ID NO 54
<211> LENGTH: 225
<212> TYPE: DNA
<213> ORGANISM: Unknown
<220> FEATURE:
<223> OTHER INFORMATION: Encodes ITS region from Alatospora

<400> SEQUENCE: 54

```
tccgtaggtg aacctgcgga ggagcatatc aataagcgga ggaccttccg taggtgaacc     60
tgcggacgca tatcattaag cggaggacat atcaataagc ggaggacctt ccgtaggtga    120
acctgcggac gcatatcaat aagcggagga tcttccgtag gtgaacctgc ggaaggatca    180
ttatgaataa gcatatcaat aagcggagga tcgtccgtag gtgaa                    225
```

<210> SEQ ID NO 55
<211> LENGTH: 225
<212> TYPE: DNA
<213> ORGANISM: Unknown
<220> FEATURE:
<223> OTHER INFORMATION: Encodes ITS region from Hypocreaceae

<400> SEQUENCE: 55

```
tccgtaggtg aacctgcgga aggatcatta tgaattataa atatttgtga atttaccaca     60
gcaaacaaaa atcatacaat caaaacaaaa ataattaaaa cttttaacaa tggatctctt    120
ggttctcgta tcgatgaaga acgcagcgaa acgcgatatt tcttgtgaat tgcagaagtg    180
aatcatcagt ttttgaacgc acattgcact ttggggtatc cccca                    225
```

<210> SEQ ID NO 56
<211> LENGTH: 225
<212> TYPE: DNA
<213> ORGANISM: Unknown
<220> FEATURE:
<223> OTHER INFORMATION: Encodes ITS region from Pichia Fermentans

<400> SEQUENCE: 56

```
tccgtaggtg aacctgcgga aggatcatta ctgtgattta tatcttatac acatgcgtga    60
gcgcaccaaa cacctaaaat tgtaataata ccagtcagta agttttaaca aaacaaaact   120
ttcaacaacg gatctcttgg ttctcgcatc gatgaagagc gcagcgaaat gcgatacctg   180
gtgtgaattg cagccatcgt gaatcatcga gttcttgaac gcaca                   225
```

<210> SEQ ID NO 57
<211> LENGTH: 225
<212> TYPE: DNA
<213> ORGANISM: Unknown
<220> FEATURE:
<223> OTHER INFORMATION: Encodes ITS region from Candida railenensis

<400> SEQUENCE: 57

```
tccgtaggtg aacctgcgga aggatcatta cagtattctt ttgccagcgc ttaattgcgc    60
ggcgaaaaac cttacacact atgttttttt aatttgaaac tattgctttg gtctggctta   120
gaaataggtt gggccaaagg ttttatcaaa acttcaatat ttattattga attgttattt   180
ttaattttat gtcaatttgt tgattatatc aaaaatcttc aaaac                   225
```

<210> SEQ ID NO 58
<211> LENGTH: 225
<212> TYPE: DNA
<213> ORGANISM: Unknown
<220> FEATURE:
<223> OTHER INFORMATION: Encodes ITS region from Hypocreaceae

<400> SEQUENCE: 58

```
tccgtaggtg aacctgcgga aggatcatta agaattataa atatttgtga aatttacaca    60
gcaaacaata attttatagt caaaacaaaa ataatcaaaa cttttaacaa tggatctctt   120
ggttctcgta tcgatgaaga acgcagcgaa acgcgatatt tcttgtgaat tgcagaagtg   180
aatcatcagt ttttgaacgc acattgcact ttggggtatc cccca                   225
```

<210> SEQ ID NO 59
<211> LENGTH: 225
<212> TYPE: DNA
<213> ORGANISM: Unknown
<220> FEATURE:
<223> OTHER INFORMATION: Encodes 16S rRNA from Clostridium XlVb

<400> SEQUENCE: 59

```
agagtttgat catggctcag gatgaacgct ggcggcgtgc ctaacacatg caagtcgagc    60
gcgtctgatt tgatgcttgc attaatgaaa gatgagcggc ggacgggtga gtaacgcgtg   120
ggtaacctgc cctatacaca tggataacat actgaaaagt ttactaatac atgataaatat  180 atatttacgg catcgtagat atatcaaagt gttagcggta tagga                   225
```

<210> SEQ ID NO 60
<211> LENGTH: 225
<212> TYPE: DNA
<213> ORGANISM: Unknown
<220> FEATURE:

<223> OTHER INFORMATION: Encodes 16S rRNA from Gemmiger

<400> SEQUENCE: 60

```
agagtttgat catggctcag gatgaacgcc ggcggtgtgc ctaatacatg caagtcgaac    60
ggtaacagga agcagcttgc tgcttcgctg acgagtggcg gacgggtgag taacgcgtga   120
gtaacctgcc ccgaagtggg ggacaacagt tggaaacgac tgctaatacc gcataagccc   180
acagagccgc atggctcaga gggaaaagga cttcggtttg cttcg                  225
```

<210> SEQ ID NO 61
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 61

```
agagtttgat cctggctcag gatgaacgct ggcggcgtgc ttaacacatg caagtcgaac    60
ggaaaggcct tgtgcttgca cagggtactc gagtggcgaa cgggtgagta acacgtgggt   120
aacctgccca agagactggg ataacacctg gaaacagatg ctaataccgg ataacaacac   180
tagacgcatg tctagagttt gaaagatggt tctgctatca ctctt                  225
```

<210> SEQ ID NO 62
<211> LENGTH: 185
<212> TYPE: DNA
<213> ORGANISM: Unknown
<220> FEATURE:
<223> OTHER INFORMATION: Encodes 16S rRNA from Clostridium XI

<400> SEQUENCE: 62

```
agagtttgat catggctcag gatgaacgct ggcggcgtgc ctattgcaca atgggcgaaa    60
gcctgatgca gcaacgccgc gtgagcgaag aaggccttcg ggtcgtaaag ctctgtcata   120
taggaagata atgacggtac ttgaggagga agccccggct aactacgtgc cagcagccgc   180
ggaat                                                              185
```

<210> SEQ ID NO 63
<211> LENGTH: 225
<212> TYPE: DNA
<213> ORGANISM: Unknown
<220> FEATURE:
<223> OTHER INFORMATION: Encodes 16S rRNA from Jeotgalicoccus

<400> SEQUENCE: 63

```
agagtttgat catggctcag gatgaacgct ggcggcgtgc ctaatacatg caagtcgagc    60
gcgaagatca ggagcttgct cctgagattc gagcggcgga cgggtgagta acacgtaggc   120
aacctaccct tgagattggg ataactaccg gaaacggtag ctaataccgg atacgacatt   180
cctgcataag taagaatgtt aaaaggcgga tttatctgcc gctca                  225
```

<210> SEQ ID NO 64
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 64

```
agagtttgat cctggctcag gacgaacgct ggcggcgtgc ctaacacatg caagttgagc    60
ggagatatga ggagcttgct ttttatatct tagcagcgaa cgggtgagta acacgtgggg   120
```

```
aacctgcccc atagtctggg ataccacttg gaaacaggtg ctaataccgg ataagaaagc      180
agatcgcatg atcagctttt aaaaggcggc gtaagctgtc gctat                    225
```

<210> SEQ ID NO 65
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 65

```
agagtttgat cctggctcag gatgaacgct ggcggcgtgc ctaatacatg caagtcgagc      60
gcatcggccc aactgattga agatgcttgc atccgattga cgatggttta ccgatgagcg    120
gcggacgggt gagtaacacg taggtaacct gcccagaagc gggggataac acctggaaac    180
agatgctaat accgcatagg tcatttgacc gcatggtcaa atgat                    225
```

<210> SEQ ID NO 66
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 66

```
agagtttgat catggctcag gacgaacgct ggcggcgtgc ctaacacatg caagtcgaac      60
ggagttgttt gaggaagttt tcggatggaa tcagatgact tagtggcgga cgggtgagta    120
acgcgtggga aacctgccct gtactggggg ataacacttg gaaacaggtg ctaataccgg    180
ataagaaagc agatcgcatg atcagctttt aaaaggcggc gtaag                    225
```

<210> SEQ ID NO 67
<211> LENGTH: 225
<212> TYPE: DNA
<213> ORGANISM: Unknown
<220> FEATURE:
<223> OTHER INFORMATION: Encodes 16S rRNA from Jeotgalicoccus

<400> SEQUENCE: 67

```
agagtttgat catggctcag gatgaacgct ggcggcgtgc ctaatacatg caagtcgagc      60
gcgagcgtta aagcttgct tctaacaatc gagcggcgga cgggtgagta acacgtgggc    120
agcctacctt tgagattggg ataactaccg gaaacggtag ctaataccgg ataggacatg    180
attacataag tagtgatgtt aaaaggcgga tttatctgcc gttca                    225
```

<210> SEQ ID NO 68
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 68

```
agagtttgat catggctcag gacgaacgct ggcggcgtgc ctaatacatg caagtcgaac      60
gaaactttct tacaccgaat gcttgcattc atcgtaagaa gttgagtggc ggacgggtga    120
gtaacacgtg gggaacctgc cccatagtct gggataccac ttggaaacag gtgctaatac    180
cggataagaa agcagatcgc atgatcagct tttaaaaggc ggcgt                    225
```

<210> SEQ ID NO 69

```
<211> LENGTH: 225
<212> TYPE: DNA
<213> ORGANISM: Unknown
<220> FEATURE:
<223> OTHER INFORMATION: Encodes 16S rRNA from Jeotgalicoccus

<400> SEQUENCE: 69
agagtttgat cctggctcag gatgaacgct ggcggcgtgc ctaatacatg caagtcgagc      60
gcgaagatca ggagcttgct cctgagattc gagcggcgga cgggtgagta acacgtaggc     120 aacctacccct tgagattggg ataactaccg gaaacggtag ctaataccgg atacgacatt    180
cctgcataag taagaatgtt aaaaggcgga tttatctgcc gctca                     225

<210> SEQ ID NO 70
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 70
agagtttgat catggctcag gatgaacgcc ggcggtgtgc ctaatacatg caagtcgagc      60
gcactggccc aacagaaatg acgtgcttgc actgatttga cgttggattc ccagtgagcg     120
gcggacgggt gagtaacacg tgggcaacct gccccaaagc ggggaagat aatgacggta     180 cccaaggagg aagccacggc taactacgtg ccagcagccg cggta                     225

<210> SEQ ID NO 71
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 71
agagtttgat catggctcag gatgaacgcc ggcggtgtgc ctaatacatg caagtcgagc      60
gcactggccc aacagaaatg acgtgcttgc actgatttga cgttggattc ccagtgagcg     120
gcggacgggt gagtaacacg tgggcaacct gccccaaagc ggggatcgc atgatcctta     180 gatgaaagat ggttctgcta tcgcttttag atggacccgc ggcgt                     225

<210> SEQ ID NO 72
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 72
agagtttgat cctggctcag gatgaacgct ggcggcgtgc ctaatacatg caagtcgagc      60
gaacagataa ggagcttgct cctttgacgt tagcggcgga cgggtgagta acacgtgggt     120
aacctaccta taagactggg ataacttcgg gaaaccggag ctaataccgg ataagaaagc     180
agatcgcatg atcagcttat aaaaggcggc gtaagctgtc gctat                     225

<210> SEQ ID NO 73
<211> LENGTH: 225
<212> TYPE: DNA
<213> ORGANISM: Unknown
<220> FEATURE:
<223> OTHER INFORMATION: Encodes 16S rRNA from Corynebacterium

<400> SEQUENCE: 73
```

```
agagtttgat catggctcag gacgaacgct ggcggcgtgc ctaatacatg caagtcgaac      60
gaaactttct tacaccgaat gcttgcattc accgtaagaa gttgagtggc ggacgggtga     120
gtaacacgtg ggtgatctgc cctgcactgt gggataagcc tgggaaactg ggtctaatac     180
catataggac cgcatcttgg atggtgtggt ggaaagcttt tgcgg                     225
```

```
<210> SEQ ID NO 74
<211> LENGTH: 197
<212> TYPE: DNA
<213> ORGANISM: Unknown
<220> FEATURE:
<223> OTHER INFORMATION: Encodes 16S rRNA from Microbacterium

<400> SEQUENCE: 74
agagtttgat cctggctcag actcctacgg gaggcagcag tggggaatat tgcacaatgg      60
gggaaaccct gatgcagcaa cgccgcgtga gggatgacgg ccttcgggtt gtaaacctct     120
tttggcaggg aagaagcgag agtgacggta cctgcagaaa aagcgccggc taactacgtg     180
ccagcagccg cggtaat                                                    197
```

```
<210> SEQ ID NO 75
<211> LENGTH: 225
<212> TYPE: DNA
<213> ORGANISM: Unknown
<220> FEATURE:
<223> OTHER INFORMATION: Encodes 16S rRNA from Jeotgalicoccus

<400> SEQUENCE: 75
agagtttgat catggctcag gatgaacgct ggcggcgtgc ctaatacatg caagtcgagc      60
gcgaagatca ggagcttgct cctgagattc gagcggcgga cgggtgagta acacgtaggc     120
aacctaccct tgagattggg ataactaccg gaaacggtag ctaataccgg atacgacatt     180
cctgcataag taagaatgtt aaaaggcgga tttatctgcc gctca                     225
```

```
<210> SEQ ID NO 76
<211> LENGTH: 225
<212> TYPE: DNA
<213> ORGANISM: Unknown
<220> FEATURE:
<223> OTHER INFORMATION: Encodes 16S rRNA from Jeotgalicoccus

<400> SEQUENCE: 76
agagtttgat catggctcag gatgaacgct ggcggcgtgc ctaatacatg caagtcgagc      60
gcgaagatca ggagcttgct cctgagattc gagcggcgga cgggtgagta acacgtaggc     120
aacctaccct tgagattggg ataactaccg gaaacggtag ctaataccgg atacgacatt     180
cctgcataag taagaatgtt aaaaggcgga tttatctgcc gctca                     225
```

```
<210> SEQ ID NO 77
<211> LENGTH: 225
<212> TYPE: DNA
<213> ORGANISM: Unknown
<220> FEATURE:
<223> OTHER INFORMATION: Encodes 16S rRNA from Glycomyces

<400> SEQUENCE: 77
agagtttgat catggctcag gacgaacgct ggcggcgtgc ttcacacatg caagtcgaac      60
ggaaaggctc cttcgggagt gctcgagtgg cgaacgggtg agtaacacgt gggtaacctg     120
cccccatctc tgggataact gctggaaacg gtggctaata ccggatacta ctgctggtcg     180
```
catggcctgg tggtggaaag cttttgcggt tggggagggg ctcgc   225

<210> SEQ ID NO 78
<211> LENGTH: 225
<212> TYPE: DNA
<213> ORGANISM: Unknown
<220> FEATURE:
<223> OTHER INFORMATION: Encodes 16S rRNA from Streptomyces

<400> SEQUENCE: 78
agagtttgat cctggctcag gacgaacgct ggcggcgtgc ttaacacatg caagtcgaac   60
gatgaaccgg ccttcgggtt ggggattagt ggcgaacggg tgagtaacac gtgggtaatc   120
tgccctgcac tctgggataa gcctgggaaa ctgggtctaa tactggatat gaccttctct   180
cgcatggggg ttggtggaaa gcttttgcgg tgcaggatgg gcccg   225

<210> SEQ ID NO 79
<211> LENGTH: 225
<212> TYPE: DNA
<213> ORGANISM: Unknown
<220> FEATURE:
<223> OTHER INFORMATION: Encodes 16S rRNA from Saccharopolyspora

<400> SEQUENCE: 79
agagtttgat cctggctcag gcggtcagtc cgagccgctc cattcgggtg gtgtgctcgg   60
cgatgagatc ggtgtgcacg gcctcgatct gcgagaccat ccgctgcacc tcgtcgtcac   120
gctcgagcgt cgagtcgcgc agcgcccgca gcaccggctc gtcgagcacc atgagcgccc   180
ggcaccacag caacgcgtcg ccgacgaccc gccgccccca catgg   225

<210> SEQ ID NO 80
<211> LENGTH: 225
<212> TYPE: DNA
<213> ORGANISM: Unknown
<220> FEATURE:
<223> OTHER INFORMATION: Encodes 16S rRNA from Brevibacterium

<400> SEQUENCE: 80
agagtttgat cctggctcag gacgaacgct ggcggcgtgc ttaacacatg caagtcgaac   60
ggaaaggcct catccttttt tgggtggggt gctcgagtgg cgaacgggtg agtaacacgt   120
gagtaacctg cccctgactc tgggataagc ctgggaaact gggtctaata ctggatatga   180
tgcctggccg catggtctgg gtgtggaaag ttttttcggt tggga   225

<210> SEQ ID NO 81
<211> LENGTH: 225
<212> TYPE: DNA
<213> ORGANISM: Unknown
<220> FEATURE:
<223> OTHER INFORMATION: Encodes 16S rRNA from Microbacterium

<400> SEQUENCE: 81
agagtttgat cctggctcag gatgaacgct ggcggcgtgc ttaacacatg caagtcgaac   60
ggtgaagcca agcttgcttg gtggatcagt ggcgaacggg tgagtaacac gtgagcaacc   120
tgccctggac tctgggataa gcgctggaaa cggcgtctaa tactggatat gagcctcttc   180
cgcatggtgg gggttggaaa gatttttggg tctgggatgg gctcg   225

<210> SEQ ID NO 82
<211> LENGTH: 225
<212> TYPE: DNA
<213> ORGANISM: Unknown

<220> FEATURE:
<223> OTHER INFORMATION: Encodes 16S rRNA from Acinetobacter

<400> SEQUENCE: 82
agagtttgat catggctcag attgaacgct ggcggcaggc ttaacacatg caagtcgagc     60
ggagagaggt agcttgctac cgatcttagc ggcggacggg tgagtaatgc ttaggaatct    120
gcctattagt gggggacaac atttcgaaag gaatgctaat accgcatacg tcctacggga    180
gaaagcaggg gatcttcgga ccttgcgcta atagatgagc ctaag                    225

<210> SEQ ID NO 83
<211> LENGTH: 225
<212> TYPE: DNA
<213> ORGANISM: Unknown
<220> FEATURE:
<223> OTHER INFORMATION: Encodes 16S rRNA from Lactococcus

<400> SEQUENCE: 83
agagtttgat cctggctcag gacgaacgct ggcggcgtgc ctaatacatg caagttgagc     60
gctgaaggtt ggtacttgta ccgactggat gagcagcgaa cgggtgagta acgcgtgggg    120 aatctgccctt tgagcggggg acaacatttg gaaacgaatg ctaataccgc ataaaaactt   180
taaacacaag ttttaagttt gaaagatgca attgcatcac tcaaa                    225

<210> SEQ ID NO 84
<211> LENGTH: 225
<212> TYPE: DNA
<213> ORGANISM: Unknown
<220> FEATURE:
<223> OTHER INFORMATION: Encodes 16S rRNA from Cloacibacterium

<400> SEQUENCE: 84
agagtttgat cctggctcag gatgaacgct agcgggaggc ctaacacatg caagccgagc     60
ggtattgttt cttcggaaat gagagagcgg cgtacgggtg cggaacacgt gtgcaacctg    120
cctttatctg ggggatagcc tttcgaaagg aagattaata ctccataata tattgattgg    180
catcaattaa tattgaaagc tccggcggat agagatgggc acgcg                    225

<210> SEQ ID NO 85
<211> LENGTH: 225
<212> TYPE: DNA
<213> ORGANISM: Unknown
<220> FEATURE:
<223> OTHER INFORMATION: Encodes 16S rRNA from Mycobacterium

<400> SEQUENCE: 85
agagtttgat catggctcag gacgaacgct ggcggcgtgc ttaacacatg caagtcgaac     60
ggaaaggccc cttcgggggt gctcgagtgg cgaacgggtg agtaacacgt gggtgatctg    120
ccctgcactc tgggataagc ctgggaaact gggtctaata ccggatagga ccacatgtcg    180
catggtgtgt ggtggaaagc ttttgcggtg tgggatgggc ccgcg                    225

<210> SEQ ID NO 86
<211> LENGTH: 225
<212> TYPE: DNA
<213> ORGANISM: Unknown
<220> FEATURE:
<223> OTHER INFORMATION: Encodes 16S rRNA from Leucobacter

<400> SEQUENCE: 86
agagtttgat catggctcag gacgaacgct ggcggcgtgc ttaacacatg caagtcgaac     60

```
gctgaagctc ccagcttgct gggggtggat gagtggcgaa cgggtgagta acacgtgagt    120
aacctgcccc gaactctggg ataagcgctg gaaacggcgt ctaatactgg atatgtccta    180
tcaccgcatg gtgtgtaggt ggaaagaatt ttggttcggg atgga                    225
```

<210> SEQ ID NO 87
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 87

```
agagtttgat catggctcag gatgaacgct ggcggcatgc cttacacatg caagtcggac    60
gggaagtggt gtttccagtg gcggacgggt gagtaacacg tgggtaacct gcctaaaaga    120
aggggataac acttggaaac aggtgctaat accgtatatc tctaaggatc gcatgatcct    180
tagatgaaag atggttctgc tatcgctttt agatggaccc gcggc                   225
```

<210> SEQ ID NO 88
<211> LENGTH: 225
<212> TYPE: DNA
<213> ORGANISM: Unknown
<220> FEATURE:
<223> OTHER INFORMATION: Encodes 16S rRNA from Rothia

<400> SEQUENCE: 88

```
agagtttgat cctggctcag gacgaacgct ggcggcgtgc ttaacacatg caagtcgaac    60
gatgaagccc agcttgctgg gtggattagt ggcgaacggg tgagtaatac gtgagtaacc    120
tgcctttaac tctgggataa gccttggaaa cggggtctaa taccggatac gaccagttcc    180
cgcatgggat gctggtggaa agggatatgt actggtttta gatgg                   225
```

<210> SEQ ID NO 89
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 89

```
agagtttgat cctggctcag gatgaacgct ggcggcgtgc ctaacacatg caagtcgagc    60
gaactcttcg gagagagcgg cggacgggtg agtaacacgt ggggaacctg ccccatagtc    120
tgggatacca cttggaaaca ggtgctaata ccggataaga aagcagatcg catgatcagc    180
tttttaaaag gcggcgtaag ctgtcgctat gggatggccc cgcgg                   225
```

<210> SEQ ID NO 90
<211> LENGTH: 225
<212> TYPE: DNA
<213> ORGANISM: Unknown
<220> FEATURE:
<223> OTHER INFORMATION: Encodes 16S rRNA from Clavibacter

<400> SEQUENCE: 90

```
agagtttgat cctggctcag gacgaacgct ggcggcgtgc ttaacacatg caagtcgaac    60
ggtgatgtca gagcttgctc tggcggatca gtggcgaacg ggtgagtaac acgtgagtaa    120
cctgcccccg actctgggat aactgctaga aatggtagct aataccggat atgacgactg    180
gccgcatggt ctggtcgtgg aaagaatttc ggttggggat ggact                   225
```

```
<210> SEQ ID NO 91
<211> LENGTH: 225
<212> TYPE: DNA
<213> ORGANISM: Unknown
<220> FEATURE:
<223> OTHER INFORMATION: Encodes 16S rRNA from Hydrogenoanaerobacterium

<400> SEQUENCE: 91
agagtttgat catggctcag gacgaacgct ggcggcgcgc ctaacacatg caagtcgaac      60
ggggatattt aagagcttgc ttttgaatat tctagtggcg gacgggtgag taacgcgtga     120
gtaacctgcc tttcagaggg ggataacagt tggaaacagc tgctaatacc gcataacata     180
tacaattcgc atgggaagta tatcaaagag atatcgctga aagac                     225

<210> SEQ ID NO 92
<211> LENGTH: 225
<212> TYPE: DNA
<213> ORGANISM: Unknown
<220> FEATURE:
<223> OTHER INFORMATION: Encodes 16S rRNA from Howardella

<400> SEQUENCE: 92
agagtttgat cctggctcag gatgaacgct ggcggcgtgc ttaacacatg caagtcgaac      60
ggacaaagag gggcttgctc ctctttgtta gtggcggacg ggtgagtaac acgtgagcaa     120
cctgcccata tctggggaat aacacagtga aaattgtgct aataccgcat aagaccacga     180
ggaggcatct ccttgcggta aaagatttat cggatatgga tgggc                     225

<210> SEQ ID NO 93
<211> LENGTH: 225
<212> TYPE: DNA
<213> ORGANISM: Unknown
<220> FEATURE:
<223> OTHER INFORMATION: Encodes 16S rRNA from Clostridium sensu stricto

<400> SEQUENCE: 93
agagtttgat cctggctcag gacgaacgct ggcggcgtgc ctaacacatg caagtcgaac      60
ggacgaggag gtgcttgcac ctccaagtta gtggcggacg ggtgagtaac gcgtgagcaa     120
cctgcctcaa agaggggat  aacgtctgga acggacgct  aataccgcat gatatattga     180
ataggcatct atttaatatc aaaggagcaa tccgctttga gatgg                     225

<210> SEQ ID NO 94
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 94
agagtttgat cctggctcag gatgaacgct ggcggcgtgc ttaacacatg caagtcgagc      60
gaagcggttt tggaagtctt cggacggaag agagcgactg agcggcggac gggtgagtaa     120
cgcgtgggta acctgcctcg tacaggggga taacagttgg aaacgactgc taataccgca     180
taagcccacg gggtcgcatg gctctgaggg aaaaggattt attcg                     225

<210> SEQ ID NO 95
<211> LENGTH: 225
<212> TYPE: DNA
<213> ORGANISM: Unknown
<220> FEATURE:
<223> OTHER INFORMATION: Encodes 16S rRNA from Hydrogenoanaerobacterium
```

```
<400> SEQUENCE: 95
agagtttgat catggctcag gacgaacgct ggcggcgcgc ctaacacatg caagtcgaac    60
ggggatattt aagagcttgc ttttaaatat tctagtggcg gacgggtgag taacgcgtga   120
gtaacctgcc tttcagaggg ggataacagc tggaaacagc tgctaatacc gcataacata   180
tacaattcgc atgggaagta tatcaaagag atatcgctga aagat                   225

<210> SEQ ID NO 96
<211> LENGTH: 225
<212> TYPE: DNA
<213> ORGANISM: Unknown
<220> FEATURE:
<223> OTHER INFORMATION: Encodes 16S rRNA from Papillibacter

<400> SEQUENCE: 96
agagtttgat cctggctcag gacgaacgct ggcggcgtgc ctaacacatg caagtcgaac    60
ggagtttgag aagcttgctt cttaaactta gtggcggacg ggtgagtaac gcgtgagtaa   120
cctgcctttc agaggggat aacgtctgga aacgacgcg aataccgcat aacgtaccga    180
gtgggcatcc acttgatacc aaaggagcaa tccgctgaaa gatgg                   225

<210> SEQ ID NO 97
<211> LENGTH: 225
<212> TYPE: DNA
<213> ORGANISM: Unknown
<220> FEATURE:
<223> OTHER INFORMATION: Encodes 16S rRNA from Butyricicoccus

<400> SEQUENCE: 97
agagtttgat cctggctcag gacgaacgct ggcggcgcgc ctaacacatg caagtcgaac    60
ggggatattt aagagcttgc ttttgaatat tctagtggcg gacgggtgag taacgcgtga   120
gtaacctgcc tttcagaggg ggataacagc tggaaacagc tgctaatacc gcataacata   180
tacaattcgc atgggaagta tatcaaagag atatcgctga aagat                   225

<210> SEQ ID NO 98
<211> LENGTH: 225
<212> TYPE: DNA
<213> ORGANISM: Unknown
<220> FEATURE:
<223> OTHER INFORMATION: Encodes 16S rRNA from Eubacterium

<400> SEQUENCE: 98
agagtttgat cctggctcag gacgaacgct ggcggcgcgc ctaacacatg caagtcgaac    60
ggggttattt tggaaagttc tttcggggac tggaatcttt aacctagtgg cggacgggtg   120
agtaacgcgt gagcaatctg cctttaggag ggggataaca gtcggaaacg gctgctaata   180
ccgcataatg catcaatttc gcatgttatt gatgccaaag gagca                   225

<210> SEQ ID NO 99
<211> LENGTH: 225
<212> TYPE: DNA
<213> ORGANISM: Unknown
<220> FEATURE:
<223> OTHER INFORMATION: Encodes 16S rRNA from Turicibacter

<400> SEQUENCE: 99
agagtttgat catggctcag gatgaacgct ggcggcgtgc ctaatacatg caagtcgagc    60
gaaccaccct ggtggtgagc ggcggacggg tgagtaacac gtaggtaacc tgcccataag   120
atggggacaa ccaccggaaa cggtggctaa taccgcataa gcccacgggg ccgcatggcc   180
```

```
ctgagggaaa aggagcacac cgctttgaga tggcctcgcg tccga            225
```

<210> SEQ ID NO 100
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 100

```
agagtttgat cctggctcag gatgaacgct ggcggcgtgc ctaatacatg caagtcgagc    60
gaaccacctt ggtggtgagc ggcggacggg tgagtaacac gtaggtaacc tgcccataag   120
atggggacaa ccaccggaaa cggtggctaa taccgcataa cgtaccgagt gggcatccac   180
ttgataccaa aggagcaatc cgctgaaaga tgggctcgcg tccga                   225
```

<210> SEQ ID NO 101
<211> LENGTH: 225
<212> TYPE: DNA
<213> ORGANISM: Unknown
<220> FEATURE:
<223> OTHER INFORMATION: Encodes 16S rRNA from Asaccharobacter

<400> SEQUENCE: 101

```
agagtttgat cctggctcag gacgaacgct ggcggcgcgc ctaacacatg caagtcgaac    60
ggttaaggcg ccttcgggcg cgaatagagt ggcgaacggg tgagtaacac gtgaccaacc   120
tgcccccctc cccgggataa cgcgaggaaa cccgcgctaa taccggatac tccgcccctc   180
ccgcatggga ggggcgggaa agccccgacg gaggggatg gggtc                    225
```

<210> SEQ ID NO 102
<211> LENGTH: 225
<212> TYPE: DNA
<213> ORGANISM: Unknown
<220> FEATURE:
<223> OTHER INFORMATION: Encodes 16S rRNA from Faecalibacterium

<400> SEQUENCE: 102

```
agagtttgat cctggctcag gatgaacgct ggcggcgtgc ctaatacatg caagtcgaac    60
gcgagccttc gggctcgagt ggcgaacggg tgagtaacgc gtgaggaacc tgcctcaaag   120
aggggacaa cagttggaaa cgactgctaa taccgcataa gcccacgggg ccgcatggct   180
ctgagggaaa aggagcaatc cgctttgaga tggcctcgcg tccga                   225
```

<210> SEQ ID NO 103
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 103

```
agagtttgat cctggctcag gatgaacgct ggcggcgtgc ctaacacatg caagtcgagc    60
gaagcggttt cgatgaagtt ttcgatggga ttcggaattg actgagcggc ggacgggtga   120
gtaacgcgtg gtaacctgc ctcacactgg ggacaacag ctgaaacga ctgctaatac    180
cgcataacgc atgaccggtg catcccggac atgccaaaga tttat                   225
```

<210> SEQ ID NO 104
<211> LENGTH: 225
<212> TYPE: DNA

```
<213> ORGANISM: Unknown
<220> FEATURE:
<223> OTHER INFORMATION: Encodes 16S rRNA from Clostridium IV

<400> SEQUENCE: 104
agagtttgat cctggctcag gatgaacgct ggcggcatgc ctaatacatg caagtcgaac       60
ggaatgcgga gaggatttat cttttctgtg tttagtggcg aacgggtgag taacgcgtga      120
gcaacctgcc cttcagaggg ggatagcgtc tggaaacgga cggtaatacc gcataacgta      180
cagggaccgc atgatctttg taccaaaact gaggtgctga aggat                      225

<210> SEQ ID NO 105
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 105
agagtttgat cctggctcag gatgaacgct ggcggcgtgc ctaacacatg caagtcgaac       60
ggagatttga gagcttgctt tcaaatctta gtggcggacg ggtgagtaac gcgtgagtaa      120
cctgcctcat acaggggggat aacagttaga aatgactgct aataccgcat aagcgcacag     180
taccgcatgg tacggtgtga aaaactccgg tggtatggga tgggc                     225

<210> SEQ ID NO 106
<211> LENGTH: 225
<212> TYPE: DNA
<213> ORGANISM: Unknown
<220> FEATURE:
<223> OTHER INFORMATION: Encodes 16S rRNA from Clostridium XlVb

<400> SEQUENCE: 106
agagtttgat cctggctcag gatgaacgct ggcggcgtgc ttaacacatg caagtcgagc       60
ggagatattc agaaagcttg ctttttgaat atcttagcgg cggacgggtg agtaacgtgt      120
gggcaacctg cctcatacag agggataatc atgtgaaaac gtgactaata ccgcatgtca     180
ttaccgaagg gcatccttag gtaagaaaag gagcaatccg gtatg                     225

<210> SEQ ID NO 107
<211> LENGTH: 225
<212> TYPE: DNA
<213> ORGANISM: Unknown
<220> FEATURE:
<223> OTHER INFORMATION: Encodes 16S rRNA from Butyricicoccus

<400> SEQUENCE: 107
agagtttgat catggctcag gatgaacgct ggcggcgtgc ctaacacatg caagtcgaac       60
ggacttattt tggaaagttc ttcggaactg gaatctataa gttagtggcg gacgggtgag      120
taacgcgtga gcaatctgcc tcggagtggg ggataacagc tggaaacggc tgctaatacc     180
gcataatgca ttctggtcgc atggcctaaa tgccaaaggc ttgct                     225

<210> SEQ ID NO 108
<211> LENGTH: 225
<212> TYPE: DNA
<213> ORGANISM: Unknown
<220> FEATURE:
<223> OTHER INFORMATION: Encodes 16S rRNA from Sporobacter

<400> SEQUENCE: 108
agagtttgat catggctcag gacgaacgct ggcggcgtgc ctaacacatg caagtcgaac       60
```

```
ggagatacag gggcttgccc ctgtatctta gtggcggacg ggcgagtaac gcgtgaggaa    120
cctgcccttc agtggggaat aacgctgga aacggtcgct aataccgcat gacacattgg    180
taccgcatga tactgatgtc aaaggagcaa tccgctgaag gatgg                   225
```

```
<210> SEQ ID NO 109
<211> LENGTH: 225
<212> TYPE: DNA
<213> ORGANISM: Unknown
<220> FEATURE:
<223> OTHER INFORMATION: Encodes 16S rRNA from Butyricicoccus

<400> SEQUENCE: 109
agagtttgat catggctcag gatgaacgct ggcggcgtgt ctaacacatg caagtcgaac    60
ggggtaccct gaaacgaggc ttcggccaag cggaaggact acctagtggc ggacgggtga   120
gtaacgcgtg agcaacctgc ctttcagatg gggataacgg ctggaaacgg ccgctaatac   180
cgcataacgc ataactgggg catcccggca atgccaaaga tttat                  225
```

```
<210> SEQ ID NO 110
<211> LENGTH: 225
<212> TYPE: DNA
<213> ORGANISM: Unknown
<220> FEATURE:
<223> OTHER INFORMATION: Encodes 16S rRNA from Hydrogenoanaerobacterium

<400> SEQUENCE: 110
agagtttgat catggctcag gacgaacgct ggcggcgcgc ctaacacatg caagtcgaac    60
ggaaatgatt gaagtttact ttggtcattt tagtggcgga cgggtgagta acacgtgagc   120
aacctgcctt tcagaggggg ataacgtttg gaaacgaacg ctaataccgc ataacgtata   180
cggatggcat cgtctgtata ccaaaggagg aatccgctga aagat                  225
```

```
<210> SEQ ID NO 111
<211> LENGTH: 225
<212> TYPE: DNA
<213> ORGANISM: Unknown
<220> FEATURE:
<223> OTHER INFORMATION: Encodes 16S rRNA from Anaerofilum

<400> SEQUENCE: 111
agagtttgat cctggctcag gacgaacgct ggcggcgcgc ctaacacatg caagtcgaac    60
ggagcttgct tgtcagatcc tttcggggtg acgacttgta agcttagtgg cgaacgggtg   120
agtaacacgt gagtaacctg ccccagagtg ggggacaaca gttggaaacg actgctaata   180
ccgcataagc ccacggaacc gcctggttca gagggaaaaa gagca                  225
```

```
<210> SEQ ID NO 112
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 112
agagtttgat catggctcag gatgaacgct ggcggcgtgc ctaacacatg caagtcgaac    60
ggagtttgtt ggatcgatcc ttcgggtgat tgaaaataaa gtgagtggcg gacgggtgag   120
taacacgtga gcaacctgcc tttcagacgg ggataacagt tggaaacgac tgctaatacc   180
gcataagacc acgctatggc atcgtagagg ggtcaaagga gaaat                  225
```

<210> SEQ ID NO 113
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 113
agagtttgat catggctcag gatgaacgct ggcggcgtgc ctaacacatg caagtcgagc    60
gaactcttcg gagtgagcgg cggacgggtg agtaacgcgt gggtaacctg cctcacactg   120
ggggataaca gatagaaata tctgctaaaa ccgcataagc gcacgaggtc gcatgaccat   180
gtgtgaaaaa ctccggtggt gtgagatgga cccgcgtctg attag                   225

<210> SEQ ID NO 114
<211> LENGTH: 225
<212> TYPE: DNA
<213> ORGANISM: Unknown
<220> FEATURE:
<223> OTHER INFORMATION: Encodes 16S rRNA from Lachnospiracea incertae
      sedis

<400> SEQUENCE: 114
agagtttgat cctggctcag gatgaacgct ggcggcgtgc ctaacacatg caagtcgagc    60
gaactcttcg gagtgagcgg cggacgggtg agtaacgcgt gggtaacctg ccctgtacag   120
ggggataaca gttagaaatg actgctaata ccgcataagc gcacagcttc gcatgaagcg   180
gtgtgaaaaa ctgaggtggt acaggatggg cccgcgttgg attag                   225

<210> SEQ ID NO 115
<211> LENGTH: 225
<212> TYPE: DNA
<213> ORGANISM: Unknown
<220> FEATURE:
<223> OTHER INFORMATION: Encodes 16S rRNA from Lachnospiracea incertae
      sedis

<400> SEQUENCE: 115
agagtttgat cctggctcag gatgaacgct ggcggcgtgc ctaacacatg caagtcgagc    60
gaactcttcg gagtgagcgg cggacgggtg agtaacgcgt gggtaacctg cctcatacag   120
ggggataaca gttagaaatg actgctaata ccgcataaga ccacagcacc gcatggtgca   180
ggggtaaaaa ctccggtggt atgagatgga cccgcgtctg attag                   225

<210> SEQ ID NO 116
<211> LENGTH: 225
<212> TYPE: DNA
<213> ORGANISM: Unknown
<220> FEATURE:
<223> OTHER INFORMATION: Encodes 16S rRNA from Butyricicoccus

<400> SEQUENCE: 116
agagtttgat cctggctcag gatgaacgct ggcggcgtgc ctaacacatg caagtcgaac    60
gggcttattt tggaaagttc ttcggaactg gaatctataa gttagtggcg gacgggtgag   120
taacgcgtga gcaatctgcc tcggagtggg ggataacagc tggaaacggc tgctaatacc   180
gcatgatgca ttctggtcgc atggcctaaa tgccaaaggc ttgct                   225

<210> SEQ ID NO 117
<211> LENGTH: 225
<212> TYPE: DNA
<213> ORGANISM: Unknown

<220> FEATURE:
<223> OTHER INFORMATION: Encodes 16S rRNA from Pediococcus

<400> SEQUENCE: 117
agagtttgat catggctcag gatgaacgct ggcggcatgc ctaagacatg caagtcgaac      60
gaggtggccc actgattaag aaggaaagtt gaaaagcttg cttggatgct ggaattctta     120
tgacgtggat cttccaccta gtggcaaacg ggtgagtaac acgtgggtta cctacctcta     180
agttggggaa aacaattgga aacgattgat aataccgaat aagct                     225

<210> SEQ ID NO 118
<211> LENGTH: 225
<212> TYPE: DNA
<213> ORGANISM: Unknown
<220> FEATURE:
<223> OTHER INFORMATION: Encodes 16S rRNA from Acetanaerobacterium

<400> SEQUENCE: 118
agagtttgat cctggctcag gatgaacgct ggcggcgtgc ctaacacatg caagtcgagc      60
gaactcttcg gagtgagcgg cggacgggtg agtaacacgt gagtaacctg cctttcagag     120
tggaataacg tttggaaacg aacgctaata ccgcataaca tgagagaacg gcatcgttct     180
ttcatcaaag attttatcgc tgagagatgg gctcgcggcc gatta                     225

<210> SEQ ID NO 119
<211> LENGTH: 225
<212> TYPE: DNA
<213> ORGANISM: Unknown
<220> FEATURE:
<223> OTHER INFORMATION: Encodes 16S rRNA from Hydrogenoanaerobacterium

<400> SEQUENCE: 119
agagtttgat catggctcag gatgaacgct ggcggcacgc ctaacacatg caagtcgaac      60
gaagttattt tgatcgaagt tttcggatgg acattgattt aacttagtgg cggacgggtg     120
agtaacacgt gagcaatctg cctttcagag tgggataccg tttggaaacg aacgttaata     180
ccgcataacg cagcgaggcc gcatgacctt gctgccaaag attta                     225

<210> SEQ ID NO 120
<211> LENGTH: 225
<212> TYPE: DNA
<213> ORGANISM: Unknown
<220> FEATURE:
<223> OTHER INFORMATION: Encodes 16S rRNA from Butyricicoccus

<400> SEQUENCE: 120
agagtttgat catggctcag gatgaacgct ggcggcgtgc ataacacatt caagtcgaac      60
ggagttatac gagtagcaat acgaatataa cttagtggcg gacgggtgag taacgcgtga     120
gcaacctacc tttcaaagcg ggataacaca tggaaacgtg tgctaatacc gcataacgta     180
tcgatgtcgc atgacaacga taccaaaagg gcaacctgat gaaag                     225

<210> SEQ ID NO 121
<211> LENGTH: 225
<212> TYPE: DNA
<213> ORGANISM: Unknown
<220> FEATURE:
<223> OTHER INFORMATION: Encodes 16S rRNA from Lachnospiracea incertae
      sedis

<400> SEQUENCE: 121
agagtttgat cctggctcag gatgaacgct ggcggcgtgc ctaacacatg caagtcgagc      60

```
gaactcttcg gagtgagcgg cggacgggtg agtaacgcgt gggtaacctg cctcatacag    120 gggataaca gttagaaatg actgctaata ccgcataaga ccacagcttc gcatggagca    180
gtggtaaaaa ctccggtggt atgagatgga cccgcgtctg attag                   225
```

<210> SEQ ID NO 122
<211> LENGTH: 225
<212> TYPE: DNA
<213> ORGANISM: Unknown
<220> FEATURE:
<223> OTHER INFORMATION: Encodes 16S rRNA from Erysipelotrichaceae
      incertae sedis

<400> SEQUENCE: 122

```
agagtttgat cctggctcag gatgaacgct ggcggcgtgc ctaatacatg caagtcgaac    60
gggaatcttc ggattccagt ggcgaacggg tgaggaatac ataggtaacc tgcccctccg    120
aggggaacaa cagacggaaa catctgctaa gaccgcatag ccacagggaa ggcatcttcc    180
ctgtgccaaa tgtcctttcg gggacagcgg ggggatggac ctatg                   225
```

<210> SEQ ID NO 123
<211> LENGTH: 225
<212> TYPE: DNA
<213> ORGANISM: Unknown
<220> FEATURE:
<223> OTHER INFORMATION: Encodes 16S rRNA from Lachnospiracea incertae
      sedis

<400> SEQUENCE: 123

```
agagtttgat catggctcag gatgaacgct ggcggcgtgc ctaacacatg caagtcgagc    60
gaactcttcg gagtgagcgg cggacgggtg attaacgcgt gggtaacctg cctcatacag    120 gggataaca gttagaaatg actgctaata ccgcataaga ccccagcttc gcatgaagcg    180
gtggtaaaaa ctccggtggt atgagatgga ttcgcgtcag attag                   225
```

<210> SEQ ID NO 124
<211> LENGTH: 225
<212> TYPE: DNA
<213> ORGANISM: Unknown
<220> FEATURE:
<223> OTHER INFORMATION: Encodes 16S rRNA from Butyricicoccus

<400> SEQUENCE: 124

```
agagtttgat cctggctcag gatgaacgct ggcggcgtgc ctaacacatg caagtcgaac    60 ggacatttt tggaaacttc ttcggaagtg gaatctaaat gttagtggcg gacgggtgag    120
taacgcgtga gcaatctgcc tcggagtggg ggataacagc cggaaacggc tgctaatacc    180
gcataatgta tgagagtcgc atggcttta taccaaaggc ttgct                    225
```

<210> SEQ ID NO 125
<211> LENGTH: 225
<212> TYPE: DNA
<213> ORGANISM: Unknown
<220> FEATURE:
<223> OTHER INFORMATION: Encodes 16S rRNA from Butyricicoccus

<400> SEQUENCE: 125

```
agagtttgat catggctcag gatgaacgct ggcggcgtgc ctaacacatg caagtcgaac    60
ggacttattt tggaaagttc ttcggaactg gaatctataa gttagtggcg tacgggtgag    120
taacgcgtga gcaatctgcc tcggagtggg ggataacagc cggaaacggc tgctaatacc    180
```
gcataatgta tgagagtcgc atggcttta taccaaaggc ttgct                           225

<210> SEQ ID NO 126
<211> LENGTH: 225
<212> TYPE: DNA
<213> ORGANISM: Unknown
<220> FEATURE:
<223> OTHER INFORMATION: Encodes 16S rRNA from Butyricicoccus

<400> SEQUENCE: 126
agagtttgat cctggctcag gatgaacgct ggcggcgtgc ctaacacatg caagtcgaac        60
gaacttattt tggaaagttc ttcggaactg gaatctataa gttagtggcg gacgggtgag       120
taacgcgtga gcaatctgcc tcggagtggg ggataacagc cggaaacggc tgctaatacc       180
gcataatgta tgagagtcgc atggcttta taccaaaggc ttgca                          225

<210> SEQ ID NO 127
<211> LENGTH: 225
<212> TYPE: DNA
<213> ORGANISM: Unknown
<220> FEATURE:
<223> OTHER INFORMATION: Encodes 16S rRNA from Butyricicoccus

<400> SEQUENCE: 127
agagtttgat catggctcag gatgaacgct ggcggcgtgc ctaacacatg caagtcgaac        60
ggagttattt tggaaagtct ttcgggactg gaatctataa cttagtggcg gacgggtgag       120
taacgcgtga gcaatctgcc tcggagtggg ggataacagc cggaaacggc tgctaatacc       180
gcataatgca ttttaatcgc atggttgaaa tgccaaaggc ttgct                         225

<210> SEQ ID NO 128
<211> LENGTH: 225
<212> TYPE: DNA
<213> ORGANISM: Unknown
<220> FEATURE:
<223> OTHER INFORMATION: Encodes 16S rRNA from Butyricicoccus

<400> SEQUENCE: 128
agagtttgat cctggctcag gacgaacgct ggcggcgcgc ctaacacatg caagtcgaac        60
ggagttattt tggaaagtct ttcgggactg gaatctataa cttagtggcg gacgggtgag       120
taacgcgtga gcaatctgcc tcggagtggg ggataacagc cggaaacggc tgctaatacc       180
gcataatgca ttctggtcgc atgacctaaa tgccaaaggc ttgct                         225

<210> SEQ ID NO 129
<211> LENGTH: 225
<212> TYPE: DNA
<213> ORGANISM: Unknown
<220> FEATURE:
<223> OTHER INFORMATION: Encodes 16S rRNA from Lachnospiracea incertae
     sedis

<400> SEQUENCE: 129
agagtttgat catggctcag gatgaacgct ggcggcgtgc ctaacacatg caagtcgagc        60
gaactcttcg gagtgagcgg cggacgggtg agtaacgcgt gggtaacctg cctcacacag       120
ggggataaca gttagaaatg actgctaata ccgcataaga ccacagcacc gcatggtgca       180
gtggtaaaaa ctccggtggt atgagatgga cccgcgtctg attag                         225

<210> SEQ ID NO 130
<211> LENGTH: 225
<212> TYPE: DNA

<213> ORGANISM: Unknown
<220> FEATURE:
<223> OTHER INFORMATION: Encodes 16S rRNA from Howardella

<400> SEQUENCE: 130
agagtttgat cctggctcag gatgaacgct ggcggcgtgc ataacacatt caagtcgaac      60
ggagacttat gcgtagcaat acaagtaagt cttagtggcg gacgggtgag taacgcgtga     120
gcaacctacc tttcaaagcg ggataacaca tggaaacgtg tgctaatacc gcataacgta     180
ccgacaccgc atgatgatgg taccaaaagg gcaacctgat gaaag                     225

<210> SEQ ID NO 131
<211> LENGTH: 225
<212> TYPE: DNA
<213> ORGANISM: Unknown
<220> FEATURE:
<223> OTHER INFORMATION: Encodes 16S rRNA from Lachnospiracea incertae
      sedis

<400> SEQUENCE: 131
agagtttgat catggctcag gatgaacgct ggcggcgtgc ctaacacatg caagtcgagc      60
gaactcttcg gagtgagcgg cggacgggtg agtaacgcgt gggtaacctg cctcatacag     120
ggggataaca gttagaaatg actgctaata ccgcataaga ccccagcttc gcatgaagcg     180
gtggtaaaaa ctccggtggt atgagatgga cccgcgtctg attag                     225

<210> SEQ ID NO 132
<211> LENGTH: 225
<212> TYPE: DNA
<213> ORGANISM: Unknown
<220> FEATURE:
<223> OTHER INFORMATION: Encodes 16S rRNA from Clavibacter

<400> SEQUENCE: 132
agagtttgat catggctcag gacgaacgct ggcggcgtgc ttaacacatg caagtcgaac      60
ggtgatgtca gagcttgctc tggcggatca gtggcgaacg ggtgagtaac acgtgagtaa     120 cctgccccccg actctgggat aactgctaga aatggtagct aataccggat atgacgactg    180
gccgcatggt ctggtcgtgg aaagaatttc ggttggggat ggact                     225

<210> SEQ ID NO 133
<211> LENGTH: 225
<212> TYPE: DNA
<213> ORGANISM: Unknown
<220> FEATURE:
<223> OTHER INFORMATION: Encodes 16S rRNA from Butyricicoccus

<400> SEQUENCE: 133
agagtttgat cctggctcag gatgaacgct ggcggcgtgc ataacacatt caagtcgaac      60
ggagacttat gcgtagcaat acaagtaagt cttagtggcg gacgggtgag taacgcgtga     120
gcaacctacc tttcaaagcg ggataacgtc tggaacgga cgctaatacc gcataacgta      180
ccgacaccgc atgatgatgg taccaaaagg gcaacctgat gaaag                     225

<210> SEQ ID NO 134
<211> LENGTH: 225
<212> TYPE: DNA
<213> ORGANISM: Unknown
<220> FEATURE:
<223> OTHER INFORMATION: Encodes 16S rRNA from Hydrogenoanaerobacterium

<400> SEQUENCE: 134

```
agagtttgat catggctcag gacgaacgct ggcggcgtgc ctaacacatg caagtcgaac    60
ggacgagcag gagcttgctt ctgcgagtaa gtggcgacg  ggtgagtaac gcgtgagcaa   120
cctgcctttc agagggggat aacgtctgga aacggacgct aataccgcat aagctccgag   180
gatcgcatgg tctcaggagc aaaggaggaa tccgctgaaa gatgg                   225
```

```
<210> SEQ ID NO 135
<211> LENGTH: 225
<212> TYPE: DNA
<213> ORGANISM: Unknown
<220> FEATURE:
<223> OTHER INFORMATION: Encodes 16S rRNA from Spiroplasma

<400> SEQUENCE: 135
agagtttgat catggctcag gatgaacgct ggcggcatgc ctaagacatg caagtcgtac    60
gaaggagccc attgatattt attgaagttt gaagtgcttg cacggatgac ggatttattt   120
ggatttggat tctctcctta gtggcaaacg ggtgagtaac acgtgggtta cctgcctcca   180
agatggggat aacaattgga aacgattgat aataccgaat gtgct                   225
```

```
<210> SEQ ID NO 136
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 136
agagtttgat cctggctcag gacgaacgct ggcggcgcgc ctaacacatg caagtcgaac    60
ggggcttaca ttttgaagtt ttcggatgga cgaatgtaag cttagtggcg gacgggtgag   120
taacgcgtgg gcaaccctacc ttatacaggg ggataacagt tagaaatgac tgctaatacc  180
gcataagacc acagcttcgc atggagcagt ggtaaaaact ccggt                  225
```

```
<210> SEQ ID NO 137
<211> LENGTH: 225
<212> TYPE: DNA
<213> ORGANISM: Unknown
<220> FEATURE:
<223> OTHER INFORMATION: Encodes 16S rRNA from Jeotgalicoccus

<400> SEQUENCE: 137
agagtttgat cctggctcag gatgaacgct ggcggcgtgc ctaatacatg caagtcgaac    60
gagatggccc aatgaagttt gagtgcttgc acaatttctg atttggattt tccatctagt   120
ggcggacggg tgagtaacac gtgggtgacc tacctttgag tctgggacaa ctactggaaa   180
cggtagctaa taccggatga tatacagttt catttctgta ttaaa                   225
```

```
<210> SEQ ID NO 138
<211> LENGTH: 225
<212> TYPE: DNA
<213> ORGANISM: Unknown
<220> FEATURE:
<223> OTHER INFORMATION: Encodes 16S rRNA from Syntrophomonas

<400> SEQUENCE: 138
agagtttgat cctggctcag gacgaacgct ggcggcgtgc ctaacacatg caagtcgaac    60
ggacgaggcc ccttcgggga ccgagttagt ggcggacggg tgagtaacgc gtgagcaacc   120
tgcctttcag tggggacaa cagttggaaa cgactgctaa taccgcataa gcgcacagga    180
ccgcatggtc aagtgcgaaa aactccggtg gtatgagatg gaccc                   225
```

<210> SEQ ID NO 139
<211> LENGTH: 225
<212> TYPE: DNA
<213> ORGANISM: Unknown
<220> FEATURE:
<223> OTHER INFORMATION: Encodes 16S rRNA from Clostridium IV

<400> SEQUENCE: 139
agagtttgat cctggctcag gacgaacgct ggcggcgcgc ctaacacatg caagtcgaac      60
ggagcattga gagcttgctt ttaatgctta gtggcggacg ggtgagtaac gcgtgaggaa     120
cctgcctcgg agtggggaat aacagcccga aagggttgct aataccgcat gatgcagttg     180
ggccgcatgg ctctgactgc caaagattta tcgctctgag atggc                     225

<210> SEQ ID NO 140
<211> LENGTH: 225
<212> TYPE: DNA
<213> ORGANISM: Unknown
<220> FEATURE:
<223> OTHER INFORMATION: Encodes 16S rRNA from Lachnospiracea incertae
      sedis

<400> SEQUENCE: 140
agagtttgat catggctcag gacgaacgct ggcggcgtgc ctaacacatg caagtcgaac      60
ggactgattt gagagcttgc tcttgaagaa agttagtggc ggacgggtga gtaacgcgtg     120
agtaacctgc ctttcagagg gggataacat cctgaaaagg atgctaatac cgcataagcg     180
cacagcttcg catgaagcgg tgtgaaaaac tccggtggta tggga                     225

<210> SEQ ID NO 141
<211> LENGTH: 225
<212> TYPE: DNA
<213> ORGANISM: Unknown
<220> FEATURE:
<223> OTHER INFORMATION: Encodes 16S rRNA from Hydrogenoanaerobacterium

<400> SEQUENCE: 141
agagtttgat catggctcag gacgaacgct ggcggcgcgc ctaacacatg caagtcgaac      60
gggactattt ggccggaagt tttcggatgg aaggcgggat agtttagtgg cggacgggtg     120
agtaacacgt gagcaacctg cctctgagag gggaataacg gctggaaacg gtcgctaata     180
ccgcataacg tatcgggggg acatccccct ggtaccaaag atttt                     225

<210> SEQ ID NO 142
<211> LENGTH: 225
<212> TYPE: DNA
<213> ORGANISM: Unknown
<220> FEATURE:
<223> OTHER INFORMATION: Encodes 16S rRNA from Oscillibacter

<400> SEQUENCE: 142
agagtttgat catggctcag gacgaacgct ggcggcgtgc ctaacacatg caagtcgagc      60
gaagcaccct tgactgaggt ttcggccaaa tgataggaat gcttagtggc ggactggtga     120
gtaacgcgtg aggaacctgc cttccagagg gggacaacag ttggaaacga ctgctaatac     180
cgcataagcg cacagggccg catggcccgg tgtgaaaagc tccgg                     225

<210> SEQ ID NO 143
<211> LENGTH: 225
<212> TYPE: DNA
<213> ORGANISM: Unknown

<220> FEATURE:
<223> OTHER INFORMATION: Encodes 16S rRNA from Clostridium IV

<400> SEQUENCE: 143
agagtttgat catggctcag gatgaacgct ggcggcgtgc ttaacacatg caagtcgaac    60
gagaatctaa ggacggagtt ttcggacaac tgaattagag gaaagtggcg gacgggtgag   120
taacgcgtga ggaacctgcc ttggagtggg gaataacagt tggaaacagc tgctaatacc   180
gcataatgca tttggatcgc atggtcctga atgccaaaga tttat                   225

<210> SEQ ID NO 144
<211> LENGTH: 225
<212> TYPE: DNA
<213> ORGANISM: Unknown
<220> FEATURE:
<223> OTHER INFORMATION: Encodes 16S rRNA from Sporobacter

<400> SEQUENCE: 144
agagtttgat cctggctcag gacgaacgct ggcggcgcgc ctaacacatg caagtcgaac    60
ggggttgaga ggagcttgct tttcttgact tagtggcgga cgggtgagta acgcgtgagc   120
aatctgcctc ggagtggggg ataacagctg gaaacggctg ctaataccgc ataatgcatt   180
ctggtcgcat ggtcggaatg ccaaaggctt gctgctctga gatga                   225

<210> SEQ ID NO 145
<211> LENGTH: 225
<212> TYPE: DNA
<213> ORGANISM: Unknown
<220> FEATURE:
<223> OTHER INFORMATION: Encodes 16S rRNA from Pediococcus

<400> SEQUENCE: 145
agagtttgat cctggctcag gatgaacgct ggcggcgtgc ctaatacatg caagtcggac    60
gcaatgcttc ggcattgagt ggcgaacggg tgagtaatac ataagcaacc tgcccctgtg   120 aggggataa ctgctggaaa cggcagctaa gaccgcataa gcgcacggta tcgcatggta   180
cagtgtgaaa aactccggtg gtatgggatg gacccgcgtc tgatt                   225

<210> SEQ ID NO 146
<211> LENGTH: 225
<212> TYPE: DNA
<213> ORGANISM: Unknown
<220> FEATURE:
<223> OTHER INFORMATION: Encodes 16S rRNA from Sporobacter

<400> SEQUENCE: 146
agagtttgat cctggctcag gacgaacgct ggcggcgcgc ctaacacatg caagtcgaac    60
ggacttattt tggaaagttc ttcggaactg gaatctataa gttagtggcg gacgggtgag   120
taacgcgtga gcaatctgcc tcggagtggg ggataacagc tggaaacggc tgctaatacc   180
gcataatgca ttctggtcgc atggcctaaa tgccaaaggc ttgct                   225

<210> SEQ ID NO 147
<211> LENGTH: 225
<212> TYPE: DNA
<213> ORGANISM: Unknown
<220> FEATURE:
<223> OTHER INFORMATION: Encodes 16S rRNA from Bacillus

<400> SEQUENCE: 147
agagtttgat cctggctcag gacgaacgct ggcggcgtgc ctaatacatg caagtcgagc    60

```
gaaccaataa aaagcttgct ttttgttggt tagcggcgga cgggtgagta acacgtgggt    120
aacctgcctg taagatcggg ataactccgg gaaaccggtg ctaataccgg atagattatc    180
tttccgcttg gagagataag gaaagatggc tattgccatc actta                    225
```

```
<210> SEQ ID NO 148
<211> LENGTH: 225
<212> TYPE: DNA
<213> ORGANISM: Unknown
<220> FEATURE:
<223> OTHER INFORMATION: Encodes 16S rRNA from Cellulomonas

<400> SEQUENCE: 148
agagtttgat cctggctcag gacgaacgct ggcggtatgc ctaacacatg caagtcgaac    60
gaggttcttc ggaacctagt ggcgaacggg tgagtaacac gtgagcaacc tgccttacac    120
tttcggatac ctacgggaaa ctgtagtcaa tacggtataa gaccacgctg tcgcatgaca    180
gagggataaa agatttatcg gtgtaagatg ggctcgcgtc gcatt                    225
```

```
<210> SEQ ID NO 149
<211> LENGTH: 225
<212> TYPE: DNA
<213> ORGANISM: Unknown
<220> FEATURE:
<223> OTHER INFORMATION: Encodes 16S rRNA from Syntrophomonas

<400> SEQUENCE: 149
agagtttgat cttggctcag gacgaacgct ggcggcgtgc ctaacacatg caagtcgaac    60
ggagattaaa gttaacaccg agagccacga ggctgccggt ggagcgtgtt caaaaaatac    120
aaagtatttt ttgaactagg cttttaaagag gtgactgaca ctgagttgag cggaatggtt    180
ttgggtattg actttaatct tagtggcgga cgggtgagta acgcg                    225
```

```
<210> SEQ ID NO 150
<211> LENGTH: 225
<212> TYPE: DNA
<213> ORGANISM: Unknown
<220> FEATURE:
<223> OTHER INFORMATION: Encodes 16S rRNA from Cryptanaerobacter

<400> SEQUENCE: 150
agagtttgat catggctcag gacgaacgct ggcggcgtgc ttaacacatg caagtcgaac    60
ggactttcca ggacagattc cttcgggatg aagacctggc gagttagtgg cggacgggtg    120
agtaacgcgt ggataatctg cccaacagac cgggacaaca gttggaaacg actgctaata    180
ccggataacg tagttttgcg gcatcgcaag attaccaaag gaggc                    225
```

```
<210> SEQ ID NO 151
<211> LENGTH: 225
<212> TYPE: DNA
<213> ORGANISM: Unknown
<220> FEATURE:
<223> OTHER INFORMATION: Encodes 16S rRNA from Sporobacter

<400> SEQUENCE: 151
agagtttgat cctggctcag gacgaacgct ggcggcgtgc ctaacacatg caagtcgaac    60
ggggctcttt ggatcgagac ttcggtcaag tgaatttgag cttagtggcg gacgggtgag    120
taacgcgtga gcaacctgcc tttcagaggg ggacaacagt tggaaacgac tgctaatacc    180
gcataacgtg tcgaggaggc atctctttga caccaaagat ttatc                    225
```

<210> SEQ ID NO 152
<211> LENGTH: 225
<212> TYPE: DNA
<213> ORGANISM: Unknown
<220> FEATURE:
<223> OTHER INFORMATION: Encodes 16S rRNA from Hydrogenoanaerobacterium

<400> SEQUENCE: 152

```
agagtttgat catggctcag gataaacgct ggcggcgcac ataagacatg caagtcgaac    60
ggaagtcgtt gtaatgaaat tggactggac agagaacttg ttcgaaggaa agaaagatag   120
acttacaaca atggctttag tggcggactg gtgagtaacg cgtgagcaac ctgcctatta   180
gagggaata acagtgagaa atcattgcta ataccgcata tacca                    225
```

<210> SEQ ID NO 153
<211> LENGTH: 225
<212> TYPE: DNA
<213> ORGANISM: Unknown
<220> FEATURE:
<223> OTHER INFORMATION: Encodes 16S rRNA from Clostridium IV

<400> SEQUENCE: 153

```
agagtttgat catggctcag gacgaacgct ggcggcgcgc ctaacacatg caagtcgaac    60
gaagtttgcc ggattgatcc ttcgggtgat tgattgtaaa cttagtggcg gacgggtgag   120
taacacgtga gcaacctgcc ttacagaggg ggataacgtt tggaaacgaa cgctaatacc   180
gcataacacc tttaagggac atcccttggg ggtcaaagga gcaat                   225
```

<210> SEQ ID NO 154
<211> LENGTH: 225
<212> TYPE: DNA
<213> ORGANISM: Unknown
<220> FEATURE:
<223> OTHER INFORMATION: Encodes 16S rRNA from Hydrogenoanaerobacterium

<400> SEQUENCE: 154

```
agagtttgat catggctcag gataaacgct ggcggcgcac ataagacatg caagtcgaac    60
ggacttaact cattctttta gattgagagc ggttagtggc ggactggtga gtaacatgta   120
agcaatctgc ctattagagg ggaataacag tgagaaatca ttgctaatac cgcatatgcc   180
ataaaaacca catggtttta gtgggaaagg agcaatccgc taata                   225
```

<210> SEQ ID NO 155
<211> LENGTH: 225
<212> TYPE: DNA
<213> ORGANISM: Unknown
<220> FEATURE:
<223> OTHER INFORMATION: Encodes 16S rRNA from Spiroplasma

<400> SEQUENCE: 155

```
agagtttgat catggctcag gatgaacgct ggcggcatgc ctaagacatg caagtcgaac    60
gaggtggccc atagaagatg gagtgcttgc acaaaatcgg acatggattc ccacctagtg   120
gcagacgggt gagtaacacg tgggtgacct acctttaaga tggggataac agttggaaac   180
gattgctaat accgaataag atataactgt cgtggttata tagaa                   225
```

<210> SEQ ID NO 156
<211> LENGTH: 225
<212> TYPE: DNA
<213> ORGANISM: Unknown
<220> FEATURE:
<223> OTHER INFORMATION: Encodes 16S rRNA from Erysipelotrichaceae
    incertae sedis

```
<400> SEQUENCE: 156
agagtttgat cctggctcag gacgaacgct ggcggcgtgc ctaatacatg caagtcgaac     60
gaagtttcga ggaagcttgc ttccaaagag acttagtggc gaacgggtga gtaacacgta   120
ggtaacctgc ccatgtgtcc gggataactg ctggaaacgg tagctaaaac cggataggta   180
tacagagcgc atgctcagta tattaaagcg cccatcaagg cgtga                   225

<210> SEQ ID NO 157
<211> LENGTH: 225
<212> TYPE: DNA
<213> ORGANISM: Unknown
<220> FEATURE:
<223> OTHER INFORMATION: Encodes 16S rRNA from Pseudoflavonifractor

<400> SEQUENCE: 157
agagtttgat cctggctcag gatgaacgct ggcggcgtgc ttaacacatg caagtcgaac     60
ggagagctat ggaaagagga ttcgtccaat tgaaatagtt tcttagtggc ggacgggtga   120
gtaacgcgtg aggaacctgc cttggagtgg ggaataacag ttagaaatga ctgctaatac   180
cgcataatat gtctgtaccg catggtagtg gacatcaaag attta                   225

<210> SEQ ID NO 158
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 158
agagtttgat cctggctcag gatgaacgct ggcggcgtgc ctaacacatg caagtcgagc     60
gaactcttcg gagtgagcgg cggacgggtg agtaacgcgt gggcaacctg ccccataccg   120
ggggataaca gagagaaatt tctgctaata ccgcataagc gcacgaggac cgcatggtcc   180
ggtgtgaaaa gccgagacgg tatacgatgg acccgcgtct gatta                   225

<210> SEQ ID NO 159
<211> LENGTH: 225
<212> TYPE: DNA
<213> ORGANISM: Unknown
<220> FEATURE:
<223> OTHER INFORMATION: Encodes 16S rRNA from Mogibacterium

<400> SEQUENCE: 159
aagtttgatc ctggctcagg atgaacgctg gcggcgtgcc taacacatgc aagtcgagcg     60
agaaatgtat ttatgaaact tcggtagatt agatacatgg aaagcggcgg acgggtgagt   120
aacgcgtagg caacctgccc cttgcagagg gatagccatt ggaaacgatg attaaaacct   180
cataacgctg cattgtcaca tgatagagca gccaaagatt tatcg                   225

<210> SEQ ID NO 160
<211> LENGTH: 225
<212> TYPE: DNA
<213> ORGANISM: Unknown
<220> FEATURE:
<223> OTHER INFORMATION: Encodes 16S rRNA from Clostridium sensu stricto

<400> SEQUENCE: 160
agagtttgat catggctcag gatgaacgct ggcggcgtgc ctaacacatg caagtcgagc     60
gaactcttcg gagtgagcgg cggacgggtg agtaacacgt gagtaacctg cctttcagag   120
```

```
tggaataacg tttggaaacg aacgctaata ccgcataaca tagtttccgg gcatccggag      180
actatcaaag attttatcgc tgagagatgg gctcgcggcc gatta                     225
```

<210> SEQ ID NO 161
<211> LENGTH: 225
<212> TYPE: DNA
<213> ORGANISM: Unknown
<220> FEATURE:
<223> OTHER INFORMATION: Encodes 16S rRNA from Clostridium IV

<400> SEQUENCE: 161

```
agagtttgat catggctcag gacgaacgct ggcggcgtgc ctaacacatg caagtcgaac       60
ggagcttttc tgaggaagtt ttcggatgga atcagttagg cttagtggcg gacgggtgag      120
taacgcgtga gcaacctgcc tttcagaggg ggataacgtt ctgaaaagaa cgctaatacc      180
gcataacata ttttctccgc atggagggga tatcaaagga gcaat                     225
```

<210> SEQ ID NO 162
<211> LENGTH: 225
<212> TYPE: DNA
<213> ORGANISM: Unknown
<220> FEATURE:
<223> OTHER INFORMATION: Encodes 16S rRNA from Citrobacter

<400> SEQUENCE: 162

```
aagttacctg gctcaggatg aacgctggcg gcgtgcctaa tacatgcaag tcggacgcaa       60
tgcttcggca ttgagtggcg aacgggtgag taagacataa gcaacctgcc cctgtgaggg      120
ggataactac tggaaacggt agctaatacc gcataacgtc gcaagaccaa agaggggggac    180 cttcgggcct cttgccatcg gatgtgccca gatgggatta gctag                     225
```

<210> SEQ ID NO 163
<211> LENGTH: 225
<212> TYPE: DNA
<213> ORGANISM: Unknown
<220> FEATURE:
<223> OTHER INFORMATION: Encodes 16S rRNA from Hydrogenoanaerobacterium

<400> SEQUENCE: 163

```
agagtttgat cctggctcag gacgaacgct ggcggcgcgc ctaacacatg caagtcgaac       60
gaagttattt tgatcgaagt tttcggatgg acattgattt aacttagtgg cggacgggtg      120
agtaacacgt gagcaatctg cctttcagag tgggataccg tttggaaacg aacgttaata      180
ccgcataacg cagcgaggcc gcatgacctt gctgccaaag attta                     225
```

<210> SEQ ID NO 164
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 164

```
agagtttgat catggctcag gatgaacgct ggcggcgtgc ttaacacatg caagtcgaac       60
gaagcacata ggcagatttc ttcggattga agtatatgtg actgagtggc ggacgggtga      120
gtaacgcgtg ggtaacctgc cttcacagg gggacaacag ctggaaacgg ctgctaatac      180
cgcataaccc gctagggccg catggcccag acggaaaagg agcaa                     225
```

<210> SEQ ID NO 165
<211> LENGTH: 225

```
<212> TYPE: DNA
<213> ORGANISM: Unknown
<220> FEATURE:
<223> OTHER INFORMATION: Encodes 16S rRNA from Clostridium XlVa

<400> SEQUENCE: 165
agagtttgat cctggctcag gatgaacgct ggcggcgtgc ttaacacatg caagtcgaac    60
gaagcacaga gacggatttc ttcggattga agtttctgtg actgagtggc ggacgggtga   120
gtaacgcgtg ggtaacctgc ctttcacagg gggacaacag ctggaaacgg ctgctaatac   180
cgcataaccc gctagggccg catggcccag acggaaaagg agcaa                   225

<210> SEQ ID NO 166
<211> LENGTH: 225
<212> TYPE: DNA
<213> ORGANISM: Unknown
<220> FEATURE:
<223> OTHER INFORMATION: Encodes 16S rRNA from Clostridium sensu stricto

<400> SEQUENCE: 166
agagtttgat cctggctcag gacgaacgct ggcggcgtgc ctaacacatg caagtcgaac    60
ggacgaggag gtgcttgcac ctccaagtta gtggcggacg ggtgagtaac gcgtgagcaa   120
cctgcctcaa agaggggat aacgtctaga aacggacgct aataccgcat gatgtattcg    180
gtaggaatct attggatacc aaaggagcaa tccgctttga gatgg                   225

<210> SEQ ID NO 167
<211> LENGTH: 225
<212> TYPE: DNA
<213> ORGANISM: Unknown
<220> FEATURE:
<223> OTHER INFORMATION: Encodes 16S rRNA from Erysipelotrichaceae
      incertae sedis

<400> SEQUENCE: 167
agagtttgat catggctcag gatgaacgct ggcggcatgc ctaatacatg caagtcgaac    60
ggacggaaga tgagcttgct cattggaagt cagtggcgaa cgggtgagta acacgtaggg   120
aatctgccca tgtgcccggg acaacagatg gaaatgtctg ctaaaaccgg ataggtggca   180
atgaggcatc ttcttgcgat taaagggggct acggccttga acatg                  225

<210> SEQ ID NO 168
<211> LENGTH: 225
<212> TYPE: DNA
<213> ORGANISM: Unknown
<220> FEATURE:
<223> OTHER INFORMATION: Encodes 16S rRNA from Clostridium XlVb

<400> SEQUENCE: 168
agagtttgat catggctcag gatgaacgct ggcggcgtgc ttaacacatg caagtcgagc    60
ggagatattc ggaaagcttg cttttttggat atcttagcgg cggacgggtg agtaacgtgt   120
gggcaacctg cctcatacag agggatagtc atgtgaaaac gtgactaata ccgcatgtca   180
ttaccaaagg gcatccttcg gtaagaaaag gagcaatccg gtatg                   225

<210> SEQ ID NO 169
<211> LENGTH: 225
<212> TYPE: DNA
<213> ORGANISM: Unknown
<220> FEATURE:
<223> OTHER INFORMATION: Encodes 16S rRNA from Clostridium XlVb

<400> SEQUENCE: 169
```

```
agagtttgat cttggctcag gatgaacgct ggcggcgtgc ttaacacatg caagtcgagc    60
ggagatattc ggaaagcttg ctttttggat atcttagcgg cggacgggtg agtaacgtgt   120
gggcaacctg cctcatacag agggatactc atgtgaaaac gtgactaata ccgcatgtca   180
ttactgcagg gcatccttcg gtaagaaaag gagaaatccg gtatg                   225

<210> SEQ ID NO 170
<211> LENGTH: 225
<212> TYPE: DNA
<213> ORGANISM: Unknown
<220> FEATURE:
<223> OTHER INFORMATION: Encodes 16S rRNA from Butyricicoccus

<400> SEQUENCE: 170
agagtttgat cctggctcag gatgaacgct ggcggcgtgc ctaacacatg caagtcgaac    60
ggagcaccct caatcgagtt ttcggacaag agagaggaat gcttagtggc ggacgggtga   120
gtaacgcgtg agcaatctgc ctttcagagg gggacaacag agggaaactt ctgctaatac   180
cgcataacgt atccggggcg catgctctgg ataccaaaga tttga                   225

<210> SEQ ID NO 171
<211> LENGTH: 225
<212> TYPE: DNA
<213> ORGANISM: Unknown
<220> FEATURE:
<223> OTHER INFORMATION: Encodes 16S rRNA from Pediococcus

<400> SEQUENCE: 171
agagtttatc ctggctcagg atgaacgctg gcggcgtgcc taatacatgc aagtcggacg    60
caatgcttcg gcattgagtg gcgaacgggt gagtaagaca taagcaacct gcccctgtga   120
gggggataac tgctggaaac ggcagctaat accgcataag cgcacagggc cgcatggcct   180
agtgtgaaaa actccggtgg tgtgggatgg gcccgcgttg gatta                   225

<210> SEQ ID NO 172
<211> LENGTH: 225
<212> TYPE: DNA
<213> ORGANISM: Unknown
<220> FEATURE:
<223> OTHER INFORMATION: Encodes 16S rRNA from Sphingomonas

<400> SEQUENCE: 172
agagtttgat catggctcag gatgaacgct ggcggcatgc ctaagacatg caagtcgaac    60
gaagtggccc aatgaagatg aagtgcttgc actgattcgg acttggattc ccacttagtg   120
gcgaaagggt gagtaacacg tgggttatct gccttcgagt ctggaataac agttagaaat   180
gattgctaat gccggatgat atatgttagg atacgtccta atata                   225

<210> SEQ ID NO 173
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 173
agagtttgat cctggctcag gatgaacgct ggcggcatgc ctaagacatg caagtcgaac    60
gaagtggccc aaggaagtag agtgcttgca cgaagcggaa ttggattccc acttagtggc   120
agacgggtga gtaacacgtg ggtaacctac cgaagagact gggataacag ttagaaatga   180
```

```
ctgctaatac cggatgattc atctttacat aagtagagat gctaa              225
```

```
<210> SEQ ID NO 174
<211> LENGTH: 225
<212> TYPE: DNA
<213> ORGANISM: Unknown
<220> FEATURE:
<223> OTHER INFORMATION: Encodes 16S rRNA from Clostridium IV

<400> SEQUENCE: 174
agagtttgat cctggctcag gacgaacgct ggcggcgtgc ctaacacatg caagtcgaac    60
ggagttatca gacggaagtt ttcgatgga agactgataa cttagtggcg gacgggtgag   120
taacgcgtga gtaacctgcc tttcagaggg ggataacgtt ttgaaaagaa cgctaatacc   180
gcataacaca gatggaccgc atggtgtgtc tgtcaaagga gcaat                    225
```

```
<210> SEQ ID NO 175
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 175
agagtttgat cctggctcag gatgaacgct ggcggcgtgc ttaacacatg caagtcgaac    60
gaagcggcgc agaggaagtt ttcgatgga atcggcgctg actgagtggc ggacgggtga   120
gtaacgcgtg ggtaacctgc ctcgcacagg gggataacag ttagaaatga ctgctaatac   180
cgcataaccc gctagggccg catggcctgg acggaaaaga tttat                    225
```

```
<210> SEQ ID NO 176
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 176
agagtttgat catggctcag gatgaacgct ggcggcgtgc ttaacacatg caagtcgaac    60
gaagcggcgc ggaggaagtt ttcgatgga atcggcgctg actgagtggc ggacgggtga   120
gtaacgcgtg ggtaacctgc ctcacacagg gggataacag ttagaaatga ctgctaatac   180
cgcataaccc gctagggccg catggcccgg acggaaaaga tttat                    225
```

```
<210> SEQ ID NO 177
<211> LENGTH: 225
<212> TYPE: DNA
<213> ORGANISM: Unknown
<220> FEATURE:
<223> OTHER INFORMATION: Encodes 16S rRNA from Methylobacterium

<400> SEQUENCE: 177
agagtttgat catggctcag agcgaacgct ggcggcaggc ttaacacatg caagtcgaac    60
gctcgtcttc ggacgggagt ggcagacggg tgagtaacac gtgggaacgt acccttggt   120 tcggaataac gcaggaaac ttgcgctaat accggatacg ccctttggg gaaaggttta   180 ctgccgaagg atcggcccgc gtctgattag ctagttggtg gggta                    225
```

```
<210> SEQ ID NO 178
<211> LENGTH: 225
<212> TYPE: DNA
<213> ORGANISM: Unknown
```

```
<220> FEATURE:
<223> OTHER INFORMATION: Encodes 16S rRNA from Salana

<400> SEQUENCE: 178
agagtttgat cctggctcag cagccgcggt aatacgtagg gcgcgagcgt tgtccggaat    60
cattgggcgt aaagagctcg taggcggttt gtcgcgtctg ctgtgaaagc ctggggctca   120
actccgggat tgcagtgggt acgggcagac tagagtgcgg taggggagac tggaattcct   180
ggtgtagcgg tggaatgcgc agatatcagg aagaacaccg atggc                   225

<210> SEQ ID NO 179
<211> LENGTH: 225
<212> TYPE: DNA
<213> ORGANISM: Unknown
<220> FEATURE:
<223> OTHER INFORMATION: Encodes 16S rRNA from Petrobacter

<400> SEQUENCE: 179
agagtttgat cctggctcag tttgcgggag cgtggtgact tgcgggttgt agcgctgctt    60
gtcgtcgttg ccgtagaagg tgcccgtcac catcaggttg cgcgtgttcg acagcagtac   120
cggatagctc aatgcaacc  cgagccgttg cgtgtcggtc aggtagcgcg attgatagcc   180
cagttgctcc agcggcagat tctcgggcat gccgcgatag tgcga                   225

<210> SEQ ID NO 180
<211> LENGTH: 225
<212> TYPE: DNA
<213> ORGANISM: Unknown
<220> FEATURE:
<223> OTHER INFORMATION: Encodes 16S rRNA from Bacillus

<400> SEQUENCE: 180
agagtttgat cctggctcag gacgaacgct ggcggcgtgc ctaatacatg caagtcgagc    60
ggactttaaa agcttgcttt taaagttagc ggcggacggg tgagtaacac gtgggcaacc   120
tgcctgtaag actgggataa cttcgggaaa ccggagctaa taccggataa tccttttcct   180
ctcatgagga aaagctgaaa gacggtttac gctgtcactt acaga                   225

<210> SEQ ID NO 181
<211> LENGTH: 225
<212> TYPE: DNA
<213> ORGANISM: Unknown
<220> FEATURE:
<223> OTHER INFORMATION: Encodes 16S rRNA from Thermovibrio

<400> SEQUENCE: 181
agagtttgat cctggctcag cgaaggtagc gtcaggcacg tcgaggtctt ccagatgttc    60
ggtgtgagaa cctccatcat cggaagacct cgaccctac ccagtgcccg acgcgccgac   120
caccatcaca ccccgcctac acccggatt gtgatgagcc cctgaaacca ccgtactgat    180
aagcagtact tctgcacact caacgagacc agcagggcca gcgga                   225

<210> SEQ ID NO 182
<211> LENGTH: 225
<212> TYPE: DNA
<213> ORGANISM: Unknown
<220> FEATURE:
<223> OTHER INFORMATION: Encodes 16S rRNA from Erysipelotrichaceae
      incertae sedis

<400> SEQUENCE: 182
agagtttgat catggctcag gatgaacgct ggcggcgtgc ctaatacatg caagtcgaac    60
```

```
ggagcacctt ggtgctcagt ggcgaacggg tgaggagaac ataggtaacc tgcccctccg    120
agggggacaa cagctggaaa cggctgctaa gaccgcatag acgcattcag ggcatcctgg    180
atgcgctaaa tgaccggatg gtcagcgggg ggatggacct atgca                    225
```

```
<210> SEQ ID NO 183
<211> LENGTH: 225
<212> TYPE: DNA
<213> ORGANISM: Unknown
<220> FEATURE:
<223> OTHER INFORMATION: Encodes 16S rRNA from Selenomonas

<400> SEQUENCE: 183
agagtttgat catggctcag gacgaacgct ggcggcgtgc ttaacacatg caagtcgaac    60
gaggctgata tttagcttgc tattttgaag ccgagtggca aacgggtgag taacgcgtag   120
acaacctgcc gcaaagatgg ggacaacagt ccgaaaggac tgctaatacc gaatgttgtc   180
agattcccgc atgggagact gattaaagat ggcctctact tgtaa                   225
```

```
<210> SEQ ID NO 184
<211> LENGTH: 225
<212> TYPE: DNA
<213> ORGANISM: Unknown
<220> FEATURE:
<223> OTHER INFORMATION: Encodes 16S rRNA from Glaciecola

<400> SEQUENCE: 184
agagtttgat catggctcag attgaacgct ggcggcaggc ctaatacatg caagtcgaac    60
ggtaacatgg aagtagcaat acttttgatg acgagtggcg gacgggtgag taatatttgg   120
gaatctacct atcagagggg gatagcaact ggaaacggtt gataagaccg cgtacgctct   180
gaggaggaaa gtaatgggat cgaaagacca ttagctgata gatga                   225
```

```
<210> SEQ ID NO 185
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 185
agagtttgat catggctcag gacgaacgct ggcggcgtgc ctaatacatg caagtcgaac    60
gagttttgtt ttaaggatca aggtgcttgc accgagagaa ttagaatgaa acgagtggcg   120
gacgggtgag taacacgtgg gtaacctacc ctaaagtggg ggataacatt tggaaacaga   180
tgctaatacc gcataacgaa cgaagccaca tggctttgtt ctgaa                   225
```

```
<210> SEQ ID NO 186
<211> LENGTH: 225
<212> TYPE: DNA
<213> ORGANISM: Unknown
<220> FEATURE:
<223> OTHER INFORMATION: Encodes 16S rRNA from Eubacterium

<400> SEQUENCE: 186
agagtttgat catggctcag gatgaacgct ggcggcgtgc ctaacacatg caagtcgaac    60
ggggttaagt gaaattttcg gatggagctt aacttagtgg cggacgggtg agtaacgcgt   120
ggataacctg cctcacactg ggggatagca gctggaaacg gctggtaata ccgcataaga   180
ccacagcacc gcatggtgca ggggtaaaag atttatcggt gtgag                   225
```

<210> SEQ ID NO 187
<211> LENGTH: 225
<212> TYPE: DNA
<213> ORGANISM: Unknown
<220> FEATURE:
<223> OTHER INFORMATION: Encodes 16S rRNA from Thermomicrobium

<400> SEQUENCE: 187
agagtttgat cctggctcag ccacacggtg tgctcggggt cgcgcacggt gacgtcgtcg    60
acctcgtcgg gcgtgctgac gatctgcacc cggtcgggcg cctcgccgct cgtgccgacg   120
acctcctcgt ggccacggtg gccgatgagc acgatgtcgt agtcctgcct cgcataccgg   180
cgcacctccc ggtgcacctt cgtgacgagc gggcaggtcg cgtcg                  225

<210> SEQ ID NO 188
<211> LENGTH: 225
<212> TYPE: DNA
<213> ORGANISM: Unknown
<220> FEATURE:
<223> OTHER INFORMATION: Encodes 16S rRNA from Acidobacteria

<400> SEQUENCE: 188
agagtttgat cctggctcag tgaaaggccc ttcctagcgg cagggcaacg tcaattgttg    60
agtggaattt gggtttgaca gatttgcctc aatgaaaggc ccttcctagc ggaagggcaa   120
ccagttcccc aacaagtgtg gcgtctccta cagtcgcctc aatgaaaggc ccttcctagc   180
ggaagggcaa catgacacga cgaatcaacg ctctggagag gagca                  225

<210> SEQ ID NO 189
<211> LENGTH: 225
<212> TYPE: DNA
<213> ORGANISM: Unknown
<220> FEATURE:
<223> OTHER INFORMATION: Encodes 16S rRNA from Chlorobaculum

<400> SEQUENCE: 189
agagtttgat cctggctcaa agtaaaagta atcctcctca agtgccttct ggctggaagg    60 ctgttttttga tgatgaatac cagacttggt attatgtaga tttatctacg aacagctctc   120
agtgggaacc accaagggga acaacatggc caagacccaa aggtcctcca ccagatgtta   180
acaatgagaa gagttctcgt caacaggcag accaggctcc tccac                  225

<210> SEQ ID NO 190
<211> LENGTH: 225
<212> TYPE: DNA
<213> ORGANISM: Unknown
<220> FEATURE:
<223> OTHER INFORMATION: Encodes 16S rRNA from Rothia

<400> SEQUENCE: 190
agagtttgat cctggctcag gacgaacgct ggcggcgtgc ttaacacatg caagtcgaac    60
gatgaagcct agcttgctag gtggattagt ggcgaacggg tgagtaatac gtgagtaacc   120
tacctttaac tctgggataa gcctgggaaa ctgggtctaa taccggatac gaccaatctc   180
cgcatggggt gttggtggaa agcgttatgt agtggttata gatgg                  225

<210> SEQ ID NO 191
<211> LENGTH: 225
<212> TYPE: DNA
<213> ORGANISM: Unknown
<220> FEATURE:
<223> OTHER INFORMATION: Encodes 16S rRNA from Selenomonas

<400> SEQUENCE: 191
agagtttgat catagctcag dacgaacgct ggcggcgtgc ttaacacatg caagtcgaac    60
gaggtgattg aaagcttgct tttgagaacc gggtggcaaa cgggtgagta acgcgtagac   120
aacctgccgc aaagatgggg acaacagtcc gaaaggactg ctaataccga atgttgtgca   180
acttccgcat gggagatgca ttaaagatgg cctctacttg taagc                   225

<210> SEQ ID NO 192
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 192
agagtttgat catggctcag gatgaacgct ggcggcgtgc ctaacacatg caagtcgaac    60
ggggttaagt gaaattttcg gatggatctt aacttagtgg cggacgggtg agtaacgcgt   120
ggataacctg cctcacacag ggggatagca gctggaaacg gctggtaata ccgcataaga   180
ccacggcccc gcatggggct gtagtaaaag atttatcggt gtgag                   225

<210> SEQ ID NO 193
<211> LENGTH: 225
<212> TYPE: DNA
<213> ORGANISM: Unknown
<220> FEATURE:
<223> OTHER INFORMATION: Encodes 16S rRNA from Virgibacillus

<400> SEQUENCE: 193
agagtttgat catggctcat ctcgagcagg agggcaagag cgagggcgac gcgcacgccg    60
aggagatccg cggcgatgtc gagcgcggca tccgcaccca gctgctgctc gacaaggtcg   120
tcgaggagct cggcgtgcag ctgagccagg acgagctgtc acagtacctg gtgcagcagt   180
cgatgcagta cggcatcgac ccgaacgagt tcttccgcat catca                   225

<210> SEQ ID NO 194
<211> LENGTH: 225
<212> TYPE: DNA
<213> ORGANISM: Unknown
<220> FEATURE:
<223> OTHER INFORMATION: Encodes 16S rRNA from Sphingomonas

<400> SEQUENCE: 194 agagtttgatc ctggctcaga acgaacgctg gcggcatgcc taacacatgc aagtcgaacg   60
agaccttcgg gtctagtggc gcacgggtgc gtaacgcgtg gaatctgcc cttgggttcg    120 gaataacttc gggaaactga agctaatacc ggatgatgac gtaagtccaa agatttatcg   180
cccaaggatg agcccgcgta ggattagcta gttggtgagg taaag                   225

<210> SEQ ID NO 195
<211> LENGTH: 225
<212> TYPE: DNA
<213> ORGANISM: Unknown
<220> FEATURE:
<223> OTHER INFORMATION: Encodes 16S rRNA from Citricoccus

<400> SEQUENCE: 195
agagtttgat catggctcag gatgaacgct ggcggcgtgc ttaacacatg caagtcgaac    60
gctgaagctc ctagcttgct gggggtggat gagtggcgaa cgggtgagta tcacgtgagt   120

```
aacctgccct tgactctggg ataagcctgg gaaactgggt ctaataccgg atgatcactt    180
ctctccgcat gggggtggt gtaaagattg tatcggtctt ggatg                    225
```

<210> SEQ ID NO 196
<211> LENGTH: 225
<212> TYPE: DNA
<213> ORGANISM: Unknown
<220> FEATURE:
<223> OTHER INFORMATION: Encodes 16S rRNA from Catenibacterium

<400> SEQUENCE: 196

```
agagtttgat cctggctcag ccctctaaaa ccacatgccc aacccggcat gggttggccg    60
cttaaactca atgtcattgg cgctcggcgc cgcgtttctc gagggtctta ccgggcgcac   120
tggatagcgc aagaaccggg ccctagaaa agagcgctgc tttataccag aaagccctgg    180
gagcaacaag gaaaaacgca ggataaaacc caaccccgag ccagc                   225
```

<210> SEQ ID NO 197
<211> LENGTH: 225
<212> TYPE: DNA
<213> ORGANISM: Unknown
<220> FEATURE:
<223> OTHER INFORMATION: Encodes 16S rRNA from Amycolatopsis

<400> SEQUENCE: 197

```
agagtttgat catggctcag gcggttggga gtgccgttgc cggttaaggt ggagcgattc    60
tggcgggggg ctcctgacag cgttctgtca ggagcgttca ggagggtggc aaagcgtgtt   120
gcagattgcc caggcagtga ataccgggcg gagggaggag cgattcagtg cggaatccaa   180
cccgccagca gccgcggtaa tctgctctta tacacatctc cgagc                   225
```

<210> SEQ ID NO 198
<211> LENGTH: 225
<212> TYPE: DNA
<213> ORGANISM: Unknown
<220> FEATURE:
<223> OTHER INFORMATION: Encodes 16S rRNA from Sphingobium

<400> SEQUENCE: 198

```
agagtttgat cctggctcag aacgaacgct ggcggcatgc ctaatacatg caagtcgaac    60
gagatcttcg gatctagtgg cgcacgggtg cgtaacgcgt gggaatctgc ccttgggttc   120
ggaataacgt cgggaaactg acgctaatac cggatgatga cgtaagtcca agatttatc    180 gcccaaggat gagcccgcgt aggattagct agttggtggg gtaaa                   225
```

<210> SEQ ID NO 199
<211> LENGTH: 225
<212> TYPE: DNA
<213> ORGANISM: Unknown
<220> FEATURE:
<223> OTHER INFORMATION: Encodes 16S rRNA from Actinomyces

<400> SEQUENCE: 199

```
agagtttgat cctggctcag gacgaacgct ggcggcgtgc ttaacacatg caagtcgaac    60
gctgaagccc agcttgctgg gtggatgagt ggcgaacggg tgagtaacac gtgagtaacc   120
tgcccccttc tttgggataa cgcccggaaa cgggtgctaa tactggatat tcactggcct   180
tcgcatgggg gttggtggaa aggttttttc tggtgggga tgggc                    225
```

<210> SEQ ID NO 200
<211> LENGTH: 225

```
<212> TYPE: DNA
<213> ORGANISM: Unknown
<220> FEATURE:
<223> OTHER INFORMATION: Encodes 16S rRNA from Succiniclasticum

<400> SEQUENCE: 200
agagtttgat cctggctcag gacgaacgct ggcggcgtgc ctaacacatg caagtcgaac      60
ggggattttg tttcggcaga atcctagtgg cgaacgggtg agtaacgcgt aggcaacctg     120
cccccggat tgggacaaca ccccgaaagg ggtgctaata ccggatacga agataacacc     180
gcatggtgat attttgaaag atggcctcta tttataagct atcgc                    225

<210> SEQ ID NO 201
<211> LENGTH: 225
<212> TYPE: DNA
<213> ORGANISM: Unknown
<220> FEATURE:
<223> OTHER INFORMATION: Encodes 16S rRNA from Beijerinckia

<400> SEQUENCE: 201
agagtttgat cctggctcag aacgaacgct ggcggcaggc ttaacacatg caagtcgaac      60
gccccgcaag gggagtggca gacgggtgag taacgcgtgg gaacataccc tttcctgcgg     120
aatagctccg ggaaactgga attaataccg catacgccct acggggggaaa gatttatcgg     180
ggaaggattg gcccgcgttg gattagctag ttggtggggt aaagg                    225

<210> SEQ ID NO 202
<211> LENGTH: 225
<212> TYPE: DNA
<213> ORGANISM: Unknown
<220> FEATURE:
<223> OTHER INFORMATION: Encodes 16S rRNA from Bosea

<400> SEQUENCE: 202
agagtttgat cctggctcag agcgaacgct ggcggcaggc ttaacacatg caagtcgaac      60
gggcacttcg gtgctagtgg cagacgggtg agtaacacgt gggaacgtac ctttcggttc     120
ggaataatcc agggaaactt ggactaatac cggatacgcc cttcggggga aagatttatc     180
gccgatagat cggcccgcgt ctgattagct agttggtgag gtaat                    225

<210> SEQ ID NO 203
<211> LENGTH: 225
<212> TYPE: DNA
<213> ORGANISM: Unknown
<220> FEATURE:
<223> OTHER INFORMATION: Encodes 16S rRNA from Sporobacter

<400> SEQUENCE: 203
agagtttgat cctggctcag gacgaacgct ggcggcgtgc ctaacacatg caagtcgaac      60
ggagattaag tttaacaccg aacacttgat gctgttaaag taagcgcatc aaaaacgcga     120
agcgttttg attaggctta ttttgagtga caaacacaaa agatatcgag tagtcggtgt     180
tgaacttaat cttagtggcg gacgggtgag taacgcgtga gtaac                    225

<210> SEQ ID NO 204
<211> LENGTH: 225
<212> TYPE: DNA
<213> ORGANISM: Unknown
<220> FEATURE:
<223> OTHER INFORMATION: Encodes 16S rRNA from Facklamia

<400> SEQUENCE: 204
```

```
agagtttgat cctggctcag gacgaacgct ggcggcgtgc ctaatacatg caagtcgaac    60
gcactgacgg agaacttgtt ctcttgacgt gagtggcgca cgggtgagta acacgtggga   120
aacctaccct tcagcggggg ataaccatcg gaaacgatga ctaataccgc atagacgaca   180
gaaccgcctg gttcaatcgg gaaagacggc ttcggctgtc actga                   225
```

<210> SEQ ID NO 205
<211> LENGTH: 225
<212> TYPE: DNA
<213> ORGANISM: Unknown
<220> FEATURE:
<223> OTHER INFORMATION: Encodes 16S rRNA from Acinetobacter

<400> SEQUENCE: 205

```
agagtttgat cctggctcag attgaacgct ggcggcaggc ttaacacatg caagtcgagc    60
ggggaagggt agcttgctac ctgacctagc ggcggacggg tgagtaatgc ttaggaatct   120
gcctattagt gggggacaac attccgaaag gaatgctaat accgcatacg ccctacgggg   180
gaaagcaggg gatcttcgga ccttgcgcta atagatgagc ctaag                   225
```

<210> SEQ ID NO 206
<211> LENGTH: 225
<212> TYPE: DNA
<213> ORGANISM: Unknown
<220> FEATURE:
<223> OTHER INFORMATION: Encodes 16S rRNA from Brevundimonas

<400> SEQUENCE: 206

```
agagtttgat catggctcag agcgaacgct ggcggcaggc ctaacacatg caagtcgaac    60
ggacccttcg gggttagtgg cggacgggtg agtaacacgt gggaacgtgc ctttaggttc   120
ggaatagctc ctggaaacgg gtggtaatgc cgaatgtgcc cttcggggga aagatttatc   180
gcctttagag cggcccgcgt ctgattagct agttggtgag gtaac                   225
```

<210> SEQ ID NO 207
<211> LENGTH: 225
<212> TYPE: DNA
<213> ORGANISM: Unknown
<220> FEATURE:
<223> OTHER INFORMATION: Encodes 16S rRNA from Ochrobactrum

<400> SEQUENCE: 207

```
agagtttgat cctggctcag aacgaacgct ggcggcaggc ttaacacatg caagtcgagc    60
gccccgcaag gggagcggca gacgggtgag taacgcgtgg gaatctacct tttgctacgg   120
aataactcag ggaaacttgt gctaataccg tatgtgccct tcgggggaaa gatttatcgg   180
caaaggatga gcccgcgttg gattagctag ttggtggggt aaagg                   225
```

<210> SEQ ID NO 208
<211> LENGTH: 225
<212> TYPE: DNA
<213> ORGANISM: Unknown
<220> FEATURE:
<223> OTHER INFORMATION: Encodes 16S rRNA from Alcaligenes

<400> SEQUENCE: 208

```
agagtttgat cctggctcag attgaacgct agcgggatgc tttacacatg caagtcgaac    60
ggcagcgcga gagagcttgc tctcttggcg gcgagtggcg gacgggtgag taatatatcg   120
gaacgtgccc agtagcgggg gataaactact cgaaagagtg gctaataccg catacgccct   180
acgggggaaa gggggggatc gcaagacctc tcactattgg agcgg                   225
```

<210> SEQ ID NO 209
<211> LENGTH: 225
<212> TYPE: DNA
<213> ORGANISM: Unknown
<220> FEATURE:
<223> OTHER INFORMATION: Encodes 16S rRNA from Pseudochrobactrum

<400> SEQUENCE: 209

```
agagtttgat catggctcag aacgaacgct ggcggcaggc ttaacacatg caagtcgaac    60
ggtctcttcg gaggcagtgg cagacgggtg agtaatgcat gggaatctac cgttctctac   120
ggaataactc agggaaactt gtgctaatac cgtatacgcc cttttgggga aagatttatc   180
ggagaatgat gagcccatgt tggattagct agttggtagg gtaaa                   225
```

<210> SEQ ID NO 210
<211> LENGTH: 225
<212> TYPE: DNA
<213> ORGANISM: Unknown
<220> FEATURE:
<223> OTHER INFORMATION: Encodes 16S rRNA from Jeotgalicoccus

<400> SEQUENCE: 210

```
agagtttgat cctggctcag gatgaacgct ggcggcgtgc ctaatacatg caagtcgagc    60
gcgagcgtta aagcttgct tctaacaatc gagcggcgga cgggtgagta acacgtgggc   120
aacctacctt tgagattggg ataactaccg gaaacggtag ctaataccgg ataggacatg   180
attacataag tagtgatgtt aaaaggcgga tttatctgcc gttca                   225
```

<210> SEQ ID NO 211
<211> LENGTH: 225
<212> TYPE: DNA
<213> ORGANISM: Unknown
<220> FEATURE:
<223> OTHER INFORMATION: Encodes 16S rRNA from Jeotgalicoccus

<400> SEQUENCE: 211

```
agagtttgat cctggctcag gatgaacgct ggcggcgtgc ctaatacatg caagtcgagc    60
gcgaatctca ggagcttgct cctgagattc gagcggcgga cgggtgagta acacgtaggc   120
aacctaccct tgagattggg ataactaccg gaaacggtag ctaataccgg atacgacatt   180
cctgcataag taagaatgtt aaaaggcgga tttatctgcc gctca                   225
```

<210> SEQ ID NO 212
<211> LENGTH: 225
<212> TYPE: DNA
<213> ORGANISM: Unknown
<220> FEATURE:
<223> OTHER INFORMATION: Encodes 16S rRNA from Acinetobacter

<400> SEQUENCE: 212

```
agagtttgat catggctcag attgaacgct ggcggcaggc ttaacacatg caagtcgagc    60
ggggcgaagg tagcttgcta ctggaaccta gcggcggacg ggtgagtaat acttaggaat   120
ctgcctatta gtgggggaca acgttccgaa aggagcgcta ataccgcata cgccctacgg   180
gggaaagcag gggatcactt gtgaccttgc gctaatagat gagcc                   225
```

<210> SEQ ID NO 213
<211> LENGTH: 225
<212> TYPE: DNA
<213> ORGANISM: Unknown
<220> FEATURE:

<223> OTHER INFORMATION: Encodes 16S rRNA from Sphingobacterium

<400> SEQUENCE: 213

```
agagtttgat catggctcag gatgaacgct agcggcaggc ctaatacatg caagtcgaac    60
gggatccagg tgttagcttg ctaacatttg gtgagagtgg cgcacgggtg cgtaacgcgt   120
gagcaaccta cccatatcag ggggatagcc cgaagaaatt cggattaaca ccgcataaga   180
ctacgagatg gcatcatcaa gtagttaaat atttatagga tatgg                   225
```

<210> SEQ ID NO 214
<211> LENGTH: 225
<212> TYPE: DNA
<213> ORGANISM: Unknown
<220> FEATURE:
<223> OTHER INFORMATION: Encodes 16S rRNA from Lachnospiracea

<400> SEQUENCE: 214

```
agagtttgat cctggctcag gatgaacgct ggcggcgtgc ttaacacatg caagtcgaac    60
ggagttattt tatggaagcc ttcgggtgga agtaaaataa cttagtggcg gacgggtgag   120
taacgcgtgg gtaacctgcc ttatacaggg ggataacagc cggaaacggt tgctaatacc   180
gcataagcgc acagtattgc atgatacagt gtgaaaagat ttatc                   225
```

<210> SEQ ID NO 215
<211> LENGTH: 225
<212> TYPE: DNA
<213> ORGANISM: Unknown
<220> FEATURE:
<223> OTHER INFORMATION: Encodes 16S rRNA from Azospirillum

<400> SEQUENCE: 215

```
agagtttgat cctggctcag aacgaacgct ggcggcatgc ctaacacatg caagtcgaac    60
gaaggcttcg gccttagtgg cgcacgggtg agtaacacgt gggaacctgc ctttcggttc   120
ggaataacgt ctggaaacgg acgctaacac cggatacgcc cttcggggga aagttcacgc   180
cgagagaggg gcccgcgtcg gattaggtag ttggtgtggt aacgg                   225
```

<210> SEQ ID NO 216
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 216

```
agagtttgat cctggctcag gacgaacgtt ggcggcgtgc ctaatacatg caagtcgaac    60
gaagtcgccc aattgattct tagtgcttgc actaagatga ttttggatcc gactgagtgg   120
cgaactggtg agtaacacgt gggtaacctg cccagaagaa ggggataaca cctggaaaca   180
gatgctaata ccgtataaca acaagaacca catggttctt gtttg                   225
```

<210> SEQ ID NO 217
<211> LENGTH: 225
<212> TYPE: DNA
<213> ORGANISM: Unknown
<220> FEATURE:
<223> OTHER INFORMATION: Encodes 16S rRNA from Clavibacter

<400> SEQUENCE: 217

```
agagtttgat cctggctcag gacgaacgct ggcggcgtgc ttaacacatg caagtcgaac    60
ggtgatgtca gagcttgctc tggcggatca gtggcgaacg ggtgagtaac acgtgagtaa   120
```

```
cctgccccg    actctgggat    aactgctaga    aatggtagct    aataccggat    atgacgactg        180
gccgcatggt   ctggtcgtgg    aaagaatttc    ggttggggat    ggact                            225
```

<210> SEQ ID NO 218
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 218

```
agagtttgat   catggctcag    gatgaacgct    ggcggcgtgc    ttaacacatg    caagtcgaac        60
ggagttattt   tacggaagcc    ttcgggtgga    agtaaaataa    cttagtggcg    gacgggtgag        120
taacgcgtgg   gtaacctgcc    ttatacaggg    ggataacagc    cggaaacggt    tgctaatacc        180
gcataagcgc   acagtattgc    atgatacggt    gtgaaaagat    ttatc                            225
```

<210> SEQ ID NO 219
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 219

```
agagtttgat   catggctcag    gatgaacgct    ggcggcgtgc    ttaacacatg    caagtcgaac        60
ggagttattt   tatggaagcc    ttcgggtgga    aataaaataa    cttagtggcg    gacgggtgag        120
taacgcgtgg   gtaacctgcc    ttatacaggg    ggataacagc    cggaaacggt    tgctaatacc        180
gcataagcgc   acagtattgc    atgatacagt    gtgaaaagat    ttatc                            225
```

<210> SEQ ID NO 220
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 220

```
agagtttgat   catggctcag    gacgaacgct    ggcggcgtgc    ttaacacatg    caagtcgaac        60
gatgaagctg   gtgcttgcac    tggtggatta    gtggcgaacg    ggtgagtaac    acgtgggtaa        120
cctgcccttg   aagtagggga    taacacttgg    aaacaggtgc    taataccgta    taacaaccaa        180
aaccacctgg   ttttggttta    aaagacggct    tcggctgtca    cttta                            225
```

<210> SEQ ID NO 221
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 221

```
agagtttgat   cctggctcag    gatgaacgct    ggcggcgtgc    ctaacacatg    caagtcgaac        60
ggagttatgc   tgaaacctag    tgaggcataa    cttagtggcg    gacgggtgag    taacgcgtgg        120
gcaacctgcc   ccacacaggg    ggataacact    tagaaatagg    tgctaatacc    gcataagcgc        180
acagcttcgc   atgaagcagt    gtgaaaagct    gcggcggtgt    gggat                            225
```

<210> SEQ ID NO 222

```
<211> LENGTH: 225
<212> TYPE: DNA
<213> ORGANISM: Unknown
<220> FEATURE:
<223> OTHER INFORMATION: Encodes 16S rRNA from Bacillus

<400> SEQUENCE: 222
agagtttgat cctggctcag gacgaacgct ggcggcgtgc ctaatacatg caagtcgagc      60
gaaccaataa gaagcttgct ttttgttggt tagcggcgga cgggtgagta acacgtgggt     120
aacctgcctg taagaccggg ataactccgg gaaaccggtg ctaataccgg atagattatc     180
tttccgcctg gagagataag gaaagatggc ttttgccatc actta                     225

<210> SEQ ID NO 223
<211> LENGTH: 225
<212> TYPE: DNA
<213> ORGANISM: Unknown
<220> FEATURE:
<223> OTHER INFORMATION: Encodes 16S rRNA from Methanoplanus

<400> SEQUENCE: 223
agagtttgat cctgccagta gtcatatgct tgtctcaaag attaagccat gcatgtgcaa      60
gtatgaacta attcgaactg tgaaactgcg aatggctcat taaatcagtt atagtttgtt     120
tgatggtacg tgctactcgg ataaccgtag taattctaga gctaatacgt gcaacaaacc     180
ccgacttccg ggaggggcgc atttattaga taaaaggctg acgcg                     225

<210> SEQ ID NO 224
<211> LENGTH: 225
<212> TYPE: DNA
<213> ORGANISM: Unknown
<220> FEATURE:
<223> OTHER INFORMATION: Encodes 16S rRNA from Mogibacterium

<400> SEQUENCE: 224
agagtttgat catggctcag gatgaacgct ggcggcgtgc ctaacacatg caagtcgagc      60
gagaaatgta tttatgaaac ttcggtagat tagatacatg gaaagcggcg gacgggtgag     120
taacgcgtag gcaacctgcc ccttgcagag ggatagccat tggaaacgat gattaaaacc     180
tcataacgct gcattgtcac atgatagagc agccaaagat ttatc                     225

<210> SEQ ID NO 225
<211> LENGTH: 225
<212> TYPE: DNA
<213> ORGANISM: Unknown
<220> FEATURE:
<223> OTHER INFORMATION: Encodes 16S rRNA from Brachybacterium

<400> SEQUENCE: 225
agagtttgat cctggctcag gacgaacgct ggcggcgtgc ttaacacatg caagtcgaac      60
gatgacggtg gtgcttgcac cgcctgatta gtggcgaacg ggtgagtaac acgtgagtaa     120
cctgccctcc acttcgggat aacctcggga aatcgtggct aataccggat atgagcactc     180
atcgcatggt gggtgttgga aagatttatc ggtgggggat ggact                     225

<210> SEQ ID NO 226
<211> LENGTH: 225
<212> TYPE: DNA
<213> ORGANISM: Unknown
<220> FEATURE:
<223> OTHER INFORMATION: Encodes 16S rRNA from Facklamia

<400> SEQUENCE: 226
```

```
agagtttgat cctggctcag gacgaacgct ggcggcgtgc ctaatacatg caagtcgaac    60
gcactgacgg agaacttgtt ctcttgacgt gagtggcgca cgggtgagta acacgtggga   120
aacctaccct tcagcggggg ataaccatcg gaaacgatga ctaataccgc atagacgaca   180
gaaccgcctg gttcaatcgg gaaagacggc ttcggctgtc actga                   225
```

<210> SEQ ID NO 227
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 227

```
agagtttgat cctggctcag gatgaacgct ggcggcgtgc ttaacacatg caagtcgaac    60
ggagttattt tatggaagcc ttcgggtgga agtaaaataa cttagtggcg gacgggtgag   120
taacgcgtgg gtaacctgcc ttatacaggg ggataacagc cggaaacggt tgctaatacc   180
gcataagcgc acagtattgc atgataccgt gtgaaaagat ttatc                   225
```

<210> SEQ ID NO 228
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 228

```
agagtttgat cctggctcag gatgaacgct ggcggcgtgc ttaacacatg caagtcgaac    60
ggacttattt tatggaagcc ttcgggtgga aataaaataa gttagtggcg gacgggtgag   120
taacgcgtgg gtaacctgcc ttatacaggg ggataacagc cggaaacggt tgctaatacc   180
gcataagcgc acagtattgc atgataccgt gtgaaaagat ttatc                   225
```

<210> SEQ ID NO 229
<211> LENGTH: 225
<212> TYPE: DNA
<213> ORGANISM: Unknown
<220> FEATURE:
<223> OTHER INFORMATION: Encodes 16S rRNA from Syntrophomonas

<400> SEQUENCE: 229

```
agagtttgat cctggctcag gacgaacgct ggcggcgtgc ctaacacatg caagtcgaac    60
ggaagtaaga gcttcggttt ttactttagt ggcgaacggg tgagtaacgc gtgaggaacc   120
tgcctttcag tggggacaa cagttggaaa cgactgctaa taccgcataa tgtttccggt    180
ctgcatggac tggaaaccaa agctttatgt gctgaaagat ggcct                   225
```

<210> SEQ ID NO 230
<211> LENGTH: 225
<212> TYPE: DNA
<213> ORGANISM: Unknown
<220> FEATURE:
<223> OTHER INFORMATION: Encodes 16S rRNA from Beijerinckia

<400> SEQUENCE: 230

```
agagtttgat cctggctcag aacgaacgct ggcggcaggc ttaacacatg caagtcgaac    60
gccccgcaag gggagtggca gacgggtgag taacgcgtgg gaacataccc tttcctgcgg   120
aatagctccg ggaaactgga attaataccg catacgccct acggggaaa gatttatcgg    180
```
ggaaggattg gcccgcgttg gattagctag ttggtggggt aaagg     225

<210> SEQ ID NO 231
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 231
agagtttgat catggctcag dacgaacgct ggcggcatgc ttaacacatg caagtcgaac     60
gggaagtggt gtttccagtg gcgaacgggt gagtaacacg tggggaacct gccccatagt    120
ctgggatacc acttggaaac aggtgctaat accggataag aaagcagatc gcatgatcag    180
cttttaaaag gcggcgtaag ctgtcgctat gggatggccc cgcgg                    225

<210> SEQ ID NO 232
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 232
agagtttgat catggctcag gatgaacgct ggcggcatgc ttaacacatg caagtcgaac     60
gggaagtggt gtttccagtg gcggacgggt gagtaacacg tggggaacct gccccatagt    120
ctgggatacc acttggaaac aggtgctaat accggataag aaagcagatc gcatgatcag    180
cttataaaag gcggcgtaag ctgtcgctat gggatggccc cgcgg                    225

<210> SEQ ID NO 233
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 233
agagtttgat cctggctcag gatgaacgct ggcggcatgc ttaacacatg caagtcgaac     60
gggaagtggt gtttccagtg gcggacgggt gagtaacacg tgggtaacct gcccaagaga    120
ctgggataac acctggaaac agatgctaat accggataac aacactagac gcatgtctag    180
agtttgaaag atggttctgc tatcactctt ggatggacct gcggt                    225

<210> SEQ ID NO 234
<211> LENGTH: 225
<212> TYPE: DNA
<213> ORGANISM: Unknown
<220> FEATURE:
<223> OTHER INFORMATION: Encodes 16S rRNA from Erysipelotrichaceae
      incertae sedis

<400> SEQUENCE: 234
agagtttgat cctggctcag gatgaacgct ggcggcgtgc ctaatacatg caagtcgaac     60
ggagcacctt ggtgctcagt ggcgaacggg tgaggagaac ataggtaacc tgcccctccg    120 aggggggacaa cagctggaaa cggctgctaa gaccgcatag acgcattcag gcatcctgg    180 atgcgctaaa tgaccggatg gtcagcgggg ggatggacct atgca                    225

<210> SEQ ID NO 235
<211> LENGTH: 225
<212> TYPE: DNA

<213> ORGANISM: Unknown
<220> FEATURE:
<223> OTHER INFORMATION: Encodes 16S rRNA from Rummeliibacillus

<400> SEQUENCE: 235

```
agagtttgat cctggctcag dacgaacgct ggcggcgtgc ctaatacatg caagtcgagc      60
gaatgatgag gagcttgctc ctctgattta gcggcggacg ggtgagtaac acgtgggcaa     120
cctgccctgt agactgggat aacttcggga aaccggagct aataccggat aattctttta     180
gcctcatggc tttaagctaa aaggcgcttc ggcgtcacta cagga                    225
```

<210> SEQ ID NO 236
<211> LENGTH: 225
<212> TYPE: DNA
<213> ORGANISM: Unknown
<220> FEATURE:
<223> OTHER INFORMATION: Encodes 16S rRNA from Acinetobacter

<400> SEQUENCE: 236

```
agagtttgat catggctcag attgaacgct ggcggcaggc ttaacacatg caagtcgagc      60
ggggataggg tgcttgcacc tgattcctag cggcggacgg gtgagtaatg cttaggaatc     120
tgcctattag tggggacaa cgttccgaaa gggacgctaa taccgcatac gtcctacggg      180
agaaagcagg ggatcttcgg accttgcgct aatagatgag cctaa                    225
```

<210> SEQ ID NO 237
<211> LENGTH: 225
<212> TYPE: DNA
<213> ORGANISM: Unknown
<220> FEATURE:
<223> OTHER INFORMATION: Encodes 16S rRNA from Lactococcus

<400> SEQUENCE: 237

```
agagtttgat cctggctcag gacgaacgct ggcggcgtgc ctaatacatg caagttgagc      60
gctgaaggtt ggtacttgta ccgactggat gagcagcgaa cgggtgagta acgcgtgggg     120
aatctgcctt tgagcggggg acaacatttg gaaacgaatg ctaataccgc ataaaaactt     180
taaacacaag tttttaagttt gaaagatgca attgcatcac tcaaa                   225
```

<210> SEQ ID NO 238
<211> LENGTH: 225
<212> TYPE: DNA
<213> ORGANISM: Unknown
<220> FEATURE:
<223> OTHER INFORMATION: Encodes 16S rRNA from Propionibacterium

<400> SEQUENCE: 238

```
agagtttgat cctggctcag gacgaacgct ggcggcgtgc ttaacacatg caagtcgtac      60
ggtaaggccc tttcgggggt acacgagtgg cgaacgggtg agtaacacgt gagtaacctg     120
cccacaactt tgggataacg ctaggaaact ggtgctaata ctggatatgt gctcctgctg     180
catggtgggg gttggaaagc tccggcggtt gtggatggac tcgcg                    225
```

<210> SEQ ID NO 239
<211> LENGTH: 225
<212> TYPE: DNA
<213> ORGANISM: Unknown
<220> FEATURE:
<223> OTHER INFORMATION: Encodes 16S rRNA from Clostridium sensu stricto

<400> SEQUENCE: 239

```
agagtttgat catggctcag gataaacgct ggcggcgcac ataagacatg caagtcgaac      60
```

```
ggacttaatc gaaatattta tattttgaag cggttagtgg cggactggtg agtaacgcgt      120
aaggaacctg cctgttagag gggaataaca gtgagaaatc actgctaata ccgcatatgc      180
catagttacc acatggtaat agtgggaaag gagcaatccg ctgac                      225
```

```
<210> SEQ ID NO 240
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 240
agagtttgat cctggctcag gatgaacgct ggcggcgtgc ctaacacatg caagtcgaac      60
gaagcgccca ggacgaagcc tacgggcaga ggaatggggg actgagtggc ggacgggtga      120
gtaacgcgtg aggaacctgc ctcatacagg gggataacag ttagaaatga ctgctaatac      180
cgcataagcg cacgagaccg catgggaacg tgtgaaaaac tgagg                     225
```

```
<210> SEQ ID NO 241
<211> LENGTH: 225
<212> TYPE: DNA
<213> ORGANISM: Unknown
<220> FEATURE:
<223> OTHER INFORMATION: Encodes 16S rRNA from Rummeliibacillus

<400> SEQUENCE: 241
agagtttgat cctggctcag gacgaacgct ggcggcgtgc ctaatacatg caagtcgagc      60
gaatgacgag aagcttgctt ctctgattta gcggcggacg ggtgagtaac acgtgggcaa      120
cctgccctgt agactgggat aacttcggga aaccggagct aataccggat aattctttta     180
gcctcatggc tttaagctaa aaggcgcttc ggcgtcacta cagga                     225
```

```
<210> SEQ ID NO 242
<211> LENGTH: 225
<212> TYPE: DNA
<213> ORGANISM: Unknown
<220> FEATURE:
<223> OTHER INFORMATION: Encodes 16S rRNA from Ralstonia

<400> SEQUENCE: 242
agagtttgat cctggctcag attgaacgct ggcggcatgc cttacacatg caagtcgaac      60
ggcagcatga tctagcttgc tagattgatg gcgagtggcg aacgggtgag taatacatcg      120
gaacgtgccc tgtagtgggg gataactagt cgaaagatta gctaataccg catacgacct      180
gagggtgaaa gtgggggacc gcaaggcctc atgctatagg agcgg                     225
```

```
<210> SEQ ID NO 243
<211> LENGTH: 225
<212> TYPE: DNA
<213> ORGANISM: Unknown
<220> FEATURE:
<223> OTHER INFORMATION: Encodes 16S rRNA from Brachybacterium

<400> SEQUENCE: 243
agagtttgat cctggctcag gacgaacgct ggcggcgtgc ttaacacatg caagtcgaac      60
gatgacgatg gtgcttgcac cgtctgatta gtggcgaacg ggtgagtaac acgtgagtaa      120
cctgccctcc tcttcgggat aaccgccgga aacggtggct aataccggat atgaatgcct     180
gccgcatggt gggtgttgga agatttatc ggtgggggat ggact                      225
```

<210> SEQ ID NO 244
<211> LENGTH: 225
<212> TYPE: DNA
<213> ORGANISM: Unknown
<220> FEATURE:
<223> OTHER INFORMATION: Encodes 16S rRNA from Ruminobacter

<400> SEQUENCE: 244

```
agagtttgat cctggctcag attgaacgct ggcggcaggc ttaacacatg caagtcgtac    60
ggtaacagag ggaagcttgc ttctctgctg acgagtggcg gacgggtgag taatgtctgg   120
gaagctgcct gcttgagggg gatagcggag cgaaagttcc gataataccg cgtaagcccg   180 agagggaaa gtgcgggacc gcaaggccgc acgcgagcag atgcg                    225
```

<210> SEQ ID NO 245
<211> LENGTH: 225
<212> TYPE: DNA
<213> ORGANISM: Unknown
<220> FEATURE:
<223> OTHER INFORMATION: Encodes 16S rRNA from Glycomyces

<400> SEQUENCE: 245

```
agagtttgat catggctcag gcggttggcc aggtacaccg agcggtggtg accaccggtg    60
cagccaatgg cgatggtcac ataggcgcgg ttgctggcgg cgaagcgtgg cagccatttt   120
tccaggtagg cgaggatgtc ctgatacatc tcctcgacct ccggttgcgc ggccaggtag   180
tcgatcactg gttgatccag cccggagtgg tcgcgcagtt ccggc                   225
```

<210> SEQ ID NO 246
<211> LENGTH: 225
<212> TYPE: DNA
<213> ORGANISM: Unknown
<220> FEATURE:
<223> OTHER INFORMATION: Encodes 16S rRNA from Psychrobacter

<400> SEQUENCE: 246

```
agagtttgat catggctcag attgaacgct ggcggcaggc ttaacacatg caagtcgagc    60
ggtaacattt ctagcttgct agaagatgac gagcggcgga cgggtgagta atacttagga   120
atctacctag tagtgggggg tagctcgggg aaactcgaat taataccgca tacgacctac   180
gggagaaagg gggcaacttg ttgctctcgc tattagatga gccta                   225
```

<210> SEQ ID NO 247
<211> LENGTH: 225
<212> TYPE: DNA
<213> ORGANISM: Unknown
<220> FEATURE:
<223> OTHER INFORMATION: Encodes 16S rRNA from Yaniella

<400> SEQUENCE: 247

```
agagtttgat cctggctcag gatgaacgct ggcggcgtgc ttaacacatg caagtcgaac    60
gctgaagctc ccagcttgct gggggtggat gagtggcgaa cgggtgagta tcacgtgagt   120
aacctgccct tgactctggg ataagcccgg gaaactgggt ctaatactgg ataggactgg   180
ccatcgcatg gtggttggtt gaaagctttt gcggttttgg atgga                   225
```

<210> SEQ ID NO 248
<211> LENGTH: 225
<212> TYPE: DNA
<213> ORGANISM: Unknown
<220> FEATURE:
<223> OTHER INFORMATION: Encodes 16S rRNA from Clostridium IV

<400> SEQUENCE: 248

```
agagtttgat catggctcag gacgaacgct ggcggcgtgc ctaacacatg caagtcgaac    60
ggagttatta gagtgaagtt ttcggatgga atgataataa cttagtggcg gacgggtgag   120
taacgcgtga gtaacctgcc catgagaggg ggataacgtt ctgaaaagaa cgctaatacc   180
gcataacata tttagttcgc atggactgaa tatcaaagga gcgat                   225
```

<210> SEQ ID NO 249
<211> LENGTH: 225
<212> TYPE: DNA
<213> ORGANISM: Unknown
<220> FEATURE:
<223> OTHER INFORMATION: Encodes 16S rRNA from Clostridium sensu stricto

<400> SEQUENCE: 249

```
agagtttgat cctggctcag gacgaacgct ggcggcgtgc ctaacacatg caagtcgagc    60
gatgatatcc cttcggggat tgattagcgg cggacgggtg agtaacacgt gggtaacctg   120
cctcaaagag ggggatagcc ctccgaaagg aggattaata ccgcataaag ttgagagttc   180
gcatgaacat tcaaccaaag gagcaatccg ctttgagatg gaccc                   225
```

<210> SEQ ID NO 250
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 250

```
agagtttgat cctggctcag gatgaacgct ggcggcgtgc ttaacacatg caagtcgaac    60
ggacttattt tacggaagcc ttcgggtgga agtaaaataa gttagtggcg gacgggtgag   120
taacgcgtgg gtaacctgcc ttatacaggg ggataacagc cggaaacggt tgctaatacc   180
gcataagcgc acagtattgc atgatacagt gtgaaaagat ttatc                   225
```

<210> SEQ ID NO 251
<211> LENGTH: 225
<212> TYPE: DNA
<213> ORGANISM: Unknown
<220> FEATURE:
<223> OTHER INFORMATION: Encodes 16S rRNA from Clostridium sensu stricto

<400> SEQUENCE: 251

```
agagtttgat cctggctcag gacgaacgct ggcggcgtgc ctaacacatg caagtcgagc    60
gagggacttc ggtccctagc ggcggacggg tgagtaacac gtgggtaacc tgcctcatag   120
aggggatag cctcccgaaa gggagattaa taccgcataa catcatgctt tcgcatggaa   180
gtatgatcaa aggagcaatc cgctatgaga tggacccgcg gcgca                   225
```

<210> SEQ ID NO 252
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 252

```
agagtttgat catggctcag gatgaacgct ggcggcgtgc ttaacacatg caagtcgaac    60
ggagttattt tacggaagcc ttcgggtgga agtaaaataa cttagtggcg gacgggtgag   120
```

```
taacgcgtgg gtaacctgcc ttatacaggg ggataacagc cggaaacggt tgctaatacc    180
gcataagcgc acagtattgc atgatacggt gtgaaaaaga ttaaa                   225

<210> SEQ ID NO 253
<211> LENGTH: 225
<212> TYPE: DNA
<213> ORGANISM: Unknown
<220> FEATURE:
<223> OTHER INFORMATION: Encodes 16S rRNA from Cohnella

<400> SEQUENCE: 253
agagtttgat cctggctcag gacgaacgct ggcggcgtgc ctaatacatg caagtcgagc    60
ggatctctga tggagcttgc tcctgatgag gttagcggcg gacgggtgag taacacgtag   120
gcaacctgcc cccaagatcg ggataacatt cggaaacgaa tgctaagacc ggatacacgg   180
tttggtcgca tgatcggatc gggaaacacg gagcaatctg tggct                  225

<210> SEQ ID NO 254
<211> LENGTH: 225
<212> TYPE: DNA
<213> ORGANISM: Unknown
<220> FEATURE:
<223> OTHER INFORMATION: Encodes 16S rRNA from
      Chthonomonas/Armatimonadetes gp3

<400> SEQUENCE: 254
agagtttgat cctggctcag cagtttccgt attgaacaaa tggactgccc caccgaacag    60
acgctgattc aagacaaact gagcaagctg gctggcatag acaagctcga tttcaatctg   120
atcaatcgcg ttcttggggt atggcacagc ttgccgtcga ccgctcttat tgaagcggcg   180
atctcatccc taggtatgca agcagaaccg ctctctgctg agggg                  225

<210> SEQ ID NO 255
<211> LENGTH: 225
<212> TYPE: DNA
<213> ORGANISM: Unknown
<220> FEATURE:
<223> OTHER INFORMATION: Encodes 16S rRNA from Streptophyta

<400> SEQUENCE: 255
agagtttgat cctggctcag gatgaacgct ggcggcatgc cttacacatg caagtcggac    60
gggaagtggt gtttccagtg gcggacgggt gagtaacgcg taagaaccta cccttgggag   120
gggaacaaca gctggaaacg actgctaata ccgcataagc ccacggggcc gcatggctct   180
gagggaaaag gagcaatccg ctttgagatg gcctcgcgtc cgatt                  225

<210> SEQ ID NO 256
<211> LENGTH: 225
<212> TYPE: DNA
<213> ORGANISM: Unknown
<220> FEATURE:
<223> OTHER INFORMATION: Encodes 16S rRNA from Acinetobacter

<400> SEQUENCE: 256
agagtttgat cctggctcag attgaacgct ggcggcaggc ttaacacatg caagtcgagc    60
ggggaaaggt agcttgctac ctgacctagc ggcggacggg tgagtaatgc ttaggaatct   120
gcctattagt gggggacaac atctcgaaag ggatgctaat accgcatacg tcctacggga   180
gaaagcaggg gaccttcggg ccttgcgcta atagatgagc ctaag                  225

<210> SEQ ID NO 257
```

```
<211> LENGTH: 225
<212> TYPE: DNA
<213> ORGANISM: Unknown
<220> FEATURE:
<223> OTHER INFORMATION: Encodes 16S rRNA from Clostridium XlVb

<400> SEQUENCE: 257
agagtttgat cctggctcag gatgaacgct ggcggcgtgc ttaacacatg caagtcgagc    60
ggagatattc ggaaagcttg ctttttggat atcttagcgg cggacgggtg agtaacgtgt   120
gggcaacctg cctcatacag agggataatc atgtgaaaac gtgactaata ccgcatgtca   180
ttactgaagg gcatccttcg gtaagaaaag gagaaatccg gtatg                   225

<210> SEQ ID NO 258
<211> LENGTH: 225
<212> TYPE: DNA
<213> ORGANISM: Unknown
<220> FEATURE:
<223> OTHER INFORMATION: Encodes 16S rRNA from Neisseria

<400> SEQUENCE: 258
agagtttgat catggctcag attgaacgct ggcggcatgc tttacacatg caagtcgaac    60
ggcagcgagg agaagcttgc ttctctgtcg gcgagtggcg aacgggtgag tatagcatcg   120
gaacgtgcca gtagtgggg gataaccaaa cgaaagtttg gctaataccg cgtaagctcc    180
aaggaggaaa gtaggggacc taaataaggc cttacgctat ttgat                   225

<210> SEQ ID NO 259
<211> LENGTH: 225
<212> TYPE: DNA
<213> ORGANISM: Unknown
<220> FEATURE:
<223> OTHER INFORMATION: Encodes 16S rRNA from Butyricicoccus

<400> SEQUENCE: 259
agagtttgat cctggctcag gatgaacgct ggcggcacgc ctaacacatg caagtcgaac    60
gaagttattt tgatcgaagt tttcggatgg acattgattt aacttagtgg cggacgggtg   120
agtaacacgt gagcaatctg cctttcagag tgggataccg tttggaaacg aacgttaata   180
ccgcataacg cagcgaggcc gcatgacctt gctgccaaag attta                   225

<210> SEQ ID NO 260
<211> LENGTH: 225
<212> TYPE: DNA
<213> ORGANISM: Unknown
<220> FEATURE:
<223> OTHER INFORMATION: Encodes 16S rRNA from Sporobacter

<400> SEQUENCE: 260
agagtttgat cctggctcag gacgaacgct ggcggcgtgc ctaacacatg caagtcgaac    60
ggagatatat tgaatgaaga tttcggttgg aatttgatat atcttagtgg cggacgggtg   120
agtaacgcgt gagtaacctg ccgatgagag tggaataacg ttctgaaaag aacgctaata   180
ccgcataaca tatgggagcc gcatgactct gatatcaaag attt                    225

<210> SEQ ID NO 261
<211> LENGTH: 225
<212> TYPE: DNA
<213> ORGANISM: Unknown
<220> FEATURE:
<223> OTHER INFORMATION: Encodes 16S rRNA from Sporobacter

<400> SEQUENCE: 261
```

```
agagtttgat cctggctcag gacgaacgct ggcggcgtgc ctaacacatg caagtcgaac      60
ggggctcttt ggatcgagac ttcggtcaag tgaatctgag cttagtggcg gacgggtgag     120
taacgcgtga gcaacctgcc tttcagaggg ggacaacagt tggaaacgac tgctaatacc     180
gcataatgtg ttttgggggc atccccgaaa caccaaagat ttatc                     225
```

<210> SEQ ID NO 262
<211> LENGTH: 225
<212> TYPE: DNA
<213> ORGANISM: Unknown
<220> FEATURE:
<223> OTHER INFORMATION: Encodes 16S rRNA from Syntrophomonas

<400> SEQUENCE: 262

```
agagtttgat catggctcag gacgaacgct ggcggcgtgc ctaacacatg caagtcgaac      60
ggggctcttt ggatcgagac ttcggtcaag tgaaactgag cttagtggcg gacgggtgag     120
taacgcgtga gcaacctgcc tttcagaggg ggacaacagt tggaaacgac tgctaatacc     180
gcataacgtg tcgaggaggc atctctttga caccaaagat ttatc                     225
```

<210> SEQ ID NO 263
<211> LENGTH: 225
<212> TYPE: DNA
<213> ORGANISM: Unknown
<220> FEATURE:
<223> OTHER INFORMATION: Encodes 16S rRNA from Desulfotomaculum

<400> SEQUENCE: 263

```
agagtttgat catggctcag gacgaacgct ggcggcgtgc ctaacacatg caagtcgaac      60
ggggttactg tgaaggagtt cttcggaacg aatttatttt aacctagtgg cggacgggcg     120
agtaacgcgt gagtaacctg cccataagag ggggataaca cagagaaatt tgtgctaata     180
ccgcatattg aagtatttct gcatggagat gctttgaaag attta                     225
```

<210> SEQ ID NO 264
<211> LENGTH: 225
<212> TYPE: DNA
<213> ORGANISM: Unknown
<220> FEATURE:
<223> OTHER INFORMATION: Encodes 16S rRNA from Streptophyta

<400> SEQUENCE: 264

```
agagtttgat cctggctcag gatgaacgct ggcggcatgc ttaacacatg caagtcgaac      60
gggaagtggt gtttccagtg gcgaacgggt gcgtaatgcg tgggaatctg ccgaacagtt     120
cgggccaaat cctgaagaaa gctaaaaagc gctgtttgat gagcctgcgt agtattaggt     180
agttggtcag gtaaaggctg accaagccaa tgatgcttag ctggt                     225
```

<210> SEQ ID NO 265
<211> LENGTH: 225
<212> TYPE: DNA
<213> ORGANISM: Unknown
<220> FEATURE:
<223> OTHER INFORMATION: Encodes 16S rRNA from Acetomicrobium

<400> SEQUENCE: 265

```
agagtttgat catggctcag gacgaacgct ggcggcgtgc ctaacacatg caagtcgagc      60
ggggacacgg ggcttcggcc ctgtgttcta gcggcggacg ggtgagtaac gcgtgaacaa     120
tctgtcccag acaggggat aacaactgga aacagttgct aataccgcat aagaccacgg     180
```
cctcgcatgg ggctggggta aaagtgggaa cacggtttgg ggtga            225

<210> SEQ ID NO 266
<211> LENGTH: 225
<212> TYPE: DNA
<213> ORGANISM: Unknown
<220> FEATURE:
<223> OTHER INFORMATION: Encodes 16S rRNA from Acinetobacter

<400> SEQUENCE: 266
agagtttgat catggctcag attgaacgct ggcggcaggc ttaacacatg caagtcgagc    60
ggggaagggt agcttgctac ctgacctagc ggcggacggg tgagtaatgc ttaggaatct   120
gcctattagt gggggacaac attccgaaag gaatgctaat accgcatacg ccctacgggg   180
gaaagcaggg gatcttcgga ccttgcgcta atagatgagc ctaag                    225

<210> SEQ ID NO 267
<211> LENGTH: 225
<212> TYPE: DNA
<213> ORGANISM: Unknown
<220> FEATURE:
<223> OTHER INFORMATION: Encodes 16S rRNA from Erysipelotrichaceae
      incertae sedis

<400> SEQUENCE: 267
agagtttgat catggctcag gatgaacgct ggcggcatgc ctaatacatg caagtcgaac    60
gaagtttcga ggaagcttgc ttccaaagag acttagtggc gaacgggtga gtaacacgta   120
ggtaacctgc ccatgtgtcc gggataactg ctggaaacgg tagctaaaac cggataggta   180
tacagagcgc atgctcagta tattaaagcg cccatcaagg cgtga                    225

<210> SEQ ID NO 268
<211> LENGTH: 225
<212> TYPE: DNA
<213> ORGANISM: Unknown
<220> FEATURE:
<223> OTHER INFORMATION: Encodes 16S rRNA from Jeotgalicoccus

<400> SEQUENCE: 268
agagtttgat cctggctcag gatgaacgct ggcggcgtgc ctaatacatg caagtcgagc    60
gcgaagatca ggagcttgct cctgagattc gagcggcgga cgggtgagta acacgtaggc   120
aacctaccct tgagattggg ataactaccg gaaacggtag ctaataccgg atacgacatt   180
cctgcataag taagaatgtt aaaaggcgga tttatctgcc gctca                    225

<210> SEQ ID NO 269
<211> LENGTH: 225
<212> TYPE: DNA
<213> ORGANISM: Unknown
<220> FEATURE:
<223> OTHER INFORMATION: Encodes 16S rRNA from Selenomonas

<400> SEQUENCE: 269
agagtttgat cctggctcag gacgaacgct ggcggcgtgc ttaacacatg caagtcgaac    60
gagacgattt agaagcttgc ttttattgag tcgagtggca aacgggtgag taacgcgtag   120
acaacctgcc gcaaagatgg ggacaacagt ccgaaaggac tgctaatacc gaatgttgta   180
tctcctccgc atggaagaga tattaaagat ggcctctact tgtaa                    225

<210> SEQ ID NO 270
<211> LENGTH: 225
<212> TYPE: DNA

<213> ORGANISM: Unknown
<220> FEATURE:
<223> OTHER INFORMATION: Encodes 16S rRNA from Howardella

<400> SEQUENCE: 270

```
agagtttgat cctggctcag gatgaacgct ggcggcgtgc ttaacacatg caagtcgaat    60
gtagtttact acatggcgga cgggtgagta acgcgtgagc aatctgccca tatctggggg   120
ataacagttg gaaacgactg ataataccgc ataatattgt ttgaaggcat cttcttacaa   180
tcaaagattt atcggatatg gatgagctcg cgtctgatta gctag                   225
```

<210> SEQ ID NO 271
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 271

```
agagtttgat cctggctcag gatgaacgct ggcggcgtgc ctaacacatg caagtcgaac    60
ggagttatgc tgaaaccagg cggtgcttgc actgccttgt gatgaataac ttagtggcgg   120
acgggtgagt aacgcgtggg caacctgccc cacacagggg gataacactt agaaataggt   180
gctaataccg cataagcgca cagcttcgca tgaagcagtg tgaaa                   225
```

<210> SEQ ID NO 272
<211> LENGTH: 225
<212> TYPE: DNA
<213> ORGANISM: Unknown
<220> FEATURE:
<223> OTHER INFORMATION: Encodes 16S rRNA from Lachnospiracea incertae
      sedis

<400> SEQUENCE: 272

```
agagtttgat cctggctcag gatgaacgct ggcggcgtgc ctaacacatg caagtcgaac    60
ggtgatatat agatgatttc ggtctgaaat atatcatagt ggcggacggg tgagtaacgc   120
gtggataacc tgccccgtac tgggggatag cagctggaaa cggctggtaa taccgcataa   180
gcgcacgagg gggcctcccc ttgtgtgaaa agattcatcg gtacg                   225
```

<210> SEQ ID NO 273
<211> LENGTH: 225
<212> TYPE: DNA
<213> ORGANISM: Unknown
<220> FEATURE:
<223> OTHER INFORMATION: Encodes 16S rRNA from Lachnospiracea incertae
      sedis

<400> SEQUENCE: 273

```
agagtttgat cctggctcag gatgaacgct ggcggcgtgc ctaacacatg caagtcgaac    60
gggactattt agagatgttt tcggactgat cttttttagtt tagtggcgga cgggtgagta   120
acgcgtggac aacctgcctt tcacaggggg atagcagctg gaaacggctg gtaataccgc   180
atacgctcaa tacaccgcat ggtgtgatga ggaaagattt atcgg                   225
```

<210> SEQ ID NO 274
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 274

```
agagtttgat cctggctcag gatgaacgct ggcggcgtgc ctaacacatg caagtcgaac    60
ggggttaaga gaaattttcg gatggacctt aacttagtgg cggacgggtg agtaacgcgt   120
ggataacctg cctcacacag ggggatagca gctggaaacg gctggtaata ccgcataaga   180
ccacggcccc gcatggagct gtagtaaaag atttatcggt gtgag                   225
```

<210> SEQ ID NO 275
<211> LENGTH: 225
<212> TYPE: DNA
<213> ORGANISM: Unknown
<220> FEATURE:
<223> OTHER INFORMATION: Encodes 16S rRNA from Lachnospiracea incertae
      sedis

<400> SEQUENCE: 275

```
agagtttgat catggctcag gatgaacgct ggcggcgtgc ctaacacatg caagtcgaac    60
gaagcacttc tggtttgaga ttcgtcaaga accggatttg acttagtggc ggacgggtga   120
gtaatgtatg agcaacctgc ctttcagagg gggacaacaa ttggaaacga ctgctaatac   180
cgcataatgt attttaaggg catccttgga ataccaaagg agcaa                   225
```

<210> SEQ ID NO 276
<211> LENGTH: 225
<212> TYPE: DNA
<213> ORGANISM: Unknown
<220> FEATURE:
<223> OTHER INFORMATION: Encodes 16S rRNA from Bacillus

<400> SEQUENCE: 276

```
agagtttgat catggctcag gacgaacgct ggcggcgtgc ctaatacatg caagtcgagc    60
ggatgaagaa gagcttgctc tttggattca gcggcggacg ggtgagtaac acgtgggcaa   120
cctgcctgta agactgggat aacttcggga aaccggagct aataccggat aaaaactttc   180
ttcacatgaa ggaaggataa aagacggttt tgctgtcact tacag                   225
```

<210> SEQ ID NO 277
<211> LENGTH: 225
<212> TYPE: DNA
<213> ORGANISM: Unknown
<220> FEATURE:
<223> OTHER INFORMATION: Encodes 16S rRNA from Paenibacillus

<400> SEQUENCE: 277

```
agagtttgat catggctcag gacgaacgct ggcggcgtgc ctaatacatg caagtcgagc    60
ggagttactt tgaaagcttg ctttcaaagt aacttagcgg cggacgggtg agtaacacgt   120
aggcaacctg cccctcagac tgggataact accggaaacg gtagctaata ccggataatt   180
tctttttcct cctgagagaa gaatgaaaga cggagcaatc tgtca                   225
```

<210> SEQ ID NO 278
<211> LENGTH: 225
<212> TYPE: DNA
<213> ORGANISM: Unknown
<220> FEATURE:
<223> OTHER INFORMATION: Encodes 16S rRNA from Eubacterium

<400> SEQUENCE: 278

```
agagtttgat catggctcag gatgaacgct ggcggcgtgc ctaacacatg caagtcgaac    60
ggggttaagg gaaattttcg gatggaactt aacttagtgg cggacgggtg agtaacgcgt   120
ggataacctg cctcacactg ggggatagca gctggaaacg gctggtaata ccgcataaga   180
```

```
ccacagcacc gcatggtgca ggggtaaaag atttatcggt gtgag         225
```

<210> SEQ ID NO 279
<211> LENGTH: 225
<212> TYPE: DNA
<213> ORGANISM: Unknown
<220> FEATURE:
<223> OTHER INFORMATION: Encodes 16S rRNA from Amphibacillus

<400> SEQUENCE: 279

```
agagtttgat cctggctcag gatgaacgct ggcggcgtgc ctaatacatg caagtcgagc   60
gcgtgaagct taactgatct cttcggagtg acgttaagtg gatcgagcgg cggatgggtg  120
agtaacacgt gggcaacctg cctataagac tgggataact tacggaaacg tgagctaata  180
ccggatgaaa ccttttgtca cctggcaaaa ggatgaaagg tggct                  225
```

<210> SEQ ID NO 280
<211> LENGTH: 225
<212> TYPE: DNA
<213> ORGANISM: Unknown
<220> FEATURE:
<223> OTHER INFORMATION: Encodes 16S rRNA from Staphylococcus

<400> SEQUENCE: 280

```
agagtttgat cctggctcag gatgaacgct ggcggcatgc ctaagacatg caagtcgaac   60
gggatggccc actgatagtt ttggaagttt ggagagcttg ctcaaagaat ggaaaaagct  120
tgacgtggat tttccatcca gtggcagacg ggtgagtaac acgtgggtaa cctaccccag  180
agactgggat aactgttgga aacgacagct aataccggat aaacc                  225
```

<210> SEQ ID NO 281
<211> LENGTH: 225
<212> TYPE: DNA
<213> ORGANISM: Unknown
<220> FEATURE:
<223> OTHER INFORMATION: Encodes 16S rRNA from Paenibacillus

<400> SEQUENCE: 281

```
agagtttgat cctggctcag gacgaacgct ggcggcgtgc ctaatacatg caagtcgagc   60
ggagttattt tgaaagcttg ctttcaaaat aacttagcgg cggacgggtg agtaacacgt  120
aggcaacctg cccctcagac tgggataact accggaaacg gtagctaata ccggataatt  180
tctttttct cctgagagaa gaatgaaaga cggagcaatc tgtca                   225
```

<210> SEQ ID NO 282
<211> LENGTH: 225
<212> TYPE: DNA
<213> ORGANISM: Unknown
<220> FEATURE:
<223> OTHER INFORMATION: Encodes 16S rRNA from Clostridium IV

<400> SEQUENCE: 282

```
agagtttgat cctggctcag gacgaacgct ggcggcgtgc ctaacacatg caagtcgaac   60
ggagttgagg agcttgctcc ttaacttagt ggcggacggg tgagtaacgc gtgagtaacc  120
tgcctctgag aggggaataa cgttctgaaa aggacgctaa taccgcataa cacatatttg  180
ccgcatgaca gatatgtcaa agattttatc gctcggagat ggact                  225
```

<210> SEQ ID NO 283
<211> LENGTH: 225
<212> TYPE: DNA

```
<213> ORGANISM: Unknown
<220> FEATURE:
<223> OTHER INFORMATION: Encodes 16S rRNA from Prevotella

<400> SEQUENCE: 283
agagtttgat cctggctcag gatgaacgct agctacaggc ttaacacatg caagtcgagg      60
ggcagcatga agtttgcttg caaactttga tggcgaccgg cgcacgggtg agtaacgcgt     120
atccaacctt ccctatacta gaggatagcc cggcgaaagt cggattaata ctctatgttc    180
ttcgtagaag acatctgaaa tgaagcaaag gtttaccggt atagg                    225

<210> SEQ ID NO 284
<211> LENGTH: 225
<212> TYPE: DNA
<213> ORGANISM: Unknown
<220> FEATURE:
<223> OTHER INFORMATION: Encodes 16S rRNA from Barnesiella

<400> SEQUENCE: 284
agagtttgat cctggctcag gatgaacgct agcgacaggc ttaacacatg caagtcgagg      60
ggcagcgcgg aggtagcaat acttctggcg gcgaccggcg cactggtgag taacacgtat    120
gcgacctgcc ccggacaggg ggataaaccc gggaaactgg gcctaatacc ccataagtat    180
cgaggatgca tgtccttgat atgaaagatc cgtcggtccg ggatg                    225

<210> SEQ ID NO 285
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 285
agagtttgat cctggctcag gatgaacgct ggcggcgtgc ctaacacatg caagtcgaac      60
ggagatgagt tgatattttc ggatggatac ttatcttagt ggcggacggg tgagtaacgc    120
gtggataacc tgcctcgtac tgggggatag cagctggaaa cggctggtaa taccgcataa    180
gcgcacgatg ccgcatggca atgtgtgaaa agatttatcg gtacg                    225

<210> SEQ ID NO 286
<211> LENGTH: 225
<212> TYPE: DNA
<213> ORGANISM: Unknown
<220> FEATURE:
<223> OTHER INFORMATION: Encodes 16S rRNA from Clostridium XlVa

<400> SEQUENCE: 286
agagtttgat catggctcag gacgaacgct ggcggcgtgc ttaacacatg caagtcgaac      60
gaggatcatt tggatgagag cttcggcagg attttgaatg attcgagtgg cggacgggtg    120
agtaacgcgt gagcaatctg tcccagacag gggaataaca cttggaaaca ggtgctaata    180
ccgcataaga ccacagtatc gcatggtaca ggggtaaaag gagga                    225

<210> SEQ ID NO 287
<211> LENGTH: 225
<212> TYPE: DNA
<213> ORGANISM: Unknown
<220> FEATURE:
<223> OTHER INFORMATION: Encodes 16S rRNA from Sharpea

<400> SEQUENCE: 287
agagtttgat cctggctcag gatgaacgct ggcggcgtgc ctaatacatg caagtcggac      60
```

```
ggagcgcttc ggcgctcagt ggcgaacggg tgagtagcac atgggcaacc tgcccttcag    120
agggggacaa cagctggaaa cggctgctaa gaccgcatag gcgcggacgg gacatcccgt    180
ccacgttaaa cgtcctttcg ggacggctg aaggatgggc ctgtg                     225
```

<210> SEQ ID NO 288
<211> LENGTH: 225
<212> TYPE: DNA
<213> ORGANISM: Unknown
<220> FEATURE:
<223> OTHER INFORMATION: Encodes 16S rRNA from Lachnospiracea incertae
      sedis

<400> SEQUENCE: 288

```
agagtttgat catggctcag gatgaacgct ggcggcgtgc ctaacacatg caagtcgagc    60
ggagtcataa gttgattctt cggatgattt ttatgactta gcggcggatg ggtgagtaac    120
acgtgggtaa tctgccctgc acaggggat aacagctgga aacggctgtt aataccgcat    180
atgcacacgt tatcgcatga tagagtgtgg aaagatttat cggtg                    225
```

<210> SEQ ID NO 289
<211> LENGTH: 225
<212> TYPE: DNA
<213> ORGANISM: Unknown
<220> FEATURE:
<223> OTHER INFORMATION: Encodes 16S rRNA from Leucobacter

<400> SEQUENCE: 289

```
agagtttgat cctggctcag gacgaacgct ggcggcgtgc ttaacacatg caagtcgaac    60
gctgaagctc ccagcttgct gggggtggat gagtggcgaa cgggtgagta acacgtgagt    120
aacctgcccc gaactctggg ataagcgctg gaaacggcgt ctaatactgg atatgtccta    180
tcaccgcatg gtgtgtaggt ggaaagaatt ttggttcggg atgga                    225
```

<210> SEQ ID NO 290
<211> LENGTH: 225
<212> TYPE: DNA
<213> ORGANISM: Unknown
<220> FEATURE:
<223> OTHER INFORMATION: Encodes 16S rRNA from Lactonifactor

<400> SEQUENCE: 290

```
agagtttgat catggctcag gatgaacgct ggcggcgtgc ttaacacatg caagtcgaac    60
gaggttaatt gagcggatta tttcggtatg aagcgctttt aactgagtgg cggacgggtg    120
agtaacgcgt gggcaacctg cctcattcag ggggatacca gttggaaacg actgttaata    180
ccgcataagc gcacggttcc gcatggaaca gtgtgaaaag ctccg                    225
```

<210> SEQ ID NO 291
<211> LENGTH: 225
<212> TYPE: DNA
<213> ORGANISM: Unknown
<220> FEATURE:
<223> OTHER INFORMATION: Encodes 16S rRNA from Lachnospiracea incertae
      sedis

<400> SEQUENCE: 291

```
agagtttgat cctggctcag gatgaacgct ggcggcgtgc ctaacacatg caagtcgaac    60
gaagcacttc tgaacggaga ttcgtcaaag tttggatttg acttagtggc ggacgggtga    120
gtaatgtatg agcaacctgc ctttcagagg gggacaacag ttggaaacga ctgctaatac    180
```

<210> SEQ ID NO 292
<211> LENGTH: 225
<212> TYPE: DNA
<213> ORGANISM: Unknown
<220> FEATURE:
<223> OTHER INFORMATION: Encodes 16S rRNA from Succiniclasticum

<400> SEQUENCE: 292

```
agagtttgat cctggctcag gacgaacgct ggcggcgtgc ctaacacatg caagtcgaac    60
ggggattttg tttcggcaga atcctagtgg cgaacgggtg agtaacgcgt aggcaacctg   120
ccctccggcc ggggacaaca ctccgaaagg ggtgctaata ccggatacga agtctgtgcc   180
gcatggtacg gatttgaaag atggcctcta tttataagct atcgc                   225
```

<210> SEQ ID NO 293
<211> LENGTH: 225
<212> TYPE: DNA
<213> ORGANISM: Unknown
<220> FEATURE:
<223> OTHER INFORMATION: Encodes 16S rRNA from Acidovorax

<400> SEQUENCE: 293

```
agagtttgat cctggctcag attgaacgct ggcggcatgc cttacacatg caagtcgaac    60
ggtaacagct cttcggaggc tgacgagtgg cgaacgggtg agtaatacat cggaacgtgc   120
ccgatcgtgg gggataacgg agcgaaagct ttgctaatac cgcatacgat ctacggatga   180
aagcagggga ccctcgggcc ttgcgcgaac ggagcggccg atggc                   225
```

<210> SEQ ID NO 294
<211> LENGTH: 225
<212> TYPE: DNA
<213> ORGANISM: Unknown
<220> FEATURE:
<223> OTHER INFORMATION: Encodes 16S rRNA from Acinetobacter

<400> SEQUENCE: 294

```
agagtttgat cctggctcag attgaacgct ggcggcaggc ttaacacatg caagtcgagc    60
ggggaaaggt agcttgctac ctaacctagc ggcggacggg tgagtaatgc ttaggaatct   120
gcctattagt gggggacaac attccgaaag gaatgctaat accgcatacg ccctacgggg   180
gaaagcaggg gatcttcgga ccttgcgcta atagatgagc ctaag                   225
```

<210> SEQ ID NO 295
<211> LENGTH: 225
<212> TYPE: DNA
<213> ORGANISM: Unknown
<220> FEATURE:
<223> OTHER INFORMATION: Encodes 16S rRNA from Comamonas

<400> SEQUENCE: 295

```
agagtttgat cctggctcag gacgaacgct ggcggcatgc tttacacatg caagtcgaac    60
ggcagcacgg acttcggtct ggtggcgagt ggcgaacggg tgagtaatac atcggaacgt   120
gcccagttgt gggggataac tactcgaaag agtagctaat accgcatgag aactgaggtt   180
gaaagcaggg gatcgtaaga ccttgcgcaa ctggagcggc cgatg                   225
```

<210> SEQ ID NO 296
<211> LENGTH: 225
<212> TYPE: DNA
<213> ORGANISM: Unknown

```
<220> FEATURE:
<223> OTHER INFORMATION: Encodes 16S rRNA from Prevotella

<400> SEQUENCE: 296
agagtttgat cctggctcag gatgaacgct agctacaggc ttaacacatg caagtcgagg      60
ggcagcatga tcgaagcttg ctttgattga tggcgaccgg cgcacgggtg agtaacgcgt     120
atccaacctt ccctgtagta gagaatagcc cggcgaaagt cggattaatg ctctatgttg     180
tatttcgatg acatctgaag aataccaaag gtttaccgct atagg                     225

<210> SEQ ID NO 297
<211> LENGTH: 225
<212> TYPE: DNA
<213> ORGANISM: Unknown
<220> FEATURE:
<223> OTHER INFORMATION: Encodes 16S rRNA from Clostridium IV

<400> SEQUENCE: 297
agagtttgat cctggctcag gacgaacgct ggcggcgtgc ctaacacatg caagtcgaac      60
ggagtcaaga agcttgcttt ttgacttagt ggcggacggg tgagtaacgc gtgagtaacc     120
tgcctctgag aggggaataa cgttctgaaa agaacgctaa taccgcataa cgtatcgaag     180
ccgcatgact ttgataccaa agattttatc gctcggagat ggact                     225

<210> SEQ ID NO 298
<211> LENGTH: 225
<212> TYPE: DNA
<213> ORGANISM: Unknown
<220> FEATURE:
<223> OTHER INFORMATION: Encodes 16S rRNA from Clostridium sensu stricto

<400> SEQUENCE: 298
agagtttgat cctggctcag gacgaacgct ggcggcgtgc ttaacacatg caagtcgagc      60
gagagaatct ggtgcttgca ccagaggatc tagcggcgga cgggtgagta acacgtgggc     120 aacctgcccct aaggagggga ataacaggcc gaaaggtctg ctaataccgc ataatatctt    180
ttcttcgcat ggagaaaaga ttaaagattt atcgccttag gatgg                     225

<210> SEQ ID NO 299
<211> LENGTH: 225
<212> TYPE: DNA
<213> ORGANISM: Unknown
<220> FEATURE:
<223> OTHER INFORMATION: Encodes 16S rRNA from Succiniclasticum

<400> SEQUENCE: 299
agagtttgat catggctcag gacgaacgct ggcggcgtgc ctaacacatg caagtcgaac      60
ggggattttg tttcggcaga atcctagtgg cgaacgggtg agtaacgcgt aggcaacctg     120
ccctccggcc ggggacaaca ctccgaaagg ggtgctaata ccggatacga agtctgtgcc     180
gcatggtacg gatttgaaag atggcctctg tttacaagct atcgc                     225

<210> SEQ ID NO 300
<211> LENGTH: 225
<212> TYPE: DNA
<213> ORGANISM: Unknown
<220> FEATURE:
<223> OTHER INFORMATION: Encodes 16S rRNA from Lachnospiracea incertae
      sedis

<400> SEQUENCE: 300
agagtttgat cctggctcag gatgaacgct ggcggcgtgc ctaacacatg caagtcgaac      60
```

```
ggggctgttt gaaagatctt tcggagtga tttcttacag cttagtggcg gacgggtgag    120
taacgcgtgg ataacctgcc tttcacaggg ggatagcagc tggaaacggc tggtaatacc   180
gcatacgctc ttaagaccgc atgatcttaa gaggaaagat ttatc                   225
```

<210> SEQ ID NO 301
<211> LENGTH: 225
<212> TYPE: DNA
<213> ORGANISM: Unknown
<220> FEATURE:
<223> OTHER INFORMATION: Encodes 16S rRNA from Pedobacter

<400> SEQUENCE: 301

```
agagtttgat cctggctcag gatgaacgct agcggcaggc ctaatacatg caagtcgaac    60
gcgattgcgg tgcttgcacc gcatgaaagt ggcgtacggg tgcgtaacgc gtgagcaacc   120
taccgttgtc tgggggatag cccggagaaa tccggattaa taccgcataa tattagagag   180
cagcattgct ttctgatcaa acatttatgg gacagcgatg ggctc                   225
```

<210> SEQ ID NO 302
<211> LENGTH: 225
<212> TYPE: DNA
<213> ORGANISM: Unknown
<220> FEATURE:
<223> OTHER INFORMATION: Encodes 16S rRNA from Clostridium XII

<400> SEQUENCE: 302

```
agagtttgat cctggctcag gatgaacgct ggcggcgtgc ctaacacatg caagtcgagc    60
gagaaagtct ttacggatcc ttcgggtgaa agaatgactg gacagcggcg gacgggtgag   120
taacgcgtgg gaaaccttcc ttatacaaag ggatagcctc gggaaaccgg gattaatacc   180
ttatgaaact ctagtaccgc atggtacatg agtcaaaact ccggt                   225
```

<210> SEQ ID NO 303
<211> LENGTH: 225
<212> TYPE: DNA
<213> ORGANISM: Unknown
<220> FEATURE:
<223> OTHER INFORMATION: Encodes 16S rRNA from Flavobacterium

<400> SEQUENCE: 303

```
agagtttgat cctggctcag gatgaacgct agcggcaggc ctaacacatg caagtcgagg    60
ggtagagtta gcttgctaac ttgagaccgg cgcacgggtg cgtaacgcgt atgcaatcta   120
ccttatactg agggatagcc cggagaaatc cggattaata ccttatagta tattaaagtg   180
gcatcatttt gatattaaag atttattggt ataagatgag catgc                   225
```

<210> SEQ ID NO 304
<211> LENGTH: 225
<212> TYPE: DNA
<213> ORGANISM: Unknown
<220> FEATURE:
<223> OTHER INFORMATION: Encodes 16S rRNA from Clostridium sensu stricto

<400> SEQUENCE: 304

```
agagtttgat cctggctcag gacgaacgct ggcggcgtgc ctaacacatg caagtcgagc    60
gaggagattc ccttcgggga tgaacctagc ggcggacggg tgagtaacac gtgggcaacc   120
tgccttgtag aggggaatag ccttccgaaa ggaagattaa taccgcataa cattgcttta   180
tcgcatgata aagtaatcaa aggagcaatc cgctacaaga tgggc                   225
```

<210> SEQ ID NO 305
<211> LENGTH: 225
<212> TYPE: DNA
<213> ORGANISM: Unknown
<220> FEATURE:
<223> OTHER INFORMATION: Encodes 16S rRNA from Alkaliphilus

<400> SEQUENCE: 305

```
agagtttgat cctggctcag gatgaacgct ggcggcgtgc ctaacacatg caagtcgagc    60
ggagatgaag aagtttactt ctgattctta gcggcggacg ggtgagtaac gcgtgggcaa   120
cctaccctgt acaggggggat aacaatggga aaccattgct aatacccccat aacgcctttg   180 aggggcatcc cttaaaggtc aaagaatttc ggtacaggat gggcc                   225
```

<210> SEQ ID NO 306
<211> LENGTH: 225
<212> TYPE: DNA
<213> ORGANISM: Unknown
<220> FEATURE:
<223> OTHER INFORMATION: Encodes 16S rRNA from Arthrobacter

<400> SEQUENCE: 306

```
agagtttgat catggctcag gatgaacgct ggcggcgtgc ttaacacatg caagtcgaac    60
gatgaagcct agcttgctgg gtggattagt ggcgaacggg tgagtaacac gtgagtaacc   120 tgccccctgac ttcgggataa gcctgggaaa ctgggtctaa taccggatat cacttcctgc   180
cgcatggtgg gtggttgaaa gatttatcgg ttggggatgg actcg                   225
```

<210> SEQ ID NO 307
<211> LENGTH: 225
<212> TYPE: DNA
<213> ORGANISM: Unknown
<220> FEATURE:
<223> OTHER INFORMATION: Encodes 16S rRNA from Flavobacterium

<400> SEQUENCE: 307

```
agagtttgat cctggctcag gatgaacgct agcggcaggc ctaacacatg caagtcgagg    60
ggtagagtta gcttgctaac ttgagaccgg cgcacgggtg cgtaacgcgt atgcaatcta   120
ccttatactg agggatagcc cggagaaatc cggattaata ccttatagtt aataaaaaag   180
gcatctttta tattataaag atttattggt ataagatgag catgc                   225
```

<210> SEQ ID NO 308
<211> LENGTH: 225
<212> TYPE: DNA
<213> ORGANISM: Unknown
<220> FEATURE:
<223> OTHER INFORMATION: Encodes 16S rRNA from Roseburia

<400> SEQUENCE: 308

```
agagtttgat cctggctcag gatgaacgct ggcggcgtgc ttaacacatg caagtcgaac    60
gaagcactta agcggatccc ttcggggtga agcttaagtg acttagtggc ggacgggtga   120
gtaacgcgtg gtaacctgc ctcatacagg gggataacag ttggaaacga ctgctaagac   180
cgcataacaa gaaggaaccg catgatttct tcttcaaata tttat                   225
```

<210> SEQ ID NO 309
<211> LENGTH: 225
<212> TYPE: DNA
<213> ORGANISM: Unknown
<220> FEATURE:
<223> OTHER INFORMATION: Encodes 16S rRNA from Paenibacillus

<400> SEQUENCE: 309

```
agagtttgat cctggctcag gacgaacgct ggcggcgtgc ctaatacatg caagtcgagc      60
ggagttcctt tgaaagcttg ctttcaaagg aacttagcgg cggacgggtg agtaacacgt     120
aggcaacctg cccctcagac tgggataact accggaaacg gtagctaata ccggataatt    180
tcttttttct cctgagagaa gaatgaaaga cggagcaatc tgtca                    225
```

<210> SEQ ID NO 310
<211> LENGTH: 225
<212> TYPE: DNA
<213> ORGANISM: Unknown
<220> FEATURE:
<223> OTHER INFORMATION: Encodes 16S rRNA from Olivibacter

<400> SEQUENCE: 310

```
agagtttgat cctggctcag gatgaacgct agcggcaggc ctaatacatg caagtcggac      60
gggattgcag tatagcttgc tatactgcat gagagtggcg cacgggtgcg taacgcgtga    120
gcaacctgcc catgtcaggg ggatagcccg ttgaaagacg gattaatacc gcataacaca    180
tagagaccac ctggtttcta tgtcaaatat ttataggaca tggat                    225
```

<210> SEQ ID NO 311
<211> LENGTH: 225
<212> TYPE: DNA
<213> ORGANISM: Unknown
<220> FEATURE:
<223> OTHER INFORMATION: Encodes 16S rRNA from Clostridium XII

<400> SEQUENCE: 311

```
agagtttgat catggctcag gatgaacgct ggcggcgtgc ctaacacatg caagtcgagc      60
gagaaagtcg ttacggatcc ttcgggtgaa agaatgactg gatagcggcg gacgggtgag    120
taacgcgtgg gaaaccttcc ttatacaaag ggatagcctc gggaaaccgg gattaatacc    180
ttatgaaact ctagtaccgc atggtacatg agtcaaaact ccggt                    225
```

<210> SEQ ID NO 312
<211> LENGTH: 225
<212> TYPE: DNA
<213> ORGANISM: Unknown
<220> FEATURE:
<223> OTHER INFORMATION: Encodes 16S rRNA from Sphingobacterium

<400> SEQUENCE: 312

```
agagtttgat cctggctcag gatgaacgct agcggcaggc ctaatacatg caagtcggac      60
gggatccggg agtagcttgc tacttccggt gagagtggcg cacgggtgcg taacgcgtga    120
gcaacctgcc catatcaggg ggatagcccg gagaaatccg gattaacacc gcatgacacg    180
ccgggacggc atcgttccgg cgtcaaatat tcataggata tggat                    225
```

<210> SEQ ID NO 313
<211> LENGTH: 225
<212> TYPE: DNA
<213> ORGANISM: Unknown
<220> FEATURE:
<223> OTHER INFORMATION: Encodes 16S rRNA from Sphingobacterium

<400> SEQUENCE: 313

```
agagtttgat cctggctcag gatgaacgct agcggcaggc ctaatacatg caagtcggac      60
gggatccgtc ggagagcttg ctcgaagacg gtgagagtgg cgcacgggtg cgtaacgcgt    120
```

```
gagcaaccta cctctatcag ggggatagcc tctcgaaaga gagattaaca ccgcataaca    180
tatctgaccg gcatcggtta gctattaaat atttatagga tagag                    225
```

```
<210> SEQ ID NO 314
<211> LENGTH: 225
<212> TYPE: DNA
<213> ORGANISM: Unknown
<220> FEATURE:
<223> OTHER INFORMATION: Encodes 16S rRNA from Anaerosporobacter

<400> SEQUENCE: 314
agagtttgat catggctcag gacgaacgct ggcggcgtgc ttaacacatg caagtcgaac    60
gaagcactta agcggatccc ttcggggtga agcttaagtg acttagtggc ggacgggtga   120
gtaacgcgtg ggtaacctgc ctcatacagg gggataacag ttggaaacga ctgctaagac   180
cgcataaaac agtagtgtcg catgacacaa ctgtcaaata tttat                   225
```

```
<210> SEQ ID NO 315
<211> LENGTH: 225
<212> TYPE: DNA
<213> ORGANISM: Unknown
<220> FEATURE:
<223> OTHER INFORMATION: Encodes 16S rRNA from Clostridium XII

<400> SEQUENCE: 315
agagtttgat cctggctcag gacgaacgct ggcggcgtgc ctaacacatg caagtcgagc    60
gaagttttca aagcagattt cttcggattg aagttttgat tatcttagcg gcggacgggt   120
gagtaacgcg tgagaaacct gcctttcaca aagggatagc ctcgggaaac tgggattaat   180
accttatgat actaattctt cgcatgaaga attagtcaaa gcgta                   225
```

```
<210> SEQ ID NO 316
<211> LENGTH: 225
<212> TYPE: DNA
<213> ORGANISM: Unknown
<220> FEATURE:
<223> OTHER INFORMATION: Encodes 16S rRNA from Clostridium XII

<400> SEQUENCE: 316
agagtttgat cctggctcag gacgaacgct ggcggcgtgc ctaacacatg caagtcgagc    60
gaagttttca aagttgattt cttcggaatg aaactttgat tatcttagcg gcggacgggt   120
gagtaacgcg tgagaaacct gcctttcaca aagggatagc ctcgggaaac tgggattaat   180
accttatgat actaaatctt cacatgaagg aatagtcaaa gcgta                   225
```

```
<210> SEQ ID NO 317
<211> LENGTH: 225
<212> TYPE: DNA
<213> ORGANISM: Unknown
<220> FEATURE:
<223> OTHER INFORMATION: Encodes 16S rRNA from Clostridium sensu stricto

<400> SEQUENCE: 317
agagttatca tggctcagga cgaacgctgg cggcgtgcct aacacatgca agtcgagcga    60
ggggagtttc ttcggaaaca aacctagcgg cggacgggtg agtaacacgt gggcaacctg   120
ccttgtagag gggaatagcc ttccgaaagg aagattaata ccgcataaca ttgcactttc   180
gcatgagaga gtaattaaag gagtaatccg ctacaagatg ggccc                   225
```

```
<210> SEQ ID NO 318
<211> LENGTH: 225
```

```
<212> TYPE: DNA
<213> ORGANISM: Unknown
<220> FEATURE:
<223> OTHER INFORMATION: Encodes 16S rRNA from Pedobacter

<400> SEQUENCE: 318
agagtttgat catggctcag gatgaacgct agcggcaggc ctaatacatg caagtcgagg      60
ggtatgggtt gcttgcaacc cagagaccgg cgcacgggtg cgtaacgcgt atgcaatcta     120
ccttaatcag ggggatagcc cggagaaatc cggattaaca ccgcataaca ttaagtaatg     180
gcatcattat ttaatcaaat atttatagga ttaagatgag catgc                     225

<210> SEQ ID NO 319
<211> LENGTH: 225
<212> TYPE: DNA
<213> ORGANISM: Unknown
<220> FEATURE:
<223> OTHER INFORMATION: Encodes 16S rRNA from Bacillus

<400> SEQUENCE: 319
agagtttgat cctggctcag gacgaacgct ggcggcgtgc ctaatacatg caagtcgagc      60
ggattgtgag agaagcttgc ttctcccaca gttagcggcg gacgggtgag taacacgtgg     120
gcaacctgcc tgtaagatcg ggataacttc gggaaaccgg agctaatacc ggataggcga     180
ttttactgca tggtagaatc gagaaagatg ctaaggcatc actta                     225

<210> SEQ ID NO 320
<211> LENGTH: 225
<212> TYPE: DNA
<213> ORGANISM: Unknown
<220> FEATURE:
<223> OTHER INFORMATION: Encodes 16S rRNA from Paenibacillus

<400> SEQUENCE: 320
agagtttgat catggctcag gacgaacgct ggcggcgtgc ctaatacatg caagtcgagc      60 ggagttatttt tgaaagcttg ctttcgaaat aacttagcgg cggacgggtg agtaacacgt    120
aggcaacctg cccctcagac tgggataact accggaaacg gtagctaata ccggataatt     180
tcttttttct cctgaagaaa gaatgaaaga cggagcaatc tgtca                     225

<210> SEQ ID NO 321
<211> LENGTH: 225
<212> TYPE: DNA
<213> ORGANISM: Unknown
<220> FEATURE:
<223> OTHER INFORMATION: Encodes 16S rRNA from Prevotella

<400> SEQUENCE: 321
agagtttgat catggctcag agctccaggc ttaacacatg caagtcgagg                 60
ggcagcaggg agatagcttg ctatctttgc tggcgaccgg cgcacgggtg agtaacgcgt     120
atccaacctt cccttacta aggaatagcc cggcgaaagt cggattaatg ccttatgttc      180 tccttttgcag gcatctaacg aggagcaaag attcatcggt aaggg                    225

<210> SEQ ID NO 322
<211> LENGTH: 225
<212> TYPE: DNA
<213> ORGANISM: Unknown
<220> FEATURE:
<223> OTHER INFORMATION: Encodes 16S rRNA from Lachnospiracea incertae
      sedis

<400> SEQUENCE: 322
```

```
agagtttgat cctggctcag gatgaacgct ggcggcgtgc ctaacacatg caagtcgaac    60
gggactattc tgagatgttt tcggactgat ctaaatagtt tagtggcgga cgggtgagta   120
acgcgtggac aacctgcctt tcacagggg atagcagctg gaaacggctg gtaataccgc   180
atacgctcag tgcaccgcat ggtgtattga ggaaagattt atcgg                  225
```

<210> SEQ ID NO 323
<211> LENGTH: 225
<212> TYPE: DNA
<213> ORGANISM: Unknown
<220> FEATURE:
<223> OTHER INFORMATION: Encodes 16S rRNA from Lachnospiracea incertae
      sedis

<400> SEQUENCE: 323

```
agagtttgat cctggctcag gatgaacgct ggcggcgtgc ctaacacatg caagtcgaac    60
gggactattt agagatgttt tcggactgat cttttttagtt tagtggcgga cgggtgagta   120
acgcgtggac aacctgcctt tcacagggg atagcagctg gaaacggctg gtaataccgc   180
atacgctcag tgcaccgcat ggtgtgctga ggaaagattt atcgg                  225
```

<210> SEQ ID NO 324
<211> LENGTH: 225
<212> TYPE: DNA
<213> ORGANISM: Unknown
<220> FEATURE:
<223> OTHER INFORMATION: Encodes 16S rRNA from Escherichia/Shigella

<400> SEQUENCE: 324

```
agagtttgat catggctcag gatgaacgct ggcggcgtgc ttaacacatg caagtcgaac    60
gctgaagctc ccagcttgct gggggtggat gagtggcgaa cgggtgagta tcacgtgagt   120
aacctgccct taactctggg ataagcccgg gaaactgggt ctaatactgg ataggactga   180
tcatcgcatg gtggttggtt gaaagttttt gacggttttg gatgg                  225
```

<210> SEQ ID NO 325
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 325

```
agagtttgat catggctcag gacgaacgct ggcggcgtgc ctaatacatg caagtcgagc    60
gagcggaact aacagattta cttcggtaat gacgttagga aagcgagcgg cggatgggtg   120
cattagctag ttggtaaggt aaaggcttac caaggcgatg atgcatagcc gagttgagag   180
actgatcggc cacattggga ctgagacacg gcccaaactc ctacg                  225
```

<210> SEQ ID NO 326
<211> LENGTH: 225
<212> TYPE: DNA
<213> ORGANISM: Unknown
<220> FEATURE:
<223> OTHER INFORMATION: Encodes 16S rRNA from Corynebacterium

<400> SEQUENCE: 326

```
agagtttgat cctggctcag gatgaacgct ggcggcgtgc ctaacacatg caagtcgaac    60
ggggttaaga gaaattttcg gatggatctt aacttagtgg cggacgggtg agtaacgcgt   120
ggataacctg cctcacacag ggggatagca gctggaaacg gctggtaata ccgcataaga   180
```

```
ccacggcccc gcatggagct gtagtaaaag atttatcggt gtgag          225
```

<210> SEQ ID NO 327
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 327

```
agagtttgat catggctcag aacgaacgct ggcggcaggc ttaacacatg caagtcgagc   60
gggcatcttc gggtgtcagc ggcggacggg ttagtaacgc gtgggaacgt gcccttTGct  120
tcggaatagc cccgggaaac tgggggtaat accggatgtg ccctgagggg gaaagattta  180
tcggcaaggg atcggcccgc gtctgattag gtagttggtg tggta                  225
```

<210> SEQ ID NO 328
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 328

```
agagtttgat cctggctcag gacgaacgct ggcggcgtgc ctaatacatg caagtcgagc   60
gagcggaaag cgagcggcgg atgggtgagt aacacgtggg gaacctgccc catagtctgg  120
gataccactt ggaaacaggt gctaataccg gataagaaag cagatcgcat gatcagcttt  180
taaaaggcgg cgtaagctgt cgctatggga tggccccgcg gtgca                  225
```

<210> SEQ ID NO 329
<211> LENGTH: 225
<212> TYPE: DNA
<213> ORGANISM: Unknown
<220> FEATURE:
<223> OTHER INFORMATION: Encodes 16S rRNA from Escherichia/Shigella

<400> SEQUENCE: 329

```
agagtttgat cctggctcag gacgaacgct ggcggcgtgc ttaacacatg caagtcgaac   60
gatgacgatg gtgcttgcac cgtctgatta gtggcgaacg ggtgagtaac acgtgagtaa  120
cctgccctcc tcttcgggat aaccgccgga aacggtggct aataccggat atgaatgcct  180
gccgcatggt gggtgttgga aagatttatc ggtgggggat ggact                  225
```

<210> SEQ ID NO 330
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 330

```
agagtttgat catggctcag attgaacgct ggcggcaggc ttaacacatg caagtcgagc   60
ggggagaagg tagcttgcta ctggaaccta gcggcggacg ggtgagtaat gcttaggaat  120
ctgcctatta gtgggggaca acgttccgaa aggagcgcta ataccgcata cgccctacgg  180
gggaaagcag gggatcactt gtgaccttgc gctaatagat gagcc                  225
```

<210> SEQ ID NO 331
<211> LENGTH: 225
<212> TYPE: DNA

```
<213> ORGANISM: Unknown
<220> FEATURE:
<223> OTHER INFORMATION: Encodes 16S rRNA from Lactobacillus

<400> SEQUENCE: 331
agagtttgat cctggctcag gacgaacgct ggcggcgtgc ctaacacatg caagtcgagc    60
gaagttttta gagaagattt cttcggaatg aaactctaat tatcttagcg gcggacgggt   120
gagtaacgcg tgagaaacct gcctttcaca aagggatagc ctcgggaaac tgggattaat   180
accttatgac acttaaattt cgcatggaaa ataagttaaa gcgta                   225

<210> SEQ ID NO 332
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 332
agagtttgat cctggctcag gacgaacgct ggcggcgtgc ttaacacatg caagtcgaac    60
gagacgattt taagcttgct tagatgagtc gagtggcaaa cgggtgagta acgcgtagac   120
aacctgccgc aaagatgggg acaacagtcc gaaaggactg ctaataccga atgttgtcag   180
tttctcgcat gagagattga ttaaagatgg cctctacttg taagc                   225

<210> SEQ ID NO 333
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 333
agagtttgat catggctcag gacgaacgct ggcggcgtgc ctaatacatg caagtcgagc    60
gagcggaact aacagattta cttcggtaat gacgttagga aagcgagcgg cggacgggtg   120
agtaacgtgt gggcaacctg cctcacacag ggggataaca gttagaaatg actgctaata   180
ccgcataaga ccacggcacc gcatggtgca ggggtaaaaa ctctg                   225

<210> SEQ ID NO 334
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 334
agagtttgat cctggctcag gacgaacgct ggcggcgtgc ttaacacatg caagtcgaac    60
gctgaagctc ccagcttgct gggggtggat gagtggcgaa cgggtgagta acacgtgagt   120
aacctgcccc gaactctggg ataagcgctg gaaacggcgt ctaatactgg atatgtccta   180
tcaccgcatg gtgtgtaggt ggaaagaatt ttggttcggg atgga                   225

<210> SEQ ID NO 335
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 335
agagtttgat cctggctcag gacgaacgct ggcggcgtgc ttaacacatg caagtcgaac    60
```

```
gatgatgccc agcttgctgg gcggattagt ggcgaacggg tgagtaatac gtgagtaacc    120
tgcccttgac tctgggataa gcctgggaaa ctgggtctaa tactggatac taccgtccac    180
cgcatggtgg gtggtggaaa gggttttact ggttttggat gggct                    225
```

```
<210> SEQ ID NO 336
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 336
agagtttgat cctggctcag gatgaacgct ggcggcgtgc ttaacacatg caagtcgaac     60
gatgatgctg gtgcttgcac tggtggatta gtggcgaacg ggtgagtaac acgtgagtaa    120 cctgccctg  acttcgggat aagcccggga aactgggtct aataccggat atgacttcct    180
gctgcatggc aggggtgga aagatttatc ggttggggat ggact                     225
```

```
<210> SEQ ID NO 337
<211> LENGTH: 225
<212> TYPE: DNA
<213> ORGANISM: Unknown
<220> FEATURE:
<223> OTHER INFORMATION: Encodes 16S rRNA from Enterococcus

<400> SEQUENCE: 337
agagtttgat cctggctcag gacgaacgct ggcggcgtgc ctaatacatg caagtcgaac     60
gcttctttcc tcccgagtgc ttgcactcaa ttggaaagag gagtggcgga cgggtgagta    120
acacgtgggt aacctaccca tcagaggggg ataacacttg gaaacaggtg ctaataccgc    180
ataacagttt atgccgcatg gcataagagt gaaaggcgct ttcgg                    225
```

```
<210> SEQ ID NO 338
<211> LENGTH: 225
<212> TYPE: DNA
<213> ORGANISM: Unknown
<220> FEATURE:
<223> OTHER INFORMATION: Encodes 16S rRNA from Corynebacterium

<400> SEQUENCE: 338
agagtttgat cctggctcag gacgaacgct ggcggcgtgc ttaacacatg caagtcgaac     60
gctgaaacca gagcttgctt tggtggatga gtggcgaacg ggtgagtaac acgtgggtga    120
tctgccctac actttgggat aagcctggga aactgggtct aataccgaat attcacacca    180
ccgtaggggt ggtgtggaaa gctttatgcg gtgtgggatg agcct                    225
```

```
<210> SEQ ID NO 339
<211> LENGTH: 225
<212> TYPE: DNA
<213> ORGANISM: Unknown
<220> FEATURE:
<223> OTHER INFORMATION: Encodes 16S rRNA from Streptococcus

<400> SEQUENCE: 339
agagtttgat cctggctcag gacgaacgct ggcggcgtgc ctaatacatg caagtggaac     60
gcatgattga taccggagct tgctccacca ttaatcatga gtcgcgaacg ggtgagtaac    120
gcgtaggtaa cctacctcat agcgggggat aactattgga aacgatagct aataccgcat    180
aagagtggat aacacatgtt attgatttaa aaggagcaat tgctt                    225
```

```
<210> SEQ ID NO 340
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 340
agagtttgat catggctcag dacgaacgct ggcggcgtgc ctaatacatg caagtcgaac      60
gagaatttct tacaccgagt gcttgcactc accgtaagaa attcgagtgg cggacgggtg     120
agtaacacgt gggtaacctg cccaaaagaa ggggataaca tttggaaaca aatgctaata    180
ccgtataacc atgatgaccg catggtcatt atgtaaaagg tggtt                   225

<210> SEQ ID NO 341
<211> LENGTH: 225
<212> TYPE: DNA
<213> ORGANISM: Unknown
<220> FEATURE:
<223> OTHER INFORMATION: Encodes 16S rRNA from Corynebacterium

<400> SEQUENCE: 341
agagtttgat cctggctcag gacgaacgct ggcggcgtgc ttaacacatg caagtcgaac      60
ggtaaggccc cagcttgctg gggtacacga gtggcgaacg ggtgagtaac acgtgggtga    120
cctgccccgc acttcgggat aagcctggga aactgggtct aataccggat aggaccgcac   180
cgtgagggtg tggtggaaag ttttcggtg tgggatgggc ccgcg                    225

<210> SEQ ID NO 342
<211> LENGTH: 225
<212> TYPE: DNA
<213> ORGANISM: Unknown
<220> FEATURE:
<223> OTHER INFORMATION: Encodes 16S rRNA from Peptostreptococcaceae
      (Clostridium Cluster XI)

<400> SEQUENCE: 342
agagtttgat catggctcag gatgaacgct ggcggcgtgc ctaacacatg caagtcgagc      60
gatcttcttc ggaagagagc ggcggacggg tgagtaacgc gtgggtaacc tgccctgtac    120
acacggataa cataccgaaa ggtatgctaa tacgagataa tatgctttta tcgcatggta   180
gaagtatcaa agctccggcg gtacaggatg gacccgcgtc tgatt                   225

<210> SEQ ID NO 343
<211> LENGTH: 225
<212> TYPE: DNA
<213> ORGANISM: Unknown
<220> FEATURE:
<223> OTHER INFORMATION: Encodes 16S rRNA from Corynebacterium

<400> SEQUENCE: 343
agagtttgat cctggctcag gacgaacgct ggcggcgtgc ttaacacatg caagtcgaac      60
ggaaaggccc ttgcttgcag gggtactcga gtggcgaacg ggtgagtaac acgtgggtga    120
tctgccttgt acttcgggat aagcctggga aactgggtct aataccggat aggaccatgc   180
tttagtgtgt gtggtggaaa gtttttcgg tacaagatga gcccg                    225

<210> SEQ ID NO 344
<211> LENGTH: 225
<212> TYPE: DNA
<213> ORGANISM: Unknown
<220> FEATURE:
```

<223> OTHER INFORMATION: Encodes 16S rRNA from Corynebacterium

<400> SEQUENCE: 344

```
agagtttgat catggctcag gatgaacgct ggcggcgtgc ttaacacatg caagtcgaac      60
ggaaaggcct gtacttgtac aggtgctcga gtggcgaacg ggtgagtaac acgtgggtga    120
tctgccctgc actgtgggat aagcccggga aactgggtct aataccatat aggaccactt    180
cttggatgtt gtggtggaaa gcttttgcgg tgtgggatga gcctg                    225
```

<210> SEQ ID NO 345
<211> LENGTH: 225
<212> TYPE: DNA
<213> ORGANISM: Unknown
<220> FEATURE:
<223> OTHER INFORMATION: Encodes 16S rRNA from Lachnospiraceae
      (Clostridium Cluster XlVa)

<400> SEQUENCE: 345

```
agagtttgat catggctcag gatgaacgct ggcggcgtgc ctaacacatg caagtcgagc      60
gaagcgattc ggatgaagtt ttcggatgga ttttggattg actgagcggc ggacgggtga    120
gtaacgcgtg ggtaacctgc ctcatacagg gggataacag ttagaaatga ctgctaatac    180
cgcataagcg cacagtaccg catggtacgg tgtgaaaaac tccgg                    225
```

<210> SEQ ID NO 346
<211> LENGTH: 225
<212> TYPE: DNA
<213> ORGANISM: Unknown
<220> FEATURE:
<223> OTHER INFORMATION: Encodes 16S rRNA from Lachnospiracea incertae
      sedis

<400> SEQUENCE: 346

```
agagtttgat catggctcag gatgaacgct ggcggcgtgc ttaacacatg caagtcgagc      60
gaagcactta cttttgattt cttcggaatg acgaggtctg tgacttagcg gcggacgggt    120
gagtaacgcg tgggcaacct gcctcacaca gggggataac agttagaaat gactgctaat    180
accgcataag accccggcac cgcatggtgc aggggtaaaa actcc                    225
```

<210> SEQ ID NO 347
<211> LENGTH: 225
<212> TYPE: DNA
<213> ORGANISM: Unknown
<220> FEATURE:
<223> OTHER INFORMATION: Encodes 16S rRNA from Ruminococcaceae
      (Clostridium Cluster III)

<400> SEQUENCE: 347

```
agagtttgat cctggctcag gacgaacgct ggcggcgtgc ttaacacatg caagtcgagc      60
ggagatgttc ggagtgcttg cacactgaac atttcagcgg cggacgggtg agtaacgcgt    120
gaacaatctg tcccatacag ggggataaca gatggaaaca tctgctaata ccgcataaga    180
ccacgacatc acatgatgat ggggtaaaag gagcaatccg gtatg                    225
```

<210> SEQ ID NO 348
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 348

```
agagtttgat catggctcag gacgaacgct ggcggcgtgc ctaatacatg caagtcgaac      60
gaactctggt attgattggt gcttgcatca tgatttacat ttgagtgagt ggcgaactgg     120
tgagtaacac gtgggaaacc tgcccagaag cgggggataa cacctggaaa cagatgctaa    180
taccgcataa caacttggac cgcatggtcc gagtttgaaa gatgg                     225
```

<210> SEQ ID NO 349
<211> LENGTH: 225
<212> TYPE: DNA
<213> ORGANISM: Unknown
<220> FEATURE:
<223> OTHER INFORMATION: Encodes 16S rRNA from Streptococcus

<400> SEQUENCE: 349

```
agagtttgat cctggctcag gacgaacgct ggcggcgtgc ctaatacatg caagtagaac      60
gctgaagaaa ggagcttgct tcttttggat gagttgcgaa cgggtgagta acgcgtaggt    120
aacctgcctt gtagcggggg ataactattg gaaacgatag ctaataccgc ataacagctt    180
ttgacacatg ttagaagctt gaaagatgca attgcatcac tacga                     225
```

<210> SEQ ID NO 350
<211> LENGTH: 225
<212> TYPE: DNA
<213> ORGANISM: Unknown
<220> FEATURE:
<223> OTHER INFORMATION: Encodes 16S rRNA from Lachnospiraceae
      (Clostridium Cluster XlVa)

<400> SEQUENCE: 350

```
agagtttgat catggctcag gatgaacgct ggcggcgtgc ttaacacatg caagtcgaac      60
gaagcggctg gacggaagtt ttcggatgga agaccggctg actgagtggc ggacgggtga    120
gtaacgcgtg ggtaacctgc cgtatacagg gggataacag agagaaattt ctgctaatac    180
cgcataagcg cacgaagacc gcatggtccg gtgtgaaaag ccgag                     225
```

<210> SEQ ID NO 351
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 351

```
agagtttgat cctggctcag gacgaacgct ggcggcgtgc ctaatacatg caagtcgagc      60
gagcagaacc agcagattta cttcggtaat gacgctgggg acgcgagcgg cggatgggtg    120
agtaacacgt ggggaacctg ccccatagtc tgggatacca cttggaaaca ggtgctaata    180
ccggataaga aagcagatcg catgatcagc ttataaaagg cggcg                     225
```

<210> SEQ ID NO 352
<211> LENGTH: 225
<212> TYPE: DNA
<213> ORGANISM: Unknown
<220> FEATURE:
<223> OTHER INFORMATION: Encodes 16S rRNA from Paracoccus

<400> SEQUENCE: 352

```
agagtttgat cctggctcag aacgaacgct ggcggcaggc ctaacacatg caagtcgagc      60 ggaccccttcg gggttagcgg cggacgggtg agtaacgcgt gggaatatgc ccttctctac    120
ggaatagtct cgggaaactg ggggtaatac cgtatacgcc ctttggggga aagatttatc    180
```
ggagaaggat tagcccgcgt tggattaggt agttggtggg gtaat      225

<210> SEQ ID NO 353
<211> LENGTH: 225
<212> TYPE: DNA
<213> ORGANISM: Unknown
<220> FEATURE:
<223> OTHER INFORMATION: Encodes 16S rRNA from Cellulosilyticum

<400> SEQUENCE: 353
agagtttgat catggctcag gacgaacgct ggcggcgcgc ctaacacatg caagtcgaac      60
gaagctatgt tgaaagcttg ctggatatat agcttagtgg cggacgggtg agtaacacgt     120
gagtaacctg cctctcagag tggaataacg tttggaaacg gacgctaata ccgcataacg     180
tgagaagagg gcatcctctt tttaccaaag atttatcgct gagag                    225

<210> SEQ ID NO 354
<211> LENGTH: 225
<212> TYPE: DNA
<213> ORGANISM: Unknown
<220> FEATURE:
<223> OTHER INFORMATION: Encodes 16S rRNA from Blautia

<400> SEQUENCE: 354
agagtttgat catggctcag gatgaacgct ggcggcgtgc ttaacacatg caagtcgaac      60
ggggaatatt ctgacagaga cttcggttga agtcgttata ttcctagtgg cggacgggtg     120
agtaacgcgt gggtaacctg ccccacacag ggggataaca accagaaatg gctgctaata     180
ccgcataagc gcacgggacc gcatggtttt gtgtgaaaaa ctccg                    225

<210> SEQ ID NO 355
<211> LENGTH: 225
<212> TYPE: DNA
<213> ORGANISM: Unknown
<220> FEATURE:
<223> OTHER INFORMATION: Encodes 16S rRNA from Corynebacterium

<400> SEQUENCE: 355
agagtttgat cctggctcag gacgaacgct ggcggcgtgc ttaacacatg caagtcgaac      60
ggaaaggccc ctagcttgct gggggtactc gagtggcgaa cgggtgagta acacgtgggt     120
gatctgccct gcacttcggg ataagcttgg gaaactgggt ctaataccgg atatgaacgg     180
tctttggtgt gattgttgga aagattttttt cggtgtggga tgagc                   225

<210> SEQ ID NO 356
<211> LENGTH: 225
<212> TYPE: DNA
<213> ORGANISM: Unknown
<220> FEATURE:
<223> OTHER INFORMATION: Encodes 16S rRNA from Lachnospiracea incertae
    sedis

<400> SEQUENCE: 356
agagtttgat catggctcag gatgaacgct ggcggcgtgc ttaacacatg caagtcgaac      60
ggacaaagaa gatttcggtt ttctttgtta gtggcggacg ggtgagtaac gcgtgggcaa     120 cctacccttat acaggggat aacagttaga aatgactgat aataccgcat aagcgcccga     180
ggtcgcatga ccttgagtga aaaactccgg tggtataaga tgggc                    225

<210> SEQ ID NO 357
<211> LENGTH: 225
<212> TYPE: DNA

```
<213> ORGANISM: Unknown
<220> FEATURE:
<223> OTHER INFORMATION: Encodes 16S rRNA from Corynebacterium

<400> SEQUENCE: 357
agagtttgat cctggctcag dacgaacgct ggcggcgtgc ttaacacatg caagtcgaac    60
gatgaagctt agcttgctag gtggattagt ggcgaacggg tgagtaacac gtaggtaatc   120
tgccctgcac tttgggataa gcctgggaaa ctgggtctaa taccgaatag dacacactat   180
ctttacggtg gtgtgtggaa agcttttgcg gtgtgggatg agcct                   225

<210> SEQ ID NO 358
<211> LENGTH: 225
<212> TYPE: DNA
<213> ORGANISM: Unknown
<220> FEATURE:
<223> OTHER INFORMATION: Encodes 16S rRNA from Corynebacterium

<400> SEQUENCE: 358
agagtttgat cctggctcag gatgaacgct ggcggcgtgc ttaacacatg caagtcgaac    60
ggaaaggcct tgtgcttgca caaggtactc gagtggcgaa cgggtgagta acacgtgggt   120
gatctgccct gcactgtggg ataagcctgg gaaactgggt ctaataccat ataggaccgc   180
actttggatg gtgtggtgga aagcttttgc ggtgtgggat gagcc                   225

<210> SEQ ID NO 359
<211> LENGTH: 225
<212> TYPE: DNA
<213> ORGANISM: Unknown
<220> FEATURE:
<223> OTHER INFORMATION: Encodes 16S rRNA from Ruminococcus

<400> SEQUENCE: 359
agagtttgat catggctcag gatgaacgct ggcggcgtgc ttaacacatg caagtcgaac    60
gaagcataca gacggaagtt ttcggacaga agactgtatg actgagtggc ggacgggtga   120
gtaacgcgtg ggtaacctgc cgtatacagg gggataacag ttagaaatgg ctgctaatac   180
cgcataagcg cacagaaccg catggttcgg tgtgaaaagc cgaga                   225

<210> SEQ ID NO 360
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 360
agagtttgat catggctcag dacgaacgct ggcggcgtgc ctaatacatg caagtcgagc    60
gagcggaacc gacagattca cttcggtgat gacgacggga aagcgagcgg cggatgggtg   120
agtaacacgt gggtaaccta cccttaagtc tgggatacca cttggaaaca ggtgctaata   180
ccggatagga attagagctg catggcttta atttaaaagg cggcg                   225

<210> SEQ ID NO 361
<211> LENGTH: 225
<212> TYPE: DNA
<213> ORGANISM: Unknown
<220> FEATURE:
<223> OTHER INFORMATION: Encodes 16S rRNA from Roseburia

<400> SEQUENCE: 361
agagtttgat catggctcag gatgaacgct ggcggcgtgc ttaacacatg caagtcgaac    60
```

```
gaagcacttc cgcatgagac ttcggtggaa tgagggagtg actgagtggc ggacgggtga    120
gtaacgcgtg ggcaacctgc cttacacagg gggataacag ttagaaatga ctgctaatac    180
cgcataagcg cacagtaccg catggtacag tgtgaaaaac tccgg                    225
```

<210> SEQ ID NO 362
<211> LENGTH: 225
<212> TYPE: DNA
<213> ORGANISM: Unknown
<220> FEATURE:
<223> OTHER INFORMATION: Encodes 16S rRNA from Lachnospiracea
      (Clostridium Cluster XlVa)

<400> SEQUENCE: 362

```
agagtttgat catggctcag gatgaacgct ggcggcgtgc ttaacacatg caagtcgaac    60
gaagcgcatg gacagattcc ttcgggttga agaccatgtg acttagtggc ggacgggtga    120
gtaacgcgtg ggtaatctgc cctgcacagg gggataacag ttggaaacga ctgctaatac    180
cgcataagcc aacagggccg catggcctgg ttggaaaaga tttat                   225
```

<210> SEQ ID NO 363
<211> LENGTH: 224
<212> TYPE: DNA
<213> ORGANISM: Unknown
<220> FEATURE:
<223> OTHER INFORMATION: Encodes 16S rRNA from Lachnospiracea
      (Clostridium Cluster XlVb)

<400> SEQUENCE: 363

```
agagtttgat cctggctcag gatgaacgct ggcggcgtgc ttaacacatg caagtcgaac    60
gaagaaggtt agaatgagag cttcggcagg atttctatct atcttagtgg cggacgggtg    120
agtaacgtgt gggcaacctg ccctgtactg gggaataatc attggaaacg atgactaata    180
ccgcatgtgg tcctcggaag gcatcttctg aggaagaaag gatt                    224
```

<210> SEQ ID NO 364
<211> LENGTH: 224
<212> TYPE: DNA
<213> ORGANISM: Unknown
<220> FEATURE:
<223> OTHER INFORMATION: Encodes 16S rRNA from Clostridium sensu stricto

<400> SEQUENCE: 364

```
agagtttgat cctggctcag gacgaacgct ggcggcgtgc ctaacacatg caagtcgagc    60
gagaagagct ccttcgggag taattctagc ggcggacggg tgagtaacac gtgggcaacc    120
cgccttagtg aggggatag cctcccgaaa gggagattaa taccgcataa cattattta    180 tcgcatgata gaataatcaa aggagcaatc cgcactaaga tggg                    224
```

<210> SEQ ID NO 365
<211> LENGTH: 225
<212> TYPE: DNA
<213> ORGANISM: Unknown
<220> FEATURE:
<223> OTHER INFORMATION: Encodes 16S rRNA from Bacteroides

<400> SEQUENCE: 365

```
agagtttgat cctggctcag gatgaacgct agctacaggc ttaacacatg caagtcgagg    60
ggcagcatgg tcttagcttg ctaaggctga tggcgaccgg cgcacgggtg agtaacacgt    120
atccaacctg ccgtctactc ttggccagcc ttctgaaagg aagattaatc caggatggga    180
```

```
tcatgagttc acatgtccgc atgattaaag gtattttccg gtaga            225

<210> SEQ ID NO 366
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 366
agagtttgat cctggctcag gatgaacgcc ggcggtgtgc ctaatacatg caagtcgtac   60
gcactggccc aactgattga tggtgcttgc accggattga cgatggatca ccagtgagtg  120
gcggacgggt gagtaacacg taggtaacct gccccggagc gggggataac atttggaaac  180
agatgctaat accgcataac aacactagac gcatgtctag agttt             225

<210> SEQ ID NO 367
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 367
agagtttgat cctggctcag gatgaacgcc ggcggtgtgc ctaatacatg caagtcgagc   60
gcactggccc aactgatatt acgtgcttgc actgaattga cgttggatta ccagtgagcg  120
gcggacgggt gagtaacacg tgggcaacct gccctggagc gggggataac atctggaaac  180
aggtgctaat accgcataac aacaaaagcc acatgacttt tgttt             225

<210> SEQ ID NO 368
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 368
agagtttgat cctggctcag gatgaacgct ggcggcgtgc ctaatacatg caagtcgagc   60
gcatcggccc aactgattga agatgcttgc atccgattga cgatggttta ccgatgagcg  120
gcggacgggt gagtaacacg taggtaacct gcccagaagc gggggataac acctggaaac  180
agatgctaat accgcatagg tcatttgacc gcatggtcaa atgat             225

<210> SEQ ID NO 369
<211> LENGTH: 224
<212> TYPE: DNA
<213> ORGANISM: Unknown
<220> FEATURE:
<223> OTHER INFORMATION: Encodes 16S rRNA from Lactobacillus
      (Ascusbbr_5796(B))

<400> SEQUENCE: 369
agagtttgat catggctcag gacgaacgct ggcggcgtgc ctaatacatg caagtcgagc   60
gagcggaact aacagattta cttcggtaat gacgttagga aagcgagcgg cggatgggtg  120
agtaacacgt ggggaacctg ccccatagtc tgggatacca cttggaaaca ggtgctaata  180
ccggataaga aagcagatcg catgatcagc ttttaaaagg cggc              224

<210> SEQ ID NO 370
<211> LENGTH: 225
<212> TYPE: DNA
```

```
<213> ORGANISM: Unknown
<220> FEATURE:
<223> OTHER INFORMATION: Encodes 16S rRNA from Lactobacillus
      (Asbusbbr_5796(C))

<400> SEQUENCE: 370
agagtttgat cctggctcag gacgaacgct ggcggcgtgc ctaatacatg caagtcgagc    60
gagcggaact aacagattta cttcggtaat gacgttagga aagcgagcgg cggatgggtg   120
agtaacacgt ggggaacctg ccccatagtc tgggatacca cttggaaaca ggtgctaata   180
ccggataaga aagcagatcg catgatcagc ttttaaaagg cggcg                   225

<210> SEQ ID NO 371
<211> LENGTH: 225
<212> TYPE: DNA
<213> ORGANISM: Unknown
<220> FEATURE:
<223> OTHER INFORMATION: Encodes 16S rRNA from Lactobacillus
      Ascusbbr_14690(B)

<400> SEQUENCE: 371
agagtttgat cctggctcag gacgaacgct ggcggcgtgc ctaatacatg caagtcgaac    60
gagaatttct tacaccgagt gcttgcactc accgtaagaa attcgagtgg cggacgggtg   120
agtaacacgt gggtaacctg cccaaaagaa ggggataaca tttggaaaca aatgctaata   180
ccgtataacc atgatgaccg catggtcatt atgtaaaagg tggtt                   225

<210> SEQ ID NO 372
<211> LENGTH: 225
<212> TYPE: DNA
<213> ORGANISM: Unknown
<220> FEATURE:
<223> OTHER INFORMATION: Encodes 16S rRNA from Lactobacillus
      Ascusbbr_14690(C)

<400> SEQUENCE: 372
agagtttgat catggctcag gacgaacgct ggcggcgtgc ctaatacatg caagtcgaac    60
gagaatttct tacaccgagt gcttgcactc accgtaagaa attcgagtgg cggacgggtg   120
agtaacacgt gggtaacctg cccaaaagaa ggggataaca tttggaaaca aatgctaata   180
ccgtataacc atgatgaccg catggtcata atgtaaatgg tggtg                   225

<210> SEQ ID NO 373
<211> LENGTH: 225
<212> TYPE: DNA
<213> ORGANISM: Unknown
<220> FEATURE:
<223> OTHER INFORMATION: Encodes 16S rRNA from Lactobacillus
      Ascusbbr_38717(B)

<400> SEQUENCE: 373
agagtttgat cctggctcag gatgaacgcc ggcggtgtgc ctaatacatg caagtcgagc    60
gcactggccc aactgatatg acgtgcttgc actgaattga cgttggatta ccagtgagcg   120
gcggacgggt gagtaacacg tgggcaacct gccctggagc gggggataac atctggaaac   180
aggtgctaat accgcataac aacgaaaacc acatggtttt cgttt                   225

<210> SEQ ID NO 374
<211> LENGTH: 225
<212> TYPE: DNA
<213> ORGANISM: Unknown
<220> FEATURE:
<223> OTHER INFORMATION: Encodes 16S rRNA from Bacillus Ascusbbr_33(B)
```

<400> SEQUENCE: 374

```
agagtttgat cctggctcag gacgaacgct ggcggcgtgc ctaatacatg caagtcgagc    60
ggacagatgg gagcttgctc cctgatgtta gcggcggacg ggtgagtaac acgtgggtaa   120
cctgcctgta agactgggat aactccggga accgggggct aataccggat ggttgtctga   180
accgcatggt tcagacataa aaggtggctt cggctaccac ttaca                   225
```

<210> SEQ ID NO 375
<211> LENGTH: 224
<212> TYPE: DNA
<213> ORGANISM: Unknown
<220> FEATURE:
<223> OTHER INFORMATION: Encodes 16S rRNA from Lactobacillus
      Ascusbbr_409(B)

<400> SEQUENCE: 375

```
agagtttgat cctggctcag gatgaacgcc ggcggtgtgc ctaatacatg caagtcgtac    60
gcactggccc aactgattga tggtgcttgc accggattga cgatggatca ccagtgagtg   120
gcggacgggt gagtaacacg taggtaacct gccccggagc ggggataac atttggaaac    180
agatgctaat accgcataac aacaaaagtc gcatggcttt tgtt                    224
```

<210> SEQ ID NO 376
<211> LENGTH: 225
<212> TYPE: DNA
<213> ORGANISM: Unknown
<220> FEATURE:
<223> OTHER INFORMATION: Encodes 16S rRNA from Lactobacillus
      Ascusbbr_409(C)

<400> SEQUENCE: 376

```
agagtttgat cctggctcag gatgaacgcc ggcggtgtgc ctaatacatg caagtcgtac    60
gcactggccc aactgattga tggtgcttgc acctgattga cgatggatta ccagtgagtg   120
gcggacgggt gagtaacacg taggtaacct gccccggagc ggggataac atttggaaac    180
agatgctaat accgcataac aacaaaagcc acatggcttt tgttt                   225
```

<210> SEQ ID NO 377
<211> LENGTH: 225
<212> TYPE: DNA
<213> ORGANISM: Unknown
<220> FEATURE:
<223> OTHER INFORMATION: Encodes 16S rRNA from Lactobacillus
      Ascusbbr_409(D)

<400> SEQUENCE: 377

```
agatttgatc atggctcagg atgaacgccg gcggtgtgcc taatacatgc aagtcgtacg    60
cactggccca actgattgat ggtgcttgca cttgattgac gttggatcac cagtgagtgg   120
cggacgggtg agtaacacgt aggtaacctg ccccggagcg gggataaca tttggaaaca   180
gatgctaata ccgcataaca acaaaagcca catggctttt gtttg                   225
```

<210> SEQ ID NO 378
<211> LENGTH: 225
<212> TYPE: DNA
<213> ORGANISM: Unknown
<220> FEATURE:
<223> OTHER INFORMATION: Encodes 16S rRNA from Lactobacillus
      Ascusbbr_331885(B)

<400> SEQUENCE: 378

```
agatttgatc ctggctcagg atgaacgccg cggtgtgcc taatacatgc aagtcgtacg    60
cactggccca actgattgat ggtgcttgca ccggattgac gatggatcac cagtgagtgg   120
cggacgggtg agtaacacgt aggtaacctg ccccggagcg ggggataaca tttggaaata   180
gatgctaata ccgcataata acaaaagcca catggctttt gtttg                   225
```

```
<210> SEQ ID NO 379
<211> LENGTH: 225
<212> TYPE: DNA
<213> ORGANISM: Unknown
<220> FEATURE:
<223> OTHER INFORMATION: Encodes 16S rRNA from Lactobacillus
      Ascusbbr_331885(C)

<400> SEQUENCE: 379
```

```
agagtttgat catggctcag gatgaacgcc ggcggtgtgt ctaatacatg caagtcgtac    60
gcactggccc aactgattga tggtgcttgc accggattga cgatggatca ccagtgagtg   120
gcggacgggt gagtaacacg taggtaacct gccccgcggc ggggataac atttggaaac    180 agatgctaat accgcatgac aacaaaagtc gcatggcttt tgttt                   225
```

```
<210> SEQ ID NO 380
<211> LENGTH: 225
<212> TYPE: DNA
<213> ORGANISM: Unknown
<220> FEATURE:
<223> OTHER INFORMATION: Encodes 16S rRNA from Clostridium
      Ascusbbr_247(B)

<400> SEQUENCE: 380
```

```
agagtttgat cctggctcag gatgaacgct ggcggcgtgc ctaacacatg caagtcgaac    60
gaagcgattt gaaagaagtt ttcggatgga atccaaattg actgagtggc ggacgggtga   120
gtaacgcgtg gtaacctgc ctcacactgg gggacaacag ctggaaacgg ctgctaatac    180
cgcataagcg cacagcttcg catgaagcag tgtgaaaaac tccgg                   225
```

```
<210> SEQ ID NO 381
<211> LENGTH: 225
<212> TYPE: DNA
<213> ORGANISM: Unknown
<220> FEATURE:
<223> OTHER INFORMATION: Encodes 16S rRNA from Chlostridium
      Ascusbbr_10593(B)

<400> SEQUENCE: 381
```

```
agagtttgat catggctcag gatgaacgct ggcggcgtgc ctaacacatg caagtcgagc    60
gaagcgattc ggatgaagtt ttcggatgga ttttggattg actgagcggc ggacgggtga   120
gtaacgcgtg gtaacctgc ctcatacagg gggataacag ttagaaatga ctgctaatac    180
cgcataagcg cacagtaccg catggtacgg tgtgaaaaac tccgg                   225
```

```
<210> SEQ ID NO 382
<211> LENGTH: 225
<212> TYPE: DNA
<213> ORGANISM: Unknown
<220> FEATURE:
<223> OTHER INFORMATION: Encodes 16S rRNA from Chlostridium
      Ascusbbr_32731(B)

<400> SEQUENCE: 382
```

```
agagtttgat cctggctcag gatgaacgct ggcggcgtgc ttaacacatg caagtcgagc    60
gaagcactta cttttggattt cttcggaatg acgaggtatt tgactgagcg gcggacgggt  120
```

```
gagtaacgcg tgggcaacct gcctcacaca gggggataac agttagaaat gactgctaat    180
accgcataag accacggcac cgcatggtgc aggggtaaaa actcc                    225
```

<210> SEQ ID NO 383
<211> LENGTH: 225
<212> TYPE: DNA
<213> ORGANISM: Unknown
<220> FEATURE:
<223> OTHER INFORMATION: Encodes 16S rRNA from Lactobacillus

<400> SEQUENCE: 383

```
agagtttgat cctggctcag gacgaacgct ggcggcgtgc ctaatacatg caagtcgaac    60
gaaactttct tacaccgaat gcttgcattc accgtaagaa gttgagtggc ggacgggtga    120
gtaacacgtg gtaacctgc ctaaaagaag gggataacac ttggaaacag gtgctaatac    180
cgtatatctc taaggatcgc atgatcctta gatgaaagat ggttc                    225
```

<210> SEQ ID NO 384
<211> LENGTH: 225
<212> TYPE: DNA
<213> ORGANISM: Unknown
<220> FEATURE:
<223> OTHER INFORMATION: Encodes 16S rRNA from Lactobacillus
      Ascusbbr_42760(B)

<400> SEQUENCE: 384

```
agagttgatc tggctcagga tgaacgccgg cggtgtgcct aatacatgca agtcgagcgc    60
actggcccaa cagaaatgac gtgcttgcac tgatttgaag ttggattccc agtgagcggc    120
ggacgggtga gtaacacgtg gcaacctgc cccaaagcgg gggataacat ttggaaacag    180
gtgctaatac cgcataactt ggaaaaccac atggttttcc aataa                    225
```

<210> SEQ ID NO 385
<211> LENGTH: 225
<212> TYPE: DNA
<213> ORGANISM: Unknown
<220> FEATURE:
<223> OTHER INFORMATION: Encodes 16S rRNA from Lactobacillus
      Ascusbbr_26500(B)

<400> SEQUENCE: 385

```
agagtttgat catggctcag gacgaacgct ggcggcgtgc ctaatacatg caagtcgagc    60
gagcagaacc agcagattta cttcggtaat gacgctgggg acgcgagcgg cggatgggtg    120
agtaacacgt ggggaacctg ccccatagtc tgggatacca cttggaaaca ggtgctaata    180
ccggataaga aagcagatcg catgatcagc ttataaaagg cggcg                    225
```

<210> SEQ ID NO 386
<211> LENGTH: 224
<212> TYPE: DNA
<213> ORGANISM: Unknown
<220> FEATURE:
<223> OTHER INFORMATION: Encodes 16S rRNA from Clostridium

<400> SEQUENCE: 386

```
agagtttgat catggctcag gacgaacgct ggcggcgtgc ttaacacatg caagtcgagc    60
gatgaagttc cttcgggaac ggattagcgg cggacgggtg agtaacacgt gggtaacctg    120
cctcatagag gggaatagcc ttccgaaagg aagattaata ccgcataaga ttgtagtttc    180
gcatgaaaca gcaattaaag gagtaatccg ctatgagatg gacc                     224
```

```
<210> SEQ ID NO 387
<211> LENGTH: 224
<212> TYPE: DNA
<213> ORGANISM: Unknown
<220> FEATURE:
<223> OTHER INFORMATION: Encodes 16S rRNA from Clostridium

<400> SEQUENCE: 387
agagtttgat cctggctcag gatgaacgct ggcggcgtgc ttaacacatg caagtcgagc        60
gaagcagttt taaggaagtt ttcggatgga attaaaattg acttagcggc ggacgggtga       120
gtaacgcgtg ggtaacctgc ctcatacagg gggataacag ttagaaatga ctgctaatac       180
cgcataagcg cacagtgctg catagcacag tgtgaaaaac tccg                        224
```

MICROBIAL COMPOSITIONS AND METHODS OF USE FOR IMPROVING FOWL PRODUCTION

CROSS-REFERENCE TO RELATED APPLICATIONS

This application is a U.S. Utility Application under 35 U.S.C. § 111 that claims priority pursuant to 35 U.S.C. § 120: (1) as a Continuation-In-Part Application, to International Application No. PCT/US2017/028015, filed on Apr. 17, 2017, which itself claims the benefit of priority to U.S. Provisional Application No. 62/323,305, filed on Apr. 15, 2016; U.S. Provisional Application No. 62/335,559, filed on May 12, 2016; and U.S. Provisional Application No. 62/425,480, filed on Nov. 22, 2016; (II) this application also claims the benefit of U.S. Provisional Application No. 62/574,031, filed on Oct. 18, 2017; the entirety of each and every one of the aforementioned applications is herein expressly incorporated by reference in their entirety.

FIELD

The present disclosure relates to isolated and biologically pure microorganisms that have applications, inter alia, in the farming of fowl. The disclosed microorganisms can be utilized in their isolated and biologically pure states, as well as being formulated into compositions. Furthermore, the disclosure provides microbial ensembles, containing at least two members of the disclosed microorganisms, as well as methods of utilizing said ensembles. Furthermore, the disclosure provides for methods of modulating the fowl microbiome.

STATEMENT REGARDING SEQUENCE LISTING

The sequence listing associated with this application is provided in text format in lieu of a paper copy, and is hereby incorporated by reference into the specification. The name of the text file containing the sequence listing is ASBI_003_03US_ST25.txt. The text file is ~166 kb, was created on Jul. 20, 2018, and is being submitted electronically via EFS-Web.

BACKGROUND

The global population is predicted to increase to over 9 billion people by the year 2050 with a concurrent reduction in the quantity of land, water, and other natural resources available per capita. Projections indicate that the average domestic income will also increase, with the projected rise in the GDP of China and India. The desire for a diet richer in animal-source proteins rises in tandem with increasing income, thus the global livestock sector will be charged with the challenge of producing more animal products using fewer resources. The Food and Agriculture Organization of the United Nations predict that 70% more food will have to be produced, yet the area of arable land available will decrease. It is clear that the food output per unit of resource input will have to increase considerably in order to support the rise in population.

Over recent decades the farm industry has seen fast growth in the meat sector, which has been underpinned by rising demand for poultry meat, which has consistently increased at about three times the rate of population growth over each of the past five decades.

Poultry meat, eggs, and components thereof are predominantly utilized in the preparation of foodstuffs in many different forms. There have been many strategies to improve poultry and egg production through nutritional modulations, hormone treatments, changes in animal management, and selective breeding; however, the need for more efficient production of edible poultry foodstuffs per animal is required.

Identifying compositions and methods for sustainably increasing poultry and egg production while balancing animal health and wellbeing have become imperative to satisfy the needs of everyday humans in an expanding population. Increasing the worldwide production of poultry by scaling up the total number of fowl on farms would not only be economically infeasible for many parts of the world, but would further result in negative environmental consequences as the poultry sector's growth and trends towards intensification and concentration have already given rise to a number of environmental concerns, led predominantly by the production of far more waste than can be managed by land disposal.

Population densities of poultry in large farms are often accompanied by an increased incidence of microbial pathogens that place the poultry yield at risk, and further place the ultimate consumer of the poultry at risk in instances of zoonotic pathogens such as those of *Clostridium* and *Salmonella*. Considering the widespread occurrence of many zoonotic pathogens, it is unlikely that poultry can be completely protected from exposure. Research has focused on investigative means of increasing resistance to colonization in poultry exposed to these pathogens.

Thus, meeting global poultry yield expectations, by simply scaling up current high-input agricultural systems—utilized in most of the developed world—is simply not feasible.

There is therefore an urgent need in the art for improved methods of increasing poultry and egg production, while also mitigating the colonization and spread of microbial pathogens.

SUMMARY OF THE DISCLOSURE

In some embodiments, the at least two microbial strains or the at least one microbial strain present in a composition, or microbial ensemble, of the disclosure exhibit an increased utility that is not exhibited when said strains occur alone or when said strains are present at a naturally occurring concentration. In some embodiments, compositions of the disclosure, comprising at least two microbial strains as taught herein, exhibit a synergistic effect on imparting at least one improved trait in an animal. In some embodiments, the compositions of the disclosure—comprising one or more isolated microbes as taught herein—exhibit markedly different characteristics/properties compared to their closest naturally occurring counterpart. That is, the compositions of the disclosure exhibit markedly different functional and/or structural characteristics/properties, as compared to their closest naturally occurring counterpart. For instance, the microbes of the disclosure are structurally different from a microbe as it naturally exists in a fowl gastrointestinal tract, for at least the following reasons: said microbe can be isolated and purified, such that it is not found in the milieu of the gastrointestinal tract, said microbe can be present at concentrations that do not occur in the gastrointestinal tract, said microbe can be associated with acceptable carriers that do not occur in the gastrointestinal tract, said microbe can be formulated to be shelf-stable and exist outside the gastrointestinal tract, and said microbe can be combined with other microbes at concentrations that do not exist in the gastrointestinal tract. Further, the microbes of the disclosure are functionally different from a microbe as it naturally exists in a gastrointestinal tract, for at least the following reasons: said microbe when applied in an isolated and purified form can lead to modulation of the gastrointestinal microbiome, increased weight gain, increased feed utilization, decreased amounts of microbial pathogens, decreased pathogen-associated GI lesions, said microbe can be formulated to be shelf-stable and able to exist outside the gastrointestinal environment, such that the microbe now has a new utility as a supplement capable of administration to a fowl, wherein the microbe could not have such a utility in it's natural state in the gastrointestinal tract, as the microbe would be unable to survive outide the gastrointestinal tract without the intervention of the hand of man to formulate the microbe into a shelf-stable state and impart this new utility that has the aforementioned functional characteristics not possessed by the microbe in it's natural state of existence in the fowl gastrointestinal tract.

In some aspects, the present disclosure is drawn to a method of decreasing feed conversion ratio, increasing fowl weight, and/or decreasing pathogen-associated lesion formation in the gastrointestinal tract of fowl, the method comprising: a) administering to a fowl an effective amount of a shelf-stable fowl supplement comprising: i) a purified microbial population of *Lactobacillus* bacteria comprising bacteria with a 16S nucleic acid sequence that is at least about 97% identical to SEQ ID NO:1, and said bacterium has a MIC score of at least about 0.1; and ii) a shelf-stable carrier suitable for fowl administration, wherein the fowl administered the effective amount of the shelf-stable fowl supplement exhibits an decrease in feed conversion ratio, an increase in weight, or a decrease in pathogen-associated lesion formation in the gastrointestinal tract, as compared to a fowl not having been administered the supplement.

In some aspects, the present disclosure is drawn to a method of decreasing feed conversion ratio, increasing fowl weight, or decreasing pathogen-associated lesion formation in the gastrointestinal tract of fowl, the method comprising: a) administering to a fowl an effective amount of a shelf-stable fowl supplement comprising: i) a purified microbial population that comprises a bacterium with a 16S nucleic acid sequence, and/or a fungus with an ITS nucleic acid sequence, which is at least about 97% identical to a nucleic acid sequence selected from the group consisting of SEQ ID NOs:1-387, and said bacterium and/or fungus have a MIC score of at least about 0.2; and ii) a shelf-stable carrier suitable for fowl administration; wherein the fowl administered the effective amount of the shelf-stable fowl supplement exhibits a decrease in feed conversion ratio, an increase in weight, and/or a decrease in pathogen-associated lesion formation in the gastrointestinal tract, as compared to a fowl not having been administered the supplement.

In some aspects, the present disclosure is drawn to a method of treating poultry for necrotic enteritis, the method comprising: a) administering to a bird an effective amount of a shelf-stable poultry supplement comprising: i) a purified microbial population that comprises a bacterium with a 16S nucleic acid sequence, and/or a fungus with an ITS nucleic acid sequence, which is at least about 97% identical to a nucleic acid sequence selected from the group consisting of SEQ ID NOs:1-387, and said bacterium and/or fungus have a MIC score of at least about 0.2; and ii) a shelf-stable carrier suitable for poultry administration, wherein the bird administered the effective amount of the shelf-stable poultry supplement exhibits a decrease in the number of necrotic enteritis-causing bacteria in the gastrointestinal tract, as compared to a bird not having been administered the supplement.

In some aspects, the present disclosure is drawn to a method of treating poultry for necrotic enteritis, the method comprising: administering to a bird an effective amount of a shelf-stable poultry supplement comprising: i) a purified microbial population of *Lactobacillus* bacteria comprising bacteria with a 16S nucleic acid sequence that is at least about 97% identical to SEQ ID NO:1, and said bacterium has a MIC score of at least about 0.2; and ii) a shelf-stable carrier suitable for poultry administration, wherein the poultry administered the effective amount of the shelf-stable poultry supplement exhibits a decrease in the number of necrotic enteritis-causing bacteria in the gastrointestinal tract, as compared to a bird not having been administered the supplement.

In some aspects, the present disclosure is drawn to a method of decreasing feed conversion ratio, increasing fowl weight, and/or decreasing pathogen-associated lesion formation in the gastrointestinal tract of fowl, the method comprising: a) administering to a fowl an effective amount of a shelf-stable fowl supplement comprising: i) a purified microbial population of *Lactobacillus* bacteria comprising bacteria with a 16S nucleic acid sequence that is at least about 97% identical to SEQ ID NO:374, and said bacterium has a MIC score of at least about 0.2; and ii) a shelf-stable carrier suitable for fowl administration, wherein the fowl administered the effective amount of the shelf-stable fowl supplement exhibits an decrease in feed conversion ratio, an increase in weight, or a decrease in pathogen-associated lesion formation in the gastrointestinal tract, as compared to a fowl not having been administered the supplement.

In some aspects, the present disclosure is drawn to a method of decreasing feed conversion ratio, increasing fowl weight, and/or decreasing pathogen-associated lesion formation in the gastrointestinal tract of fowl, the method comprising: a) administering to a fowl an effective amount of a shelf-stable fowl supplement comprising: i) a purified microbial population of *Lactobacillus* bacteria comprising bacteria with a 16S nucleic acid sequence that is at least about 97% identical to SEQ ID NO:382, and said bacterium has a MIC score of at least about 0.2; and ii) a shelf-stable carrier suitable for fowl administration, wherein the fowl administered the effective amount of the shelf-stable fowl supplement exhibits an decrease in feed conversion ratio, an increase in weight, or a decrease in pathogen-associated lesion formation in the gastrointestinal tract, as compared to a fowl not having been administered the supplement.

In aspects, the aforementioned microbial species—that is, a purified microbial population that comprises a bacteria with a 16S nucleic acid sequence, and/or a fungi with an ITS nucleic acid sequence, which is at least about 97% identical to a nucleic acid sequence selected from the group consisting of: SEQ ID NOs: 1-387—are members of a Markush group, as the present disclosure illustrates that the members belong to a class of microbes characterized by various physical and functional attributes, which can include any of the following: a) the ability to convert a carbon source into a volatile fatty acid such as acetate, butyrate, propionate, or combinations thereof; b) the ability to degrade a soluble or insoluble carbon source; c) the ability to impart an increase in weight gain to fowl administered the microbe(s); d) the ability to modulate the microbiome of the gastrointestinal tract of fowl administered the microbe; e) the ability to be formulated into a shelf-stable composition; f) the ability to exhibit a decrease in feed conversion ratio in fowl having been administered the microbe(s); g) the ability to impart a decrease in pathogen-associated lesion formation in the gastrointestinal tract; h) the ability to impart a decrease in pathogenic microbes in the gastrointestinal tract; and/or i) possessing a MIC score of at least about 0.2 if a bacteria and possessing a MIC score of at least about 0.2 if a fungi. Thus, the members of the Markush group possess at least one property in common, which can be responsible for their function in the claimed relationship.

In some aspects, the fowl is a broiler. In some aspects, the fowl supplement is stable under ambient conditions for at least one week. In some aspects, the fowl supplement is formulated as an: encapsulation, tablet, capsule, pill, feed additive, food ingredient, food additive, food preparation, food supplement, water additive, water-mixed additive, heat-stabilized additive, moisterure-stabilized additive, consumable solution, consumable spray additive, consumable solid, consumable gel, injection, suppository, drench, or combinations thereof.

In some aspects, administration comprises feeding the fowl supplement to a fowl or spraying the fowl supplement onto a fowl. In some aspects, the purified microbial population is present in the fowl supplement at a concentration of at least $10^2$ cells. In some aspects, the purified microbial population comprises a bacterium with a 16S nucleic acid sequence that is at least about 97% identical to a nucleic acid sequence selected from the group consisting of: SEQ ID NOs:1-50 and 59-387. In some aspects, the purified microbial population comprises a fungus with an ITS nucleic acid sequence that is at least about 97% identical to a nucleic acid sequence selected from the group consisting of: SEQ ID NOs:51-58. In some aspects, the purified microbial population comprises a bacterium with a 16S nucleic acid sequence that is at least about 99% identical to a nucleic acid sequence selected from the group consisting of: SEQ ID NOs:1-50 and 59-387. In some aspects, the purified microbial population comprises a fungus with an ITS nucleic acid sequence that is at least about 99% identical to a nucleic acid sequence selected from the group consisting of: SEQ ID NOs:51-58. In some aspects, the purified microbial population comprises a bacterium with a 16S nucleic acid sequence selected from the group consisting of: SEQ ID NOs:1-50 and 59-387. In some aspects, the purified microbial population comprises a fungus with an ITS nucleic acid sequence selected from the group consisting of: SEQ ID NOs:51-58.

In some aspects, the purified microbial population comprises a bacterium with a 16S nucleic acid sequence and a fungus with an ITS nucleic acid sequence that is at least about 97% identical to a nucleic acid sequence selected from the group consisting of: SEQ ID NOs:1-387. In some aspects, the purified microbial population comprises a bacteria with a 16S nucleic acid sequence that is at least about 97% identical to SEQ ID NO:1. In some aspects, the purified microbial population comprises a bacterium with a 16S nucleic acid sequence comprising SEQ ID NO:1, and wherein the bacterium is as deposited as PATENT201703004.

In some aspects, the purified microbial population only contains organisms that are members of a group selected from: *Lactobacillus, Clostridium, Faecalibacter, Hydrogenoanaerobacterium, Acrocarpospora, Bacillus, Subdoligranulum, Leuconostoc, Lachnospiracea, Anaerofilum, Microbacterium, Verrucosispora, Anaerofilum, Blautia, Pseudomonas, Sporobacter, Corynebacterium, Streptococcus, Paracoccus, Cellulosilyticum, Ruminococcus, Rosebura, Bacteroides, Filobasidium, Gibberella, Alatospora, Pichia,* and *Candida.*

In some aspects, the fowl administered the effective amount of the fowl supplement exhibits at least a 1% decrease in feed conversion ratio, at least a 1% increase in weight, and/or at least a 1% decrease in pathogen-associated lesion formation in the gastrointestinal tract. In some aspects, the fowl administered the effective amount of the fowl supplement exhibits at least a 10% decrease in feed conversion ratio, at least a 10% increase in weight, and/or at least a 10% decrease in pathogen-associated lesion formation in the gastrointestinal tract.

A shelf-stable fowl supplement capable of decreasing feed conversion ratio, increasing fowl weight, or decreasing pathogen-associated lesion formation in the gastrointestinal tract of fowl, comprising: a) a purified population that comprises a bacterium with a 16S nucleic acid sequence and/or a fungus with an ITS nucleic acid sequence, which is at least about 97% identical to a nucleic acid sequence selected from the group consisting of SEQ ID NOs:1-387; and b) a shelf-stable carrier suitable for fowl administration, wherein the purified population of bacteria and/or fungi of a) is present in the supplement in an amount effective to decrease feed conversion ratio, increase fowl weight, and/or decrease pathogen-associated lesion formation in the gastrointestinal tract of fowl, as compared to a fowl not having been administered the supplement. In some aspects, the fowl administered the supplement exhibits a decrease in feed conversion ratio as compared to fowl not having been administered the supplement. In some aspects, fowl administered the supplement exhibits a decrease in feed conversion ratio as compared to fowl not having been administered the supplement.

In some aspects, the purified population of bacteria and/or fungi comprises bacteria with a 16S nucleic acid sequence that is at least about 97% identical to SEQ ID NO:1. In some aspects, the purified population of bacteria and/or fungi comprises bacteria with a 16S nucleic acid sequence that is at least about 99% identical to SEQ ID NO:1. In some aspects, the purified population of bacteria and/or fungi comprises bacteria with a 16S nucleic acid sequence comprising SEQ ID NO:1. In some aspects, the purified population of bacteria and/or fungi comprises bacteria with a 16S nucleic acid sequence comprising SEQ ID NO:1, and wherein the bacteria are as deposited as PATENT201703004.

In some aspects, the shelf-stable fowl supplement further comprises: (i) a purified population of bacteria comprising a 16S nucleic acid sequence that is at least about 97% identical to a nucleic acid sequence selected from the group consisting of: SEQ ID NO:1-50 and 59-387, and/or (ii) a purified population of fungi that comprise fungi with an ITS nucleic acid sequence that is at least about 97% identical to a nucleic acid sequence selected from the group consisting of: SEQ ID NO:51-58.

In some aspects, the purified population of bacteria comprises bacteria with a 16S nucleic acid sequence that is at least about 99% identical to a nucleic acid sequence selected from the group consisting of: SEQ ID NO:1-50 and 59-387. In some aspects, the purified population of fungi comprises fungi with an ITS nucleic acid sequence that is at least about 99% identical to a nucleic acid sequence selected from the group consisting of: SEQ ID NO:51-58. In some aspects, the purified population of bacteria comprises bacteria with a 16S nucleic acid sequence selected from the group consisting of SEQ ID NO:1-50 and 59-387. In some aspects, the purified population of fungi comprises fungi with an ITS nucleic acid sequence selected from the group consisting of: SEQ ID NO:51-58. In some aspects, the purified population of bacteria comprises bacteria with a 16S nucleic acid sequence that is at least about 97% identical to SEQ ID NO:3. In some aspects, the purified population of bacteria comprises bacteria with a 16S nucleic acid sequence that is at least about 99% identical to SEQ ID NO:3. In some aspects, the purified population of bacteria comprises bacteria with a 16S nucleic acid sequence comprising SEQ ID NO:3. In some aspects, the purified population of bacteria comprises SEQ ID NO:1, and wherein the bacteria are as deposited as PATENT201703001. In some aspects, both a purified population of bacteria (i) and a purified population of fungi (ii) are present in the supplement.

In some aspects, the fowl supplement is formulated for administration to a broiler. In some aspects, the supplement is stable under ambient conditions for at least one week. In some aspects, the supplement formulated as an: encapsulation, encapsulation, tablet, capsule, pill, feed additive, food ingredient, food additive, food preparation, food supplement, water additive, water-mixed additive, heat-stabilized additive, moisture-stabilized additive, consumable solution, consumable spray additive, consumable solid, consumable gel, injection, suppository, drench, or combinations thereof.

In some aspects, the purified population of bacteria and/or fungi is present in the fowl supplement at a concentration of at least $10^2$ cells. In some aspects, the fowl administered the supplement exhibits an increase in weight as compared to fowl not having been administered the supplement. In some aspects, the fowl administered the supplement exhibits a decrease in pathogen-associated lesion formation in the gastrointestinal tract as compared to fowl not having been administered the supplement.

In some aspects, the fowl administered the supplement exhibits a decreased incidence of *Clostridium perfringens*-associated lesion formation in the gastrointestinal tract as compared to fowl not having been administered the supplement. In some aspects, the fowl administered the supplement exhibits a 1% decreased incidence of *Clostridium perfringens*-associated lesion formation in the gastrointestinal tract as compared to fowl not having been administered the supplement. In some aspects, the fowl administered the supplement exhibits a 10% decreased incidence of *Clostridium perfringens*-associated lesion formation in the gastrointestinal tract as compared to fowl not having been administered the supplement. In some aspects, the fowl administered the supplement exhibits a 20% decreased incidence of *Clostridium perfringens*-associated lesion formation in the gastrointestinal tract as compared to fowl not having been administered the supplement.

In some aspects, the shelf-stable supplement further comprises: (i) a purified population of bacteria comprising a 16S nucleic acid sequence that is at least about 97% identical to a nucleic acid sequence selected from the group consisting of: SEQ ID NO:1-50 and 59-387, and/or (ii) a purified population of fungi comprising an ITS nucleic acid sequence that is at least about 97% identical to a nucleic acid sequence selected from the group consisting of: SEQ ID NO:51-58.

In some embodiments, the present disclosure is drawn to a method for decreasing feed conversion ratio, increasing fowl weight, or decreasing pathogen-associated lesion formation in the gastrointestinal tract of fowl, the method comprising: a) administering to a fowl an effective amount of a shelf-stable fowl supplement comprising: i) a purified microbial population that comprises a bacterium with a 16S nucleic acid sequence at least about 97% identical to SEQ ID NOs:13, 346, 19, or 22, and said bacterium has a MIC score of at least about 0.2; and ii) a shelf-stable carrier suitable for fowl administration, wherein the fowl administered the effective amount of the shelf-stable fowl supplement exhibits a decrease in feed conversion ratio, an increase in weight, and/or a decrease in pathogen-associated lesion formation in the gastrointestinal tract, as compared to a fowl not having been administered the supplement.

A shelf-stable fowl supplement capable of decreasing feed conversion ratio, increasing fowl weight, or decreasing pathogen-associated lesion formation in the gastrointestinal tract of fowl, comprising: a) a purified population that comprises a bacterium with a 16S nucleic acid sequence at least about 97% identical to SEQ ID NOs:13, 346, 19, or 22; and b) a shelf-stable carrier suitable for fowl administration; wherein the purified population of bacteria of a) is present in the supplement in an amount effective to decrease feed conversion ratio, increase fowl weight, and/or decrease pathogen-associated lesion formation in the gastrointestinal tract of fowl, as compared to a fowl not having been administered the supplement.

A method for decreasing feed conversion ratio, increasing fowl weight, and/or decreasing pathogen-associated lesion formation in the gastrointestinal tract of fowl, the method comprising: a) administering to a fowl an effective amount of a shelf-stable fowl supplement comprising: i) a purified microbial population of *Bacillus, Lactobacillus*, or *Eubacterium* bacteria comprising bacteria with a 16S nucleic acid sequence selected from SEQ ID NOs:13, 346, 19, or 22, and said bacterium has a MIC score of at least about 0.2; and ii) a shelf-stable carrier suitable for fowl administration, wherein the fowl administered the effective amount of the shelf-stable fowl supplement exhibits an decrease in feed conversion ratio, an increase in weight, or a decrease in pathogen-associated lesion formation in the gastrointestinal tract, as compared to a fowl not having been administered the supplement.

A shelf-stable fowl supplement capable of decreasing feed conversion ratio, increasing fowl weight, or decreasing pathogen-associated lesion formation in the gastrointestinal tract of fowl, comprising: a) a purified population of *Bacillus, Lactobacillus*, or *Eubacterium* bacteria comprising bacteria with a 16S nucleic acid sequence that is at least about 97% identical to SEQ ID NOs:13, 346, 19, or 22; and b) a shelf-stable carrier suitable for fowl administration, wherein the purified population of *Bacillus, Lactobacillus*, or *Eubacterium* bacteria of a) is present in the supplement in an amount effective to decrease feed conversion ratio, increase fowl weight, or decrease pathogen-associated lesion formation in the gastrointestinal tract of fowl, as compared to a fowl not having been administered the supplement.

A method of treating poultry for necrotic enteritis, the method comprising: a) administering to a bird an effective amount of a shelf-stable poultry supplement comprising: i) a purified microbial population that comprises a bacterium with a 16S nucleic acid sequence at least about 97% identical to a nucleic acid sequence selected from SEQ ID NOs:13, 346, 19, or 22, and said bacterium has a MIC score of at least about 0.2; and ii) a shelf-stable carrier suitable for poultry administration, wherein the bird administered the effective amount of the shelf-stable poultry supplement exhibits a decrease in the number of necrotic enteritis-causing bacteria in the gastrointestinal tract, as compared to a bird not having been administered the supplement.

A method of treating poultry for necrotic enteritis, the method comprising: a) administering to a bird an effective amount of a shelf-stable poultry supplement comprising: i)

a purified microbial population of *Bacillus, Lactobacillus*, or *Eubacterium* bacteria comprising bacteria with a 16S nucleic acid sequence selected from SEQ ID NOs:13, 346, 19, or 22, and said bacterium has a MIC score of at least about 0.2; and ii) a shelf-stable carrier suitable for poultry administration, wherein the poultry administered the effective amount of the shelf-stable poultry supplement exhibits a decrease in the number of necrotic enteritis-causing bacteria in the gastrointestinal tract, as compared to a bird not having been administered the supplement.

In aspects, the aforementioned microbial species—that is, a purified microbial population that comprises a bacteria with a 16S nucleic acid sequence, and/or a fungi with an ITS nucleic acid sequence, which is at least about 97% identical to a nucleic acid sequence selected from the group consisting of: SEQ ID NOs: 1-387—are members of a Markush group, as the present disclosure illustrates that the members belong to a class of microbes characterized by various physical and functional attributes, which can include any of the following: a) the ability to convert a carbon source into a volatile fatty acid such as acetate, butyrate, propionate, or combinations thereof; b) the ability to degrade a soluble or insoluble carbon source; c) the ability to impart an increase in weight gain to fowl administered the microbe(s); d) the ability to modulate the microbiome of the gastrointestinal tract of fowl administered the microbe; e) the ability to be formulated into a shelf-stable composition; f) the ability to exhibit a decrease in feed conversion ratio in fowl having been administered the microbe(s); g) the ability to impart a decrease in pathogen-associated lesion formation in the gastrointestinal tract; h) the ability to impart a decrease in pathogenic microbes in the gastrointestinal tract; and/or i) possessing a MIC score of at least about 0.2 if a bacteria and possessing a MIC score of at least about 0.2 if a fungi. Thus, the members of the Markush group possess at least one property in common, which can be responsible for their function in the claimed relationship.

Budapest Treaty on the International Recognition of the Deposit of Microorganisms for the Purpose of Patent Procedures Some microorganisms described in this application were deposited with the United States Department of Agriculture (USDA) Agricultural Research Service (ARS) Culture Collection (NRRL®), located at 1815 N. University St., Peoria, Ill. 61604, USA. Some microorganisms described in this application were deposited with the Bigelow National Center for Marine Algae and Microbiota, located at 60 Bigelow Drive, East Boothbay, Me. 04544, USA. Some microorganisms described in this application were deposited with the American Type Culture Collection (ATCC), located at 10801 University Boulevard, Manassas, Va. 20108, USA.

The deposits were made under the terms of the Budapest Treaty on the International Recognition of the Deposit of Microorganisms for the Purposes of Patent Procedure. The NRRL®, ATCC, and Bigelow National Center for Marine Algae and Microbiota accession numbers for the aforementioned Budapest Treaty deposits are provided in Table 3. The accession numbers and corresponding dates of deposit for the microorganisms described in this application are separately provided in Table 45.

The strains designated in the below table have been deposited in the labs of Ascus Biosciences, Inc. since at least Mar. 1, 2016. Strains comprising SEQ ID NOs: 386 and 387 were isolated prior to, and stored since Summer 2017.

In Table 1, the closest predicted hits for taxonomy of the microbes are listed in columns 2 and 5. Column 2 is the top taxonomic hit predicated by BLAST, and column 5 is the top taxonomic hit for genus+species predicted by BLAST. The strains designated in the below table have been deposited in the labs of Ascus Biosciences, Inc. since at least Mar. 1, 2016.

Table 1 lists strain designations of the bacteria and fungi of the present disclosure. If a letter in parentheses follows any of the strain designations, then that indicates that each of those strains have variants that share at least 97% sequence identity with the reference strain with the (A) parenthetical. Ascusbbr_5796(A) has two variants, Ascusbbr_5796(B) and Ascusbbr_5796(C) that share 97.8% and 98.2% sequence identity, respectively, with Ascusbbr_5796 (A). Ascusbbr_14690(A) has two variants, Ascusbbr_14690 (B) and Ascusbbr_14690(C) that share 97.8% and 98.2% sequence identity, respectively, with Ascusbbr_14690(A). Ascusbbr_38717(A) shares 98.6% sequence identity with Ascusbbr_38717(B). Ascusbbr_33(A) shares 98.2% sequence identity with Ascusbbr_33(B). Ascusbbr_409(B), Ascusbbr_409(C), Ascusbbr_409(D), share 98.2%, 97.3%, and 97.8% sequence identity, respectively, with Ascusbbr_409(B). Ascus_331885(B) and Ascus_331885(C) share 97.8% and 97.3% sequence identity, respectively, with Ascus_331885(A). Ascusbbr_247(A) shares 97.8% sequence identity with Ascusbbr_247(B). Ascusbbr_10593 (A) shares 99.6% sequence identity with Ascusbbr_10593 (B). Ascusbbr_32731(A) shares 97.3% sequence identity with Ascusbbr_32731(B). Ascusbbr_1436(A) shares 97.8% sequence identity with Ascusbbr_1436(B). Ascusbbr_265 (A) shares 99.6% sequence identity with Ascusbbr_265(B).

TABLE 1

Microbes of the present disclosure, including bacteria (1-99) and fungi (100-107).

| | Predicted Closest Taxa of Isolated Microbes | BLAST Taxonomic Top Hit | BLAST % Ident. | Query Cover | BLAST Taxonomic Top Hit w/Genus + Species | BLAST % Ident. | Query Cover | Strain Designation | Sequence Identifier for Associated Marker | MIC Score |
|---|---|---|---|---|---|---|---|---|---|---|
| 1. | *Lactobacillus* (Genus) | *Lactobacillus crispatus* | 98% | 100% | *Lactobacillus crispatus* | 98% | 100% | Ascusbbr_4729 | SEQ ID NO: 1 | 0.76676 |
| 2. | Lachnospiraceae *Clostridium* Cluster XIVa (Family + Cluster) | Bacterium ic1296 | 98% | 91% | *Ruminococcus gnavus* | 95% | 98% | Ascusbbr_339 | SEQ ID NO: 2 | 0.62924 |
| 3. | *Lactobacillus* (Genus) | *Lactobacillus crispatus* | 100% | 100% | *Lactobacillus crispatus* | 100% | 100% | Ascusbbr_5796(A) | SEQ ID NO: 3 | 0.61325 |

TABLE 1-continued

Microbes of the present disclosure, including bacteria (1-99) and fungi (100-107).

| | Predicted Closest Taxa of Isolated Microbes | BLAST Taxonomic Top Hit | BLAST % Ident. | Query Cover | BLAST Taxonomic Top Hit w/Genus + Species | BLAST % Ident. | Query Cover | Strain Designation | Sequence Identifier for Associated Marker | MIC Score |
|---|---|---|---|---|---|---|---|---|---|---|
| 4. | Lactobacillus (Genus) | Lactobacillus crispatus | 100% | 100% | Lactobacillus crispatus | 100% | 100% | Ascusbbr_5796(B) | SEQ ID NO: 369 | 0.61325 |
| 5. | Lactobacillus (Genus) | Lactobacillus crispatus | 100% | 100% | Lactobacillus crispatus | 100% | 100% | Ascusbbr_5796(C) | SEQ ID NO: 370 | 0.61325 |
| 6. | Lactobacillus (Genus) | Lactobacillus vaginalis | 99% | 100% | Lactobacillus vaginalis | 99% | 100% | Ascusbbr_38717(A) | SEQ ID NO: 4 | 0.59229 |
| 7. | Lactobacillus (Genus) | Lactobacillus vaginalis | 99% | 100% | Lactobacillus vaginalis | 99% | 100% | Ascusbbr_38717(B) | SEQ ID NO: 373 | 0.59229 |
| 8. | Lactobacillus (Genus) | Lactobacillus vaginalis | 99% | 98% | Lactobacillus vaginalis | 99% | 98% | Ascusbbr_170211 | SEQ ID NO: 5 | 0.58403 |
| 9. | Lactobacillus (Genus) | Lactobacillus johnsonii | 99% | 100% | Lactobacillus johnsonii | 99% | 100% | Ascusbbr_1686 | SEQ ID NO: 6 | 0.57845 |
| 10. | Faecalibacterium (Genus) | Faecalibacterium sp. | 90% | 98% | Faecalibacterium prausnitzii | 89% | 97% | Ascusbbr_1789 | SEQ ID NO: 7 | 0.56099 |
| 11. | Lactobacillus (Genus) | Lactobacillus johnsonii | 99% | 100% | Lactobacillus johnsonii | 99% | 100% | Ascusbbr_3820 | SEQ ID NO: 8 | 0.55862 |
| 12. | Hydrogenoanaerobacterium (Genus) | Clostridium sp. | 91% | 98% | Butyrivibrio hungatei | 86% | 82% | Ascusbbr_173 | SEQ ID NO: 9 | 0.55675 |
| 13. | Peptostreptococcaceae Clostridium Cluster XI (Family + Cluster) | Clostridium sp. | 92% | 100% | [Eubacterium] tenue | 91% | 98% | Ascusbbr_3089 | SEQ ID NO: 10 | 0.55548 |
| 14. | Acrocarpospora (Genus) | Nonomuraea sp. | 99% | 88% | Microbispora rosea | 95% | 100% | Ascusbbr_167 | SEQ ID NO: 11 | 0.5442 |
| 15. | Lactobacillus (Genus) | Lactobacillus helveticus | 99% | 98% | Lactobacillus helveticus | 99% | 98% | Ascusbbr_301568 | SEQ ID NO: 12 | 0.53873 |
| 16. | Bacillus (Genus) | Bacillus subtilis | 99% | 100% | Bacillus subtilis | 99% | 100% | Ascusbbr_33(A) | SEQ ID NO: 13 | 0.53686 |
| 17. | Bacillus (Genus) | Bacillus subtilis | 99% | 100% | Bacillus subtilis | 99% | 100% | Ascusbbr_33(B) | SEQ ID NO: 374 | 0.53686 |
| 18. | Lactobacillus (Genus) | Lactobacillus coleohominis | 99% | 95% | Lactobacillus coleohominis | 99% | 95% | Ascusbbr_25200 | SEQ ID NO: 14 | 0.52435 |
| 19. | Subdoligranulum (Genus) | Bacterium ic1340 | 90% | 98% | Anaerofilum pentosovorans | 88% | 91% | Ascusbbr_84 | SEQ ID NO: 15 | 0.52174 |
| 20. | Subdoligranulum (Genus) | Firmicutes bacterium | 99% | 100% | Faecalibacterium prausnitzii | 96% | 100% | Ascusbbr 136 | SEQ ID NO: 16 | 0.51373 |
| 21. | Lachnospiraceae Clostridium Cluster XIVa (Family + Cluster) | Clostridium sp. | 95% | 100% | Eubacterium fissicatena | 94% | 98% | Ascusbbr_128 | SEQ ID NO: 17 | 0.51348 |
| 22. | Lactobacillus (Genus) | Lactobacillus coleohominis | 99% | 95% | Lactobacillus coleohominis | 99% | 95% | Ascusbbr_322104 | SEQ ID NO: 18 | 0.50724 |
| 23. | Lactobacillus (Genus) | Lactobacillus reuteri | 100% | 100% | Lactobacillus reuteri | 100% | 100% | Ascusbbr_409(A) | SEQ ID NO: 19 | 0.50572 |
| 24. | Lactobacillus (Genus) | Lactobacillus reuteri | 100% | 100% | Lactobacillus reuteri | 100% | 100% | Ascusbbr_409(B) | SEQ ID NO: 375 | 0.50572 |
| 25. | Lactobacillus (Genus) | Lactobacillus reuteri | 100% | 100% | Lactobacillus reuteri | 100% | 100% | Ascusbbr_409(C) | SEQ ID NO: 376 | 0.50572 |
| 26. | Lactobacillus (Genus) | Lactobacillus reuteri | 100% | 100% | Lactobacillus reuteri | 100% | 100% | Ascusbbr_409(D) | SEQ ID NO: 377 | 0.50572 |
| 27. | Leuconostoc (Genus) | Leuconostoc mesenteroides | 99% | 100% | Leuconostoc mesenteroides | 99% | 100% | Ascusbbr_127 | SEQ ID NO: 20 | 0.4955 |
| 28. | Lachnospiracea incertae sedis (Genus) | Lachnospiraceae bacterium | 96% | 100% | Eubacterium hallii | 91% | 100% | Ascusbbr_14834 | SEQ ID NO: 21 | 0.49531 |
| 29. | Lactobacillus (Genus) | Lactobacillus reuteri | 99% | 100% | Lactobacillus reuteri | 99% | 100% | Ascusbbr_331885(A) | SEQ ID NO: 22 | 0.49378 |
| 30. | Lactobacillus (Genus) | Lactobacillus reuteri | 99% | 100% | Lactobacillus reuteri | 99% | 100% | Ascusbbr_331885(B) | SEQ ID NO: 378 | 0.49378 |
| 31. | Lactobacillus (Genus) | Lactobacillus reuteri | 99% | 100% | Lactobacillus reuteri | 99% | 100% | Ascusbbr_331885(C) | SEQ ID NO: 379 | 0.49378 |
| 32. | Anaerofilum (Genus) | Clostridiales bacterium | 88% | 97% | Ruthenibacterium lactatiformans | 88% | 98% | Ascusbbr_31 | SEQ ID NO: 23 | 0.48633 |
| 33. | Lachnospiracea incertae sedis (Genus) | Blautia hydrogenotrophica | 96% | 100% | Blautia hydrogenotrophica | 96% | 100% | Ascusbbr_2307 | SEQ ID NO: 24 | 0.48546 |

TABLE 1-continued

Microbes of the present disclosure, including bacteria (1-99) and fungi (100-107).

| | Predicted Closest Taxa of Isolated Microbes | BLAST Taxonomic Top Hit | BLAST % Ident. | Query Cover | BLAST Taxonomic Top Hit w/Genus + Species | BLAST % Ident. | Query Cover | Strain Designation | Sequence Identifier for Associated Marker | MIC Score |
|---|---|---|---|---|---|---|---|---|---|---|
| 34. | Lachnospiraceae Clostridium Cluster XIVa (Family + Cluster) | Clostridium saccharolyticum-like K10 | 98% | 100% | Clostridium clostridioforme | 91% | 100% | Ascusbbr_247(A) | SEQ ID NO: 25 | 0.48546 |
| 35. | Lachnospiraceae Clostridium Cluster XIVa (Family + Cluster) | Clostridium saccharolyticum-like K10 | 98% | 100% | Clostridium clostridioforme | 91% | 100% | Ascusbbr_247(B) | SEQ ID NO: 380 | 0.48546 |
| 36. | Microbacterium (Genus) | Pseudoclavibacter sp. | 95% | 99% | Pseudoclavibacter caeni | 99% | 79% | Ascusbbr_19 | SEQ ID NO: 26 | 0.47772 |
| 37. | Verrucosispora (Genus) | Verrucosispora sp. | 99% | 100% | Verrucosispora wenchangensis | 97% | 98% | Ascusbbr_69 | SEQ ID NO: 27 | 0.47757 |
| 38. | Anaerofilum (Genus) | Faecalibacterium prausnitzii | 93% | 100% | Faecalibacterium prausnitzii | 93% | 100% | Ascusbbr_94 | SEQ ID NO: 28 | 0.46645 |
| 39. | Clostridium sensu stricto (Genus) | Candidatus Arthromitus sp | 90% | 91% | Peptoclostridium difficile | 89% | 91% | Ascusbbr_313454 | SEQ ID NO: 29 | 0.46594 |
| 40. | Lactobacillus (Genus) | Lactobacillus helveticus | 96% | 100% | Lactobacillus helveticus | 96% | 100% | Ascusbbr_351000 | SEQ ID NO: 30 | 0.46296 |
| 41. | Lactobacillus (Genus) | Lactobacillus salivarius | 99% | 100% | Lactobacillus salivarius | 99% | 100% | Ascusbbr_1436(A) | SEQ ID NO: 31 | 0.46076 |
| 42. | Lactobacillus (Genus) | Lactobacillus salivarius | 99% | 100% | Lactobacillus salivarius | 99% | 100% | Ascusbbr_1436(B) | SEQ ID NO: 383 | 0.46076 |
| 43. | Lachnospiraceae Clostridium Cluster XIVa (Family + Cluster) | Roseburia inulinivorans | 93% | 100% | Roseburia inulinivorans | 93% | 100% | Ascusbbr_28 | SEQ ID NO: 32 | 0.46028 |
| 44. | Blautia (Genus) | Ruminococcus obeum | 94% | 100% | Ruminococcus obeum | 94% | 100% | Ascusbbr_144 | SEQ ID NO: 33 | 0.45742 |
| 45. | Lactobacillus (Genus) | Lactobacillus oris | 99% | 99% | Lactobacillus oris | 99% | 99% | Ascusbbr_42760(A) | SEQ ID NO: 34 | 0.43682 |
| 46. | Lactobacillus (Genus) | Lactobacillus oris | 99% | 99% | Lactobacillus oris | 99% | 99% | Ascusbbr_42760(B) | SEQ ID NO: 384 | 0.43682 |
| 47. | Lactobacillus (Genus) | Lactobacillus crispatus | 99% | 83% | Lactobacillus crispatus | 99% | 83% | Ascusbbr_134994 | SEQ ID NO: 35 | 0.434 |
| 48. | Lactobacillus (Genus) | Lactobacillus reuteri | 94% | 88% | Lactobacillus reuteri | 94% | 88% | Ascusbbr_358773 | SEQ ID NO: 36 | 0.43348 |
| 49. | Pseudomonas (Genus) | Pseudomonas chengduensis | 99% | 100% | Pseudomonas chengduensis | 99% | 100% | Ascusbbr_2503 | SEQ ID NO: 37 | 0.42622 |
| 50. | Sporobacter (Genus) | Syntrophomonadaceae bacterium | 86% | 82% | Clostridium sphenoides | 84% | 82% | Ascusbbr_312 | SEQ ID NO: 39 | 0.42622 |
| 51. | Lactobacillus (Genus) | Lactobacillus crispatus | 99% | 83% | Lactobacillus crispatus | 99% | 83% | Ascusbbr_140914 | SEQ ID NO: 40 | 0.40935 |
| 52. | Lactobacillus (Genus) | Lactobacillus salivarius | 98% | 82% | Lactobacillus salivarius | 98% | 82% | Ascusbbr_257627 | SEQ ID NO: 41 | 0.40775 |
| 53. | Lactobacillus (Genus) | Lactobacillus helveticus | 98% | 82% | Lactobacillus helveticus | 98% | 82% | Ascusbbr_310088 | SEQ ID NO: 42 | 0.40576 |
| 54. | Lachnospiracea incertae sedis (Genus) | Blautia hydrogenotrophica | 96% | 100% | Blautia hydrogenotrophica | 96% | 100% | Ascusbbr_91 | SEQ ID NO:43 | 0.40345 |
| 55. | Lactobacillus (Genus) | Lactobacillus crispatus | 97% | 83% | Lactobacillus crispatus | 97% | 83% | Ascusbbr_150100 | SEQ ID NO: 44 | 0.40128 |
| 56. | Lactobacillus (Genus) | Lactobacillus vaginalis | 97% | 100% | Lactobacillus vaginalis | 97% | 100% | Ascusbbr_252028 | SEQ ID NO: 45 | 0.3998 |
| 57. | Peptostreptococcaceae Clostridium Cluster XI (Family + Cluster) | Clostridium sp. | 93% | 100% | Romboutsia lituseburensis | 92% | 100% | Ascusbbr_2158 | SEQ ID NO: 46 | 0.39816 |
| 58. | Lactobacillus (Genus) | Lactobacillus crispatus | 96% | 100% | Lactobacillus crispatus | 96% | 100% | Ascusbbr_373 | SEQ ID NO: 47 | 0.37614 |
| 59. | Lactobacillus (Genus) | Lactobacillus johnsonii | 98% | 94% | Lactobacillus johnsonii | 98% | 94% | Ascusbbr_1802 | SEQ ID NO: 48 | 0.37123 |
| 60. | Lactobacillus (Genus) | Lactobacillus reuteri | 96% | 100% | Lactobacillus reuteri | 96% | 100% | Ascusbbr_107 | SEQ ID NO: 49 | 0.37123 |

TABLE 1-continued

Microbes of the present disclosure, including bacteria (1-99) and fungi (100-107).

| | Predicted Closest Taxa of Isolated Microbes | BLAST Taxonomic Top Hit | BLAST % Ident. | Query Cover | BLAST Taxonomic Top Hit w/Genus + Species | BLAST % Ident. | Query Cover | Strain Designation | Sequence Identifier for Associated Marker | MIC Score |
|---|---|---|---|---|---|---|---|---|---|---|
| 61. | Lactobacillus (Genus) | Lactobacillus crispatus | 93% | 83% | Lactobacillus crispatus | 93% | 83% | Ascusbbr_1727 | SEQ ID NO: 50 | 0.36309 |
| 62. | Corynebacterium (Genus) | Corynebacterium glutamicum | 100% | 100% | Corynebacterium glutamicum | 100% | 100% | Ascusbbr_226 | SEQ ID NO: 338 | 0.75897 |
| 63. | Streptococcus (Genus) | Streptococcus hyovaginalis | 97% | 94% | Streptococcus hyovaginalis | 97% | 94% | Ascusbbr_17 | SEQ ID NO: 339 | 0.62924 |
| 64. | Lactobacillus (Genus) | Lactobacillus aviarius | 99% | 100% | Lactobacillus aviarius | 99% | 100% | Ascusbbr_14690(A) | SEQ ID NO: 340 | 0.60061 |
| 65. | Lactobacillus (Genus) | Lactobacillus aviarius | 99% | 100% | Lactobacillus aviarius | 99% | 100% | Ascusbbr_14690(B) | SEQ ID NO: 371 | 0.60061 |
| 66. | Lactobacillus (Genus) | Lactobacillus aviarius | 99% | 100% | Lactobacillus aviarius | 99% | 100% | Ascusbbr_14690(C) | SEQ ID NO: 372 | 0.60061 |
| 67. | Corynebacterium (Genus) | Corynebacterium xerosis | 100% | 100% | Corynebacterium xerosis | 100% | 100% | Ascusbbr_18 | SEQ ID NO: 341 | 0.58366 |
| 68. | Peptostreptococcaceae (Clostridium Cluster XI) (Family + Cluster) | Romboutsia lituseburensis | 98% | 100% | Romboutsia lituseburensis | 98% | 100% | Ascusbbr_7363 | SEQ ID NO: 342 | 0.57242 |
| 69. | Corynebacterium (Genus) | Corynebacterium falsenii | 100% | 100% | Corynebacterium falsenii | 100% | 100% | Ascusbbr_35 | SEQ ID NO: 343 | 0.49929 |
| 70. | Corynebacterium (Genus) | Corynebacterium ammoniagenes | 98% | 97% | Corynebacterium ammoniagenes | 98% | 97% | Ascusbbr_7779 | SEQ ID NO: 344 | 0.48127 |
| 71. | Lachnospiraceae (Clostridium Cluster XIVa) (Family + Cluster) | Desulfotomaculum sp. | 96% | 100% | Clostridium sphenoides | 95% | 100% | Ascusbbr_10593(A) | SEQ ID NO: 345 | 0.47763 |
| 72. | Lachnospiraceae (Clostridium Cluster XIVa) (Family + Cluster) | Desulfotomaculum sp. | 96% | 100% | Clostridium sphenoides | 95% | 100% | Ascusbbr_10593(B) | SEQ ID NO: 381 | 0.47763 |
| 73. | Lachnospiracea incertae sedis (Genus) | Eubacterium sp. | 98% | 100% | Eubacterium fissicatena | 93% | 98% | Ascusbbr_32731(A) | SEQ ID NO: 346 | 0.47124 |
| 74. | Lachnospiracea incertae sedis (Genus) | Eubacterium sp. | 98% | 100% | Eubacterium fissicatena | 93% | 98% | Ascusbbr_32731(B) | SEQ ID NO: 382 | 0.47124 |
| 75. | Ruminococcaceae (Clostridium Cluster III) (Family + Cluster) | Bacterium | 89% | 78% | Ruminiclostridium thermocellum | 86% | 79% | Ascusbbr_359892 | SEQ ID NO: 347 | 0.39553 |
| 76. | Lactobacillus (Genus) | Lactobacillus pentosus | 100% | 100% | Lactobacillus pentosus | 100% | 100% | Ascusbbr_25721 | SEQ ID NO: 348 | 0.39537 |
| 77. | Streptococcus (Genus) | Swine fecal bacterium | 100% | 100% | Streptococcus alactolyticus | 99% | 100% | Ascusbbr_72076 | SEQ ID NO: 349 | 0.38425 |
| 78. | Lachnospiraceae (Clostridium Cluster XIVa) (Family + Cluster) | Lachnospiraceae bacterium | 91% | 92% | Blautia producta | 89% | 97% | Ascusbbr_6097 | SEQ ID NO: 350 | 0.37484 |
| 79. | Lactobacillus (Genus) | Lactobacillus helveticus | 100% | 100% | Lactobacillus helveticus | 100% | 100% | Ascusbbr_265(A) | SEQ ID NO: 351 | 0.37167 |
| 80. | Lactobacillus (Genus) | Lactobacillus helveticus | 100% | 100% | Lactobacillus helveticus | 100% | 100% | Ascusbbr_265(B) | SEQ ID NO: 385 | 0.37167 |
| 81. | Paracoccus (Genus) | Paracoccus alcaliphilus | 99% | 99% | Paracoccus alcaliphilus | 99% | 99% | Ascusbbr_323376 | SEQ ID NO: 352 | 0.36852 |
| 82. | Cellulosilyticum (Genus) | Ruminococcus sp. | 97% | 100% | Hydrogenoanaerobacterium saccharovorans | 84% | 98% | Ascusbbr_36257 | SEQ ID NO: 353 | 0.36078 |
| 83. | Blautia (Genus) | Blautia glucerasea | 89% | 100% | Blautia glucerasea | 89% | 100% | Ascusbbr_6957 | SEQ ID NO: 354 | 0.35528 |
| 84. | Corynebacterium (Genus) | Corynebacterium flavescens | 99% | 100% | Corynebacterium flavescens | 99% | 100% | Ascusbbr_38 | SEQ ID NO: 355 | 0.35488 |
| 85. | Lachnospiracea incertae sedis (Genus) | Eubacteriaceae bacterium | 98% | 92% | Coprococcus catus | 87% | 99% | Ascusbbr_13398 | SEQ ID NO: 356 | 0.34774 |

TABLE 1-continued

Microbes of the present disclosure, including bacteria (1-99) and fungi (100-107).

| | Predicted Closest Taxa of Isolated Microbes | BLAST Taxonomic Top Hit | BLAST % Ident. | Query Cover | BLAST Taxonomic Top Hit w/Genus + Species | BLAST % Ident. | Query Cover | Strain Designation | Sequence Identifier for Associated Marker | MIC Score |
|---|---|---|---|---|---|---|---|---|---|---|
| 86. | *Corynebacterium* (Genus) | *Corynebacterium callunae* | 100% | 100% | *Corynebacterium callunae* | 100% | 100% | Ascusbbr_57 | SEQ ID NO: 357 | 0.34405 |
| 87. | *Corynebacterium* (Genus) | *Corynebacterium stationis* | 99% | 100% | *Corynebacterium stationis* | 99% | 100% | Ascusbbr_285160 | SEQ ID NO: 358 | 0.32892 |
| 88. | *Ruminococcus* (Genus) | *Clostridium* sp. | 92% | 96% | *Blautia producta* | 91% | 96% | Ascusbbr_37385 | SEQ ID NO: 359 | 0.3236 |
| 89. | *Lactobacillus* (Genus) | *Lactobacillus intestinalis* | 92% | 100% | *Lactobacillus intestinalis* | 92% | 100% | Ascusbbr_118124 | SEQ ID NO: 360 | 0.31115 |
| 90. | *Roseburia* (Genus) | Bacterium AC2012 | 92% | 99% | *Frisingicoccus caecimuris* | 91% | 100% | Ascusbbr_32592 | SEQ ID NO: 361 | 0.29912 |
| 91. | Lachnospiraceae (*Clostridium* Cluster XIVa) (Family + Cluster) | *Clostridium* sp. | 90% | 99% | *Eubacterium ventriosum* | 92% | 91% | Ascusbbr_110856 | SEQ ID NO: 362 | 0.29418 |
| 92. | Lachnospiraceae (*Clostridium* Cluster XIVb) (Family + Cluster) | Clostridiales bacterium | 99% | 99% | *Clostridium lactatifermentans* | 97% | 99% | Ascusbbr_185064 | SEQ ID NO: 363 | 0.21604 |
| 93. | *Clostridium* sensu stricto (Genus) | *Clostridium* sp. | 99% | 100% | *Clostridium thermobutyricum* | 99% | 99% | Ascusbbr_3315 | SEQ ID NO: 364 | 0.20534 |
| 94. | *Bacteroides dorei* | *Bacteroides dorei* | 100% | 100% | *Bacteroides dorei* | 100% | 100% | Ascusbbr_578 | SEQ ID NO: 365 | 0.74887 |
| 95. | *Lactobacillus* (Genus) | *Lactobacillus reuteri* | 95% | 100% | *Lactobacillus reuteri* | 95% | 100% | Ascusbbr_21169 | SEQ ID NO: 366 | 0.47787 |
| 96. | *Lactobacillus* (Genus) | *Lactobacillus reuteri* | 96% | 98% | *Lactobacillus reuteri* | 96% | 98% | Ascusbbr_110856 | SEQ ID NO: 367 | 0.39178 |
| 97. | *Lactobacillus* (Genus) | *Lactobacillus saerimneri* | 100% | 100% | *Lactobacillus saerimneri* | 100% | 100% | Ascusbbr_830 | SEQ ID NO: 368 | 0.33782 |
| 98. | *Clostridium* (Genus) | *Clostridium beijerinckii* | 99% | 100% | *Clostridium beijerinckii* | 99% | 100% | Ascusbbr_2676 | SEQ ID NO: 386 | 0.40777 |
| 99. | *Clostridium* (Genus) | *Clostridium saccharolyticum* | 100% | 99% | *Clostridium saccharolyticum* | 100% | 99% | Ascusbbr_105932 | SEQ ID NO: 387 | 0.47763 |
| 100. | Nectriaceae (Family) | *Fusarium annulatum* | 100% | 100% | *Fusarium annulatum* | 100% | 100% | Ascusfbr_15 | SEQ ID NO: 51 | 0.42622 |
| 101. | *Filobasidium floriforme* (Genus + species) | Uncultured fungus | 100% | 100% | *Cryptococcus magnus* | 100% | 100% | Ascusfbr_131 | SEQ ID NO: 52 | 0.42622 |
| 102. | *Gibberella zeae* (Genus + species) | *Fusarium asiaticum* | 100% | 100% | *Fusarium asiaticum* | 100% | 100% | Ascusfbr_26 | SEQ ID NO: 53 | 0.36913 |
| 103. | *Alatospora* (Genus) | Uncultured *Gymnoascus* | 83% | 81% | *Gymnoascus reesii* | 83% | 81% | Ascusfbr_2616 | SEQ ID NO: 54 | 0.33927 |
| 104. | Hypocreaceae (Family) | *Geotrichum* sp. | 100% | 100% | *Geotrichum candidum* | 100% | 100% | Ascusfbr_12 | SEQ ID NO: 55 | 0.32217 |
| 105. | *Pichia fermentans* (Genus + species) | *Pichia fermentans* | 100% | 100% | *Pichia fermentans* | 100% | 100% | Ascusfbr_53 | SEQ ID NO: 56 | 0.30645 |
| 106. | *Candida railenensis* (Genus + species) | *Candida railenensis* | 99% | 100% | *Candida railenensis* | 99% | 100% | Ascusfbr_1379 | SEQ ID NO: 57 | 0.28513 |
| 107. | Hypocreaceae (Family) | Uncultured fungus | 100% | 100% | *Geotrichum candidum* | 100% | 100% | Ascusfbr_122 | SEQ ID NO: 58 | 0.25801 |

In some embodiments, the isolated microbial strains of the present disclosure further encompass mutants thereof. In some embodiments, the present disclosure further contemplates microbial strains having all of the identifying characteristics of the presently disclosed microbial strains.

TABLE 2

Microbial Deposits Corresponding to the Microbes of Table 1

| Predicted Taxa of Isolated Microbes | Strain Designation | Sequence Identifier for Associated Marker | Deposit # | Predicted Taxa of Isolated Microbes | Strain Designation | Sequence Identifier for Associated Marker | Deposit # |
|---|---|---|---|---|---|---|---|
| *Lactobacillus* (Genus) | Ascusbbr_4729 | SEQ ID NO: 1 | PATENT201703004 | Peptostreptococcaceae *Clostridium* Cluster XI (Family + Cluster) | Ascusbbr_2158 | SEQ ID NO: 46 | PTA-124039 |
| Lachnospiraceae *Clostridium* Cluster XIVa (Family + Cluster) | Ascusbbr_339 | SEQ ID NO: 2 | PTA-124016, PTA-124039 | *Lactobacillus* (Genus) | Ascusbbr_373 | SEQ ID NO: 47 | |
| *Lactobacillus* (Genus) | Ascusbbr_5796(A) | SEQ ID NO: 3 | PATENT201703001, PATENT201703003, PATENT201703004, B-67267 | *Lactobacillus* (Genus) | Ascusbbr_1802 | SEQ ID NO: 48 | |
| *Lactobacillus* (Genus) | Ascusbbr_5796(B) | SEQ ID NO: 369 | PTA-124039 | | | | |
| *Lactobacillus* (Genus) | Ascusbbr_5796(C) | SEQ ID NO: 370 | PATENT201703002 | | | | |
| *Lactobacillus* (Genus) | Ascusbbr_38717(A) | SEQ ID NO: 4 | PATENT201703002, PATENT201703003, PATENT201703004, B-67268 | *Lactobacillus* (Genus) | Ascusbbr_107 | SEQ ID NO: 49 | PATENT201703002 |
| *Lactobacillus* (Genus) | Ascusbbr_38717(B) | SEQ ID NO: 373 | PATENT201703001 | | | | |
| *Lactobacillus* (Genus) | Ascusbbr_170211 | SEQ ID NO: 5 | PATENT201703002 | *Lactobacillus* (Genus) | Ascusbbr_1727 | SEQ ID NO: 50 | |
| *Lactobacillus* (Genus) | Ascusbbr_1686 | SEQ ID NO: 6 | PTA-124016, PTA-124039, PATENT201703001, PATENT201703002, PATENT201703003, PATENT201703004, B-67270 | *Corynebacterium* (Genus) | Ascusbbr_226 | SEQ ID NO: 338 | PATENT201703003 |
| *Faecalibacterium* (Genus) | Ascusbbr_1789 | SEQ ID NO: 7 | PTA-124016, PTA-124039, PATENT201703001 | *Streptococcus* (Genus) | Ascusbbr_17 | SEQ ID NO: 339 | PATENT201703002, PATENT201703003, PATENT201703004 |
| *Lactobacillus* (Genus) | Ascusbbr_3820 | SEQ ID NO: 8 | PTA-124039, PATENT201703002 | *Lactobacillus* (Genus) | Ascusbbr_14690(A) | SEQ ID NO: 340 | PTA-124039, PATENT201703001, PATENT201703002, PATENT201703003, PATENT201703004 |
| | | | | *Lactobacillus* (Genus) | Ascusbbr_14690(B) | SEQ ID NO: 371 | PTA-124016, |
| | | | | *Lactobacillus* (Genus) | Ascusbbr_14690(C) | SEQ ID NO: 372 | PATENT201703004 |
| *Hydrogenoanaero bacterium* (Genus) | Ascusbbr_173 | SEQ ID NO: 9 | PTA-124016, PTA-124039 | *Corynebacterium* (Genus) | Ascusbbr_18 | SEQ ID NO: 341 | PATENT201703003 |
| Peptostreptococcaceae *Clostridium* Cluster XI (Family + Cluster) | Ascusbbr_3089 | SEQ ID NO: 10 | PTA-124016 | Peptostreptococcaceae (*Clostridium* Cluster XI) (Family + Cluster) | Ascusbbr_7363 | SEQ ID NO: 342 | PTA-124016 |
| *Acrocarpospora* (Genus) | Ascusbbr_167 | SEQ ID NO: 11 | | *Corynebacterium* (Genus) | Ascusbbr_35 | SEQ ID NO: 343 | PATENT201703002, PATENT201703003, PATENT201703004 |
| *Lactobacillus* (Genus) | Ascusbbr_301568 | SEQ ID NO: 12 | | *Corynebacterium* (Genus) | Ascusbbr_7779 | SEQ ID NO: 344 | PATENT201703002, PATENT201703003, PATENT201703004 |

TABLE 2-continued

Microbial Deposits Corresponding to the Microbes of Table 1

| Predicted Taxa of Isolated Microbes | Strain Designation | Sequence Identifier for Associated Marker | Deposit # | Predicted Taxa of Isolated Microbes | Strain Designation | Sequence Identifier for Associated Marker | Deposit # |
|---|---|---|---|---|---|---|---|
| Bacillus (Genus) | Ascusbbr_33(A) | SEQ ID NO: 13 | PATENT201703002, PATENT201703003, B-67266 | Lachnospiraceae (Clostridium Cluster XIVa) (Family + Cluster) | Ascusbbr_10593(A) | SEQ ID NO: 345 | PTA-124039, PATENT201703001, PATENT201703002, PATENT201703003 |
| Bacillus (Genus) | Ascusbbr_33(B) | SEQ ID NO: 374 | PATENT201703001, | Lachnospiraceae (Clostridium Cluster XIVa) (Family + Cluster) | Ascusbbr_10593(B) | SEQ ID NO: 381 | PTA-124016, |
| Lactobacillus (Genus) | Ascusbbr_25200 | SEQ ID NO: 14 | PATENT201703001, PATENT201703002, PATENT201703003, PATENT201703004 | Lachnospiracea incertae sedis (Genus) | Ascusbbr_32731(A) | SEQ ID NO: 346 | PTA-124016, PATENT201703001, PATENT201703002 |
| | | | | Lachnospiracea incertae sedis (Genus) | Ascusbbr_32731(B) | SEQ ID NO: 382 | PTA-124039 |
| Subdoligranulum (Genus) | Ascusbbr_84 | SEQ ID NO: 15 | PTA-124039, PATENT201703003 | Ruminococcaceae (Clostridium Cluster III) (Family + Cluster) | Ascusbbr_359892 | SEQ ID NO: 347 | PTA-124039 |
| Subdoligranulum (Genus) | Ascusbbr_136 | SEQ ID NO: 16 | PTA-124016 | Lactobacillus (Genus) | Ascusbbr_25721 | SEQ ID NO: 348 | |
| Lachnospiraceae Clostridium Cluster XIVa (Family + Cluster) | Ascusbbr_128 | SEQ ID NO: 17 | PATENT201703004 | Streptococcus (Genus) | Ascusbbr_72076 | SEQ ID NO: 349 | PTA-124039, PATENT201703001, PATENT201703002, PATENT201703003, PATENT201703004 |
| Lactobacillus (Genus) | Ascusbbr_322104 | SEQ ID NO: 18 | PATENT201703001 | Lachnospiraceae (Clostridium Cluster XIVa) (Family + Cluster) | Ascusbbr_6097 | SEQ ID NO: 350 | PTA-124016, PTA-124039, PATENT201703002, PATENT201703003, PATENT201703004 |
| Lactobacillus (Genus) | Ascusbbr_409(A) | SEQ ID NO: 19 | PTA-124039, PATENT201703002, PATENT201703003, | Lactobacillus (Genus) | Ascusbbr_265 (A) | SEQ ID NO: 351 | PATENT201703001, PATENT201703002 |
| Lactobacillus (Genus) | Ascusbbr_409(B) | SEQ ID NO: 375 | PATENT201703004 | | | | PATENT201703004 |
| Lactobacillus (Genus) | Ascusbbr_409(C) | SEQ ID NO: 376 | PATENT201703001 | | | | |
| Lactobacillus (Genus) | Ascusbbr_409(D) | SEQ ID NO: 377 | PATENT201703001 | Lactobacillus (Genus) | Ascusbbr_265 (B) | SEQ ID NO: 385 | PATENT201703001, PATENT201703002, PATENT201703004 |
| Leuconostoc (Genus) | Ascusbbr_127 | SEQ ID NO: 20 | B-67265 | Paracoccus (Genus) | Ascusbbr_323376 | SEQ ID NO: 352 | PATENT201703002 |
| Lachnospiracea incertae sedis (Genus) | Ascusbbr_14834 | SEQ ID NO: 21 | PTA-124016, PTA-124039, PATENT201703001, PATENT201703002, PATENT201703003 | Cellulosilyticum (Genus) | Ascusbbr_36257 | SEQ ID NO: 353 | PTA-124039 |
| Lactobacillus (Genus) | Ascusbbr_331885(A) | SEQ ID NO: 22 | PTA-124039, PATENT201703002, PATENT201703003, B-67269 | Blautia (Genus) | Ascusbbr_6957 | SEQ ID NO: 354 | PTA-124039, PATENT201703002, PATENT201703003 |
| Lactobacillus (Genus) | Ascusbbr_331885(B) | SEQ ID NO: 378 | PATENT201703001 | | | | |

TABLE 2-continued

Microbial Deposits Corresponding to the Microbes of Table 1

| Predicted Taxa of Isolated Microbes | Strain Designation | Sequence Identifier for Associated Marker | Deposit # | Predicted Taxa of Isolated Microbes | Strain Designation | Sequence Identifier for Associated Marker | Deposit # |
|---|---|---|---|---|---|---|---|
| *Lactobacillus* (Genus) | Ascusbbr__331885(C) | SEQ ID NO: 379 | PATENT201703004 | | | | |
| *Anaerofilum* (Genus) | Ascusbbr__31 | SEQ ID NO: 23 | PTA-124039, PATENT201703002 | *Corynebacterium* (Genus) | Ascusbbr__38 | SEQ ID NO: 355 | PATENT201703003 |
| *Lachnospiracea incertae sedis* (Genus) | Ascusbbr__2307 | SEQ ID NO: 24 | PTA-124039 | *Lachnospiracea incertae sedis* (Genus) | Ascusbbr__13398 | SEQ ID NO: 356 | PTA-124039, PATENT201703003 |
| *Lachnospiraceae* *Clostridium* Cluster XIVa (Family + Cluster) | Ascusbbr__247(A) | SEQ ID NO: 25 | PTA-124039, PATENT201703004 | *Corynebacterium* (Genus) | Ascusbbr__57 | SEQ ID NO: 357 | PATENT201703003 |
| *Lachnospiraceae* *Clostridium* Cluster XIVa (Family + Cluster) | Ascusbbr__247(B) | SEQ ID NO: 380 | PTA-124016 | | | | |
| *Microbacterium* (Genus) | Ascusbbr__19 | SEQ ID NO: 26 | PATENT201703001, B-67264 | *Corynebacterium* (Genus) | Ascusbbr__285160 | SEQ ID NO: 358 | PTA-124039, PATENT201703001, PATENT201703002, PATENT201703003, PATENT201703004 |
| *Verrucosispora* (Genus) | Ascusbbr__69 | SEQ ID NO: 27 | | *Ruminococcus* (Genus) | Ascusbbr__37385 | SEQ ID NO: 359 | |
| *Anaerofilum* (Genus) | Ascusbbr__94 | SEQ ID NO: 28 | PATENT201703001, PATENT201703004 | *Lactobacillus* (Genus) | Ascusbbr__118124 | SEQ ID NO: 360 | PATENT201703001 |
| *Clostridium sensu stricto* (Genus) | Ascusbbr__313454 | SEQ ID NO: 29 | PATENT201703003, PATENT201703004 | *Roseburia* (Genus) | Ascusbbr__32592 | SEQ ID NO: 361 | PATENT201703002 |
| *Lactobacillus* (Genus) | Ascusbbr__351000 | SEQ ID NO: 30 | | *Lachnospiraceae* (*Clostridium* Cluster XIVa) (Family + Cluster) | Ascusbbr__110856 | SEQ ID NO: 362 | PATENT201703004 |
| *Lactobacillus* (Genus) | Ascusbbr__1436(A) | SEQ ID NO: 31 | PTA-124039, PATENT201703001, PATENT201703002, PATENT201703003, PATENT201703004 | *Lachnospiraceae* (*Clostridium* Cluster XIVb) (Family + Cluster) | Ascusbbr__185064 | SEQ ID NO: 363 | PTA-124039, PATENT201703001, PATENT201703002 |
| *Lactobacillus* (Genus) | Ascusbbr__1436(B) | SEQ ID NO: 383 | PTA-124016 | | | | |
| *Lachnospiraceae* *Clostridium* Cluster XIVa (Family + Cluster) | Ascusbbr__28 | SEQ ID NO: 32 | PTA-124016, PTA-124039, PATENT201703002 | *Clostridium sensu stricto* (Genus) | Ascusbbr __3315 | SEQ ID NO: 364 | |
| *Blautia* (Genus) | Ascusbbr__144 | SEQ ID NO: 33 | PTA-124039, PATENT201703002 | *Bacteroides dorei* | Ascusbbr__578 | SEQ ID NO: 365 | PTA-124039 |
| *Lactobacillus* (Genus) | Ascusbbr__42760(A) | SEQ ID NO: 34 | PTA-124039, PATENT201703002, PATENT201703003, PATENT201703004 | *Lactobacillus* (Genus) | Ascusbbr__21169 | SEQ ID NO: 366 | PATENT201703001 |
| *Lactobacillus* (Genus) | Ascusbbr__42760(B) | SEQ ID NO: 384 | PATENT201703001 | | | | |
| *Lactobacillus* (Genus) | Ascusbbr__134994 | SEQ ID NO: 35 | | *Lactobacillus* (Genus) | Ascusbbr__48584 | SEQ ID NO: 367 | PATENT201703004 |

TABLE 2-continued

Microbial Deposits Corresponding to the Microbes of Table 1

| Predicted Taxa of Isolated Microbes | Strain Designation | Sequence Identifier for Associated Marker | Deposit # | Predicted Taxa of Isolated Microbes | Strain Designation | Sequence Identifier for Associated Marker | Deposit # |
|---|---|---|---|---|---|---|---|
| *Lactobacillus* (Genus) | Ascusbbr__358773 | SEQ ID NO: 36 | | Nectriaceae (Family) | Ascusfbr__15 | SEQ ID NO: 51 | |
| *Pseudomonas* (Genus) | Ascusbbr__2503 | SEQ ID NO: 37 | PATENT201703001 | *Filobasidium floriforme* (Genus + species) | Ascusfbr __131 | SEQ ID NO: 52 | |
| *Sporobacter* (Genus) | Ascusbbr__312 | SEQ ID NO: 39 | PATENT201703002 | *Gibberella zeae* (Genus + species) | Ascusfbr __26 | SEQ ID NO: 53 | |
| *Lactobacillus* (Genus) | Ascusbbr__140914 | SEQ ID NO: 40 | | *Alatospora* (Genus) | Ascusfbr __2616 | SEQ ID NO: 54 | |
| *Lactobacillus* (Genus) | Ascusbbr__257627 | SEQ ID NO: 41 | | Hypocreaceae (Family) | Ascusfbr __12 | SEQ ID NO: 55 | |
| *Lactobacillus* (Genus) | Ascusbbr__310088 | SEQ ID NO: 42 | | *Pichia fermentans* (Genus + species) | Ascusfbr __53 | SEQ ID NO: 56 | |
| Lachnospiracea incertae sedis (Genus) | Ascusbbr__91 | SEQ ID NO: 43 | PTA-124016, PTA-124039, PATENT201703002, PATENT201703003 | *Candida railenensis* (Genus + species) | Ascusfbr __1379 | SEQ ID NO: 57 | |
| *Lactobacillus* (Genus) | Ascusbbr__150100 | SEQ ID NO: 44 | | Hypocreaceae (Family) | Ascusfbr __122 | SEQ ID NO: 58 | |
| *Lactobacillus* (Genus) | Ascusbbr__252028 | SEQ ID NO: 45 | | *Lactobacillus* (Genus) | Ascusbbr__830 | SEQ ID NO: 368 | PTA-124039 |
| *Clostridium beijerinckii* (Genus + species) | Ascusbbr__2676 | SEQ ID NO: 386 | PATENT201703003 PATENT201703004 | *Clostridium saccharolyticum* (Genus + species) | Ascusbbr__105932 | SEQ ID NO: 387 | PATENT201703001 PATENT201703002 |

TABLE 3

Bacteria of the present disclosure.

| | Predicted Closest Taxa of Isolated Microbes | Strain Designation | Sequence Identifier for Associated Marker | Predicted Closest Taxa of Isolated Microbes | Strain Designation | Sequence Identifier for Associated Marker |
|---|---|---|---|---|---|---|
| 1. | *Clostridium* XIVb (Cluster) | Ascusbbr_6 | SEQ ID NO: 59 | *Actinomyces* (Genus) | Ascusbbr_2226 | SEQ ID NO: 199 |
| 2. | *Gemmiger* (Genus) | Ascusbbr_113 | SEQ ID NO: 60 | *Succiniclasticum* (Genus) | Ascusbbr_2227 | SEQ ID NO: 200 |
| 3. | *Lactobacillus* (Genus) | Ascusbbr_116 | SEQ ID NO: 61 | *Beijerinckia* (Genus) | Ascusbbr_2229 | SEQ ID NO: 201 |
| 4. | *Clostridium* XI (Cluster) | Ascusbbr_129 | SEQ ID NO: 62 | *Bosea* (Genus) | Ascusbbr_2235 | SEQ ID NO: 202 |
| 5. | *Jeotgalicoccus* (Genus) | Ascusbbr_265 | SEQ ID NO: 63 | *Sporobacter* (Genus) | Ascusbbr_2237 | SEQ ID NO: 203 |
| 6. | *Lactobacillus* (Genus) | Ascusbbr_275 | SEQ ID NO: 64 | *Facklamia* (Genus) | Ascusbbr_2251 | SEQ ID NO: 204 |
| 7. | *Lactobacillus* (Genus) | Ascusbbr_343 | SEQ ID NO: 65 | *Acinetobacter* (Genus) | Ascusbbr_2266 | SEQ ID NO: 205 |
| 8. | *Lactobacillus* (Genus) | Ascusbbr_363 | SEQ ID NO: 66 | *Brevundimonas* (Genus) | Ascusbbr_2284 | SEQ ID NO: 206 |
| 9. | *Jeotgalicoccus* (Genus) | Ascusbbr_399 | SEQ ID NO: 67 | *Ochrobactrum* (Genus) | Ascusbbr_2285 | SEQ ID NO: 207 |
| 10. | *Lactobacillus* (Genus) | Ascusbbr_444 | SEQ ID NO: 68 | *Alcaligenes* (Genus) | Ascusbbr_2290 | SEQ ID NO: 208 |
| 11. | *Jeotgalicoccus* (Genus) | Ascusbbr_498 | SEQ ID NO: 69 | *Pseudochrobactrum* (Genus) | Ascusbbr_2291 | SEQ ID NO: 209 |
| 12. | *Lactobacillus* (Genus) | Ascusbbr_542 | SEQ ID NO: 70 | *Jeotgalicoccus* (Genus) | Ascusbbr_2292 | SEQ ID NO: 210 |
| 13. | *Lactobacillus* (Genus) | Ascusbbr_561 | SEQ ID NO: 71 | *Jeotgalicoccus* (Genus) | Ascusbbr_2293 | SEQ ID NO: 211 |

TABLE 3-continued

Bacteria of the present disclosure.

| Predicted Closest Taxa of Isolated Microbes | Strain Designation | Sequence Identifier for Associated Marker | Predicted Closest Taxa of Isolated Microbes | Strain Designation | Sequence Identifier for Associated Marker |
|---|---|---|---|---|---|
| 14. *Lactobacillus* (Genus) | Ascusbbr_570 | SEQ ID NO: 72 | *Acinetobacter* (Genus) | Ascusbbr_2294 | SEQ ID NO: 212 |
| 15. *Corynebacterium* (Genus) | Ascusbbr_616 | SEQ ID NO: 73 | *Sphingobacterium* (Genus) | Ascusbbr_2295 | SEQ ID NO: 213 |
| 16. *Microbacterium* (Genus) | Ascusbbr_620 | SEQ ID NO: 74 | Lachnospiracea (Genus) | Ascusbbr_2301 | SEQ ID NO: 214 |
| 17. *Jeotgalicoccus* (Genus) | Ascusbbr_690 | SEQ ID NO: 75 | *Azospirillum* (Genus) | Ascusbbr_2302 | SEQ ID NO: 215 |
| 18. *Jeotgalicoccus* (Genus) | Ascusbbr_705 | SEQ ID NO: 76 | *Lactobacillus* (Genus) | Ascusbbr_2313 | SEQ ID NO: 216 |
| 19. *Glycomyces* (Genus) | Ascusbbr_793 | SEQ ID NO: 77 | *Clavibacter* (Genus) | Ascusbbr_2320 | SEQ ID NO: 217 |
| 20. *Streptomyces* (Genus) | Ascusbbr_795 | SEQ ID NO: 78 | *Clostridium* XIVa (Cluster) | Ascusbbr_2324 | SEQ ID NO: 218 |
| 21. *Saccharopolyspora* (Genus) | Ascusbbr_796 | SEQ ID NO: 79 | *Clostridium* XIVa (Cluster) | Ascusbbr_2325 | SEQ ID NO: 219 |
| 22. *Brevibacterium* (Genus) | Ascusbbr_803 | SEQ ID NO: 80 | *Lactobacillus* (Genus) | Ascusbbr_2328 | SEQ ID NO: 220 |
| 23. *Microbacterium* (Genus) | Ascusbbr_804 | SEQ ID NO: 81 | *Clostridium* XIVa (Cluster) | Ascusbbr_2331 | SEQ ID NO: 221 |
| 24. *Acinetobacter* (Genus) | Ascusbbr_840 | SEQ ID NO: 82 | *Bacillus* (Genus) | Ascusbbr_2337 | SEQ ID NO: 222 |
| 25. *Lactococcus* (Genus) | Ascusbbr_846 | SEQ ID NO: 83 | *Methanoplanus* (Genus) | Ascusbbr_2354 | SEQ ID NO: 223 |
| 26. *Cloacibacterium* (Genus) | Ascusbbr_867 | SEQ ID NO: 84 | *Mogibacterium* (Genus) | Ascusbbr_2361 | SEQ ID NO: 224 |
| 27. *Mycobacterium* (Genus) | Ascusbbr_929 | SEQ ID NO: 85 | *Brachybacterium* (Genus) | Ascusbbr_2368 | SEQ ID NO: 225 |
| 28. *Leucobacter* (Genus) | Ascusbbr_944 | SEQ ID NO: 86 | *Facklamia* (Genus) | Ascusbbr_2376 | NO: 226 SEQ ID NO: 226 |
| 29. *Lactobacillus* (Genus) | Ascusbbr_950 | SEQ ID NO: 87 | *Clostridium* XIVa (Cluster) | Ascusbbr_2378 | SEQ ID NO: 227 |
| 30. *Rothia* (Genus) | Ascusbbr_951 | SEQ ID NO: 88 | *Clostridium* XIVa (Cluster) | Ascusbbr_2380 | SEQ ID NO: 228 |
| 31. *Lactobacillus* (Genus) | Ascusbbr_996 | SEQ ID NO: 89 | *Syntrophomonas* (Genus) | Ascusbbr_2383 | SEQ ID NO: 229 |
| 32. *Clavibacter* (Genus) | Ascusbbr_1005 | SEQ ID NO: 90 | *Beijerinckia* (Genus) | Ascusbbr_2386 | SEQ ID NO: 230 |
| 33. *Hydrogenoanaerobacterium* (Genus) | Ascusbbr_1029 | SEQ ID NO: 91 | *Lactobacillus* (Genus) | Ascusbbr_2390 | SEQ ID NO: 231 |
| 34. *Howardella* (Genus) | Ascusbbr_1036 | SEQ ID NO: 92 | *Lactobacillus* (Genus) | Ascusbbr_2391 | SEQ ID NO: 232 |
| 35. *Clostridium* (Genus) | Ascusbbr_1069 | SEQ ID NO: 93 | *Lactobacillus* (Genus) | Ascusbbr_2395 | SEQ ID NO: 233 |
| 36. | Ascusbbr_1128 | SEQ ID NO: 94 | Erysipelotrichaceae (Family) | Ascusbbr_2397 | SEQ ID NO: 234 |
| 37. *Hydrogenoanaerobacterium* (Genus) | Ascusbbr_1139 | SEQ ID NO: 95 | *Rummeliibacillus* (Genus) | Ascusbbr_2399 | SEQ ID NO: 235 |
| 38. *Papillibacter* (Genus) | Ascusbbr_1169 | SEQ ID NO: 96 | *Acinetobacter* (Genus) | Ascusbbr_2402 | SEQ ID NO: 236 |
| 39. *Butyricicoccus* (Genus) | Ascusbbr_1185 | SEQ ID NO: 97 | *Lactococcus* (Genus) | Ascusbbr_2403 | SEQ ID NO: 237 |
| 40. *Eubacterium* (Genus) | Ascusbbr_1245 | SEQ ID NO: 98 | *Propionibacterium* (Genus) | Ascusbbr_2412 | SEQ ID NO: 238 |
| 41. *Turicibacter* (Genus) | Ascusbbr_1258 | SEQ ID NO: 99 | *Clostridium* (Genus) | Ascusbbr_2413 | SEQ ID NO: 239 |
| 42. *Lactobacillus* (Genus) | Ascusbbr_1264 | SEQ ID NO: 100 | *Clostridium* XIVa (Cluster) | Ascusbbr_2416 | SEQ ID NO: 240 |
| 43. *Asaccharobacter* (Genus) | Ascusbbr_1332 | SEQ ID NO: 101 | *Rummeliibacillus* (Genus) | Ascusbbr_2419 | SEQ ID NO: 241 |
| 44. *Faecalibacterium* (Genus) | Ascusbbr_1360 | SEQ ID NO: 102 | *Ralstonia* (Genus) | Ascusbbr_2420 | SEQ ID NO: 242 |
| 45. *Clostridium* XIVa (Cluster) | Ascusbbr_1363 | SEQ ID NO: 103 | *Brachybacterium* (Genus) | Ascusbbr_2421 | SEQ ID NO: 243 |
| 46. *Clostridium* XIVa (Cluster) | Ascusbbr_1422 | SEQ ID NO: 104 | *Ruminobacter* (Genus) | Ascusbbr_2423 | SEQ ID NO: 244 |
| 47. *Clostridium* IV (Cluster) | Ascusbbr_1424 | SEQ ID NO: 105 | *Glycomyces* (Genus) | Ascusbbr_2427 | SEQ ID NO: 245 |
| 48. *Clostridium* XIVb (Cluster) | Ascusbbr_1433 | SEQ ID NO: 106 | *Psychrobacter* (Genus) | Ascusbbr_2428 | SEQ ID NO: 246 |
| 49. *Butyricicoccus* (Genus) | Ascusbbr_1456 | SEQ ID NO: 107 | *Yaniella* (Genus) | Ascusbbr_2429 | SEQ ID NO: 247 |

TABLE 3-continued

Bacteria of the present disclosure.

| Predicted Closest Taxa of Isolated Microbes | Strain Designation | Sequence Identifier for Associated Marker | Predicted Closest Taxa of Isolated Microbes | Strain Designation | Sequence Identifier for Associated Marker |
|---|---|---|---|---|---|
| 50. *Sporobacter* (Genus) | Ascusbbr_1485 | SEQ ID NO: 108 | *Clostridium* IV (Cluster) | Ascusbbr_2431 | SEQ ID NO: 248 |
| 51. *Butyricicoccus* (Genus) | Ascusbbr_1488 | SEQ ID NO: 109 | *Clostridium* (Genus) | Ascusbbr_2434 | SEQ ID NO: 249 |
| 52. *Hydrogenoanaerobacterium* (Genus) | Ascusbbr_1490 | SEQ ID NO: 110 | *Clostridium* XIVa (Cluster) | Ascusbbr_2435 | SEQ ID NO: 250 |
| 53. *Anaerofilum* (Genus) | Ascusbbr_1493 | SEQ ID NO: 111 | *Clostridium* (Genus) | Ascusbbr_2436 | SEQ ID NO: 251 |
| 54. *Clostridium* XIVa (Cluster) | Ascusbbr_1536 | SEQ ID NO: 112 | *Clostridium* XIVa (Cluster) | Ascusbbr_2437 | SEQ ID NO: 252 |
| 55. *Clostridium* XIVa (Cluster) | Ascusbbr_1541 | SEQ ID NO: 113 | *Cohnella* (Genus) | Ascusbbr_2438 | SEQ ID NO: 253 |
| 56. Lachnospiracea (Family) | Ascusbbr_1572 | SEQ ID NO: 114 | *Chthonomonas* (Genus) | Ascusbbr_2441 | SEQ ID NO: 254 |
| 57. Lachnospiracea (Family) | Ascusbbr_1592 | SEQ ID NO: 115 | *Streptophyta* (Unranked Clade) | Ascusbbr_2445 | SEQ ID NO: 255 |
| 58. *Butyricicoccus* (Genus) | Ascusbbr_1611 | SEQ ID NO: 116 | *Acinetobacter* (Genus) | Ascusbbr_2452 | SEQ ID NO: 256 |
| 59. *Pediococcus* (Genus) | Ascusbbr_1614 | SEQ ID NO: 117 | *Clostridium* XIVb | Ascusbbr_2456 | SEQ ID NO: 257 |
| 60. *Acetanaerobacterium* (Genus) | Ascusbbr_1616 | SEQ ID NO: 118 | *Neisseria* | Ascusbbr_2465 | SEQ ID NO: 258 |
| 61. *Hydrogenoanaerobacterium* (Genus) | Ascusbbr_1623 | SEQ ID NO: 119 | *Butyricicoccus* | Ascusbbr_2471 | SEQ ID NO: 259 |
| 62. *Butyricicoccus* (Genus) | Ascusbbr_1625 | SEQ ID NO: 120 | *Sporobacter* | Ascusbbr_2472 | SEQ ID NO: 260 |
| 63. Lachnospiracea (Family) | Ascusbbr_1632 | SEQ ID NO: 121 | *Sporobacter* | Ascusbbr_2476 | SEQ ID NO: 261 |
| 64. Erysipelotrichaceae (Family) | Ascusbbr_1634 | SEQ ID NO: 122 | *Syntrophomonas* | Ascusbbr_2477 | SEQ ID NO: 262 |
| 65. Lachnospiracea (Family) | Ascusbbr_1635 | SEQ ID NO: 123 | *Desulfotomaculum* | Ascusbbr_2478 | SEQ ID NO: 263 |
| 66. *Butyricicoccus* (Genus) | Ascusbbr_1646 | SEQ ID NO: 124 | *Streptophyta* | Ascusbbr_2482 | SEQ ID NO: 264 |
| 67. *Butyricicoccus* (Genus) | Ascusbbr_1669 | SEQ ID NO: 125 | *Acetomicrobium* | Ascusbbr_2489 | SEQ ID NO: 265 |
| 68. *Butyricicoccus* (Genus) | Ascusbbr_1670 | SEQ ID NO: 126 | *Acinetobacter* | Ascusbbr_2492 | SEQ ID NO: 266 |
| 69. *Butyricicoccus* (Genus) | Ascusbbr_1674 | SEQ ID NO: 127 | Erysipelotrichaceae | Ascusbbr_2493 | SEQ ID NO: 267 |
| 70. *Butyricicoccus* (Genus) | Ascusbbr_1678 | SEQ ID NO: 128 | *Jeotgalicoccus* | Ascusbbr_2496 | SEQ ID NO: 268 |
| 71. Lachnospiracea (Family) | Ascusbbr_1679 | SEQ ID NO: 129 | *Selenomonas* | Ascusbbr_2497 | SEQ ID NO: 269 |
| 72. *Howardella* (Genu) | Ascusbbr_1684 | SEQ ID NO: 130 | *Howardella* | Ascusbbr_2498 | SEQ ID NO: 270 |
| 73. Lachnospiracea (Family) | Ascusbbr_1685 | SEQ ID NO: 131 | *Clostridium* XIVa | Ascusbbr_2500 | SEQ ID NO: 271 |
| 74. *Clavibacter* (Genus) | Ascusbbr_1694 | SEQ ID NO: 132 | Lachnospiracea | Ascusbbr_2501 | SEQ ID NO: 272 |
| 75. *Butyricicoccus* (Genus) | Ascusbbr_1695 | SEQ ID NO: 133 | Lachnospiracea | Ascusbbr_2504 | SEQ ID NO: 273 |
| 76. *Hydrogenoanaerobacterium* (Genus) | Ascusbbr_1715 | SEQ ID NO: 134 | *Clostridium* XIVa | Ascusbbr_2506 | SEQ ID NO: 274 |
| 77. *Spiroplasma* (Genus) | Ascusbbr_1720 | SEQ ID NO: 135 | Lachnospiracea | Ascusbbr_2508 | SEQ ID NO: 275 |
| 78. *Clostridium* XIVa (Cluster) | Ascusbbr_1722 | SEQ ID NO: 136 | *Bacillus* | Ascusbbr_2509 | SEQ ID NO: 276 |
| 79. *Jeotgalicoccus* (Genus) | Ascusbbr_1723 | SEQ ID NO: 137 | *Paenibacillus* | Ascusbbr_2510 | SEQ ID NO: 277 |
| 80. *Syntrophomonas* (Genus) | Ascusbbr_1743 | SEQ ID NO: 138 | *Eubacterium* | Ascusbbr_2511 | SEQ ID NO: 278 |
| 81. *Clostridium* IV (Cluster) | Ascusbbr_1746 | SEQ ID NO: 139 | *Amphibacillus* | Ascusbbr_2512 | SEQ ID NO: 279 |
| 82. Lachnospiracea (Family) | Ascusbbr_1748 | SEQ ID NO: 140 | *Staphylococcus* | Ascusbbr_2513 | SEQ ID NO: 280 |
| 83. *Hydrogenoanaerobacterium* (Genus) | Ascusbbr_1753 | SEQ ID NO: 141 | *Paenibacillus* | Ascusbbr_2514 | SEQ ID NO: 281 |
| 84. *Oscillibacter* (Genus) | Ascusbbr_1756 | SEQ ID NO: 142 | *Clostridium* IV | Ascusbbr_2515 | SEQ ID NO: 282 |
| 85. *Clostridium* IV (Cluster) | Ascusbbr_1785 | SEQ ID NO: 143 | *Prevotella* | Ascusbbr_2516 | SEQ ID NO: 283 |

TABLE 3-continued

Bacteria of the present disclosure.

| Predicted Closest Taxa of Isolated Microbes | Strain Designation | Sequence Identifier for Associated Marker | Predicted Closest Taxa of Isolated Microbes | Strain Designation | Sequence Identifier for Associated Marker |
|---|---|---|---|---|---|
| 86. *Sporobacter* (Genus) | Ascusbbr_1812 | SEQ ID NO: 144 | *Barnesiella* | Ascusbbr_2518 | SEQ ID NO: 284 |
| 87. *Pediococcus* (Genus) | Ascusbbr_1821 | SEQ ID NO: 145 | *Clostridium* XIVa | Ascusbbr_2519 | SEQ ID NO: 285 |
| 88. *Sporobacter* (Genus) | Ascusbbr_1824 | SEQ ID NO: 146 | *Clostridium* XI/Va | Ascusbbr_2520 | SEQ ID NO: 286 |
| 89. *Bacillus* (Genus) | Ascusbbr_1866 | SEQ ID NO: 147 | *Sharpea* | Ascusbbr_2521 | SEQ ID NO: 287 |
| 90. *Cellulomonas* (Genus) | Ascusbbr_1882 | SEQ ID NO: 148 | Lachnospiracea | Ascusbbr_2522 | SEQ ID NO: 288 |
| 91. *Syntrophomonas* (Genus) | Ascusbbr_1887 | SEQ ID NO: 149 | *Leucobacter* | Ascusbbr_2523 | SEQ ID NO: 289 |
| 92. *Cryptanaerobacter* (Genus) | Ascusbbr_1928 | SEQ ID NO: 150 | *Lactonifactor* | Ascusbbr_2524 | SEQ ID NO: 290 |
| 93. *Sporobacter* (Genus) | Ascusbbr_1932 | SEQ ID NO: 151 | Lachnospiracea | Ascusbbr_2525 | SEQ ID NO: 291 |
| 94. *Hydrogenoanaerobacterium* (Genus) | Ascusbbr_1933 | SEQ ID NO: 152 | *Succiniclasticum* | Ascusbbr_2526 | SEQ ID NO: 292 |
| 95. *Clostridium* IV (Cluster) | Ascusbbr_1937 | SEQ ID NO: 153 | *Acidovorax* | Ascusbbr_2528 | SEQ ID NO: 293 |
| 96. *Hydrogenoanaerobacterium* (Genus) | Ascusbbr_1953 | SEQ ID NO: 154 | *Acinetobacter* | Ascusbbr_2530 | SEQ ID NO: 294 |
| 97. *Spiroplasma* (Genus) | Ascusbbr_1955 | SEQ ID NO: 155 | *Comamonas* | Ascusbbr_2531 | SEQ ID NO: 295 |
| 98. Erysipelotrichaceae (Family) | Ascusbbr_1956 | SEQ ID NO: 156 | *Prevotella* | Ascusbbr_2533 | SEQ ID NO: 296 |
| 99. *Pseudoflavonifractor* (Genus) | Ascusbbr_1957 | SEQ ID NO: 157 | *Clostridium* IV | Ascusbbr_2534 | SEQ ID NO: 297 |
| 100. *Clostridium* XIVa (Cluster) | Ascusbbr_1967 | SEQ ID NO: 158 | *Clostridium* | Ascusbbr_2535 | SEQ ID NO: 298 |
| 101. *Mogibacterium* (Genus) | Ascusbbr_1969 | SEQ ID NO: 159 | *Succiniclasticum* | Ascusbbr_2536 | SEQ ID NO: 299 |
| 102. *Clostridium* (Genus) | Ascusbbr_1973 | SEQ ID NO: 160 | Lachnospiracea | Ascusbbr_2538 | SEQ ID NO: 300 |
| 103. *Clostridium* IV (Cluster) | Ascusbbr_2020 | SEQ ID NO: 161 | *Pedobacter* | Ascusbbr_2539 | SEQ ID NO: 301 |
| 104. *Citrobacter* (Genus) | Ascusbbr_2023 | SEQ ID NO: 162 | *Clostridium* XII | Ascusbbr_2540 | SEQ ID NO: 302 |
| 105. *Hydrogenoanaerobacterium* (Genus) | Ascusbbr_2033 | SEQ ID NO: 163 | *Flavobacterium* | Ascusbbr_2544 | SEQ ID NO: 303 |
| 106. *Clostridium* XIVa (Cluster) | Ascusbbr_2047 | SEQ ID NO: 164 | *Clostridium* | Ascusbbr_2545 | SEQ ID NO: 304 |
| 107. *Clostridium* XIVa (Cluster) | Ascusbbr_2049 | SEQ ID NO: 165 | *Alkaliphilus* | Ascusbbr_2547 | SEQ ID NO: 305 |
| 108. *Clostridium* (Genus) | Ascusbbr_2057 | SEQ ID NO: 166 | *Arthrobacter* | Ascusbbr_2548 | SEQ ID NO: 306 |
| 109. Erysipelotrichaceae (Family) | Ascusbbr_2069 | SEQ ID NO: 167 | *Flavobacterium* | Ascusbbr_2549 | SEQ ID NO: 307 |
| 110. *Clostridium* XIVb (Cluster) | Ascusbbr_2073 | SEQ ID NO: 168 | *Roseburia* | Ascusbbr_2550 | SEQ ID NO: 308 |
| 111. *Clostridium* XIVb (Cluster) | Ascusbbr_2076 | SEQ ID NO: 169 | *Paenibacillus* | Ascusbbr_2551 | SEQ ID NO: 309 |
| 112. *Butyricicoccus* (Genus) | Ascusbbr_2101 | SEQ ID NO: 170 | *Olivibacter* | Ascusbbr_2553 | SEQ ID NO: 310 |
| 113. *Pediococcus* (Genus) | Ascusbbr_2118 | SEQ ID NO: 171 | *Clostridium* XII | Ascusbbr_2554 | SEQ ID NO: 311 |
| 114. *Sphingomonas* (Genus) | Ascusbbr_2127 | SEQ ID NO: 172 | *Sphingobacterium* | Ascusbbr_2555 | SEQ ID NO: 312 |
| 115. *Clostridium* XIVa (Cluster) | Ascusbbr_2131 | SEQ ID NO: 173 | *Sphingobacterium* | Ascusbbr_2556 | SEQ ID NO: 313 |
| 116. *Clostridium* IV (Cluster) | Ascusbbr_2132 | SEQ ID NO: 174 | *Anaerosporobacter* | Ascusbbr_2557 | SEQ ID NO: 314 |
| 117. *Clostridium* XIVb (Cluster) | Ascusbbr_2136 | SEQ ID NO: 175 | *Clostridium* XII | Ascusbbr_2560 | SEQ ID NO: 315 |
| 118. *Clostridium* XIVb (Cluster) | Ascusbbr_2137 | SEQ ID NO: 176 | *Clostridium* XII | Ascusbbr_2561 | SEQ ID NO: 316 |
| 119. *Methylobacterium* (Genus) | Ascusbbr_2149 | SEQ ID NO: 177 | *Clostridium* | Ascusbbr_2562 | SEQ ID NO: 317 |
| 120. *Solana* (Genus) | Ascusbbr_2177 | SEQ ID NO: 178 | *Pedobacter* | Ascusbbr_2563 | SEQ ID NO: 318 |
| 121. *Petrobacter* (Genus) | Ascusbbr_2178 | SEQ ID NO: 179 | *Bacillus* | Ascusbbr_2564 | SEQ ID NO: 319 |

TABLE 3-continued

Bacteria of the present disclosure.

| | Predicted Closest Taxa of Isolated Microbes | Strain Designation | Sequence Identifier for Associated Marker | Predicted Closest Taxa of Isolated Microbes | Strain Designation | Sequence Identifier for Associated Marker |
|---|---|---|---|---|---|---|
| 122. | *Bacillus* (Genus) | Ascusbbr_2180 | SEQ ID NO: 180 | *Paenibacillus* | Ascusbbr_2565 | SEQ ID NO: 320 |
| 123. | *Thermovibrio* (Genus) | Ascusbbr_2183 | SEQ ID NO: 181 | *Prevotella* | Ascusbbr_2566 | SEQ ID NO: 321 |
| 124. | Erysipelotrichaceae (Family) | Ascusbbr_2184 | SEQ ID NO: 182 | Lachnospiracea (Family) | Ascusbbr_2567 | SEQ ID NO: 322 |
| 125. | *Selenomonas* (Genus) | Ascusbbr_2192 | SEQ ID NO: 183 | Lachnospiracea (Family) | Ascusbbr_2568 | SEQ ID NO: 323 |
| 126. | *Glaciecola* (Genus) | Ascusbbr_2193 | SEQ ID NO: 184 | *Escherichia/Shigella* (Genus) | Ascusbbr_2594 | SEQ ID NO: 324 |
| 127. | *Lactobacillus* (Genus) | Ascusbbr_2195 | SEQ ID NO: 185 | *Lactobacillus* (Genus) | Ascusbbr_2603 | SEQ ID NO: 325 |
| 128. | *Eubacterium* (Genus) | Ascusbbr_2200 | SEQ ID NO: 186 | *Corynebacterium* (Genus) | Ascusbbr_2605 | SEQ ID NO: 326 |
| 129. | *Thermomicrobium* (Genus) | Ascusbbr_2201 | SEQ ID NO: 187 | *Lactobacillus* (Genus) | Ascusbbr_2615 | SEQ ID NO: 327 |
| 130. | *Acidobacteria* (Genus) | Ascusbbr_2204 | SEQ ID NO: 188 | *Lactobacillus* (Genus) | Ascusbbr_2625 | SEQ ID NO: 328 |
| 131. | *Chlorobaculum* (Genus) | Ascusbbr_2205 | SEQ ID NO: 189 | *Escherichia/Shigella* (Genus) | Ascusbbr_2640 | SEQ ID NO: 329 |
| 132. | *Rothia* (Genus) | Ascusbbr_2208 | SEQ ID NO: 190 | *Lactobacillus* (Genus) | Ascusbbr_2644 | SEQ ID NO: 330 |
| 133. | *Selenomonas* (Genus) | Ascusbbr_2210 | SEQ ID NO: 191 | *Lactobacillus* (Genus) | Ascusbbr_2665 | SEQ ID NO: 331 |
| 134. | *Clostridium* XIVa (Cluster) | Ascusbbr_2215 | SEQ ID NO: 192 | *Lactobacillus* (Genus) | Ascusbbr_2684 | SEQ ID NO: 332 |
| 135. | *Virgibacillus* (Genus) | Ascusbbr_2216 | SEQ ID NO: 193 | *Lactobacillus* (Genus) | Ascusbbr_2694 | SEQ ID NO: 333 |
| 136. | *Sphingomonas* (Genus) | Ascusbbr_2218 | SEQ ID NO: 194 | *Lactobacillus* (Genus) | Ascusbbr_2699 | SEQ ID NO: 334 |
| 137. | *Citricoccus* (Genus) | Ascusbbr_2219 | SEQ ID NO: 195 | *Lactobacillus* (Genus) | Ascusbbr_2709 | SEQ ID NO: 335 |
| 138. | *Catenibacterium* (Genus) | Ascusbbr_2220 | SEQ ID NO: 196 | *Lactobacillus* (Genus) | Ascusbbr_2710 | SEQ ID NO: 336 |
| 139. | *Amycolatopsis* (Genus) | Ascusbbr_2224 | SEQ ID NO: 197 | *Enterococcus* (Genus) | Ascusbbr_2714 | SEQ ID NO: 337 |
| 140. | *Sphingobium* (Genus) | Ascusbbr_2225 | SEQ ID NO: 198 | *Clostridium* sensu stricto (Genus) | Ascusbbr_2676 | SEQ ID NO: 386 |
| 141. | Clostridium_XIVa (Cluster) | Ascusbbr_105932 | SEQ ID NO: 387 | | | |

BRIEF DESCRIPTION OF THE FIGURES

FIG. 3 is a graphical representation of the timeline of actions/events which occurred over the 21 study days of the Phase I study which utilized Cobb 500 broiler chickens.

FIG. 4 is a graphical representation of the timeline of actions/events which occurred over the 21 study days of the Phase II study which utilized Ross 708 broiler chickens.

FIG. 10 depicts an undegraded carbon source (Day 0) and a degraded carbon source (Day 7), as utilized in the insoluble carbon source assays.

DETAILED DESCRIPTION

Definitions

Figure 1:
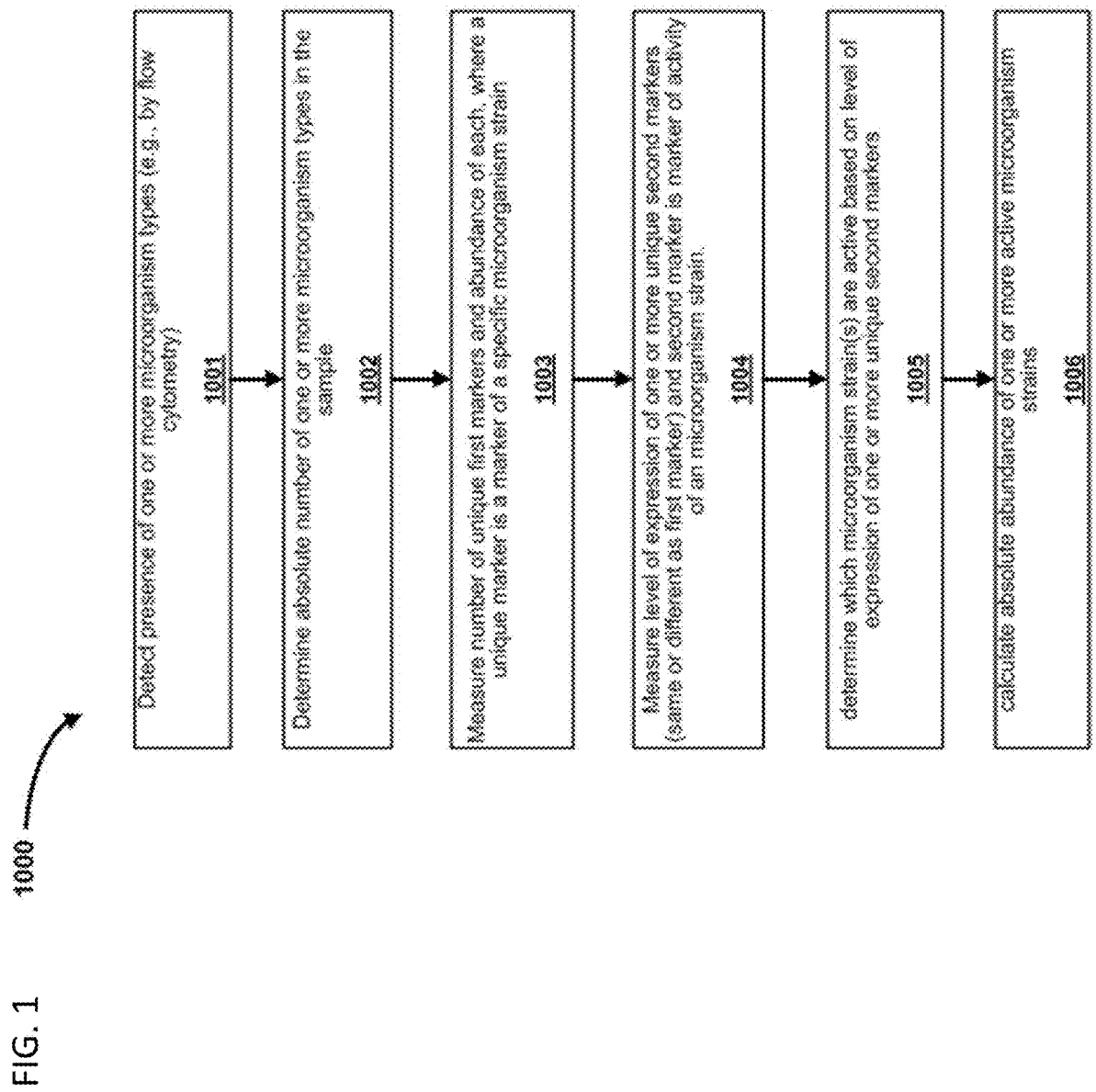
FIG. 1 shows a general workflow of one embodiment of the method for determining the absolute abundance of one or more active microorganism strains.

While the following terms are believed to be well understood by one of ordinary skill in the art, the following definitions are set forth to facilitate explanation of the presently disclosed subject matter.

The term "a" or "an" may refer to one or more of that entity, i.e. can refer to plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

Reference throughout this specification to "one embodiment", "an embodiment", "one aspect", or "an aspect" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments.

As used herein, in particular embodiments, the terms "about" or "approximately" when preceding a numerical value indicates the value plus or minus a range of 10%.

As used herein the terms "microorganism" or "microbe" should be taken broadly. These terms are used interchangeably and include, but are not limited to, the two prokaryotic domains, Bacteria and Archaea, eukaryotic fungi and protists, as well as viruses. In some embodiments, the disclosure refers to the "microbes" of Table 1 and/or Table 3, or the "microbes" incorporated by reference. This characterization can refer to not only the predicted taxonomic microbial identifiers of the table, but also the identified strains of the microbes listed in the table.

The term "microbial ensemble" or "microbial synthetic ensemble" refers to a subset of a microbial community of individual microbial species, or strains of a species, which can be described as carrying out a common function, or can be described as participating in, or leading to, or correlating with, a recognizable parameter, such as a phenotypic trait of interest (e.g. increased feed efficiency in poultry). The community may comprise two or more species, or strains of a species, of microbes. In some instances, the microbes coexist within the community symbiotically.

The term "microbial community" means a group of microbes comprising two or more species or strains. Unlike microbial ensembles, a microbial community does not have to be carrying out a common function, or does not have to be participating in, or leading to, or correlating with, a recognizable parameter, such as a phenotypic trait of interest (e.g. increased feed efficiency in poultry).

As used herein, "isolate," "isolated," "isolated microbe," and like terms, are intended to mean that the one or more microorganisms has been separated from at least one of the materials with which it is associated in a particular environment (for example soil, water, animal tissue).

Microbes of the present disclosure may include spores and/or vegetative cells. In some embodiments, microbes of the present disclosure include microbes in a viable but non-culturable (VBNC) state, or a quiescent state. See Liao and Zhao (US Publication US2015267163A1). In some embodiments, microbes of the present disclosure include microbes in a biofilm. See Merritt et al. (U.S. Pat. No. 7,427,408).

Thus, an "isolated microbe" does not exist in its naturally occurring environment; rather, it is through the various techniques described herein that the microbe has been removed from its natural setting and placed into a non-naturally occurring state of existence. Thus, the isolated strain or isolated microbe may exist as, for example, a biologically pure culture, or as spores (or other forms of the strain) in association with an acceptable carrier.

As used herein, "spore" or "spores" refer to structures produced by bacteria and fungi that are adapted for survival and dispersal. Spores are generally characterized as dormant structures; however, spores are capable of differentiation through the process of germination. Germination is the differentiation of spores into vegetative cells that are capable of metabolic activity, growth, and reproduction. The germination of a single spore results in a single fungal or bacterial vegetative cell. Fungal spores are units of asexual reproduction, and in some cases are necessary structures in fungal life cycles. Bacterial spores are structures for surviving conditions that may ordinarily be nonconductive to the survival or growth of vegetative cells.

As used herein, "microbial composition" refers to a composition comprising one or more microbes of the present disclosure, wherein a microbial composition, in some embodiments, is administered to animals of the present disclosure.

As used herein, "carrier", "acceptable carrier", or "pharmaceutical carrier" refers to a diluent, adjuvant, excipient, or vehicle with which the compound is administered. Such carriers can be sterile liquids, such as water and oils, including those of petroleum, animal, vegetable, or synthetic origin; such as peanut oil, soybean oil, mineral oil, sesame oil, and the like. Water or aqueous solution saline solutions and aqueous dextrose and glycerol solutions are preferably employed as carriers, in some embodiments as injectable solutions. Alternatively, the carrier can be a solid dosage form carrier, including but not limited to one or more of a binder (for compressed pills), a glidant, an encapsulating agent, a flavorant, and a colorant. The choice of carrier can be selected with regard to the intended route of administration and standard pharmaceutical practice. See Hardee and Baggo (1998. Development and Formulation of Veterinary Dosage Forms. 2$^{nd}$ Ed. CRC Press. 504 pg.); E. W. Martin (1970. Remington's Pharmaceutical Sciences. 17$^{th}$ Ed. Mack Pub. Co.); and Blaser et al. (US Publication US20110280840A1).

In some aspects, carriers may be granular in structure, such as sand or sand particles. In further aspects, the carriers may be dry, as opposed to a moist or wet carrier. In some aspects, carriers can be nutrititve substances and/or prebiotic substances selected from fructo-oligosaccharides, inulins, isomalto-oligosaccharides, lactitol, lactosucruse, lactulose, pyrodextrines, soy oligosaccharides, transgalacto-oligosaccharides, xylo-oligosaccharides, and vitamins. In some aspects, carriers can be in solid or liquid form. In some aspects, carriers can be zeolites, calcium carbonate, magnesium carbonate, trehalose, chitosan, shellac, albumin, starch, skim-milk powder, sweet-whey powder, maltodextrin, lactose, and inulin. In some aspects, a carrier is water or physiological saline.

In certain aspects of the disclosure, the isolated microbes exist as isolated and biologically pure cultures. It will be appreciated by one of skill in the art, that an isolated and biologically pure culture of a particular microbe, denotes that said culture is substantially free (within scientific reason) of other living organisms and contains only the individual microbe in question. The culture can contain varying concentrations of said microbe. The present disclosure notes that isolated and biologically pure microbes often "necessarily differ from less pure or impure materials." See, e.g. In re Bergstrom, 427 F.2d 1394, (CCPA 1970) (discussing purified prostaglandins), see also, In re Bergy, 596 F.2d 952 (CCPA 1979) (discussing purified microbes), see also, *Parke-Davis & Co. v. H. K. Mulford & Co.*, 189 F. 95 (S.D.N.Y. 1911) (Learned Hand discussing purified adrenaline), aff'd in part, rev'd in part, 196 F. 496 (2d Cir. 1912), each of which are incorporated herein by reference. Furthermore, in some aspects, the disclosure provides for certain quantitative measures of the concentration, or purity limitations, that must be found within an isolated and biologically pure microbial culture. The presence of these purity values, in certain embodiments, is a further attribute that distinguishes the presently disclosed microbes from those microbes existing in a natural state. See, e.g., *Merck & Co. v. Olin Mathieson Chemical Corp.*, 253 F.2d 156 (4th Cir. 1958) (discussing purity limitations for vitamin B12 produced by microbes), incorporated herein by reference.

As used herein, "individual isolates" should be taken to mean a composition, or culture, comprising a predominance of a single genera, species, or strain, of microorganism, following separation from one or more other microorganisms. The phrase should not be taken to indicate the extent to which the microorganism has been isolated or purified. However, "individual isolates" can comprise substantially only one genus, species, or strain, of microorganism.

As used herein, "microbiome" refers to the collection of microorganisms that inhabit the digestive tract or gastrointestinal tract of an animal and the microorganisms' physical environment (i.e., the microbiome has a biotic and physical component). The microbiome is fluid and may be modulated by numerous naturally occurring and artificial conditions (e.g., change in diet, disease, antimicrobial agents, influx of additional microorganisms, etc.). The modulation of the gastrointestinal microbiome can be achieved via administration of the compositions of the disclosure can take the form of: (a) increasing or decreasing a particular Family, Genus, Species, or functional grouping of a microbe (i.e., alteration of the biotic component of the gastrointestinal microbiome) and/or (b) increasing or decreasing gastrointestinal pH, increasing or decreasing volatile fatty acids in the gastrointestinal tract, increasing or decreasing any other physical parameter important for gastrointestinal health (i.e., alteration of the abiotic component of the gut microbiome).

As used herein, "probiotic" refers to a substantially pure microbe (i.e., a single isolate) or a mixture of desired microbes, and may also include any additional components that can be administered to poultry for restoring microbiota. Probiotics or microbial inoculant compositions of the invention may be administered with an agent to allow the microbes to survive the environment of the gastrointestinal tract, i.e., to resist low pH and to grow in the gastrointestinal environment. In some embodiments, the present compositions (e.g., microbial compositions) are probiotics in some aspects.

As used herein, "prebiotic" refers to an agent that increases the number and/or activity of one or more desired microbes. Non-limiting examples of prebiotics that may be useful in the methods of the present disclosure include fructooligosaccharides (e.g., oligofructose, inulin, inulin-type fructans), galactooligosaccharides, amino acids, alcohols, isomalto-oligosaccharides, lactitol, lactosucruse, lactulose, pyrodextrines, soy oligosaccharides, transgalacto-oligosaccharides, xylo-oligosaccharides, vitamins, and mixtures thereof. See Ramirez-Farias et al. (2008. *Br. J. Nutr.* 4:1-10) and Pool-Zobel and Sauer (2007. *J. Nutr.* 137:2580-2584 and supplemental).

The term "growth medium" as used herein, is any medium which is suitable to support growth of a microbe. By way of example, the media may be natural or artificial including gastrin supplemental agar, LB media, blood serum, and tissue culture gels. It should be appreciated that the media may be used alone or in combination with one or more other media. It may also be used with or without the addition of exogenous nutrients.

The medium may be amended or enriched with additional compounds or components, for example, a component which may assist in the interaction and/or selection of specific groups of microorganisms. For example, antibiotics (such as penicillin) or sterilants (for example, quaternary ammonium salts and oxidizing agents) could be present and/or the physical conditions (such as salinity, nutrients (for example organic and inorganic minerals (such as phosphorus, nitrogenous salts, ammonia, potassium and micronutrients such as cobalt and magnesium), pH, and/or temperature) could be amended.

As used herein, the term "fowl" and "poultry" are used interchangeably to include both domesticated and non-domesticated birds belonging to the orders of Galliformes and Anseriformes. Fowl include chickens (broilers/fryers/roasters/capons/roosters/stewing hens), turkeys, grouse, New World quail, Old World quail, partridges, ptarmigans, junglefowl, peafowl, ducks, geese, swans, emus, and ostriches.

Broiler chickens of the present disclosure include: Cobb 500, Cobb 700, Cobb Avian 48, Cobb Sasso, Ross 308, Ross 708, Ross PM3, Jersey Giant, Cornish Cross, Delaware, Dorking, Buckeye, Campine, Chantecler, Crevecoeur, Holland, Modern Game, Nankin, Redcap, Russian, Orloff, Spanish, Sultan, Sumatra, Yokohama, Andalusian, Buttercup, Cubalaya, Faverolles, Java, Lakenvelder, Langshan, Malay, Phoenix, Ancona, Aseel, Brahma, Catalana, Cochin, Cornish, Dominique, Hamburg, Houdan, La Fleche, Minorca, New Hampshire, Old English Game, Polish, Rhode Island White, Sebright, Shamo, Australorp, Leghorn, Orpington, Plymouth Rock, Rhode Island Red, Sussex, Wyandotte, Araucana, Iowa Blue, Lamona, Manx Rumpy, Naked Neck, Asil, Kadacknath Bursa, Hubbard, Hubbard, Cobb, Hubbard, Lohman, Anak 2000, Avian-34, Starbra, Sam Rat, Bowans, Hyline, BV-300, H & N Nick, Dekalb Lohman, ILI-80, Golden-92, Priya, Sonali, Devendra, B-77, Caribro-91, Varna, Caribro naked necked, Caribro multicolored, Aviagen, Ross, Arbor Acres, Indian River, Peterson, Cobb-Vantress, Avian Sasso, Hybro, Groupe Grimaud, Grimaud Frere, Ameraucana, Silkie, Marans, Rosecomb, Welsummer, Barnevelder, Bantam, Asil, Chantecler, Croad, Houdan, Pekin, Frizzle, Serama, Orloff, Ac, Aseel, Baheij, Bandara, and hybrids thereof.

Egg-laying chickens of the present disclosure include: Ameraucana, Ancona, Andalusian, Appenzeller, Araucana, Australorp, Barnevelder, Brahma, Buckeye, Buttercup, Campine, Catalana, Chantecler, Cochin, Cornish, Crevecoeur, Cubalaya, Delaware, Dominique, Dorking, Faverolles, Fayoumi, Hamburg, Holland, Houdan, Jaerhon, Java, Jersey Giant, La Fleche, Lakenvelder, Lamona, Langsham, Leghorn, Marans, Minorca, Nacked Neck, New Hampshire, Orloff, Orpington, Penedesenca, Phoenix, Plymouth Rock, Polish, Redcap, Rhode Island, Spanish, Sultan, Sussex, Welsumer, Wyandotte, Yokohama, and hybrids thereof.

While distinctions are made between broiler chickens and egg-laying chickens, embodiments of the present disclosure utilize broiler chickens, egg-laying chickens, and/or multi-purpose chickens.

As used herein, "improved" should be taken broadly to encompass improvement of a characteristic of interest, as compared to a control group, or as compared to a known average quantity associated with the characteristic in question. For example, "improved" feed efficiency associated with application of a beneficial microbe, or microbial ensemble, of the disclosure can be demonstrated by comparing the feed efficiency of poultry treated by the microbes taught herein to the feed efficiency of poultry not treated. In the present disclosure, "improved" does not necessarily demand that the data be statistically significant (i.e. $p<0.05$); rather, any quantifiable difference demonstrating that one value (e.g. the average treatment value) is different from another (e.g. the average control value) can rise to the level of "improved."

As used herein, "inhibiting and suppressing" and like terms should not be construed to require complete inhibition or suppression, although this may be desired in some embodiments.

The term "marker" or "unique marker" as used herein is an indicator of unique microorganism type, microorganism strain or activity of a microorganism strain. A marker can be measured in biological samples and includes without limitation, a nucleic acid-based marker such as a ribosomal RNA gene, a peptide- or protein-based marker, and/or a metabolite or other small molecule marker.

The term "metabolite" as used herein is an intermediate or product of metabolism. A metabolite in one embodiment is a small molecule. Metabolites have various functions, including in fuel, structural, signaling, stimulatory and inhibitory effects on enzymes, as a cofactor to an enzyme, in defense, and in interactions with other organisms (such as pigments, odorants and pheromones). A primary metabolite is directly involved in normal growth, development and reproduction. A secondary metabolite is not directly involved in these processes but usually has an important ecological function. Examples of metabolites include but are not limited to antibiotics and pigments such as resins and terpenes, etc. Some antibiotics use primary metabolites as precursors, such as actinomycin which is created from the primary metabolite, tryptophan. Metabolites, as used herein, include small, hydrophilic carbohydrates; large, hydrophobic lipids and complex natural compounds.

As used herein, the term "genotype" refers to the genetic makeup of an individual cell, cell culture, tissue, organism, or group of organisms.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes. Since the present disclosure, in embodiments, relates to QTLs, i.e. genomic regions that may comprise one or more genes or regulatory sequences, it is in some instances more accurate to refer to "haplotype" (i.e. an allele of a chromosomal segment) instead of "allele", however, in those instances, the term "allele" should be understood to comprise the term "haplotype". Alleles are considered identical when they express a similar phenotype. Differences in sequence are possible but not important as long as they do not influence phenotype.

As used herein, the term "locus" (loci plural) means a specific place or places or a site on a chromosome where for example a gene or genetic marker is found.

As used herein, the term "genetically linked" refers to two or more traits that are co-inherited at a high rate during breeding such that they are difficult to separate through crossing.

A "recombination" or "recombination event" as used herein refers to a chromosomal crossing over or independent assortment. The term "recombinant" refers to an organism having a new genetic makeup arising as a result of a recombination event.

As used herein, the term "molecular marker" or "genetic marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARS), cleaved amplified polymorphic sequence (CAPS) markers or isozyme markers or combinations of the markers described herein which defines a specific genetic and chromosomal location. Markers further include polynucleotide sequences encoding 16S or 18S rRNA, and internal transcribed spacer (ITS) sequences, which are sequences found between small-subunit and large-subunit rRNA genes that have proven to be especially useful in elucidating relationships or distinctions among when compared against one another. Mapping of molecular markers in the vicinity of an allele is a procedure which can be performed by the average person skilled in molecular-biological techniques.

The primary structure of major rRNA subunit 16S comprise a particular combination of conserved, variable, and hypervariable regions that evolve at different rates and enable the resolution of both very ancient lineages such as domains, and more modern lineages such as genera. The secondary structure of the 16S subunit include approximately 50 helices which result in base pairing of about 67% of the residues. These highly conserved secondary structural features are of great functional importance and can be used to ensure positional homology in multiple sequence alignments and phylogenetic analysis. Over the previous few decades, the 16S rRNA gene has become the most sequenced taxonomic marker and is the cornerstone for the current systematic classification of bacteria and archaea (Yarza et al. 2014. *Nature Rev. Micro.* 12:635-45).

A sequence identity of 94.5% or lower for two 16S rRNA genes is strong evidence for distinct genera, 86.5% or lower is strong evidence for distinct families, 82% or lower is strong evidence for distinct orders, 78.5% is strong evidence for distinct classes, and 75% or lower is strong evidence for distinct phyla. The comparative analysis of 16S rRNA gene sequences enables the establishment of taxonomic thresholds that are useful not only for the classification of cultured microorganisms but also for the classification of the many environmental sequences. Yarza et al. 2014. *Nature Rev. Micro.* 12:635-45).

As used herein, the term "trait" refers to a characteristic or phenotype. For example, in the context of some embodiments of the present disclosure; quantity of eggs produced, efficiency of feed utilization, amount of feces produced, susceptibility to gut pathogens, and a decrease in mortality rates, reduced production variability, among others. Desirable traits may also include other characteristics, including but not limited to: an increase in weight; an increase in egg production; an increase of musculature; an increase of vitamins in eggs; an increase of fatty acid concentration in the gastrointestinal tract; and increase in egg volume; an improved efficiency in feed utilization and digestibility; an increase in polysaccharide and lignin degradation; an increase in fat, starch, and protein digestion; an increase in vitamin availability; an increase in mineral availability; an increase in amino acid availability; improved gastrointestinal development; increasing villi length and surface area; pH balance in the gastrointestinal tract; pH increase in the gastrointestinal tract, pH decrease in the gastrointestinal tract, a reduction in methane and/or nitrous oxide emissions; a reduction in manure production; an improved efficiency of nitrogen utilization; an improved efficiency of phosphorous utilization; an increased resistance to colonization of pathogenic microbes that colonize chickens; an improvement in meat properties, reduced mortality, reduced production variability, increased production of antimicrobials, increased clearance of pathogenic microbes, increased resistance to colonization of pathogenic microbes that infect chickens, increased resistance to colonization of pathogenic microbes that infect humans improved gut health, etc.; wherein said increase, decrease, or reduction is determined by comparing against an animal not having been administered a composition of the present disclosure.

A trait may be inherited in a dominant or recessive manner, or in a partial or incomplete-dominant manner. A trait may be monogenic (i.e. determined by a single locus) or polygenic (i.e. determined by more than one locus) or may also result from the interaction of one or more genes with the environment.

In the context of this disclosure, traits may also result from the interaction of one or more avian genes and one or more microorganism genes.

As used herein, the term "homozygous" means a genetic condition existing when two identical alleles reside at a specific locus, but are positioned individually on corresponding pairs of homologous chromosomes in the cell of a diploid organism. Conversely, as used herein, the term "heterozygous" means a genetic condition existing when two different alleles reside at a specific locus, but are positioned individually on corresponding pairs of homologous chromosomes in the cell of a diploid organism.

As used herein, the term "phenotype" refers to the observable characteristics of an individual cell, cell culture, organism (e.g., bird), or group of organisms which results from the interaction between that individual's genetic makeup (i.e., genotype) and the environment.

As used herein, the term "chimeric" or "recombinant" when describing a nucleic acid sequence or a protein sequence refers to a nucleic acid, or a protein sequence, that links at least two heterologous polynucleotides, or two heterologous polypeptides, into a single macromolecule, or that re-arranges one or more elements of at least one natural nucleic acid or protein sequence. For example, the term "recombinant" can refer to an artificial combination of two otherwise separated segments of sequence, e.g., by chemical synthesis or by the manipulation of isolated segments of nucleic acids by genetic engineering techniques.

As used herein, a "synthetic nucleotide sequence" or "synthetic polynucleotide sequence" is a nucleotide sequence that is not known to occur in nature or that is not naturally occurring. Generally, such a synthetic nucleotide sequence will comprise at least one nucleotide difference when compared to any other naturally occurring nucleotide sequence.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "homologous" or "homologue" or "ortholog" is known in the art and refers to related sequences that share a common ancestor or family member and are determined based on the degree of sequence identity. The terms "homology," "homologous," "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, Calif.). Another alignment program is Sequencher (Gene Codes, Ann Arbor, Mich.), using default parameters.

As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art.

As used herein, the term "at least a portion" or "fragment" of a nucleic acid or polypeptide means a portion having the minimal size characteristics of such sequences, or any larger fragment of the full length molecule, up to and including the full length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids.

Variant polynucleotides also encompass sequences derived from a mutagenic and recombinogenic procedure such as DNA shuffling. Strategies for such DNA shuffling are known in the art. See, for example, Stemmer (1994) PNAS 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) PNAS 94:4504-4509; Crameri et al. (1998) Nature 391:288-291; and U.S. Pat. Nos. 5,605,793 and 5,837,458. For PCR amplifications of the polynucleotides disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) Molecular Cloning: A Laboratory Manual (2nd ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

The terms "stringency" or "stringent hybridization conditions" refer to hybridization conditions that affect the stability of hybrids, e.g., temperature, salt concentration, pH, formamide concentration and the like. These conditions are empirically optimized to maximize specific binding and minimize non-specific binding of primer or probe to its target nucleic acid sequence. The terms as used include reference to conditions under which a probe or primer will hybridize to its target sequence, to a detectably greater degree than other sequences (e.g. at least 2-fold over background). Stringent conditions are sequence dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridizes to a perfectly matched probe or primer. Typically, stringent conditions will be those in which the salt concentration is less than about 1.0 M Na+ ion, typically about 0.01 to 1.0 M Na+ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1M NaCl, 1% SDS at 37° C., and a wash in 0.1×SSC at 60° C. Hybridization procedures are well known in the art and are described by e.g. Ausubel et al., 1998 and Sambrook et al., 2001. In some embodiments, stringent conditions are hybridization in 0.25M Na2HPO4 buffer (pH 7.2) containing 1 mM Na2EDTA, 0.5-20% sodium dodecyl sulfate at 45° C., such as 0.5%, 1%, 2%, 3%, 4%, 5%, 6%, 7%, 8%, 9%, 10%, 11%, 12%, 13%, 14%, 15%, 16%, 17%, 18%, 19% or 20%, followed by a wash in 5×SSC, containing 0.1% (w/v) sodium dodecyl sulfate, at 55° C. to 65° C.

As used herein, "promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

As used herein, a "constitutive promoter" is a promoter which is active under most conditions and/or during most development stages. There are several advantages to using constitutive promoters in expression vectors used in biotechnology, such as: high level of production of proteins used to select transgenic cells or organisms; high level of expression of reporter proteins or scorable markers, allowing easy detection and quantification; high level of production of a transcription factor that is part of a regulatory transcription system; production of compounds that requires ubiquitous activity in the organism; and production of compounds that are required during all stages of development. Non-limiting exemplary constitutive promoters include, CaMV 35S promoter, opine promoters, ubiquitin promoter, alcohol dehydrogenase promoter, etc.

As used herein, a "non-constitutive promoter" is a promoter which is active under certain conditions, in certain types of cells, and/or during certain development stages. For example, tissue specific, tissue preferred, cell type specific, cell type preferred, inducible promoters, and promoters under development control are non-constitutive promoters. Examples of promoters under developmental control include promoters that preferentially initiate transcription in certain tissues.

As used herein, "inducible" or "repressible" promoter is a promoter which is under chemical or environmental factors control. Examples of environmental conditions that may affect transcription by inducible promoters include anaerobic conditions, certain chemicals, the presence of light, acidic or basic conditions, etc.

As used herein, a "tissue specific" promoter is a promoter that initiates transcription only in certain tissues. Unlike constitutive expression of genes, tissue-specific expression is the result of several interacting levels of gene regulation. As such, in the art sometimes it is preferable to use promoters from homologous or closely related species to achieve efficient and reliable expression of transgenes in particular tissues. This is one of the main reasons for the large amount of tissue-specific promoters isolated from particular tissues found in both scientific and patent literature.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the disclosure can be operably linked, either directly or indirectly, 5' to the target mRNA, or 3' to the target mRNA, or within the target mRNA, or a first complementary region is 5' and its complement is 3' to the target mRNA.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

In some embodiments, the cell or organism has at least one heterologous trait. As used herein, the term "heterologous trait" refers to a phenotype imparted to a transformed host cell or transgenic organism by an exogenous DNA segment, heterologous polynucleotide or heterologous nucleic acid. Various changes in phenotype are of interest to the present disclosure, including but not limited to increasing a fowl's yield of an economically important trait (e.g., eggs, egg volume, fowl weight, etc.) and the like. These results can be achieved by providing expression of heterologous products or increased expression of endogenous products in organisms using the methods and compositions of the present disclosure. In some embodiments, the isolated microbial strains of the present disclosure further encompass mutants thereof. In some embodiments, the present disclosure further contemplates microbial strains having all of the identifying characteristics of the presently disclosed microbial strains.

As used herein, the term "MIC" means maximal information coefficient. MIC is a type of nonparamentric analysis that identifies a score (MIC score) between active microbial strains of the present disclosure and at least one measured metadata (e.g., increase in weight). Further, U.S. application Ser. No. 15/217,575, filed on Jul. 22, 2016 (issued as U.S. Pat. No. 9,540,676 on Jan. 10, 2017) is hereby incorporated by reference in its entirety.

Figure 2:
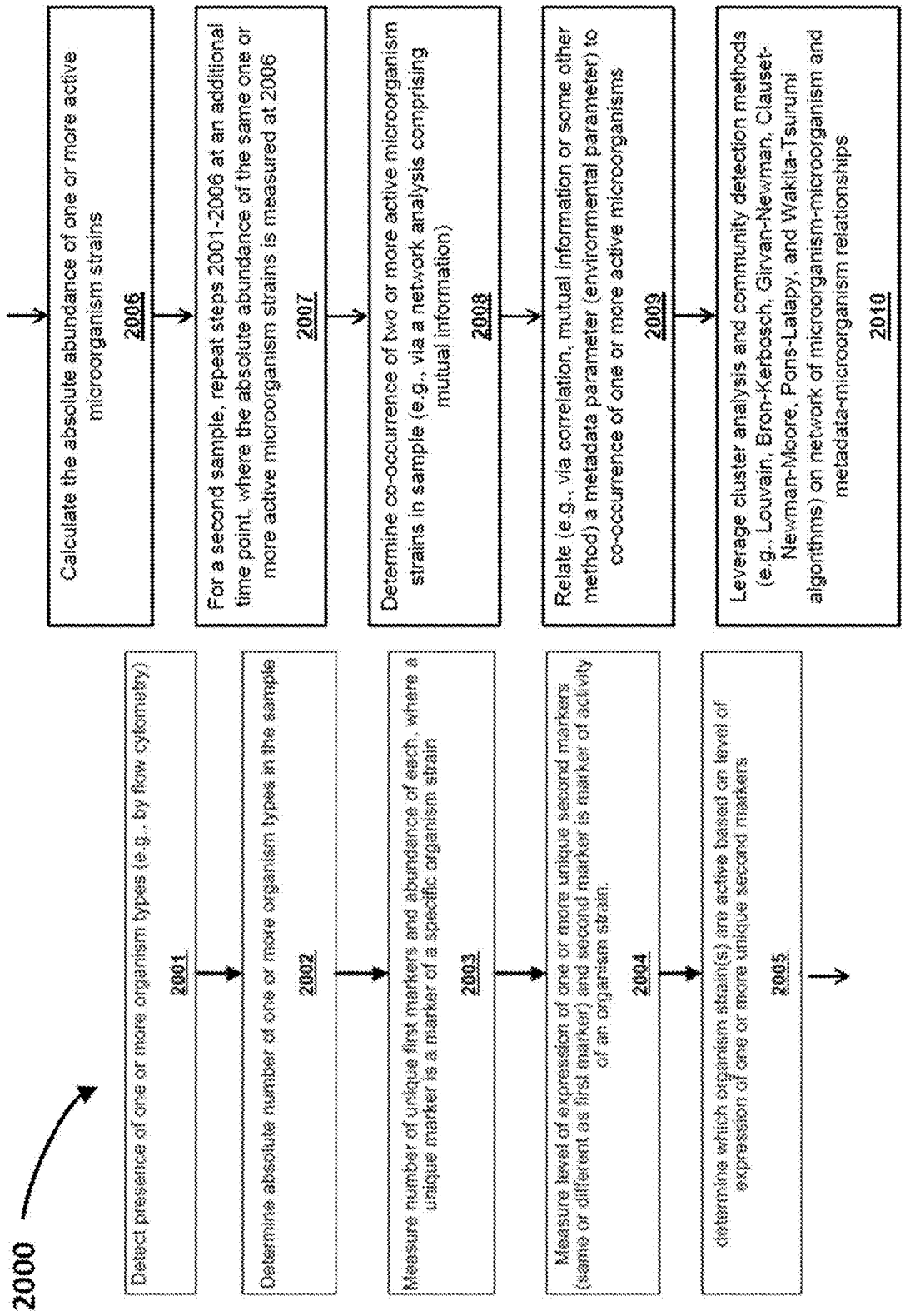
FIG. 2 shows a general workflow of one embodiment of a method for determining the co-occurrence of one or more, or two or more, active microorganism strains in a sample with one or more metadata (environmental) parameters, followed by leveraging cluster analysis and community detection methods on the network of determined relationships.

The maximal information coefficient (MIC) is then calculated between strains and metadata and between strains as seen in FIG. 2, 2009. Results are pooled to create a list of all relationships and their corresponding MIC scores. If the relationship scores below a given threshold, the relationship is deemed/identified as irrelevant. If the relationship is above a given threshold, the relationship deemed/identified as relevant, and is further subject to network analysis. The following code fragment shows an exemplary methodology for such analysis, according to one embodiment:

```
Read total list of relationships file as links
threshold = 0.8
for i in range(len(links)):
    if links >= threshold
        multiplier[i] = 1
    else
        multiplier[i] = 0
end if
links_temp = multiplier*links
final_links = links_temp[links_temp != 0]
savetxt(output_file,final_links)
output_file.close( )
```

In some embodiments, the compositions of the present disclosure comprise one or more bacteria and/or one or more fungus that have a MIC score of at least about 0.1, 0.15, 0.2, 0.25, 0.3, 0.35, 0.4, 0.45, 0.5, 0.55, 0.6, 0.7, 0.75, 0.8, 0.85, 0.9, or 0.95.

Figure 15:
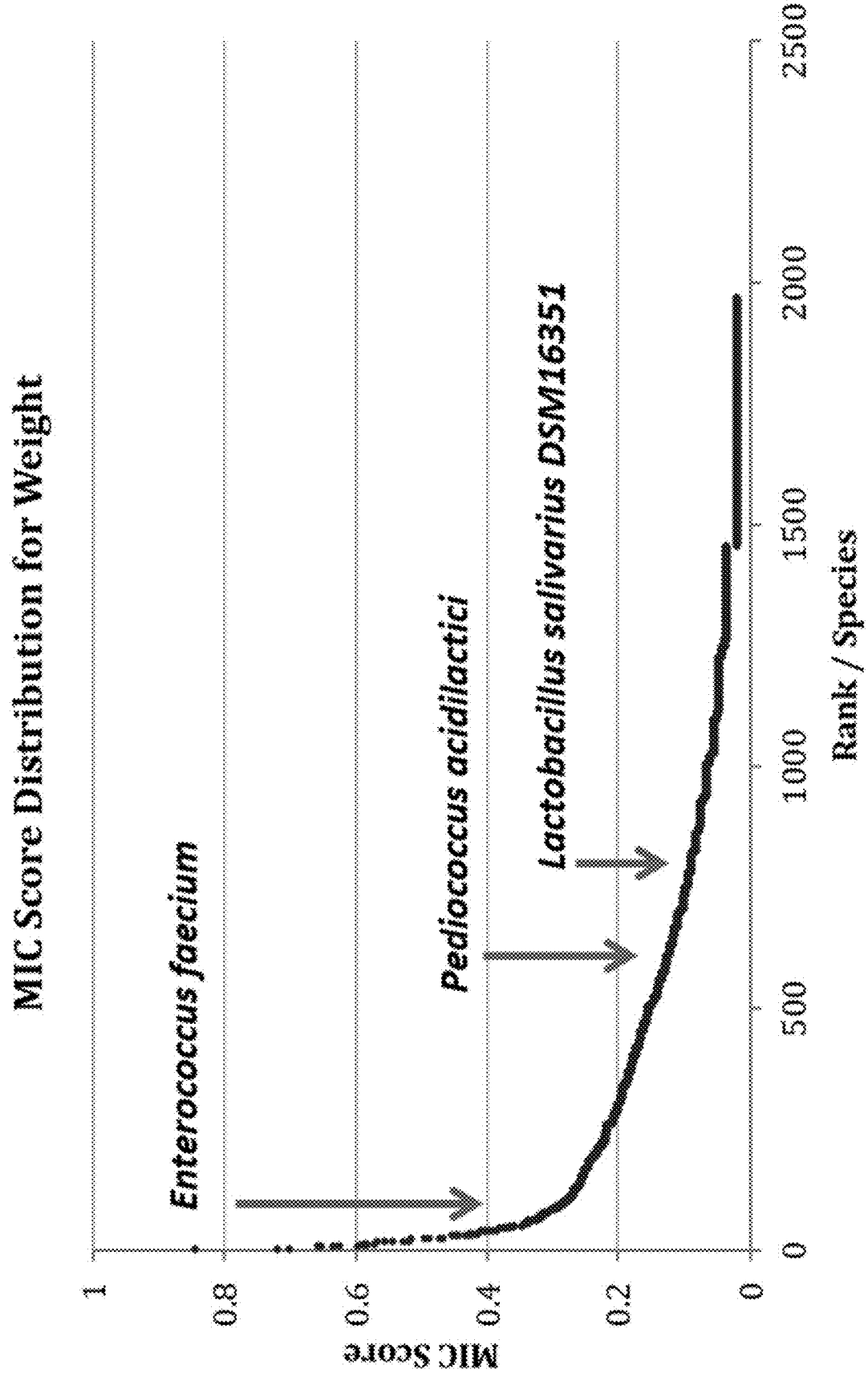
FIG. 15 depicts the MIC score distribution for gastrointestinal bacteria and broiler weight with three species of bacteria and their MIC scores, in which the species have been evaluated in 3$^{rd}$ party studies. The lower the MIC score, the less likely the species/strains are capable of positively modulating broiler weight.
Figure 16:
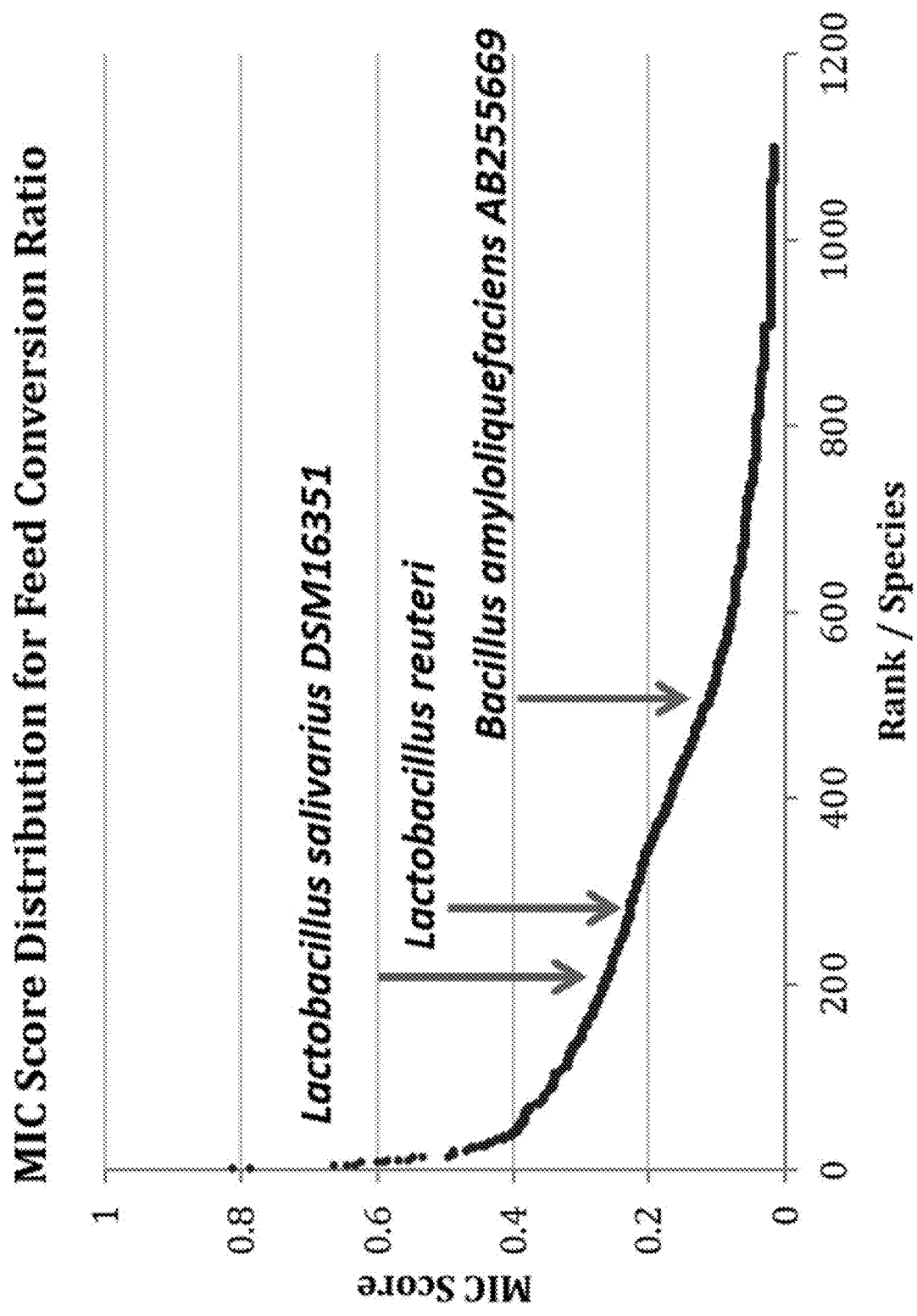
FIG. 16 depicts the MIC score distribution for gastrointestinal bacteria and broiler feed conversion ration with three species of bacteria and their MIC scores, in which the species have been evaluated in 3$^{rd}$ party studies. The lower the MIC score, the less likely the species/strains are capable of positively modulating broiler feed conversion ratio.

With regard to MIC scores, and in view of FIG. 15 and FIG. 16. a cut-off based on this score is used to define useful and non-useful microorganisms with respect to the improvement of specific traits. The point on FIG. 15 and FIG. 16 at which the data points on the curve move transition from the log scale to the linear scale (with regard to the slope) is the inflection point. The organisms with MIC scores that fall below the inflection point are generally non-useful, while the organisms with MIC scores that are found above the inflection point are generally useful, as it pertains to the specific characteristic being evaluated for the MIC score.

Based on the output of the network analysis, active strains are selected for preparing products (e.g., ensembles, aggregates, and/or other synthetic groupings) containing the selected strains. The output of the network analysis can also be used to inform the selection of strains for further product composition testing, as seen in FIG. 2, 2010.

The use of thresholds is discussed above for analyses and determinations. Thresholds can be, depending on the implementation and application: (1) empirically determined (e.g., based on distribution levels, setting a cutoff at a number that removes a specified or significant portion of low level reads); (2) any non-zero value; (3) percentage/percentile based; (4) only strains whose normalized second marker (i.e., activity) reads is greater than normalized first marker (cell count) reads; (5) log 2 fold change between activity and quantity or cell count; (6) normalized second marker (activity) reads is greater than mean second marker (activity) reads for entire sample (and/or sample set); and/or any magnitude threshold described above in addition to a statistical threshold (i.e., significance testing). The following example provides thresholding detail for distributions of RNA-based second marker measurements with respect to DNA-based first marker measurements, according to one embodiment.

As used herein "shelf-stable" refers to a functional attribute and new utility acquired by the microbes formulated according to the disclosure, which enable said microbes to exist in a useful/active state outside of their natural environment in the gastrointestinal tract (i.e. a markedly different characteristic). Thus, shelf-stable is a functional attribute created by the formulations/compositions of the disclosure and denoting that the microbe formulated into a shelf-stable composition can exist outside the gastrointestinal tract and under ambient conditions for a period of time that can be determined depending upon the particular formulation utilized, but in general means that the microbes can be formulated to exist in a composition that is stable under ambient conditions for at least a few days and generally at least one week. Accordingly, a "shelf-stable fowl supplement" is a composition comprising one or more microbes of the disclosure, said microbes formulated in a composition, such that the composition is stable under ambient conditions for at least one week, meaning that the microbes comprised in the composition (e.g. whole cell, spore, or lysed cell) are able to impart one or more beneficial phenotypic properties to a fowl when administered (e.g. increased weight gain, increased eggshell density, improved gastrointestinal health, and/or modulation of the gastrointestinal microbiome).

Isolated Microbes

In some aspects, the present disclosure provides isolated microbes, including novel strains of microbes, presented in Table 1 and Table 3.

In other aspects, the present disclosure provides isolated whole microbial cultures of the microbes identified in Table 1 and Table 3. These cultures may comprise microbes at various concentrations.

In some aspects, the disclosure provides for utilizing one or more microbes selected from Table 1 and Table 3 to increase a phenotypic trait of interest in poultry.

In some embodiments, the disclosure provides isolated microbial species belonging to taxonomic families of Lactobacillaceae, Lachnospiraceae, Ruminococcaceae, Peptostreptococcaceae, Streptosporangiaceae, Leuconostocaceae, Microbacteriaceae, Micromonosporaceae, Clostridiaceae, Pseudomonadaceae, Streptococcaceae, Bacillaceae, Bacteroidaceae, Nectriaceae, Corynebacteriaceae, Rhodobacteraceae, and Hypocreaceae.

In further embodiments, isolated microbial species may be selected from genera of family Lactobacillaceae, including *Acetatifactor, Acetitomaculum, Anaerostipes, Butyrivibrio, Catonella, Cellulosilyticum, Coprococcus, Dorea, Hespellia, Johnsonella, Lachnoanaerobaculum, Lachnobacterium, Lachnospira, Marvinbryantia, Moryella, Oribacterium, Parasporobacterium, Pseudobutyrivibrio, Robinsoniella, Roseburia, Shuttleworthia, Sporobacterium, Stomabaculum*, and *Syntrophococcus*.

In further embodiments, isolated microbial species may be selected from genera of family Lachnospiraceae, including *Butyrivibrio, Roseburia, Lachnospira, Acetitomaculum, Coprococcus, Johnsonella, Catonella, Pseudobutyrivibrio, Syntrophococcus, Sporobacterium, Parasporobacterium, Lachnobacterium, Shuttleworthia, Dorea, Anaerostipes, Hespellia, Marvinbryantia, Oribacterium, Moryella, Blautia, Robinsoniella, Cellulosilyticum, Lachnoanaerobaculum, Stomatobaculum, Fusicatenibacter, Acetatifactor*, and *Eisenbergiella*.

In further embodiments, isolated microbial species may be selected from genera of family Ruminococcaceae, including *Ruminococcus, Acetivibrio, Sporobacter, Anaerofilium, Papillibacter, Oscillospira, Gemmiger, Faecalibacterium, Fastidiosipila, Anaerotruncus, Ethanolingenens, Acetanaerobacterium, Subdoligranulum, Hydrogenoanaerobacterium*, and *Candidadus Soleaferrea*.

In further embodiments, isolated microbial species may be selected from genera of family Peptostreptococcaceae, including *Anaerosphaera, Filifactor, Peptostreptococcus, Sporacetigenium*, and *Tepidibacter*.

In further embodiments, isolated microbial species may be selected from genera of family Streptosporangiaceae, including *Acrocarpospora, Herbidospora, Microbispora, Microtetraspora, Nonomuraea, Planobispora, Planomono-*

*spora, Planotetraspora, Sphaerisporangium, Streptosporangium, Thermoactinospora, Thermocatellispora,* and *Thermopolyspora.*

In further embodiments, isolated microbial species may be selected from genera of family Leuconostocaceae, including *Fructobacillus, Leuconostoc, Oenococcus,* and *Weissella.*

In further embodiments, isolated microbial species may be selected from genera of family Microbacteriaceae, including *Agreia, Agrococcus, Agromyces, Alpinomonas, Amnibacterium, Aureobacterium, Chryseoglobus, Clavibacter, Compostimonas, Cryobacterium, Curtobacterium, Diaminobutyricimonas, Frigoribacterium, Frondihabitans, Glacibacter, Gryllotalpicola, Gulosibacter, Herbiconiux, Homoserinimonas, Humibacter, Klugiella, Labedella, Leifsonia, Leucobacter, Lysinimonas, Marisediminicola, Microbacterium, Microcella, Microterricola, Mycetocola, Okibacterium, Phycicola, Plantibacter, Pontimonas, Pseudoclavibacter, Rathayibacter, Rhodoglobus, Salinibacterium, Schumanella, Subtercola, Yonghaparkia,* and *Zimmermannella.*

In further embodiments, isolated microbial species may be selected from genera of family Micromonosporaceae, including *Actinaurispora, Actinocatenispora, Actinoplanes, Allocatelliglobosispora, Amorphosporangium, Ampullariella, Asanoa, Catelliglobosispora, Catenuloplanes, Couchioplanes, Dactylosporangium, Hamadaea, Jishengella, Krasilnikovia, Longispora, Luedemannella, Micromonospora, Phytohabitans, Phytomonospora, Pilimelia, Planopolyspora, Planosporangium, Plantactinospora, Polymorphospora, Pseudosporangium, Rugosimonospora, Salinispora, Spirilliplanes, Verrucosispora, Virgisporangium,* and *Xiangella.*

In further embodiments, isolated microbial species may be selected from genera of family Clostridiaceae, including *Acetanaerobacterium, Acetivibrio, Acidaminobacter, Alkaliphilus, Anaerobacter, Anaerostipes, Anaerotruncus, Anoxynatronum, Bryantella, Butyricicoccus, Caldanaerocella, Caloramator, Caloranaerobacter, Caminicella, Candidatus Arthromitus, Clostridium, Coprobacillus, Dorea, Ethanologenbacterium, Faecalibacterium, Garciella, Guggenheimella, Hespellia, Linmingia, Natronincola, Oxobacter, Parasporobacterium, Sarcina, Soehngenia, Sporobacter, Subdoligranulum, Tepidibacter, Tepidimicrobium, Thermobrachium, Thermohalobacter,* and *Tindallia.*

In further embodiments, isolated microbial species may be selected from genera of family Pseudomonadaceae.

In further embodiments, isolated microbial species may be selected from genera of family Nectriaceae.

In some embodiments, the disclosure provides isolated microbial species belonging to genera of: Hypocreaceae.

In some embodiments, one or more microbes from the taxa disclosed herein are utilized to impart one or more beneficial properties or improved traits to poultry production.

Furthermore, the disclosure relates to microbes having characteristics substantially similar to that of a microbe identified in Table 1 and/or Table 3.

The isolated microbial species, and novel strains of said species, identified in the present disclosure, are able to impart beneficial properties or traits to poultry production.

For instance, the isolated microbes described in Table 1 and Table 3, or microbial ensembles of said microbes, are able to increase feed efficiency. The increase can be quantitatively measured, for example, by measuring the effect that said microbial application has upon the modulation of feed efficiency. In some embodiments, feed efficiency is represented by the feed conversion ratio, which is calculated by measuring desirable animal output produced per pound of feed consumed. With regard to fowl, the desirable output is typically pounds of meat produced per pound of feed consumed.

In some embodiments, the isolated microbial strains are microbes of the present disclosure that have been genetically modified. In some embodiments, the genetically modified or recombinant microbes comprise polynucleotide sequences which do not naturally occur in said microbes. In some embodiments, the microbes may comprise heterologous polynucleotides. In further embodiments, the heterologous polynucleotides may be operably linked to one or more polynucleotides native to the microbes. In some embodiments, the isolated microbial strains of the present disclosure further encompass mutants thereof. In some embodiments, the present disclosure further contemplates microbial strains having all of the identifying characteristics of the presently disclosed microbial strains.

In some embodiments, the heterologous polynucleotides may be reporter genes or selectable markers. In some embodiments, reporter genes may be selected from any of the family of fluorescence proteins (e.g., GFP, RFP, YFP, and the like), β-galactosidase, luciferase. In some embodiments, selectable markers may be selected from neomycin phosphotransferase, hygromycin phosphotransferase, aminoglycoside adenyltransferase, dihydrofolate reductase, acetolactase synthase, bromoxynil nitrilase, β-glucuronidase, dihydrogolate reductase, and chloramphenicol acetyltransferase. In some embodiments, the heterologous polynucleotide may be operably linked to one or more promoter.

In some embodiments the isolated microbial strains express transgenic or native enzymes selected from cellulases (endocellulases, exocellulases, glucosidases), pectinases, amylases, amylopectinases, ligninases, and phytases In some embodiments, the species of the taxa provided in Table 4 are not known to have been utilized in compositions for administration to animals.

TABLE 4

| Taxa (largely Genera) of the present disclosure not known to have been utilized in animal agriculture. ||
|---|---|
| Corynebacterium | Verrucosispora |
| Clostridium XIVa | Clostridium |
| Clostridium XI | Blautia |
| Faecalibacterium | Pseudomonas |
| Hydrogenoanaerobacterium | Sporobacter |
| Acrocarpospora | Clostridium III |
| Subdoligranulum | Paracoccus |
| Leuconostoc | Cellulosilyticum |
| Lachnospiracea | Ruminococcus |
| Anaerofilum | Roseburia |
| Microbacterium | Clostridium XIVb |
| Verrucosispora | Bacteroides |

Microbial Ensembles

In some aspects, the disclosure provides microbial ensembles comprising a combination of at least any two microbes selected from amongst the microbes identified in Table 1 and Table 3.

In certain embodiments, the microbial ensembles of the present disclosure comprise two microbes, or three microbes, or four microbes, or five microbes, or six microbes, or seven microbes, or eight microbes, or nine microbes, or ten or more microbes. Said microbes of the microbial ensembles are different microbial species, or different strains of a microbial species.

In some embodiments, the disclosure provides microbial ensembles, comprising: at least one or at least two isolated microbial species belonging to genera of: *Lactobacillus, Clostridium, Faecalibacter, Hydrogenoanaerobacterium, Acrocarpospora, Bacillus, Subdoligranulum, Leuconostoc, Lachnospiracea, Anaerofilum, Microbacterium, Verrucosispora, Anaerofilum, Blautia, Pseudomonas, Sporobacter, Corynebacterium, Streptococcus, Paracoccus, Cellulosilyticum, Ruminococcus, Rosebura, Bacteroides, Filobasidium, Gibberella, Alatospora, Pichia,* and *Candida.* Particular novel strains of species of these aforementioned genera can be found in Table 1 and Table 3.

In some embodiments, the disclosure provides microbial ensembles, comprising: at least one or at least two isolated microbial species belonging to the family of: Lactobacilaceae, Lachnospiraceae, Ruminococcaceae, Peptostreptococcaceae, Streptosporangiaceae, Leuconostocaceae, Microbacteriaceae, Micromonosporaceae, Clostridiaceae, Pseudomonadales, Nectriaceae, and Hypocreaceae; wherein Lachnospiraceae can be further specific to *Clostridium* clusters XIVa and XIVb; and wherein Peptostreptococcaceae can be further specific to *Clostridium* cluster XI. Particular novel strains of species of these aforementioned genera can be found in Table 1 and Table 3.

In particular aspects, the disclosure provides microbial ensembles, comprising species as grouped in Tables 5-11. With respect to Tables 5-11, the letters A through I represent a non-limiting selection of microbes of the present disclosure, defined as:

A=Strain designation Ascusbbr_578 identified in Table 1;

B=Strain designation Ascusbbr_1436 identified in Table 1;

C=Strain designation Ascusbbr_33 identified in Table 1;

D=Strain designation Ascusbbr_105932 identified in Table 1;

E=Strain designation Ascusbbr_2676 identified in Table 1;

F=Strain designation Ascusbbr_5796 identified in Table 1;

G=Strain designation Ascusbbr_25721 identified in Table 1;

H=Strain designation Ascusbbr_4729 identified in Table 1; and

I=Strain designation Ascusbbr_7363 identified in Table 1.

TABLE 5

Eight and Nine Strain Microbial Ensembles

| | | | | | | |
|---|---|---|---|---|---|---|
| A, B, C, D, E, F, G, H | A, B, C, D, E, F, G, I | A, B, C, D, E, F, H, I | A, B, C, D, E, G, H, I | A, B, C, D, F, G, H, I | A, B, C, E, F, G, H, I |
| A, B, D, E, F, G, H, I | A, C, D, E, F, G, H, I | B, C, D, E, F, G, H, I | A, B, C, D, E, F, G, H, I | | |

TABLE 6

Seven Strain Microbial Ensembles

| | | | | | | |
|---|---|---|---|---|---|---|
| A, B, C, D, E, F, G | A, B, C, D, E, F, H | A, B, C, D, E, F, I | A, B, C, D, E, G, H | A, B, C, D, E, G, I | A, B, C, D, E, H, I |
| A, B, C, D, F, G, H | A, B, C, D, F, G, I | A, B, C, D, F, H, I | A, B, C, D, G, H, I | A, B, C, E, F, G, H | A, B, C, E, F, G, I |
| A, B, C, E, F, H, I | A, B, C, E, G, H, I | A, B, C, F, G, H, I | A, B, D, E, F, G, H | A, B, D, E, F, G, I | A, B, D, E, F, H, I |
| A, B, D, E, G, H, I | A, B, D, F, G, H, I | A, B, E, F, G, H, I | A, C, D, E, F, G, H | A, C, D, E, F, G, I | A, C, D, E, F, H, I |
| A, C, D, E, G, H, I | A, C, D, F, G, H, I | A, C, E, F, G, H, I | A, D, E, F, G, H, I | B, C, D, E, F, G, H | B, C, D, E, F, G, I |
| B, C, D, E, F, H, I | B, C, D, E, G, H, I | B, C, D, F, G, H, I | B, C, E, F, G, H, I | B, D, E, F, G, H, I | C, D, E, F, G, H, I |

TABLE 7

Six Strain Microbial Ensembles

| | | | | | | |
|---|---|---|---|---|---|---|
| A, B, C, D, E, F | A, B, C, D, E, G | A, B, C, D, E, H | A, B, C, D, E, I | A, B, C, D, F, G | A, B, C, D, F, H | A, B, C, D, F, I |
| A, B, C, D, G, H | A, B, C, D, G, I | A, B, C, D, H, I | A, B, C, E, F, G | A, B, C, E, F, H | A, B, C, E, F, I | A, B, C, E, G, H |
| A, B, C, E, G, I | A, B, C, E, H, I | A, B, C, F, G, H | A, B, C, F, G, I | A, B, C, F, H, I | A, B, C, G, H, I | A, B, D, E, F, G |
| A, B, D, E, F, H | A, B, D, E, F, I | A, B, D, E, G, H | A, B, D, E, G, I | A, B, D, E, H, I | A, B, D, F, G, H | A, B, D, F, G, I |
| D, E, F, G, H, I | C, E, F, G, H, I | A, B, D, F, H, I | A, B, D, G, H, I | A, B, E, F, G, H | A, B, E, F, G, I | A, B, E, F, H, I |
| A, B, E, G, H, I | A, B, F, G, H, I | A, C, D, E, F, G | A, C, D, E, F, H | A, C, D, E, F, I | A, C, D, E, G, H | A, C, D, E, G, I |
| A, C, D, E, H, I | A, C, D, F, G, H | A, C, D, F, G, I | A, C, D, F, H, I | A, C, D, G, H, I | A, C, E, F, G, H | A, C, E, F, G, I |
| A, C, E, F, H, I | A, C, E, G, H, I | A, C, F, G, H, I | A, D, E, F, G, H | A, D, E, F, G, I | A, D, E, F, H, I | A, D, E, G, H, I |
| A, D, F, G, H, I | A, E, F, G, H, I | B, C, D, E, F, G | B, C, D, E, F, H | B, C, D, E, F, I | B, C, D, E, G, H | B, C, D, E, G, I |
| B, C, D, E, H, I | B, C, D, F, G, H | B, C, D, F, G, I | B, C, D, F, H, I | B, C, D, G, H, I | B, C, E, F, G, H | B, C, E, F, G, I |
| B, C, E, F, H, I | B, C, E, G, H, I | B, C, F, G, H, I | B, D, E, F, G, H | B, D, E, F, G, I | B, D, E, F, H, I | B, D, E, G, H, I |
| B, D, F, G, H, I | B, E, F, G, H, I | C, D, E, F, G, H | C, D, E, F, G, I | C, D, E, F, H, I | C, D, E, G, H, I | C, D, F, G, H, I |

TABLE 8

Five Strain Microbial Ensembles

| | | | | | | | |
|---|---|---|---|---|---|---|---|
| A, B, C, D, E | A, B, C, D, F | A, B, C, D, G | A, B, C, D, H | A, B, C, D, I | A, B, C, E, F | A, B, C, E, G | A, B, C, E, H |
| A, B, C, F, H | A, B, C, F, G | A, B, C, F, I | A, B, C, G, H | A, B, C, G, I | A, B, C, H, I | A, B, D, E, F | A, B, D, E, G |

TABLE 8-continued

Five Strain Microbial Ensembles

| | | | | | | | |
|---|---|---|---|---|---|---|---|
| A, B, D, E, I | A, B, D, F, G | A, B, D, F, H | A, B, D, F, I | A, B, D, G, H | A, B, D, G, I | A, B, D, H, I | A, B, E, F, G |
| A, B, E, F, I | A, B, E, G, H | A, B, E, G, I | A, B, E, H, I | A, B, F, G, H | A, B, F, G, I | A, B, F, H, I | A, B, G, H, I |
| A, C, D, E, G | A, C, D, E, H | A, C, D, E, I | A, C, D, F, G | A, C, D, F, H | A, C, D, F, I | A, C, D, G, H | A, C, D, G, I |
| A, C, E, F, G | A, C, E, F, H | A, C, E, F, I | A, C, E, G, H | A, C, E, G, I | A, C, E, H, I | A, C, F, G, H | A, C, F, G, I |
| A, C, G, H, I | A, D, E, F, G | A, D, E, F, H | A, D, E, F, I | A, D, E, G, H | A, D, E, G, I | A, D, E, H, I | A, D, F, G, H |
| A, D, F, H, I | A, D, G, H, I | A, E, F, G, H | A, E, F, G, I | A, E, F, H, I | A, E, G, H, I | A, F, G, H, I | B, C, D, E, F |
| B, C, D, E, H | B, C, D, E, I | B, C, D, F, G | B, C, D, F, H | B, C, D, F, I | B, C, D, G, H | B, C, D, G, I | B, C, D, H, I |
| B, C, E, F, H | B, C, E, F, I | B, C, E, G, H | B, C, E, G, I | B, C, E, H, I | B, C, F, G, H | B, C, F, G, I | B, C, F, H, I |
| B, D, E, F, G | B, D, E, F, H | B, D, E, F, I | B, D, E, G, H | B, D, E, G, I | B, D, E, H, I | B, D, F, G, H | B, D, F, G, I |
| B, D, G, H, I | B, E, F, G, H | B, E, F, G, I | B, E, F, H, I | B, E, G, H, I | B, F, G, H, I | C, D, E, F, G | C, D, E, F, H |
| C, D, E, G, H | C, D, E, G, I | C, D, E, H, I | C, D, F, G, H | C, D, F, G, I | C, D, F, H, I | C, D, G, H, I | C, E, F, G, H |
| C, E, F, H, I | C, E, G, H, I | C, F, G, H, I | D, E, F, G, H | D, E, F, G, I | D, E, F, H, I | D, E, G, H, I | D, F, G, H, I |
| A, B, C, E, I | A, B, D, E, H | A, B, E, F, H | A, C, D, E, F | A, C, D, H, I | A, C, F, H, I | A, D, F, G, I | B, C, D, E, G |
| B, C, E, F, G | B, C, G, H, I | B, D, F, H, I | C, D, E, F, I | C, E, F, G, I | E, F, G, H, I | | |

TABLE 9

Four Strain Microbial Ensembles

| | | | | | | | | |
|---|---|---|---|---|---|---|---|---|
| A, B, C, D | A, B, C, E | A, B, C, F | A, B, C, G | A, B, C, H | A, B, C, I | A, B, D, E | A, B, D, F | D, G, H, I |
| A, B, D, G | A, B, D, H | A, B, D, I | A, B, E, F | A, B, E, G | A, B, E, H | A, B, E, I | A, B, F, G | E, F, G, H |
| A, B, F, H | A, D, F, H | A, D, F, I | A, D, G, H | A, D, G, I | A, E, F, G | A, E, F, H | E, F, G, I | |
| A, B, F, I | A, B, G, H | A, B, G, I | A, B, H, I | A, C, D, E | A, C, D, F | A, C, D, G | A, C, D, H | E, F, H, I |
| A, C, D, I | A, C, E, F | A, C, E, G | A, C, E, H | A, C, E, I | A, C, F, G | A, C, F, H | A, C, F, I | E, G, H, I |
| A, C, G, H | A, C, G, I | A, C, H, I | A, D, E, F | A, D, E, G | A, D, E, H | A, D, E, I | A, D, F, G | F, G, H, I |
| A, E, F, I | A, E, G, H | A, E, G, I | A, E, H, I | A, F, G, I | A, F, H, I | A, G, H, I | D, E, F, H | |
| B, C, D, E | B, C, D, F | B, C, D, G | B, C, D, H | B, C, D, I | B, C, E, F | B, C, E, G | B, C, E, H | D, E, F, I |
| B, C, E, I | B, C, F, G | B, C, F, H | B, C, F, I | B, C, G, H | B, C, G, I | B, C, H, I | B, D, E, F | D, E, G, H |
| B, D, E, G | B, D, E, H | B, D, E, I | B, D, F, G | B, D, F, H | B, D, F, I | B, D, G, H | B, D, G, I | D, E, G, I |
| B, D, H, I | B, E, F, G | B, E, F, H | B, E, F, I | B, E, G, H | B, E, G, I | B, F, G, H | B, F, G, H | D, E, H, I |
| B, F, G, I | B, F, H, I | B, G, H, I | C, D, E, F | C, D, E, G | C, D, E, H | C, D, E, I | C, D, F, G | D, F, G, H |
| C, D, F, H | C, D, F, I | C, D, G, H | C, D, G, I | C, D, H, I | C, E, F, G | C, E, F, H | C, E, F, I | D, F, G, I |
| C, E, G, H | C, E, G, I | C, E, H, I | C, F, G, H | C, F, G, I | C, F, H, I | C, G, H, I | D, E, F, G | D, F, H, I |

TABLE 10

Three Strain Microbial Ensembles

| | | | | | | | | | |
|---|---|---|---|---|---|---|---|---|---|
| A, B, C | A, B, D | A, B, E | A, B, F | A, B, G | A, B, H | A, B, I | A, C, D | A, C, E | G, H, I | E, F, H |
| A, C, F | A, C, G | A, C, H | A, C, I | A, D, E | A, D, F | A, D, G | A, D, H | A, D, I | F, H, I | E, F, G |
| A, E, F | A, E, G | A, E, H | A, E, I | A, F, G | A, F, H | A, F, I | A, G, H | A, G, I | F, G, I | D, H, I |
| A, H, I | B, C, D | B, C, E | B, C, F | B, C, G | B, C, H | B, C, I | B, D, E | B, D, F | B, G, H | D, G, I |
| B, D, G | B, D, H | B, D, I | B, E, F | B, E, G | B, E, H | B, E, I | B, F, G | B, F, H | E, H, I | E, F, I |
| B, F, I | B, G, H | B, G, I | B, H, I | C, D, E | C, D, F | C, D, G | C, D, H | C, D, I | E, G, I | D, G, H |
| C, E, F | C, E, G | C, E, H | C, E, I | C, F, G | C, F, H | C, F, I | C, G, H | C, G, I | E, G, H | D, F, I |
| C, H, I | D, E, F | D, E, G | D, E, H | D, E, I | D, F, G | D, F, H | | | | |

TABLE 11

Two Strain Microbial Ensembles

| | | | | | | | | | | | | | | |
|---|---|---|---|---|---|---|---|---|---|---|---|---|---|---|
| A, B | A, C | A, D | A, E | A, F | A, G | A, H | A, I | B, C | B, D | B, E | B, F | B, G | B, H | B, I | C, D |
| C, E | C, F | C, G | C, H | C, I | D, E | D, F | D, G | D, H | D, I | E, F | E, G | E, H | E, I | F, G | F, H |
| F, I | G, H | G, I | H, I | | | | | | | | | | | | |

In some embodiments, the microbial ensembles may be selected from any member group from Tables 5-11.

Isolated Microbes—Source Material

The microbes of the present disclosure were obtained, among other places, at various locales in the United States from the gastrointestinal tract of poultry.

Isolated Microbes—Microbial Culture Techniques

The microbes of Table 1 and Table 3 were matched to their nearest taxonomic groups by utilizing classification tools of the Ribosomal Database Project (RDP) for 16s rRNA sequences and the User-friendly Nordic ITS Ectomycorrhiza (UNITE) database for ITS rRNA sequences. Examples of matching microbes to their nearest taxa may be found in Lan et al. (2012. *PLOS one.* 7(3):e32491), Schloss and Westcott (2011. *Appl. Environ. Microbiol.* 77(10):3219-3226), and Koljalg et al. (2005. *New Phytologist.* 166(3): 1063-1068).

The isolation, identification, and culturing of the microbes of the present disclosure can be effected using standard microbiological techniques. Examples of such techniques may be found in Gerhardt, P. (ed.) Methods for General and Molecular Microbiology. American Society for Microbiology, Washington, D.C. (1994) and Lennette, E. H. (ed.) Manual of Clinical Microbiology, Third Edition. American Society for Microbiology, Washington, D.C. (1980), each of which is incorporated by reference.

Isolation can be effected by streaking the specimen on a solid medium (e.g., nutrient agar plates) to obtain a single colony, which is characterized by the phenotypic traits described hereinabove (e.g., Gram positive/negative, capable of forming spores aerobically/anaerobically, cellular morphology, carbon source metabolism, acid/base production, enzyme secretion, metabolic secretions, etc.) and to reduce the likelihood of working with a culture which has become contaminated.

For example, for microbes of the disclosure, biologically pure isolates can be obtained through repeated subculture of biological samples, each subculture followed by streaking onto solid media to obtain individual colonies or colony forming units. Methods of preparing, thawing, and growing lyophilized bacteria are commonly known, for example, Gherna, R. L. and C. A. Reddy. 2007. Culture Preservation, p 1019-1033. In C. A. Reddy, T. J. Beveridge, J. A. Breznak, G. A. Marzluf, T. M. Schmidt, and L. R. Snyder, eds. American Society for Microbiology, Washington, D.C., 1033 pages; herein incorporated by reference. Thus freeze dried liquid formulations and cultures stored long term at −70° C. in solutions containing glycerol are contemplated for use in providing formulations of the present disclosure.

The microbes of the disclosure can be propagated in a liquid medium under aerobic conditions, or alternatively anaerobic conditions. Medium for growing the bacterial strains of the present disclosure includes a carbon source, a nitrogen source, and inorganic salts, as well as specially required substances such as vitamins, amino acids, nucleic acids and the like. Examples of suitable carbon sources which can be used for growing the microbes include, but are not limited to, starch, peptone, yeast extract, amino acids, sugars such as glucose, arabinose, mannose, glucosamine, maltose, and the like; salts of organic acids such as acetic acid, fumaric acid, adipic acid, propionic acid, citric acid, gluconic acid, malic acid, pyruvic acid, malonic acid and the like; alcohols such as ethanol and glycerol and the like; oil or fat such as soybean oil, rice bran oil, olive oil, corn oil, sesame oil. The amount of the carbon source added varies according to the kind of carbon source and is typically between 1 to 100 gram(s) per liter of medium. Preferably, glucose, starch, and/or peptone is contained in the medium as a major carbon source, at a concentration of 0.1-5% (W/V). Examples of suitable nitrogen sources which can be used for growing the bacterial strains of the present disclosure include, but are not limited to, amino acids, yeast extract, tryptone, beef extract, peptone, potassium nitrate, ammonium nitrate, ammonium chloride, ammonium sulfate, ammonium phosphate, ammonia or combinations thereof. The amount of nitrogen source varies according to the type of nitrogen source, typically between 0.1 to 30 grams per liter of media. The inorganic salts, potassium dihydrogen phosphate, dipotassium hydrogen phosphate, disodium hydrogen phosphate, magnesium sulfate, magnesium chloride, ferric sulfate, ferrous sulfate, ferric chloride, ferrous chloride, manganous sulfate, manganous chloride, zinc sulfate, zinc chloride, cupric sulfate, calcium chloride, sodium chloride, calcium carbonate, sodium carbonate can be used alone or in combination. The amount of inorganic acid varies according to the kind of the inorganic salt, typically between 0.001 to 10 grams per liter of medium. Examples of specially required substances include, but are not limited to, vitamins, nucleic acids, yeast extract, peptone, meat extract, malt extract, dried yeast and combinations thereof. Cultivation can be effected at a temperature, which allows the growth of the microbial strains, essentially, between 20° C. and 46° C. In some aspects, a temperature range is 30° C.-39° C. For optimal growth, in some embodiments, the medium can be adjusted to pH 6.0-7.4. It will be appreciated that commercially available media may also be used to culture the microbial strains, such as Nutrient Broth or Nutrient Agar available from Difco, Detroit, Mich. It will be appreciated that cultivation time may differ depending on the type of culture medium used and the concentration of sugar as a major carbon source.

In some aspects, cultivation lasts between 24-96 hours. Microbial cells thus obtained are isolated using methods, which are well known in the art. Examples include, but are not limited to, membrane filtration and centrifugal separation. The pH may be adjusted using sodium hydroxide and the like and the culture may be dried using a freeze dryer, until the water content becomes equal to 4% or less. Microbial co-cultures may be obtained by propagating each strain as described hereinabove. In some aspects, microbial multi-strain cultures may be obtained by propagating two or more of the strains described hereinabove. It will be appreciated that the microbial strains may be cultured together when compatible culture conditions can be employed.

Isolated Microbes—Microbial Strains

Microbes can be distinguished into a genus based on polyphasic taxonomy, which incorporates all available phenotypic and genotypic data into a consensus classification (Vandamme et al. 1996. Polyphasic taxonomy, a consensus approach to bacterial systematics. *Microbiol Rev* 1996, 60:407-438). One accepted genotypic method for defining species is based on overall genomic relatedness, such that strains which share approximately 70% or more relatedness using DNA-DNA hybridization, with 5° C. or less $\Delta T_m$ (the difference in the melting temperature between homologous and heterologous hybrids), under standard conditions, are considered to be members of the same species. Thus, populations that share greater than the aforementioned 70% threshold can be considered to be variants of the same species. Another accepted genotypic method for defining species is to isolate marker genes of the present disclosure, sequence these genes, and align these sequenced genes from multiple isolates or variants. The microbes are interpreted as belonging to the same species if one or more of the sequenced genes share at least 97% sequence identity.

The 16S or 18S rRNA sequences or ITS sequences are often used for making distinctions between species and strains, in that if one of the aforementioned sequences shares less than a specified % sequence identity from a reference sequence, then the two organisms from which the sequences were obtained are said to be of different species or strains.

Thus, one could consider microbes to be of the same species, if they share at least 80%, 85%, 90%, 95%, 97%, 98%, or 99% sequence identity across the 16S or 18S rRNA sequence, or the ITS1 or ITS2 sequence.

Further, one could define microbial strains of a species, as those that share at least 80%, 85%, 90%, 95%, 97%, 98%, or 99% sequence identity across the 16S or 18S rRNA sequence, or the ITS 1 or ITS2 sequence.

Sequence identifiers of the present disclosure consist of SEQ ID NOs:1-387. SEQ ID NOs:1-50 and 59-387 are bacterial polynucleotide sequences encoding 16S rRNA. SEQ ID NOs:51-58 are fungal polynucleotide sequences encoding ITS sequences.

In one embodiment, microbial strains of the present disclosure include those that comprise polynucleotide sequences that share at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with any one of SEQ ID NOs:1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, 32, 33, 34, 35, 36, 37, 38, 39, 40, 41, 42, 43, 44, 45, 46, 47, 48, 49, 50, 51, 52, 53, 54, 55, 56, 57, 58, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, and 387. In a further embodiment, microbial strains of the present disclosure include those that comprise polynucleotide sequences that share at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with any one of SEQ ID NOs:1-387.

Comparisons may also be made with 23S rRNA sequences against reference sequences.

Unculturable microbes often cannot be assigned to a definite species in the absence of a phenotype determination, the microbes can be given a *candidatus* designation within a genus provided their 16S or 18S rRNA sequences or ITS sequences subscribes to the principles of identity with known species.

One approach is to observe the distribution of a large number of strains of closely related species in sequence space and to identify clusters of strains that are well resolved from other clusters. This approach has been developed by using the concatenated sequences of multiple core (housekeeping) genes to assess clustering patterns, and has been called multilocus sequence analysis (MLSA) or multilocus sequence phylogenetic analysis. MLSA has been used successfully to explore clustering patterns among large numbers of strains assigned to very closely related species by current taxonomic methods, to look at the relationships between small numbers of strains within a genus, or within a broader taxonomic grouping, and to address specific taxonomic questions. More generally, the method can be used to ask whether bacterial species exist—that is, to observe whether large populations of similar strains invariably fall into well-resolved clusters, or whether in some cases there is a genetic continuum in which clear separation into clusters is not observed.

In order to more accurately make a determination of genera, a determination of phenotypic traits, such as morphological, biochemical, and physiological characteristics are made for comparison with a reference genus archetype. The colony morphology can include color, shape, pigmentation, production of slime, etc. Features of the cell are described as to shape, size, Gram reaction, extracellular material, presence of endospores, flagella presence and location, motility, and inclusion bodies. Biochemical and physiological features describe growth of the organism at different ranges of temperature, pH, salinity and atmospheric conditions, growth in presence of different sole carbon and nitrogen sources. One of ordinary skill in the art would be reasonably apprised as to the phenotypic traits that define the genera of the present disclosure.

In one embodiment, the microbes taught herein were identified utilizing 16S rRNA gene sequences and ITS sequences. It is known in the art that 16S rRNA contains hypervariable regions that can provide species/strain-specific signature sequences useful for bacterial identification, and that ITS sequences can also provide species/strain-specific signature sequences useful for fungal identification.

Phylogenetic analysis using the rRNA genes and/or ITS sequences are used to define "substantially similar" species belonging to common genera and also to define "substantially similar" strains of a given taxonomic species. Furthermore, physiological and/or biochemical properties of the isolates can be utilized to highlight both minor and significant differences between strains that could lead to advantageous behavior in poultry.

Compositions of the present disclosure may include combinations of fungal spores and bacterial spores, fungal spores and bacterial vegetative cells, fungal vegetative cells and bacterial spores, fungal vegetative cells and bacterial vegetative cells. In some embodiments, compositions of the present disclosure comprise bacteria only in the form of spores. In some embodiments, compositions of the present disclosure comprise bacteria only in the form of vegetative cells. In some embodiments, compositions of the present disclosure comprise bacteria in the absence of fungi. In some embodiments, compositions of the present disclosure comprise fungi in the absence of bacteria. In some embodiments, compositions of the present disclosure comprise VBNC bacteria and/or fungi. In some embodiments, compositions of the present disclosure include dormant bacteria and/or fungi.

Bacterial spores may include endospores and akinetes. Fungal spores may include statismospores, ballistospores, autospores, aplanospores, zoospores, mitospores, megaspores, microspores, meiospores, chlamydospores, urediniospores, teliospores, oospores, carpospores, tetraspores, sporangiospores, zygospores, basidiospores, ascospores, and asciospores.

In some embodiments, spores of the composition germinate upon administration to animals of the present disclosure. In some embodiments, spores of the composition germinate only upon administration to animals of the present disclosure.

Microbial Compositions

In some embodiments, the microbes of the disclosure are combined into microbial compositions.

In some embodiments, the microbial compositions include poultry feed, such as cereals (barley, maize, oats, and the like); starches (tapioca and the like); oilseed cakes; and vegetable wastes. In some embodiments, the microbial compositions include vitamins, minerals, trace elements, emulsifiers, aromatizing products, binders, colorants, odorants, thickening agents, and the like. In some embodiments, the microbial compositions include one or more of an ionophore; vaccine; antibiotic; antihelmintic; virucide; nematicide; amino acids such as methionine, glycine, and arginine; fish oil; oregano; and biologically active molecules such as enzymes.

In some embodiments, the microbial compositions of the present disclosure are solid. Where solid compositions are used, it may be desired to include one or more carrier materials including, but not limited to: mineral earths such as silicas, talc, kaolin, limestone, chalk, clay, dolomite, diatomaceous earth; calcium sulfate; magnesium sulfate; magnesium oxide; zeolites, calcium carbonate; magnesium carbonate; trehalose; chitosan; shellac; albumins; starch; skim-milk powder; sweet-whey powder; maltodextrin; lactose; inulin; dextrose; products of vegetable origin such as cereal meals, tree bark meal, wood meal, and nutshell meal.

In some embodiments, the microbial compositions of the present disclosure are liquid. In further embodiments, the liquid comprises a solvent that may include water or an alcohol or a saline or carbohydrate solution, and other animal-safe solvents. In some embodiments, the microbial compositions of the present disclosure include binders such as animal-safe polymers, carboxymethylcellulose, starch, polyvinyl alcohol, and the like.

In some embodiments, the microbial compositions of the present disclosure comprise thickening agents such as silica, clay, natural extracts of seeds or seaweed, synthetic derivatives of cellulose, guar gum, locust bean gum, alginates, and methylcelluloses. In some embodiments, the microbial compositions comprise anti-settling agents such as modified starches, polyvinyl alcohol, xanthan gum, and the like.

In some embodiments, the microbial compositions of the present disclosure comprise colorants including organic chromophores classified as nitroso; nitro; azo, including monoazo, bisazo and polyazo; acridine, anthraquinone, azine, diphenylmethane, indamine, indophenol, methine, oxazine, phthalocyanine, thiazine, thiazole, triarylmethane, xanthene. In some embodiments, the microbial compositions of the present disclosure comprise trace nutrients such as salts of iron, manganese, boron, copper, cobalt, molybdenum and zinc. In some embodiments, the microbial compositions comprise dyes, both natural and artificial. In some embodiments, the dye is green in color.

In some embodiments, the microbial compositions of the present disclosure comprise an animal-safe virucide, bacteriocide, or nematicide.

In some embodiments, microbial compositions of the present disclosure comprise saccharides (e.g., monosaccharides, disaccharides, trisaccharides, polysaccharides, oligosaccharides, and the like), polymeric saccharides, lipids, polymeric lipids, lipopolysaccharides, proteins, polymeric proteins, lipoproteins, nucleic acids, nucleic acid polymers, silica, inorganic salts and combinations thereof. In a further embodiment, microbial compositions comprise polymers of agar, agarose, gelrite, and gellan gum, and the like. In some embodiments, microbial compositions comprise plastic capsules, emulsions (e.g., water and oil), membranes, and artificial membranes. In some embodiments, emulsions or linked polymer solutions may comprise microbial compositions of the present disclosure. See Harel and Bennett (U.S. Pat. No. 8,460,726B2). In one embodiment, the microbial composition comprises glucose. In one embodiment, formulations of the microbial composition comprise glucose.

In some embodiments, microbial compositions of the present disclosure comprise one or more oxygen scavengers, denitrifiers, nitrifiers, heavy metal chelators, and/or dechlorinators; and combinations thereof. In one embodiment, the one or more oxygen scavengers, denitrifiers, nitrifiers, heavy metal chelators, and/or dechlorinators are not chemically active once the microbial compositions are mixed with food and/or water to be administered to the fowl. In one embodiment, the one or more oxygen scavengers, denitrifiers, nitrifiers, heavy metal chelators, and/or dechlorinators are not chemically active when administered to the fowl.

In some embodiments, microbial compositions of the present disclosure occur in a solid form (e.g., dispersed lyophilized spores) or a liquid form (microbes interspersed in a storage medium). In some embodiments, microbial compositions of the present disclosure are added in dry form to a liquid to form a suspension immediately prior to administration.

In some embodiments, microbial compositions of the present disclosure comprise one or more preservatives. The preservatives may be in liquid or gas formulations. The preservatives may be selected from one or more of monosaccharide, disaccharide, trisaccharide, polysaccharide, acetic acid, ascorbic acid, calcium ascorbate, erythorbic acid, iso-ascorbic acid, erythrobic acid, potassium nitrate, sodium ascorbate, sodium erythorbate, sodium iso-ascorbate, sodium nitrate, sodium nitrite, nitrogen, benzoic acid, calcium sorbate, ethyl lauroyl arginate, methyl-p-hydroxy benzoate, methyl paraben, potassium acetate, potassium benzoiate, potassium bisulphite, potassium diacetate, potassium lactate, potassium metabisulphite, potassium sorbate, propyl-p-hydroxy benzoate, propyl paraben, sodium acetate, sodium benzoate, sodium bisulphite, sodium nitrite, sodium diacetate, sodium lactate, sodium metabisulphite, sodium salt of methyl-p-hydroxy benzoic acid, sodium salt of propyl-p-hydroxy benzoic acid, sodium sulphate, sodium sulfite, sodium dithionite, sulphurous acid, calcium propionate, dimethyl dicarbonate, natamycin, potassium sorbate, potassium bisulfite, potassium metabisulfite, propionic acid, sodium diacetate, sodium propionate, sodium sorbate, sorbic acid, ascorbic acid, ascorbyl palmitate, ascorbyl stearate, butylated hydro-xyanisole, butylated hydroxytoluene (BHT), butylated hydroxyl anisole (BHA), citric acid, citric acid esters of mono- and/or diglycerides, L-cysteine, L-cysteine hydrochloride, gum guaiacum, gum guaiac, lecithin, lecithin citrate, monoglyceride citrate, monoisopropyl citrate, propyl gallate, sodium metabisulphite, tartaric acid, tertiary butyl hydroquinone, stannous chloride, thiodipropionic acid, dilauryl thiodipropionate, distearyl thiodipropionate, ethoxyquin, sulfur dioxide, formic acid, or tocopherol(s).

In some embodiments, microbial compositions of the present disclosure include bacterial and/or fungal cells in spore form, vegetative cell form, dormant cell form, and/or lysed cell form. In one embodiment, the lysed cell form acts as a mycotoxin binder, e.g. mycotoxins binding to dead cells.

In some embodiments, the microbial compositions are shelf stable in a refrigerator (35-40° F.) for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days. In some embodiments, the microbial compositions are shelf stable in a refrigerator (35-40° F.) for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 weeks.

In some embodiments, the microbial compositions are shelf stable at room temperature (68-72° F.) or between 50-77° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days. In some embodiments, the microbial compositions are shelf stable at room temperature (68-72° F.) or between 50-77° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 weeks.

In some embodiments, the microbial compositions are shelf stable at −23-35° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days. In some embodiments, the microbial compositions are shelf stable at −23-35° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 weeks.

In some embodiments, the microbial compositions are shelf stable at 77-100° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days. In some embodiments, the microbial compositions are shelf stable at 77-100° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 weeks.

In some embodiments, the microbial compositions are shelf stable at 101-213° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days. In some embodiments, the microbial compositions are shelf stable at 101-213° F. for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 weeks.

In some embodiments, the microbial compositions of the present disclosure are shelf stable at refrigeration temperatures (35-40° F.), at room temperature (68-72° F.), between 50-77° F., between −23-35° F., between 70-100° F., or between 101-213° F. for a period of about 1 to 100, about 1 to 95, about 1 to 90, about 1 to 85, about 1 to 80, about 1 to 75, about 1 to 70, about 1 to 65, about 1 to 60, about 1 to 55, about 1 to 50, about 1 to 45, about 1 to 40, about 1 to 35, about 1 to 30, about 1 to 25, about 1 to 20, about 1 to 15, about 1 to 10, about 1 to 5, about 5 to 100, about 5 to 95, about 5 to 90, about 5 to 85, about 5 to 80, about 5 to 75, about 5 to 70, about 5 to 65, about 5 to 60, about 5 to 55, about 5 to 50, about 5 to 45, about 5 to 40, about 5 to 35, about 5 to 30, about 5 to 25, about 5 to 20, about 5 to 15, about 5 to 10, about 10 to 100, about 10 to 95, about 10 to 90, about 10 to 85, about 10 to 80, about 10 to 75, about 10 to 70, about 10 to 65, about 10 to 60, about 10 to 55, about 10 to 50, about 10 to 45, about 10 to 40, about 10 to 35, about 10 to 30, about 10 to 25, about 10 to 20, about 10 to 15, about 15 to 100, about 15 to 95, about 15 to 90, about 15 to 85, about 15 to 80, about 15 to 75, about 15 to 70, about 15 to 65, about 15 to 60, about 15 to 55, about 15 to 50, about 15 to 45, about 15 to 40, about 15 to 35, about 15 to 30, about 15 to 25, about 15 to 20, about 20 to 100, about 20 to 95, about 20 to 90, about 20 to 85, about 20 to 80, about 20 to 75, about 20 to 70, about 20 to 65, about 20 to 60, about 20 to 55, about 20 to 50, about 20 to 45, about 20 to 40, about 20 to 35, about 20 to 30, about 20 to 25, about 25 to 100, about 25 to 95, about 25 to 90, about 25 to 85, about 25 to 80, about 25 to 75, about 25 to 70, about 25 to 65, about 25 to 60, about 25 to 55, about 25 to 50, about 25 to 45, about 25 to 40, about 25 to 35, about 25 to 30, about 30 to 100, about 30 to 95, about 30 to 90, about 30 to 85, about 30 to 80, about 30 to 75, about 30 to 70, about 30 to 65, about 30 to 60, about 30 to 55, about 30 to 50, about 30 to 45, about 30 to 40, about 30 to 35, about 35 to 100, about 35 to 95, about 35 to 90, about 35 to 85, about 35 to 80, about 35 to 75, about 35 to 70, about 35 to 65, about 35 to 60, about 35 to 55, about 35 to 50, about 35 to 45, about 35 to 40, about 40 to 100, about 40 to 95, about 40 to 90, about 40 to 85, about 40 to 80, about 40 to 75, about 40 to 70, about 40 to 65, about 40 to 60, about 40 to 55, about 40 to 50, about 40 to 45, about 45 to 100, about 45 to 95, about 45 to 90, about 45 to 85, about 45 to 80, about 45 to 75, about 45 to 70, about 45 to 65, about 45 to 60, about 45 to 55, about 45 to 50, about 50 to 100, about 50 to 95, about 50 to 90, about 50 to 85, about 50 to 80, about 50 to 75, about 50 to 70, about 50 to 65, about 50 to 60, about 50 to 55, about 55 to 100, about 55 to 95, about 55 to 90, about 55 to 85, about 55 to 80, about 55 to 75, about 55 to 70, about 55 to 65, about 55 to 60, about 60 to 100, about 60 to 95, about 60 to 90, about 60 to 85, about 60 to 80, about 60 to 75, about 60 to 70, about 60 to 65, about 65 to 100, about 65 to 95, about 65 to 90, about 65 to 85, about 65 to 80, about 65 to 75, about 65 to 70, about 70 to 100, about 70 to 95, about 70 to 90, about 70 to 85, about 70 to 80, about 70 to 75, about 75 to 100, about 75 to 95, about 75 to 90, about 75 to 85, about 75 to 80, about 80 to 100, about 80 to 95, about 80 to 90, about 80 to 85, about 85 to 100, about 85 to 95, about 85 to 90, about 90 to 100, about 90 to 95, or 95 to 100 weeks.

In some embodiments, the microbial compositions of the present disclosure are shelf stable at refrigeration temperatures (35-40° F.), at room temperature (68-72° F.), between 50-77° F., between −23-35° F., between 70-100° F., or between 101-213° F. for a period of 1 to 100, 1 to 95, 1 to 90, 1 to 85, 1 to 80, 1 to 75, 1 to 70, 1 to 65, 1 to 60, 1 to 55, 1 to 50, 1 to 45, 1 to 40, 1 to 35, 1 to 30, 1 to 25, 1 to 20, 1 to 15, 1 to 10, 1 to 5, 5 to 100, 5 to 95, 5 to 90, 5 to 85, 5 to 80, 5 to 75, 5 to 70, 5 to 65, 5 to 60, 5 to 55, 5 to 50, 5 to 45, 5 to 40, 5 to 35, 5 to 30, 5 to 25, 5 to 20, 5 to 15, 5 to 10, 10 to 100, 10 to 95, 10 to 90, 10 to 85, 10 to 80, 10 to 75, 10 to 70, 10 to 65, 10 to 60, 10 to 55, 10 to 50, 10 to 45, 10 to 40, 10 to 35, 10 to 30, 10 to 25, 10 to 20, 10 to 15, 15 to 100, 15 to 95, 15 to 90, 15 to 85, 15 to 80, 15 to 75, 15 to 70, 15 to 65, 15 to 60, 15 to 55, 15 to 50, 15 to 45, 15 to 40, 15 to 35, 15 to 30, 15 to 25, 15 to 20, 20 to 100, 20 to 95, 20 to 90, 20 to 85, 20 to 80, 20 to 75, 20 to 70, 20 to 65, 20 to 60, 20 to 55, 20 to 50, 20 to 45, 20 to 40, 20 to 35, 20 to 30, 20 to 25, 25 to 100, 25 to 95, 25 to 90, 25 to 85, 25 to 80, 25 to 75, 25 to 70, 25 to 65, 25 to 60, 25 to 55, 25 to 50, 25 to 45, 25 to 40, 25 to 35, 25 to 30, 30 to 100, 30 to 95, 30 to 90, 30 to 85, 30 to 80, 30 to 75, 30 to 70, 30 to 65, 30 to 60, 30 to 55, 30 to 50, 30 to 45, 30 to 40, 30 to 35, 35 to 100, 35 to 95, 35 to 90, 35 to 85, 35 to 80, 35 to 75, 35 to 70, 35 to 65, 35 to 60, 35 to 55, 35 to 50, 35 to 45, 35 to 40, 40 to 100, 40 to 95, 40 to 90, 40 to 85, 40 to 80, 40 to 75, 40 to 70, 40 to 65, 40 to 60, 40 to 55, 40 to 50, 40 to 45, 45 to 100, 45 to 95, 45 to 90, 45 to 85, 45 to 80, 45 to 75, 45 to 70, 45 to 65, 45 to 60, 45 to 55, 45 to 50, 50 to 100, 50 to 95, 50 to 90, 50 to 85, 50 to 80, 50 to 75, 50 to 70, 50 to 65, 50 to 60, 50 to 55, 55 to 100, 55 to 95, 55 to 90, 55 to 85, 55 to 80, 55 to 75, 55 to 70, 55 to 65, 55 to 60, 60 to 100, 60 to 95, 60 to 90, 60 to 85, 60 to 80, 60 to 75, 60 to 70, 60 to 65, 65 to 100, 65 to 95, 65 to 90, 65 to 85, 65 to 80, 65 to 75, 65 to 70, 70 to 100, 70 to 95, 70 to 90, 70 to 85, 70 to 80, 70 to 75, 75 to 100, 75 to 95, 75 to 90, 75 to 85, 75 to 80, 80 to 100, 80 to 95, 80 to 90, 80 to 85, 85 to 100, 85 to 95, 85 to 90, 90 to 100, 90 to 95, or 95 to 100 weeks.

In some embodiments, the microbial compositions of the present disclosure are shelf stable at refrigeration temperatures (35-40° F.), at room temperature (68-72° F.), between 50-77° F., between −23-35° F., between 70-100° F., or between 101-213° F. for a period of about 1 to 36, about 1 to 34, about 1 to 32, about 1 to 30, about 1 to 28, about 1 to 26, about 1 to 24, about 1 to 22, about 1 to 20, about 1 to 18, about 1 to 16, about 1 to 14, about 1 to 12, about 1 to 10, about 1 to 8, about 1 to 6, about 1 one 4, about 1 to 2, about 4 to 36, about 4 to 34, about 4 to 32, about 4 to 30, about 4 to 28, about 4 to 26, about 4 to 24, about 4 to 22, about 4 to 20, about 4 to 18, about 4 to 16, about 4 to 14, about 4 to 12, about 4 to 10, about 4 to 8, about 4 to 6, about 6 to 36, about 6 to 34, about 6 to 32, about 6 to 30, about 6 to 28, about 6 to 26, about 6 to 24, about 6 to 22, about 6 to 20, about 6 to 18, about 6 to 16, about 6 to 14, about 6 to 12, about 6 to 10, about 6 to 8, about 8 to 36, about 8 to 34, about 8 to 32, about 8 to 30, about 8 to 28, about 8 to 26, about 8 to 24, about 8 to 22, about 8 to 20, about 8 to 18, about 8 to 16, about 8 to 14, about 8 to 12, about 8 to 10, about 10 to 36, about 10 to 34, about 10 to 32, about 10 to 30, about 10 to 28, about 10 to 26, about 10 to 24, about 10 to 22, about 10 to 20, about 10 to 18, about 10 to 16, about 10 to 14, about 10 to 12, about 12 to 36, about 12 to 34, about 12 to 32, about 12 to 30, about 12 to 28, about 12 to 26, about 12 to 24, about 12 to 22, about 12 to 20, about 12 to 18, about 12 to 16, about 12 to 14, about 14 to 36, about 14 to 34, about 14 to 32, about 14 to 30, about 14 to 28, about 14 to 26, about 14 to 24, about 14 to 22, about 14 to 20, about 14 to 18, about 14 to 16, about 16 to 36, about 16 to 34, about 16 to 32, about 16 to 30, about 16 to 28, about 16 to 26, about 16 to 24, about 16 to 22, about 16 to 20, about 16 to 18, about 18 to 36, about 18 to 34, about 18 to 32, about 18 to 30, about 18 to 28, about 18 to 26, about 18 to 24, about 18 to 22, about 18 to 20, about 20 to 36, about 20 to 34, about 20 to 32, about 20 to 30, about 20 to 28, about 20 to 26, about 20 to 24, about 20 to 22, about 22 to 36, about 22 to 34, about 22 to 32, about 22 to 30, about 22 to 28, about 22 to 26, about 22 to 24, about 24 to 36, about 24 to 34, about 24 to 32, about 24 to 30, about 24 to 28, about 24 to 26, about 26 to 36, about 26 to 34, about 26 to 32, about 26 to 30, about 26 to 28, about 28 to 36, about 28 to 34, about 28 to 32, about 28 to 30, about 30 to 36, about 30 to 34, about 30 to 32, about 32 to 36, about 32 to 34, or about 34 to 36 months.

In some embodiments, the microbial compositions of the present disclosure are shelf stable at refrigeration temperatures (35-40° F.), at room temperature (68-72° F.), between 50-77° F., between −23-35° F., between 70-100° F., or between 101-213° F. for a period of 1 to 36 1 to 34 1 to 32 1 to 30 1 to 28 1 to 26 1 to 24 1 to 22 1 to 20 1 to 18 1 to 16 1 to 14 1 to 12 1 to 10 1 to 8 1 to 6 1 one 4 1 to 2 4 to 36 4 to 34 4 to 32 4 to 30 4 to 28 4 to 26 4 to 24 4 to 22 4 to 20 4 to 18 4 to 16 4 to 14 4 to 12 4 to 10 4 to 8 4 to 6 6 to 36 6 to 34 6 to 32 6 to 30 6 to 28 6 to 26 6 to 24 6 to 22 6 to 20 6 to 18 6 to 16 6 to 14 6 to 12 6 to 10 6 to 8 8 to 36 8 to 34 8 to 32 8 to 30 8 to 28 8 to 26 8 to 24 8 to 22 8 to 20 8 to 18 8 to 16 8 to 14 8 to 12 8 to 10 10 to 36 10 to 34 10 to 32 10 to 30 10 to 28 10 to 26 10 to 24 10 to 22 10 to 20 10 to 18 10 to 16 10 to 14 10 to 12 12 to 36 12 to 34 12 to 32 12 to 30 12 to 28 12 to 26 12 to 24 12 to 22 12 to 20 12 to 18 12 to 16 12 to 14 14 to 36 14 to 34 14 to 32 14 to 30 14 to 28 14 to 26 14 to 24 14 to 22 14 to 20 14 to 18 14 to 16 16 to 36 16 to 34 16 to 32 16 to 30 16 to 28 16 to 26 16 to 24 16 to 22 16 to 20 16 to 18 18 to 36 18 to 34 18 to 32 18 to 30 18 to 28 18 to 26 18 to 24 18 to 22 18 to 20 20 to 36 20 to 34 20 to 32 20 to 30 20 to 28 20 to 26 20 to 24 20 to 22 22 to 36 22 to 34 22 to 32 22 to 30 22 to 28 22 to 26 22 to 24 24 to 36 24 to 34 24 to 32 24 to 30 24 to 28 24 to 26 26 to 36 26 to 34 26 to 32 26 to 30 26 to 28 28 to 36 28 to 34 28 to 32 28 to 30 30 to 36 30 to 34 30 to 32 32 to 36 32 to 34, or about 34 to 36 months.

In some embodiments, the microbial compositions of the present disclosure are shelf stable at any of the disclosed temperatures and/or temperature ranges and spans of time at a relative humidity of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, or 98%.

Moisture content is a measurement of the total amount of water in a composition, usually expressed as a percentage of the total weight. The moisture content is a useful measurement for determining the dry weight of a composition, and it can be used to confirm whether the desiccation/drying process of a composition is complete. The moisture content is calculated by dividing the (wet weight of the composition minus the weight after desiccating/drying) by the wet weight of the composition, and multiplying by 100.

Moisture content defines the amount of water in a composition, but water activity explains how the water in the composition will react with microorganisms. The greater the water activity, the faster microorganisms are able to grow. Water activity is calculated by finding the ratio of the vapor pressure in a composition to the vapor pressure of pure water. More specifically, the water activity is the partial vapor pressure of water in a composition divided by the standard state partial vapor pressure of pure water. Pure distilled water has a water activity of 1. A determination of water activity of a composition is not the amount of water in a composition, rather it is the amount of excess amount of water that is available for microorganisms to use. Microorganisms have a minimal and optimal water activity for growth.

In some embodiments, the microbial compositions of the present disclosure are desiccated. A microbial composition is desiccated if the moisture content of the composition is between 0% and 20%.

In some embodiments, the microbial compositions of the present disclosure have a moisture content of about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

In some embodiments, the microbial compositions of the present disclosure have a moisture content of less than 0.5%, less than 0.6%, less than 0.7%, less than 0.8%, less than 0.9%, less than 1%, less than 2%, less than 3%, less than 4%, less than 5%, less than 6%, less than 7%, less than 8%, less than 9%, less than 10%, less than 11%, less than 12%, less than 13%, less than 14%, less than 15%, less than 16%, less than 17%, less than 18%, less than 19%, less than 20%, less than 21%, less than 22%, less than 23%, less than 24%, less than 25%, less than 26%, less than 27%, less than 28%, less than 29%, less than 30%, less than 31%, less than 32%, less than 33%, less than 34%, less than 35%, less than 36%, less than 37%, less than 38%, less than 39%, less than 40%, less than 41%, less than 42%, less than 43%, less than 44%, less than 45%, less than 46%, less than 47%, less than 48%, less than 49%, less than 50%, less than 51%, less than 52%, less than 53%, less than 54%, less than 55%, less than 56%, less than 57%, less than 58%, less than 59%, less than 60%, less than 61%, less than 62%, less than 63%, less than 64%, less than 65%, less than 66%, less than 67%, less than 68%, less than 69%, less than 70%, less than 71%, less than 72%, less than 73%, less than 74%, less than 75%, less than 76%, less than 77%, less than 78%, less than 79%, less than 80%, less than 81%, less than 82%, less than 83%, less than 84%, less than 85%, less than 86%, less than 87%, less than 88%, less than 89%, less than 90%, less than 91%, less than 92%, less than 93%, less than 94%, less than 95%, less than 96%, less than 97%, less than 98%, less than 99%, or less than 100%.

In some embodiments, the microbial compositions of the present disclosure have a moisture content of less than about 0.5%, less than about 0.6%, less than about 0.7%, less than about 0.8%, less than about 0.9%, less than about 1%, less than about 2%, less than about 3%, less than about 4%, less than about 5%, less than about 6%, less than about 7%, less than about 8%, less than about 9%, less than about 10%, less than about 11%, less than about 12%, less than about 13%, less than about 14%, less than about 15%, less than about 16%, less than about 17%, less than about 18%, less than about 19%, less than about 20%, less than about 21%, less than about 22%, less than about 23%, less than about 24%, less than about 25%, less than about 26%, less than about 27%, less than about 28%, less than about 29%, less than about 30%, less than about 31%, less than about 32%, less than about 33%, less than about 34%, less than about 35%, less than about 36%, less than about 37%, less than about 38%, less than about 39%, less than about 40%, less than about 41%, less than about 42%, less than about 43%, less than about 44%, less than about 45%, less than about 46%, less than about 47%, less than about 48%, less than about 49%, less than about 50%, less than about 51%, less than about 52%, less than about 53%, less than about 54%, less than about 55%, less than about 56%, less than about 57%, less than about 58%, less than about 59%, less than about 60%, less than about 61%, less than about 62%, less than about 63%, less than about 64%, less than about 65%, less than about 66%, less than about 67%, less than about 68%, less than about 69%, less than about 70%, less than about 71%, less than about 72%, less than about 73%, less than about 74%, less than about 75%, less than about 76%, less than about 77%, less than about 78%, less than about 79%, less than about 80%, less than about 81%, less than about 82%, less than about 83%, less than about 84%, less than about 85%, less than about 86%, less than about 87%, less than about 88%, less than about 89%, less than about 90%, less than about 91%, less than about 92%, less than about 93%, less than about 94%, less than about 95%, less than about 96%, less than about 97%, less than about 98%, less than about 99%, or less than about 100%.

In some embodiments, the microbial compositions of the present disclosure have a moisture content of 1% to 100%, 1% to 95%, 1% to 90%, 1% to 85%, 1% to 80%, 1% to 75%, 1% to 70%, 1% to 65%, 1% to 60%, 1% to 55%, 1% to 50%, 1% to 45%, 1% to 40%, 1% to 35%, 1% to 30%, 1% to 25%, 1% to 20%, 1% to 15%, 1% to 10%, 1% to 5%, 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 5% to 35%, 5% to 30%, 5% to 25%, 5% to 20%, 5% to 15%, 5% to 10%, 10% to 100%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, 10% to 40%, 10% to 35%, 10% to 30%, 10% to 25%, 10% to 20%, 10% to 15%, 15% to 100%, 15% to 95%, 15% to 90%, 15% to 85%, 15% to 80%, 15% to 75%, 15% to 70%, 15% to 65%, 15% to 60%, 15% to 55%, 15% to 50%, 15% to 45%, 15% to 40%, 15% to 35%, 15% to 30%, 15% to 25%, 15% to 20%, 20% to 100%, 20% to 95%, 20% to 90%, 20% to 85%, 20% to 80%, 20% to 75%, 20% to 70%, 20% to 65%, 20% to 60%, 20% to 55%, 20% to 50%, 20% to 45%, 20% to 40%, 20% to 35%, 20% to 30%, 20% to 25%, 25% to 100%, 25% to 95%, 25% to 90%, 25% to 85%, 25% to 80%, 25% to 75%, 25% to 70%, 25% to 65%, 25% to 60%, 25% to 55%, 25% to 50%, 25% to 45%, 25% to 40%, 25% to 35%, 25% to 30%, 30% to 100%, 30% to 95%, 30% to 90%, 30% to 85%, 30% to 80%, 30% to 75%, 30% to 70%, 30% to 65%, 30% to 60%, 30% to 55%, 30% to 50%, 30% to 45%, 30% to 40%, 30% to 35%, 35% to 100%, 35% to 95%, 35% to 90%, 35% to 85%, 35% to 80%, 35% to 75%, 35% to 70%, 35% to 65%, 35% to 60%, 35% to 55%, 35% to 50%, 35% to 45%, 35% to 40%, 40% to 100%, 40% to 95%, 40% to 90%, 40% to 85%, 40% to 80%, 40% to 75%, 40% to 70%, 40% to 65%, 40% to 60%, 40% to 55%, 40% to 50%, 40% to 45%, 45% to 100%, 45% to 95%, 45% to 90%, 45% to 85%, 45% to 80%, 45% to 75%, 45% to 70%, 45% to 65%, 45% to 60%, 45% to 55%, 45% to 50%, 50% to 100%, 50% to 95%, 50% to 90%, 50% to 85%, 50% to 80%, 50% to 75%, 50% to 70%, 50% to 65%, 50% to 60%, 50% to 55%, 55% to 100%, 55% to 95%, 55% to 90%, 55% to 85%, 55% to 80%, 55% to 75%, 55% to 70%, 55% to 65%, 55% to 60%, 60% to 100%, 60% to 95%, 60% to 90%, 60% to 85%, 60% to 80%, 60% to 75%, 60% to 70%, 60% to 65%, 65% to 100%, 65% to 95%, 65% to 90%, 65% to 85%, 65% to 80%, 65% to 75%, 65% to 70%, 70% to 100%, 70% to 95%, 70% to 90%, 70% to 85%, 70% to 80%, 70% to 75%, 75% to 100%, 75% to 95%, 75% to 90%, 75% to 85%, 75% to 80%, 80% to 100%, 80% to 95%, 80% to 90%, 80% to 85%, 85% to 100%, 85% to 95%, 85% to 90%, 90% to 100%, 90% to 95%, or 95% to 100%.

In some embodiments, the microbial compositions of the present disclosure have a water activity of about 0.1, about 0.15, about 0.2, about 0.25, about 0.30, about 0.35, about 0.4, about 0.5, about 0.55, about 0.60, about 0.65, about 0.70, about 0.75, about 0.8, about 0.85, about 0.90, or about 0.95.

In some embodiments, the microbial compositions of the present disclosure have a water activity of less than about 0.1, less than about 0.15, less than about 0.2, less than about 0.25, less than about 0.30, less than about 0.35, less than about 0.4, less than about 0.5, less than about 0.55, less than about 0.60, less than about 0.65, less than about 0.70, less than about 0.75, less than about 0.8, less than about 0.85, less than about 0.90, or less than about 0.95.

In some embodiments, the microbial compositions of the present disclosure have a water activity of less than 0.1, less than 0.15, less than 0.2, less than 0.25, less than 0.30, less than 0.35, less than 0.4, less than 0.5, less than 0.55, less than 0.60, less than 0.65, less than 0.70, less than 0.75, less than 0.8, less than 0.85, less than 0.90, or less than 0.95.

In some embodiments, the microbial compositions of the present disclosure have a water activity of 0.1 to 0.95, 0.1 to 0.90, 0.1 to 0.85, 0.1 to 0.8, 0.1 to 0.75, 0.1 to 0.70, 0.1 to 0.65, 0.1 to 0.55, 0.1 to 0.50, 0.1 to 0.45, 0.1 to 0.40, 0.1 to 0.35, 0.1 to 0.3, 0.1 to 0.25, 0.1 to 0.2, 0.1 to 0.15, 0.15 to 0.95, 0.15 to 0.90, 0.15 to 0.85, 0.15 to 0.8, 0.15 to 0.75, 0.15 to 0.70, 0.15 to 0.65, 0.15 to 0.55, 0.15 to 0.50, 0.15 to 0.45, 0.15 to 0.40, 0.15 to 0.35, 0.15 to 0.3, 0.15 to 0.25, 0.15 to 0.2, 0.2 to 0.95, 0.2 to 0.90, 0.2 to 0.85, 0.2 to 0.8, 0.2 to 0.75, 0.2 to 0.70, 0.2 to 0.65, 0.2 to 0.55, 0.2 to 0.50, 0.2 to 0.45, 0.2 to 0.40, 0.2 to 0.35, 0.2 to 0.3, 0.2 to 0.25, 0.25 to 0.95, 0.25 to 0.90, 0.25 to 0.85, 0.25 to 0.8, 0.25 to 0.75, 0.25 to 0.70, 0.25 to 0.65, 0.25 to 0.55, 0.25 to 0.50, 0.25 to 0.45, 0.25 to 0.40, 0.25 to 0.35, 0.25 to 0.3, 0.3 to 0.95, 0.3 to 0.90, 0.3 to 0.85, 0.3 to 0.8, 0.3 to 0.75, 0.3 to 0.70, 0.3 to 0.65, 0.3 to 0.55, 0.3 to 0.50, 0.3 to 0.45, 0.3 to 0.40, 0.3 to 0.35, 0.35 to 0.95, 0.35 to 0.90, 0.35 to 0.85, 0.35 to 0.8, 0.35 to 0.75, 0.35 to 0.70, 0.35 to 0.65, 0.35 to 0.55, 0.35 to 0.50, 0.35 to 0.45, 0.35 to 0.40, 0.4 to 0.95, 0.4 to 0.90, 0.4 to 0.85, 0.4 to 0.8, 0.4 to 0.75, 0.4 to 0.70, 0.4 to 0.65, 0.4 to 0.55, 0.4 to 0.50, 0.4 to 0.45, 0.45 to 0.95, 0.45 to 0.90, 0.45 to 0.85, 0.45 to 0.8, 0.45 to 0.75, 0.45 to 0.70, 0.45 to 0.65, 0.45 to 0.55, 0.45 to 0.50, 0.5 to 0.95, 0.5 to 0.90, 0.5 to 0.85, 0.5 to 0.8, 0.5 to 0.75, 0.5 to 0.70, 0.5 to 0.65, 0.5 to 0.55, 0.55 to 0.95, 0.55 to 0.90, 0.55 to 0.85, 0.55 to 0.8, 0.55 to 0.75, 0.55 to 0.70, 0.55 to 0.65, 0.6 to 0.95, 0.6 to 0.90, 0.6 to 0.85, 0.6 to 0.8, 0.6 to 0.75, 0.6 to 0.70, 0.65 to 0.95, 0.65 to 0.90, 0.65 to 0.85, 0.65 to 0.8, 0.65 to 0.75, 0.7 to 0.95, 0.7 to 0.90, 0.7 to 0.85, 0.7 to 0.8, 0.75 to 0.95, 0.75 to 0.90, 0.75 to 0.85, 0.8 to 0.95, 0.8 to 0.90, 0.8 to 0.85, 0.85 to 0.95, 0.85 to 0.90, or 0.9 to 0.95.

Encapsulation Compositions

In some embodiments, the microbes or microbial compositions of the disclosure are encapsulated in an encapsulating composition. An encapsulating composition protects the microbes from external stressors prior to entering the gastrointestinal tract of poultry. In some embodiments, external stressors include thermal and physical stressors associated with pelleting and extrusion. In some embodiments, external stressors include chemicals present in the compositions to which Encapsulating compositions further create an environment that may be beneficial to the microbes, such as minimizing the oxidative stresses of an aerobic environment on anaerobic microbes, preserving the viability of the microbes wherein vegetative cells or spores form during the pelleting/extrusion process, etc. See Kalsta et al. (U.S. Pat. No. 5,104,662A), Ford (U.S. Pat. No. 5,733,568A), and Mosbach and Nilsson (U.S. Pat. No. 4,647,536A) for encapsulation compositions of microbes, and methods of encapsulating microbes.

In one embodiment, the compositions of the present disclosure exhibit a thermal tolerance, which is used interchangeably with heat tolerance and heat resistance. In one embodiment, thermal tolerant compositions of the present disclosure are tolerant of the high temperatures associated with feed manufacturing, mixing of feed and compositions of the present disclosure, storage in high heat environments, etc. In one embodiment, thermal tolerant compositions of the present disclosure are resistant to heat-killing and denaturation of the cell wall components and the intracellular environment.

In one embodiments, the encapsulation is a reservoir-type encapsulation. In one embodiment, the encapsulation is a matrix-type encapsulation. In one embodiment, the encapsulation is a coated matrix-type encapsulation. Burgain et al. (2011. J. Food Eng. 104:467-483) discloses numerous encapsulation embodiments and techniques, all of which are incorporated by reference.

In some embodiments, the compositions of the present disclosure are encapsulated in one or more of the following: gellan gum, xanthan gum, K-Carrageenan, cellulose acetate phthalate, chitosan, starch, milk fat, whey protein, Ca-alginate, raftilose, raftiline, pectin, saccharide, glucose, maltodextrin, gum arabic, guar, seed flour, alginate, dextrins, dextrans, celluloase, gelatin, gelatin, albumin, casein, gluten, acacia gum, tragacanth, wax, paraffin, stearic acid, monodiglycerides, and diglycerides. In some embodiments, the compositions of the present disclosure are encapsulated by one or more of a polymer, carbohydrate, sugar, plastic, glass, polysaccharide, lipid, wax, oil, fatty acid, or glyceride. In one embodiment, the microbial composition is encapsulated by a glucose. In one embodiment, the microbial composition is encapsulated by a glucose-containing composition. In one embodiment, formulations of the microbial composition comprise a glucose encapsulant. In one embodiment, formulations of the microbial composition comprise a glucose-encapsulated composition.

In some embodiments, the encapsulation of the compositions of the present disclosure is carried out by an extrusion, emulsification, coating, agglomeration, lyophilization, vacuum-drying, or spray-drying.

In one embodiment, the encapsulating composition comprises microcapsules having a multiplicity of liquid cores encapsulated in a solid shell material. For purposes of the disclosure, a "multiplicity" of cores is defined as two or more.

A first category of useful fusible shell materials is that of normally solid fats, including fats which are already of suitable hardness and animal or vegetable fats and oils which are hydrogenated until their melting points are sufficiently high to serve the purposes of the present disclosure. Depending on the desired process and storage temperatures and the specific material selected, a particular fat can be either a normally solid or normally liquid material. The terms "normally solid" and "normally liquid" as used herein refer to the state of a material at desired temperatures for storing the resulting microcapsules. Since fats and hydrogenated oils do not, strictly speaking, have melting points, the term "melting point" is used herein to describe the minimum temperature at which the fusible material becomes sufficiently softened or liquid to be successfully emulsified and spray cooled, thus roughly corresponding to the maximum temperature at which the shell material has sufficient integrity to prevent release of the choline cores. "Melting point" is similarly defined herein for other materials which do not have a sharp melting point.

Specific examples of fats and oils useful herein (some of which require hardening) are as follows: animal oils and fats, such as beef tallow, mutton tallow, lamb tallow, lard or pork fat, fish oil, and sperm oil; vegetable oils, such as canola oil, cottonseed oil, peanut oil, corn oil, olive oil, soybean oil, sunflower oil, safflower oil, coconut oil, palm oil, linseed oil, tung oil, and castor oil; fatty acid monoglycerides and diglycerides; free fatty acids, such as stearic acid, palmitic acid, and oleic acid; and mixtures thereof. The above listing of oils and fats is not meant to be exhaustive, but only exemplary.

Specific examples of fatty acids include linoleic acid, γ-linoleic acid, dihomo-γ-linolenic acid, arachidonic acid, docosatetraenoic acid, vaccenic acid, nervonic acid, mead acid, erucic acid, gondoic acid, elaidic acid, oleic acid, palitoleic acid, stearidonic acid, eicosapentaenoic acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecyclic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, heptatriacontanoic acid, and octatriacontanoic acid.

Another category of fusible materials useful as encapsulating shell materials is that of waxes. Representative waxes contemplated for use herein are as follows: animal waxes, such as beeswax, lanolin, shell wax, and Chinese insect wax; vegetable waxes, such as carnauba, candelilla, bayberry, and sugar cane; mineral waxes, such as paraffin, microcrystalline petroleum, ozocerite, ceresin, and montan; synthetic waxes, such as low molecular weight polyolefin (e.g., CARBOWAX), and polyol ether-esters (e.g., sorbitol); Fischer-Tropsch process synthetic waxes; and mixtures thereof. Water-soluble waxes, such as CARBOWAX and sorbitol, are not contemplated herein if the core is aqueous.

Still other fusible compounds useful herein are fusible natural resins, such as rosin, balsam, shellac, and mixtures thereof.

Various adjunct materials are contemplated for incorporation in fusible materials according to the present disclosure. For example, antioxidants, light stabilizers, dyes and lakes, flavors, essential oils, anti-caking agents, fillers, pH stabilizers, sugars (monosaccharides, disaccharides, trisaccharides, and polysaccharides) and the like can be incorporated in the fusible material in amounts which do not diminish its utility for the present disclosure.

The core material contemplated herein constitutes from about 0.1% to about 50%, about 1% to about 35%. or about 5% to about 30% by weight of the microcapsules. In some embodiments, the core material contemplated herein constitutes no more than about 30% by weight of the microcapsules. In some embodiments, the core material contemplated herein constitutes about 5% by weight of the microcapsules. The core material is contemplated as either a liquid or solid at contemplated storage temperatures of the microcapsules.

The cores may include other additives well-known in the pharmaceutical art, including edible sugars, such as sucrose, glucose, maltose, fructose, lactose, cellobiose, monosaccharides, disaccharides, trisaccharides, and polysaccharides, and mixtures thereof; artificial sweeteners, such as aspartame, saccharin, cyclamate salts, and mixtures thereof; edible acids, such as acetic acid (vinegar), citric acid, ascorbic acid, tartaric acid, and mixtures thereof; edible starches, such as corn starch; hydrolyzed vegetable protein; water-soluble vitamins, such as Vitamin C; water-soluble medicaments; water-soluble nutritional materials, such as ferrous sulfate; flavors; salts; monosodium glutamate; anti-microbial agents, such as sorbic acid; antimycotic agents, such as potassium sorbate, sorbic acid, sodium benzoate, and benzoic acid; food grade pigments and dyes; and mixtures thereof. Other potentially useful supplemental core materials will be apparent to those of ordinary skill in the art.

Emulsifying agents may be employed to assist in the formation of stable emulsions. Representative emulsifying agents include glyceryl monostearate, polysorbate esters, ethoxylated mono- and diglycerides, and mixtures thereof.

For ease of processing, and particularly to enable the successful formation of a reasonably stable emulsion, the viscosities of the core material and the shell material should be similar at the temperature at which the emulsion is formed. In particular, the ratio of the viscosity of the shell to the viscosity of the core, expressed in centipoise or comparable units, and both measured at the temperature of the emulsion, should be from about 22:1 to about 1:1, desirably from about 8:1 to about 1:1, and preferably from about 3:1 to about 1:1. A ratio of 1:1 would be ideal, but a viscosity ratio within the recited ranges is useful.

Encapsulating compositions are not limited to microcapsule compositions as disclosed above. In some embodiments encapsulating compositions encapsulate the microbial compositions in an adhesive polymer that can be natural or synthetic without toxic effect. In some embodiments, the encapsulating composition may be a matrix selected from sugar matrix, gelatin matrix, polymer matrix, silica matrix, starch matrix, foam matrix, etc. In some embodiments, the encapsulating composition may be selected from polyvinyl acetates; polyvinyl acetate copolymers; ethylene vinyl acetate (EVA) copolymers; polyvinyl alcohols; polyvinyl alcohol copolymers; celluloses, including ethylcelluloses, methylcelluloses, hydroxymethylcelluloses, hydroxypropylcelluloses and carboxymethylcellulose; polyvinylpyrolidones; polysaccharides, including starch, modified starch, dextrins, maltodextrins, alginate and chitosans; monosaccharides; fats; fatty acids, including oils; proteins, including gelatin and zeins; gum arabics; shellacs; vinylidene chloride and vinylidene chloride copolymers; calcium lignosulfonates; acrylic copolymers; polyvinylacrylates; polyethylene oxide; acrylamide polymers and copolymers; polyhydroxyethyl acrylate, methylacrylamide monomers; and polychloroprene.

In some embodiments, the microbial composition or a subcomponent thereof is encapsulated in a solid glass matrix or a flexible glass matrix (rubber matrix) comprising one or more polysaccharides, one or more saccharides, and/or one or more sugar alcohols. In some embodiments, the matrix comprises a monosaccharide or a disaccharide. In some embodiments, the disaccharide may be selected from sucrose, maltose, lactose, lactulose, trehalose, cellobiose, and chitobiose. In some embodiments, the polysaccharides, saccharides, and/or sugar alcohols are added to the microbial composition or a subcomponent thereof exogenously. In some embodiments, the matrix is an amorphous matrix. In some embodiments, the microbial composition or a subcompenent thereof is vitrified. In some embodiments, the microbial composition or a subcompenent thereof is desiccated. In some embodiments, the microbial composition or a subcompenent thereof is lyophilized. In some embodiments, the microbial composition or a subcompenent thereof is spray dried. In some embodiments, the microbial composition or a subcompenent thereof is spray congealed. See Harel and Kohavi-Beck (U.S. Pat. No. 8,097,245).

In some embodiments, the encapsulating shell of the present disclosure can be up to 10 µm, 20 µm, 30 µm, 40 µm, 60 µm, 70 µm, 80 µm, 90 µm, 100 µm, 110 µm, 120 µm, 130 µm, 140 µm, 150 µm, 160 µm, 170 µm, 180 µm, 190 µm, 200 µm, 210 µm, 220 µm, 230 µm, 240 µm, 250 µm, 260 µm, 270 µm, 280 µm, 290 µm, 300 µm, 310 µm, 320 µm, 330 µm, 340 µm, 350 µm, 360 µm, 370 µm, 380 µm, 390 µm, 400 µm, 410 µm, 420 µm, 430 µm, 440 µm, 450 µm, 460 µm, 470 µm, 480 µm, 490 µm, 500 µm, 510 µm, 520 µm, 530 µm, 540 µm, 550 µm, 560 µm, 570 µm, 580 µm, 590 µm, 600 µm, 610 µm, 620 µm, 630 µm, 640 µm, 650 µm, 660 µm, 670 µm, 680 µm, 690 µm, 700 µm, 710 µm, 720 µm, 730 µm, 740 µm, 750 µm, 760 µm, 770 µm, 780 µm, 790 µm, 800 µm, 810 µm, 820 µm, 830 µm, 840 µm, 850 µm, 860 µm, 870 µm, 880 µm, 890 µm, 900 µm, 910 µm, 920 µm, 930 µm, 940 µm, 950 µm, 960 µm, 970 µm, 980 µm, 990 µm, 1000 µm, 1010 µm, 1020 µm, 1030 µm, 1040 µm, 1050 µm, 1060 µm, 1070 µm, 1080 µm, 1090 µm, 1100 µm, 1110 µm, 1120 µm, 1130 µm, 1140 µm, 1150 µm, 1160 µm, 1170 µm, 1180 µm, 1190 µm, 1200 µm, 1210 µm, 1220 µm, 1230 µm, 1240 µm, 1250 µm, 1260 µm, 1270 µm, 1280 µm, 1290 µm, 1300 µm, 1310 µm, 1320 µm, 1330 µm, 1340 µm, 1350 µm, 1360 µm, 1370 µm, 1380 µm, 1390 µm, 1400 µm, 1410 µm, 1420 µm, 1430 µm, 1440 µm, 1450 µm, 1460 µm, 1470 µm, 1480 µm, 1490 µm, 1500 µm, 1510 µm, 1520 µm, 1530 µm, 1540 µm, 1550 µm, 1560 µm, 1570 µm, 1580 µm, 1590 µm, 1600 µm, 1610 µm, 1620 µm, 1630 µm, 1640 µm, 1650 µm, 1660 µm, 1670 µm, 1680 µm, 1690 µm, 1700 µm, 1710 µm, 1720 µm, 1730 µm, 1740 µm, 1750 µm, 1760 µm, 1770 µm, 1780 µm, 1790 µm, 1800 µm, 1810 µm, 1820 µm, 1830 µm, 1840 µm, 1850 µm, 1860 µm, 1870 µm, 1880 µm, 1890 µm, 1900 µm, 1910 µm, 1920 µm, 1930 µm, 1940 µm, 1950 µm, 1960 µm, 1970 µm, 1980 µm, 1990 µm, 2000 µm, 2010 µm, 2020 µm, 2030 µm, 2040 µm, 2050 µm, 2060 µm, 2070 µm, 2080 µm, 2090 µm, 2100 µm, 2110 µm, 2120 µm, 2130 µm, 2140 µm, 2150 µm, 2160 µm, 2170

µm, 2180 µm, 2190 µm, 2200 µm, 2210 µm, 2220 µm, 2230 µm, 2240 µm, 2250 µm, 2260 µm, 2270 µm, 2280 µm, 2290 µm, 2300 µm, 2310 µm, 2320 µm, 2330 µm, 2340 µm, 2350 µm, 2360 µm, 2370 µm, 2380 µm, 2390 µm, 2400 µm, 2410 µm, 2420 µm, 2430 µm, 2440 µm, 2450 µm, 2460 µm, 2470 µm, 2480 µm, 2490 µm, 2500 µm, 2510 µm, 2520 µm, 2530 µm, 2540 µm, 2550 µm, 2560 µm, 2570 µm, 2580 µm, 2590 µm, 2600 µm, 2610 µm, 2620 µm, 2630 µm, 2640 µm, 2650 µm, 2660 µm, 2670 µm, 2680 µm, 2690 µm, 2700 µm, 2710 µm, 2720 µm, 2730 µm, 2740 µm, 2750 µm, 2760 µm, 2770 µm, 2780 µm, 2790 µm, 2800 µm, 2810 µm, 2820 µm, 2830 µm, 2840 µm, 2850 µm, 2860 µm, 2870 µm, 2880 µm, 2890 µm, 2900 µm, 2910 µm, 2920 µm, 2930 µm, 2940 µm, 2950 µm, 2960 µm, 2970 µm, 2980 µm, 2990 µm, or 3000 µm thick.

Animal Feed

In some embodiments, compositions of the present disclosure are mixed with animal feed. In some embodiments, animal feed may be present in various forms such as pellets, capsules, granulated, powdered, mash, liquid, or semi-liquid. In some embodiments, compositions of the present disclosure are mixed with pre-pelleted feed. In some embodiments, compositions of the present disclosure are mixed with pelleted feed. In some embodiments, compositions of the present disclosure are mixed with feed after it has been pelleted.

In some embodiments, compositions of the present disclosure are mixed into the premix or mash at the feed mill, alone as a standalone premix, and/or alongside other feed additives such as MONENSIN, vitamins, etc. In one embodiment, the compositions of the present disclosure are mixed into or onto the feed at the feed mill. In another embodiment, compositions of the present disclosure are mixed into the feed itself.

In some embodiments, feed of the present disclosure may be supplemented with water, premix or premixes, forage, fodder, beans (e.g., whole, cracked, or ground), grains (e.g., whole, cracked, or ground), bean- or grain-based oils, bean- or grain-based meals, bean- or grain-based haylage or silage, bean- or grain-based syrups, fatty acids, sugar alcohols (e.g., polyhydric alcohols), commercially available formula feeds, oyster shells and those of other bivalves, and mixtures thereof.

In some embodiments, forage encompasses hay, haylage, and silage. In some embodiments, hays include grass hays (e.g., sudangrass, orchardgrass, or the like), alfalfa hay, and clover hay. In some embodiments, haylages include grass haylages, sorghum haylage, and alfalfa haylage. In some embodiments, silages include maize, oat, wheat, alfalfa, clover, and the like.

In some embodiments, premix or premixes may be utilized in the feed. Premixes may comprise micro-ingredients such as vitamins, minerals, amino acids; chemical preservatives; pharmaceutical compositions such as antibiotics and other medicaments; fermentation products, and other ingredients. In some embodiments, premixes are blended into the feed.

In some embodiments, the feed may include feed concentrates such as soybean hulls, soybean oils, sugar beet pulp, molasses, high protein soybean meal, ground corn, shelled corn, wheat midds, distiller grain, cottonseed hulls, and grease. See Anderson et al. (U.S. Pat. No. 3,484,243), Iritani et al. (U.S. Pat. No. 6,090,416), Axelrod et al. (U.S. Publication US20060127530A1), and Katsumi et al. (U.S. Pat. No. 5,741,508) for animal feed and animal feed supplements capable of use in the present compositions and methods.

In some embodiments, feed occurs as a compound, which includes, in a mixed composition capable of meeting the basic dietary needs, the feed itself, vitamins, minerals, amino acids, and other necessary components. Compound feed may further comprise premixes.

In some embodiments, microbial compositions of the present disclosure may be mixed with animal feed, premix, and/or compound feed. Individual components of the animal feed may be mixed with the microbial compositions prior to feeding to poultry. The microbial compositions of the present disclosure may be applied into or on a premix, into or on a feed, and/or into or on a compound feed.

Administration of Microbial Compositions

Figure 12:
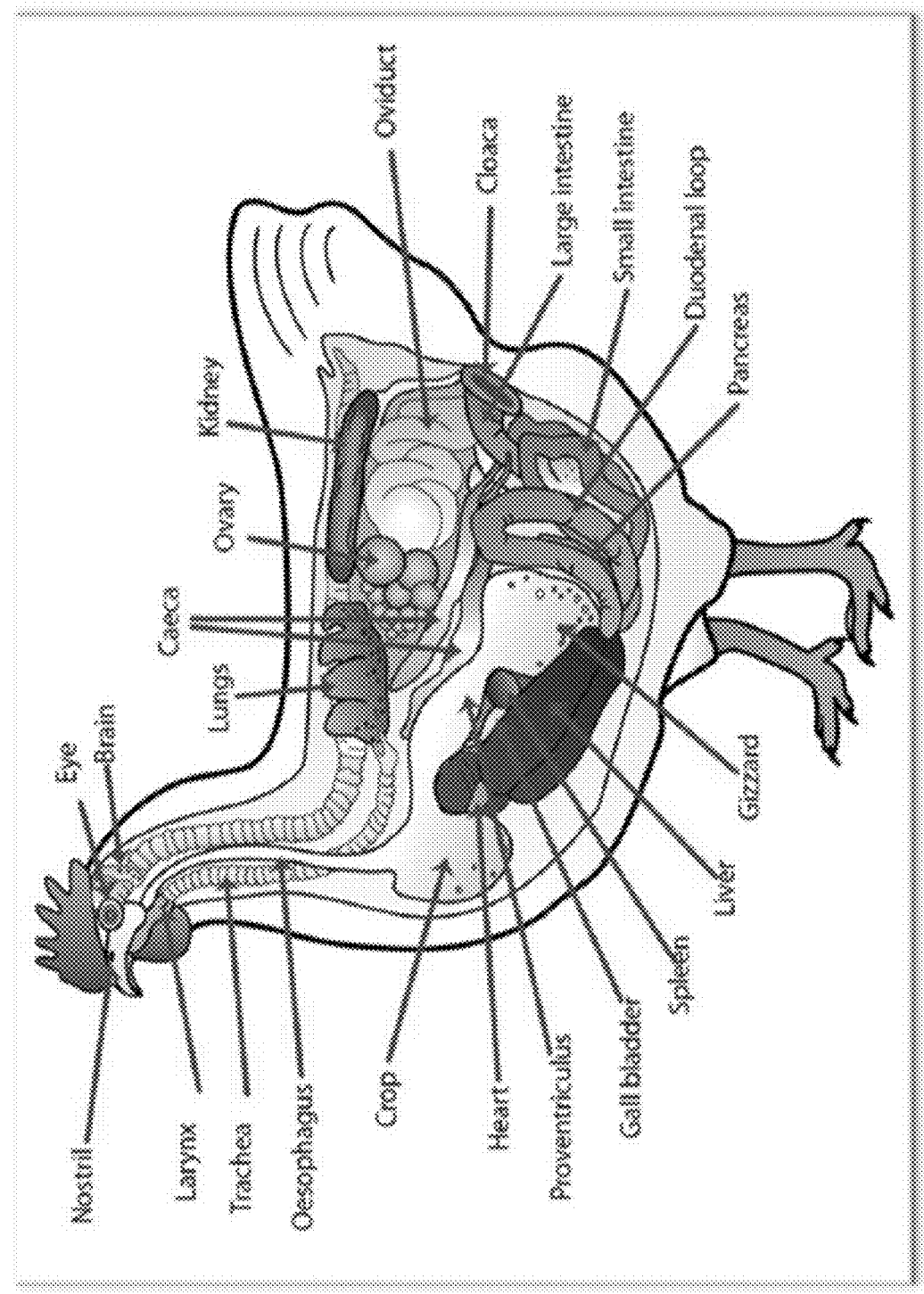
FIG. 12 is a cartoon depiction of an exemplary chicken's anatomy.
Figure 13:
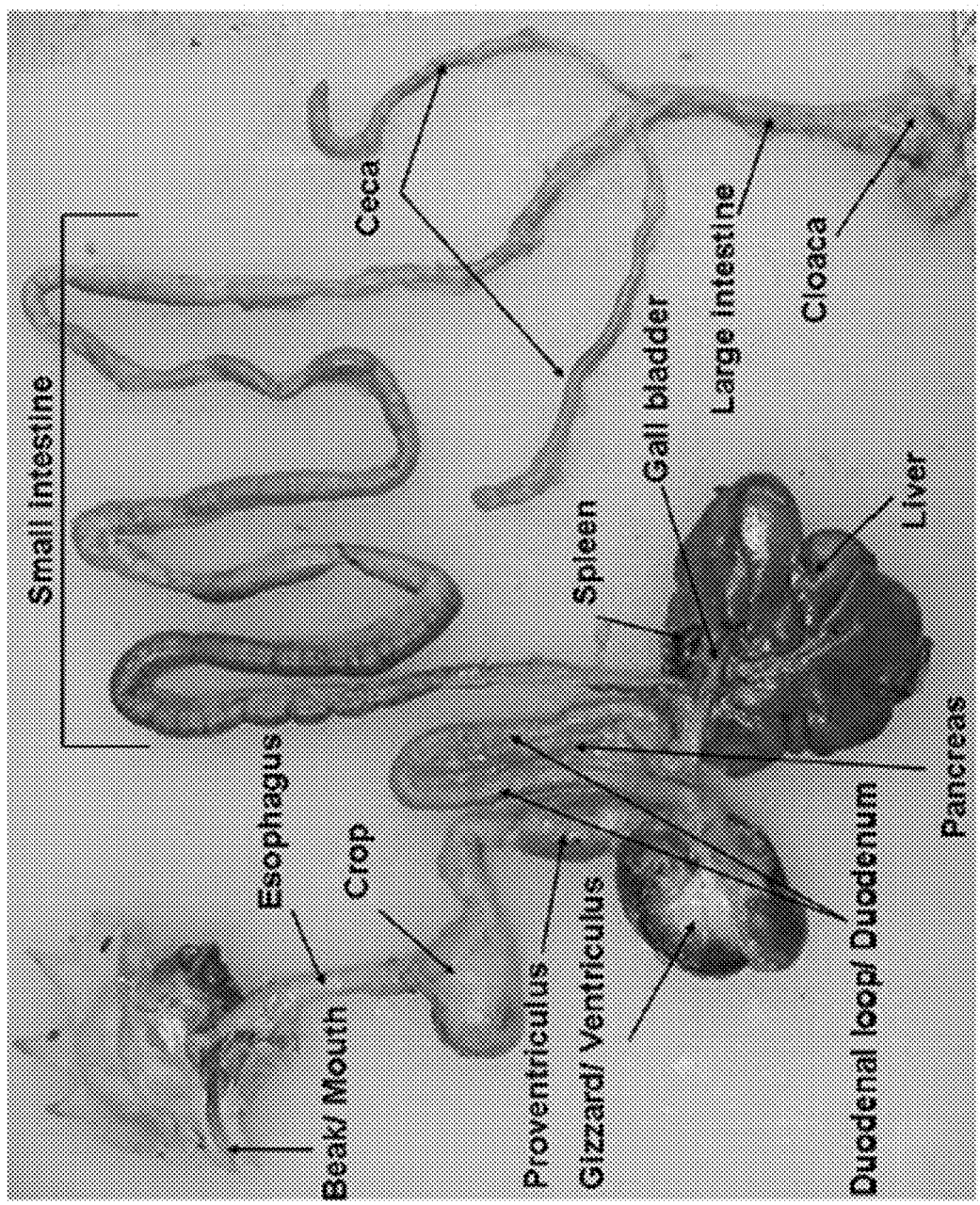
FIG. 13 is an image of a dissected gastrointestinal track of a chicken from the beak to the cloaca.

In some embodiments, the microbial compositions of the present disclosure are administered to poultry via the oral route. In some embodiments the microbial compositions are administered via a direct injection route into the gastrointestinal tract. In further embodiments, the direct injection administration delivers the microbial compositions directly to one or more of the crop, gizzard, cecum, small intestine, and large intestine. FIG. 12 and FIG. 13 provide a detailed anatomical view of the gastrointestinal tract of a chicken. In some embodiments, the microbial compositions of the present disclosure are administered to animals through the cloaca. In further embodiments, cloacal administration is in the form of an inserted suppository.

In some embodiments, the microbial compositions are administered through drinking water, spraying on litter in which the animal is in contact with, mixing with medications or vaccines, and gavage. In some embodiments, the microbial compositions are sprayed directly on the animal, wherein the animal ingests the composition having been sprayed on the animal. In some embodiments, the microbial compositions are sprayed on and/or sprayed in feed, and the feed is administered to the animal. In further embodiments, the animal ingests the composition through the preening of feathers that have come into contact with the sprayed composition.

In some embodiments, the microbial compositions of the present disclosure are administered to poultry on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 post-hatching. In some embodiments, the microbial compositions are administered to the exterior surface of an egg as a liquid, semi-liquid, or solid on day 22, 21, 20, 19, 18, 17, 16, 15, 14, 13, 12, 11, 10, 9, 8, 7, 6, 5, 4, 3, 2, 1, or 0 pre-hatching. In some embodiments, the microbial compositions of the present disclosure are administered to poultry in multiple dosing sessions in week(s) 1, 2, 3, 4, 5, 6, 7, 8, 9, 10, 11, 12, 13, 14, 15, 16, 17, 18, 19, 20, 21, 22, 23, 24, 25, 26, 27, 28, 29, and/or 30 week(s) post-hatching. In some embodiments, the microbial compositions are administed immediately after hatching. In some embodiments, the microbial compositions are administered into the egg (e.g., injection) by itself or administered along with other products such as vaccines.

In some embodiments, the microbial composition is administered in a dose comprise a total of, or at least, 1 ml, 2 ml, 3 ml, 4 ml, 5 ml, 6 ml, 7 ml, 8 ml, 9 ml, 10 ml, 11 ml, 12 ml, 13 ml, 14 ml, 15 ml, 16 ml, 17 ml, 18 ml, 19 ml, 20 ml, 21 ml, 22 ml, 23 ml, 24 ml, 25 ml, 26 ml, 27 ml, 28 ml, 29 ml, 30 ml, 31 ml, 32 ml, 33 ml, 34 ml, 35 ml, 36 ml, 37 ml, 38 ml, 39 ml, 40 ml, 41 m, 42 ml, 43 ml, 44 ml, 45 ml, 46 ml, 47 ml, 48 ml, 49 ml, 50 ml, 60 ml, 70 ml, 80 ml, 90 ml, 100 ml, 200 ml, 300 ml, 400 ml, 500 ml, 600 ml, 700 ml, 800 ml, 900 ml, or 1,000 ml.

In some embodiments, the microbial composition is administered in a dose comprising a total of, or at least, $10^{18}$, $10^{17}$, $10^{16}$, $10^{15}$, $10^{14}$, $10^{13}$, $10^{12}$, $10^{11}$, $10^{10}$, $10^9$, $10^8$, $10^7$, $10^6$, $10^5$, $10^4$, $10^3$, or $10^2$ microbial cells.

In some embodiments, the microbial compositions are mixed with feed, and the administration occurs through the ingestion of the microbial compositions along with the feed. In some embodiments, the dose of the microbial composition is administered such that there exists $10^2$ to $10^{12}$, $10^3$ to $10^{12}$, $10^4$ to $10^{12}$, $10^5$ to $10^{12}$, $10^6$ to $10^{12}$, $10^7$ to $10^{12}$, $10^8$ to $10^{12}$, $10^9$ to $10^{12}$, $10^{10}$ to $10^{12}$, $10^{11}$ to $10^{12}$, $10^2$ to $10^{11}$, $10^3$ to $10^{11}$, $10^4$ to $10^{11}$, $10^5$ to $10^{11}$, $10^6$ to $10^{11}$, $10^7$ to $10^{11}$, $10^8$ to $10^{11}$, $10^9$ to $10^{11}$, $10^{10}$ to $10^{11}$, $10^2$ to $10^{10}$, $10^3$ to $10^{10}$, $10^4$ to $10^{10}$, $10^5$ to $10^{10}$, $10^6$ to $10^{10}$, $10^7$ to $10^{10}$, $10^8$ to $10^{10}$, $10^9$ to $10^{10}$, $10^2$ to $10^9$, $10^3$ to $10^9$, $10^4$ to $10^9$, $10^5$ to $10^9$, $10^6$ to $10^9$, $10^7$ to $10^9$, $10^8$ to $10^9$, $10^2$ to $10^8$, $10^3$ to $10^8$, $10^4$ to $10^8$, $10^5$ to $10^8$, $10^6$ to $10^8$, $10^7$ to $10^8$, $10^2$ to $10^7$, $10^3$ to $10^7$, $10^4$ to $10^7$, $10^5$ to $10^7$, $10^6$ to $10^7$, $10^2$ to $10^6$, $10^3$ to $10^6$, $10^4$ to $10^6$, $10^5$ to $10^6$, $10^2$ to $10^5$, $10^3$ to $10^5$, $10^4$ to $10^5$, $10^2$ to $10^4$, $10^3$ to $10^4$, $10^2$ to $10^3$, $10^{12}$, $10^{11}$, $10^{10}$, $10^9$, $10^8$, $10^7$, $10^6$, $10^5$, $10^4$, $10^3$, or $10^2$ total microbial cells per gram or milliliter of the composition.

In some embodiments, the administered dose of the microbial composition comprises $10^2$ to $10^{18}$, $10^3$ to $10^{18}$, $10^4$ to $10^{18}$, $10^5$ to $10^{18}$, $10^6$ to $10^{18}$, $10^7$ to $10^{18}$, $10^8$ to $10^{18}$, $10^9$ to $10^{18}$, $10^{10}$ to $10^{18}$, $10^{11}$ to $10^{18}$, $10^{12}$ to $10^{18}$, $10^{13}$ to $10^{18}$, $10^{14}$ to $10^{18}$, $10^{15}$ to $10^{18}$, $10^{16}$ to $10^{18}$, $10^{17}$ to $10^{18}$, $10^2$ to $10^{12}$, $10^3$ to $10^{12}$, $10^4$ to $10^{12}$, $10^5$ to $10^{12}$, $10^6$ to $10^{12}$, $10^7$ to $10^{12}$, $10^8$ to $10^{12}$, $10^9$ to $10^{12}$, $10^{10}$ to $10^{12}$, $10^{11}$ to $10^{12}$, $10^2$ to $10^{11}$, $10^3$ to $10^{11}$, $10^4$ to $10^{11}$, $10^5$ to $10^{11}$, $10^6$ to $10^{11}$, $10^7$ to $10^{11}$, $10^8$ to $10^{11}$, $10^9$ to $10^{11}$, $10^{10}$ to $10^{11}$, $10^2$ to $10^{10}$, $10^3$ to $10^{10}$, $10^4$ to $10^{10}$, $10^5$ to $10^{10}$, $10^6$ to $10^{10}$, $10^7$ to $10^{10}$, $10^8$ to $10^{10}$, $10^9$ to $10^{10}$, $10^2$ to $10^9$, $10^3$ to $10^9$, $10^4$ to $10^9$, $10^5$ to $10^9$, $10^6$ to $10^9$, $10^7$ to $10^9$, $10^8$ to $10^9$, $10^2$ to $10^8$, $10^3$ to $10^8$, $10^4$ to $10^8$, $10^5$ to $10^8$, $10^6$ to $10^8$, $10^7$ to $10^8$, $10^2$ to $10^7$, $10^3$ to $10^7$, $10^4$ to $10^7$, $10^5$ to $10^7$, $10^6$ to $10^7$, $10^2$ to $10^6$, $10^3$ to $10^6$, $10^4$ to $10^6$, $10^5$ to $10^6$, $10^2$ to $10^5$, $10^3$ to $10^5$, $10^4$ to $10^5$, $10^2$ to $10^4$, $10^3$ to $10^4$, $10^2$ to $10^3$, $10^{18}$, $10^{17}$, $10^{16}$, $10^{15}$, $10^{14}$, $10^{13}$, $10^{12}$, $10^{11}$, $10^{10}$, $10^9$, $10^8$, $10^7$, $10^6$, $10^5$, $10^4$, $10^3$, or $10^2$ total microbial cells.

In some embodiments, the composition is administered 1 or more times per day. In some aspects, the composition is administered with food each time the animal is fed. In some embodiments, the composition is administered 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10, 1, 2, 3, 4, 5, 6, 7, 8, 9, or 10 times per day.

In some embodiments, the microbial composition is administered 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10, 1, 2, 3, 4, 5, 6, 7, 8, 9, or 10 times per week.

In some embodiments, the microbial composition is administered 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10, 1, 2, 3, 4, 5, 6, 7, 8, 9, or 10 times per month.

In some embodiments, the microbial composition is administered 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10, 1, 2, 3, 4, 5, 6, 7, 8, 9, or 10 times per year.

In some embodiments, the feed can be uniformly coated with one or more layers of the microbes and/or microbial compositions disclosed herein, using conventional methods of mixing, spraying, or a combination thereof through the use of treatment application equipment that is specifically designed and manufactured to accurately, safely, and efficiently apply coatings. Such equipment uses various types of coating technology such as rotary coaters, drum coaters, fluidized bed techniques, spouted beds, rotary mists, or a combination thereof. Liquid treatments such as those of the present disclosure can be applied via either a spinning "atomizer" disk or a spray nozzle, which evenly distributes the microbial composition onto the feed as it moves though the spray pattern. In some aspects, the feed is then mixed or tumbled for an additional period of time to achieve additional treatment distribution and drying.

In some embodiments, the feed coats of the present disclosure can be up to 10 µm, 20 µm, 30 µm, 40 µm, 50 µm, 60 µm, 70 µm, 80 µm, 90 µm, 100 µm, 110 µm, 120 µm, 130 µm, 140 µm, 150 µm, 160 µm, 170 µm, 180 µm, 190 µm, 200 µm, 210 µm, 220 µm, 230 µm, 240 µm, 250 µm, 260 µm, 270 µm, 280 µm, 290 µm, 300 µm, 310 µm, 320 µm, 330 µm, 340 µm, 350 µm, 360 µm, 370 µm, 380 µm, 390 µm, 400 µm, 410 µm, 420 µm, 430 µm, 440 µm, 450 µm, 460 µm, 470 µm, 480 µm, 490 µm, 500 µm, 510 µm, 520 µm, 530 µm, 540 µm, 550 µm, 560 µm, 570 µm, 580 µm, 590 µm, 600 µm, 610 µm, 620 µm, 630 µm, 640 µm, 650 µm, 660 µm, 670 µm, 680 µm, 690 µm, 700 µm, 710 µm, 720 µm, 730 µm, 740 µm, 750 µm, 760 µm, 770 µm, 780 µm, 790 µm, 800 µm, 810 µm, 820 µm, 830 µm, 840 µm, 850 µm, 860 µm, 870 µm, 880 µm, 890 µm, 900 µm, 910 µm, 920 µm, 930 µm, 940 µm, 950 µm, 960 µm, 970 µm, 980 µm, 990 µm, 1000 µm, 1010 µm, 1020 µm, 1030 µm, 1040 µm, 1050 µm, 1060 µm, 1070 µm, 1080 µm, 1090 µm, 1100 µm, 1110 µm, 1120 µm, 1130 µm, 1140 µm, 1150 µm, 1160 µm, 1170 µm, 1180 µm, 1190 µm, 1200 µm, 1210 µm, 1220 µm, 1230 µm, 1240 µm, 1250 µm, 1260 µm, 1270 µm, 1280 µm, 1290 µm, 1300 µm, 1310 µm, 1320 µm, 1330 µm, 1340 µm, 1350 µm, 1360 µm, 1370 µm, 1380 µm, 1390 µm, 1400 µm, 1410 µm, 1420 µm, 1430 µm, 1440 µm, 1450 µm, 1460 µm, 1470 µm, 1480 µm, 1490 µm, 1500 µm, 1510 µm, 1520 µm, 1530 µm, 1540 µm, 1550 µm, 1560 µm, 1570 µm, 1580 µm, 1590 µm, 1600 µm, 1610 µm, 1620 µm, 1630 µm, 1640 µm, 1650 µm, 1660 µm, 1670 µm, 1680 µm, 1690 µm, 1700 µm, 1710 µm, 1720 µm, 1730 µm, 1740 µm, 1750 µm, 1760 µm, 1770 µm, 1780 µm, 1790 µm, 1800 µm, 1810 µm, 1820 µm, 1830 µm, 1840 µm, 1850 µm, 1860 µm, 1870 µm, 1880 µm, 1890 µm, 1900 µm, 1910 µm, 1920 µm, 1930 µm, 1940 µm, 1950 µm, 1960 µm, 1970 µm, 1980 µm, 1990 µm, 2000 µm, 2010 µm, 2020 µm, 2030 µm, 2040 µm, 2050 µm, 2060 µm, 2070 µm, 2080 µm, 2090 µm, 2100 µm, 2110 µm, 2120 µm, 2130 µm, 2140 µm, 2150 µm, 2160 µm, 2170 µm, 2180 µm, 2190 µm, 2200 µm, 2210 µm, 2220 µm, 2230 µm, 2240 µm, 2250 µm, 2260 µm, 2270 µm, 2280 µm, 2290 µm, 2300 µm, 2310 µm, 2320 µm, 2330 µm, 2340 µm, 2350 µm, 2360 µm, 2370 µm, 2380 µm, 2390 µm, 2400 µm, 2410 µm, 2420 µm, 2430 µm, 2440 µm, 2450 µm, 2460 µm, 2470 µm, 2480 µm, 2490 µm, 2500 µm, 2510 µm, 2520 µm, 2530 µm, 2540 µm, 2550 µm, 2560 µm, 2570 µm, 2580 µm, 2590 µm, 2600 µm, 2610 µm, 2620 µm, 2630 µm, 2640 µm, 2650 µm, 2660 µm, 2670 µm, 2680 µm, 2690 µm, 2700 µm, 2710 µm, 2720 µm, 2730 µm, 2740 µm, 2750 µM, 2760 µm, 2770

μm, 2780 μm, 2790 μm, 2800 μm, 2810 μm, 2820 μm, 2830 μm, 2840 μm, 2850 μm, 2860 μm, 2870 μm, 2880 μm, 2890 μm, 2900 μm, 2910 μm, 2920 μm, 2930 μm, 2940 μm, 2950 μm, 2960 μm, 2970 μm, 2980 μm, 2990 μm, or 3000 μm thick.

In some embodiments, the microbial cells can be coated freely onto any number of compositions or they can be formulated in a liquid or solid composition before being coated onto a composition. For example, a solid composition comprising the microorganisms can be prepared by mixing a solid carrier with a suspension of the spores until the solid carriers are impregnated with the spore or cell suspension. This mixture can then be dried to obtain the desired particles.

In some other embodiments, it is contemplated that the solid or liquid microbial compositions of the present disclosure further contain functional agents e.g., activated carbon, minerals, vitamins, and other agents capable of improving the quality of the products or a combination thereof.

Methods of coating and compositions in use of said methods that are known in the art can be particularly useful when they are modified by the addition of one of the embodiments of the present disclosure. Such coating methods and apparatus for their application are disclosed in, for example: U.S. Pat. Nos. 8,097,245 and 7,998,502; and PCT Pat. App. Publication Nos. WO 2008/076975, WO 2010/138522, WO2011/094469, WO 2010/111347, and WO 2010/111565, each of which is incorporated by reference herein.

In some embodiments, the microbes or microbial ensembles of the present disclosure exhibit a synergistic effect, on one or more of the traits described herein, in the presence of one or more of the microbes or microbial ensembles coming into contact with one another. The synergistic effect obtained by the taught methods can be quantified, for example, according to Colby's formula (i.e., (E)=X+Y−(X*Y/100)). See Colby, R. S., "Calculating Synergistic and Antagonistic Responses of Herbicide Combinations," 1967. Weeds. Vol. 15, pp. 20-22, incorporated herein by reference in its entirety. Thus, "synergistic" is intended to reflect an outcome/parameter/effect that has been increased by more than an additive amount.

In some embodiments, the microbes or microbial ensembles of the present disclosure may be administered via drench. In one embodiment, the drench is an oral drench. A drench administration comprises utilizing a drench kit/applicator/syringe that injects/releases a liquid comprising the microbes or microbial ensembles into the buccal cavity and/or esophagas of the animal.

In some embodiments, the microbes or microbial ensembles of the present disclosure may be administered in a time-released fashion. The composition may be coated in a chemical composition, or may be contained in a mechanical device or capsule that releases the microbes or microbial ensembles over a period of time instead all at once. In one embodiment, the microbes or microbial ensembles are administered to an animal in a time-release capsule. In one embodiment, the composition may be coated in a chemical composition, or may be contained in a mechanical device or capsul that releases the mcirobes or microbial ensembles all at once a period of time hours post ingestion.

In some embodiments, the microbes or microbial ensembles are administered in a time-released fashion between 1 to 5, 1 to 10, 1 to 15, 1 to 20, 1 to 24, 1 to 25, 1 to 30, 1 to 35, 1 to 40, 1 to 45, 1 to 50, 1 to 55, 1 to 60, 1 to 65, 1 to 70, 1 to 75, 1 to 80, 1 to 85, 1 to 90, 1 to 95, or 1 to 100 hours.

In some embodiments, the microbes or microbial ensembles are administered in a time-released fashion between 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 1 to 16, 1 to 17, 1 to 18, 1 to 19, 1 to 20, 1 to 21, 1 to 22, 1 to 23, 1 to 24, 1 to 25, 1 to 26, 1 to 27, 1 to 28, 1 to 29, or 1 to 30 days.

Microorganisms

As used herein the term "microorganism" should be taken broadly. It includes, but is not limited to, the two prokaryotic domains, Bacteria and Archaea, as well as eukaryotic fungi, protists, and viruses.

By way of example, the microorganisms may include species of the genera of: *Lactobacillus, Clostridium, Faecalibacter, Hydrogenoanaerobacterium, Acrocarpospora, Bacillus, Subdoligranulum, Leuconostoc, Lachnospira, Anaerofilum, Microbacterium, Verrucosispora, Blautia, Pseudomonas, Sporobacter, Corynebacterium Streptococcus, Paracoccus, Celulosilyticum, Ruminococcus, Bacteroides, Filobasidium, Gibberella, Alatospora, Pichia,* and *Candida*. In some embodiments, the microorganisms may include species of any general disclosed herein.

In certain embodiments, the microorganism is unculturable. This should be taken to mean that the microorganism is not known to be culturable or is difficult to culture using methods known to one skilled in the art.

In one embodiment, the microbes are obtained from animals (e.g., mammals, reptiles, birds, and the like), soil (e.g., rhizosphere), air, water (e.g., marine, freshwater, wastewater sludge), sediment, oil, plants (e.g., roots, leaves, stems), agricultural products, and extreme environments (e.g., acid mine drainage or hydrothermal systems). In a further embodiment, microbes obtained from marine or freshwater environments such as an ocean, river, or lake. In a further embodiment, the microbes can be from the surface of the body of water, or any depth of the body of water (e.g., a deep sea sample).

The microorganisms of the disclosure may be isolated in substantially pure or mixed cultures. They may be concentrated, diluted, or provided in the natural concentrations in which they are found in the source material. For example, microorganisms from saline sediments may be isolated for use in this disclosure by suspending the sediment in fresh water and allowing the sediment to fall to the bottom. The water containing the bulk of the microorganisms may be removed by decantation after a suitable period of settling and either administered to the GI tract of poultry, or concentrated by filtering or centrifugation, diluted to an appropriate concentration and administered to the GI tract of poultry with the bulk of the salt removed. By way of further example, microorganisms from mineralized or toxic sources may be similarly treated to recover the microbes for application to poultry to minimize the potential for damage to the animal.

In another embodiment, the microorganisms are used in a crude form, in which they are not isolated from the source material in which they naturally reside. For example, the microorganisms are provided in combination with the source material in which they reside; for example, fecal matter or other composition found in the gastrointestinal tract. In this embodiment, the source material may include one or more species of microorganisms.

In some embodiments, a mixed population of microorganisms is used in the methods of the disclosure.

In embodiments of the disclosure where the microorganisms are isolated from a source material (for example, the material in which they naturally reside), any one or a combination of a number of standard techniques which will be readily known to skilled persons may be used. However, by way of example, these in general employ processes by which a solid or liquid culture of a single microorganism can be obtained in a substantially pure form, usually by physical separation on the surface of a solid microbial growth medium or by volumetric dilutive isolation into a liquid microbial growth medium. These processes may include isolation from dry material, liquid suspension, slurries or homogenates in which the material is spread in a thin layer over an appropriate solid gel growth medium, or serial dilutions of the material made into a sterile medium and inoculated into liquid or solid culture media.

Whilst not essential, in one embodiment, the material containing the microorganisms may be pre-treated prior to the isolation process in order to either multiply all microorganisms in the material. Microorganisms can then be isolated from the enriched materials as disclosed above.

In certain embodiments, as mentioned herein before, the microorganism(s) may be used in crude form and need not be isolated from an animal or a media. For example, feces, or growth media which includes the microorganisms identified to be of benefit to increased feed efficiency may be obtained and used as a crude source of microorganisms for the next round of the method or as a crude source of microorganisms at the conclusion of the method. For example, fresh feces could be obtained and optionally processed.

Microbiome Shift and Abundance of Microbes

In some embodiments, the microbiome of poultry, including the gut microbiome (crop, gizzard, cecum, small intestine, and large intestine) comprises a diverse arrive of microbes with a wide variety of metabolic capabilities. The microbiome is influenced by a range of factors including diet, variations in animal metabolism, and breed, among others. Most poultry diets are plant-based and rich in complex polysaccharides that enrich the gastrointestinal microbial community for microbes capable of breaking down specific polymeric components in the diet such as cellulose, hemicellulose, lignin, etc. The end products of primary degradation sustain a chain of microbes that ultimately produce a range of organic acids together with hydrogen and carbon dioxide. Because of the complex and interlinked nature of the microbiome, changing the diet and thus substrates for primary degradation may have a cascading effect on gut microbial metabolism, with changes in both the organic acid profiles and the methane levels produced, thus impacting the quality and quantity of animal production and or the products produced by the animal. See Menezes et al. (2011. *FEMS Microbiol. Ecol.* 78(2):256-265.)

In some aspects, the present disclosure is drawn to administering microbial compositions described herein to modulate or shift the microbiome of poultry.

In some embodiments, the microbiome is shifted through the administration of one or more microbes to the gastrointestinal tract. In further embodiments, the one or more microbes are those selected from Table 1 and/or Table 3. In some embodiments, the microbiome shift or modulation includes a decrease or loss of specific microbes that were present prior to the administration of one or more microbes of the present disclosure. In some embodiments, the microbiome shift or modulation includes an increase in microbes that were present prior to the administration of one or more microbes of the present disclosure. In some embodiments, the microbiome shift or modulation includes a gain of one or more microbes that were not present prior to the administration of one or more microbes of the present disclosure. In a further embodiment, the gain of one or more microbes is a microbe that was not specifically included in the administered microbial ensemble.

In some embodiments, the administration of microbes of the present disclosure results in a sustained modulation of the microbiome such that the administered microbes are present in the microbiome for a period of at least 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10, 1, 2, 3, 4, 5, 6, 7, 8, 9, or 10 days.

In some embodiments, the administration of microbes of the present disclosure results in a sustained modulation of the microbiome such that the administered microbes are present in the microbiome for a period of at least 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10, 1, 2, 3, 4, 5, 6, 7, 8, 9, or 10 weeks.

In some embodiments, the administration of microbes of the present disclosure results in a sustained modulation of the microbiome such that the administered microbes are present in the microbiome for a period of at least 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9, 9 to 10, 1, 2, 3, 4, 5, 6, 7, 8, 9, 10, 11, or 12 months.

In some embodiments, the presence of the administered microbes are detected by sampling the gastrointestinal tract and using primers to amplify the 16S or 18S rDNA sequences, or the ITS rDNA sequences of the administered microbes. In some embodiments, the administered microbes are one or more of those selected from Table 1 and/or Table 3, and the corresponding rDNA sequences are those selected from SEQ ID NOs:1-387.

In some embodiments, the microbiome of a bird is measured by amplifying polynucleotides collected from gastrointestinal samples, wherein the polynucleotides may be 16S or 18S rDNA fragments, or ITS rDNA fragments of microbial rDNA. In one embodiment, the microbiome is fingerprinted by a method of denaturing gradient gel electrophoresis (DGGE) wherein the amplified rDNA fragments are sorted by where they denature, and form a unique banding pattern in a gel that may be used for comparing the microbiome of the same bird over time or the microbiomes of multiple birds. In another embodiment, the microbiome is fingerprinted by a method of terminal restriction fragment length polymorphism (T-RFLP), wherein labelled PCR fragments are digested using a restriction enzyme and then sorted by size. In a further embodiment, the data collected from the T-RFLP method is evaluated by nonmetric multidimensional scaling (nMDS) ordination and PERMANOVA statistics identify differences in microbiomes, thus allowing for the identification and measurement of shifts in the microbiome. See also Shanks et al. (2011. *Appl. Environ. Microbiol.* 77(9):2992-3001), Petri et al. (2013. *PLOS one.* 8(12):e83424), and Menezes et al. (2011. *FEMS Microbiol. Ecol.* 78(2):256-265.)

In some embodiments, the administration of microbes of the present disclosure results in a modulation or shift of the microbiome which further results in a desired phenotype or improved trait.

MIC Scoring

According to the methods provided herein, a sample is processed to detect the presence of one or more microorganism types in the sample (FIG. 1, 1001; FIG. 2, 2001). The absolute number of one or more microorganism organism type in the sample is determined (FIG. 1, 1002; FIG. 2, 2002). The determination of the presence of the one or more organism types and the absolute number of at least one organism type can be conducted in parallel or serially. For example, in the case of a sample comprising a microbial community comprising bacteria (i.e., one microorganism type) and fungi (i.e., a second microorganism type), the user in one embodiment detects the presence of one or both of the organism types in the sample (FIG. 1, 1001; FIG. 2, 2001). The user, in a further embodiment, determines the absolute number of at least one organism type in the sample—in the case of this example, the number of bacteria, fungi or combination thereof, in the sample (FIG. 1, 1002; FIG. 2, 2002).

In one embodiment, the sample, or a portion thereof is subjected to flow cytometry (FC) analysis to detect the presence and/or number of one or more microorganism types (FIG. 1, 1001, 1002; FIG. 2, 2001, 2002). In one flow cytometer embodiment, individual microbial cells pass through an illumination zone, at a rate of at least about 300 $*s^{-1}$, or at least about 500 $*s^{-1}$, or at least about 1000 $*s^{-1}$. However, one of ordinary skill in the art will recognize that this rate can vary depending on the type of instrument is employed. Detectors which are gated electronically measure the magnitude of a pulse representing the extent of light scattered. The magnitudes of these pulses are sorted electronically into "bins" or "channels," permitting the display of histograms of the number of cells possessing a certain quantitative property (e.g., cell staining property, diameter, cell membrane) versus the channel number. Such analysis allows for the determination of the number of cells in each "bin" which in embodiments described herein is an "microorganism type" bin, e.g., a bacteria, fungi, nematode, protozoan, archaea, algae, dinoflagellate, virus, viroid, etc.

In one embodiment, a sample is stained with one or more fluorescent dyes wherein a fluorescent dye is specific to a particular microorganism type, to enable detection via a flow cytometer or some other detection and quantification method that harnesses fluorescence, such as fluorescence microscopy. The method can provide quantification of the number of cells and/or cell volume of a given organism type in a sample. In a further embodiment, as described herein, flow cytometry is harnessed to determine the presence and quantity of a unique first marker and/or unique second marker of the organism type, such as enzyme expression, cell surface protein expression, etc. Two- or three-variable histograms or contour plots of, for example, light scattering versus fluorescence from a cell membrane stain (versus fluorescence from a protein stain or DNA stain) may also be generated, and thus an impression may be gained of the distribution of a variety of properties of interest among the cells in the population as a whole. A number of displays of such multiparameter flow cytometric data are in common use and are amenable for use with the methods described herein.

In one embodiment of processing the sample to detect the presence and number of one or more microorganism types, a microscopy assay is employed (FIG. 1, 1001, 1002). In one embodiment, the microscopy is optical microscopy, where visible light and a system of lenses are used to magnify images of small samples. Digital images can be captured by a charge-couple device (CCD) camera. Other microscopic techniques include, but are not limited to, scanning electron microscopy and transmission electron microscopy. Microorganism types are visualized and quantified according to the aspects provided herein.

In another embodiment of in order to detect the presence and number of one or more microorganism types, the sample, or a portion thereof is subjected to fluorescence microscopy. Different fluorescent dyes can be used to directly stain cells in samples and to quantify total cell counts using an epifluorescence microscope as well as flow cytometry, described above. Useful dyes to quantify microorganisms include but are not limited to acridine orange (AO), 4,6-di-amino-2 phenylindole (DAPI) and 5-cyano-2,3 Dytolyl Tetrazolium Chloride (CTC). Viable cells can be estimated by a viability staining method such as the LIVE/DEAD® Bacterial Viability Kit (Bac-Light™) which contains two nucleic acid stains: the green-fluorescent SYTO 9TM dye penetrates all membranes and the red-fluorescent propidium iodide (PI) dye penetrates cells with damaged membranes. Therefore, cells with compromised membranes will stain red, whereas cells with undamaged membranes will stain green. Fluorescent in situ hybridization (FISH) extends epifluorescence microscopy, allowing for the fast detection and enumeration of specific organisms. FISH uses fluorescent labelled oligonucleotides probes (usually 15-25 basepairs) which bind specifically to organism DNA in the sample, allowing the visualization of the cells using an epifluorescence or confocal laser scanning microscope (CLSM). Catalyzed reporter deposition fluorescence in situ hybridization (CARD-FISH) improves upon the FISH method by using oligonucleotide probes labelled with a horse radish peroxidase (HRP) to amplify the intensity of the signal obtained from the microorganisms being studied. FISH can be combined with other techniques to characterize microorganism communities. One combined technique is high affinity peptide nucleic acid (PNA)-FISH, where the probe has an enhanced capability to penetrate through the Extracellular Polymeric Substance (EPS) matrix. Another example is LIVE/DEAD-FISH which combines the cell viability kit with FISH and has been used to assess the efficiency of disinfection in drinking water distribution systems.

In another embodiment, the sample, or a portion thereof is subjected to Raman micro-spectroscopy in order to determine the presence of a microorganism type and the absolute number of at least one microorganism type (FIG. 1, 1001-1002; FIG. 2, 2001-2002). Raman micro-spectroscopy is a non-destructive and label-free technology capable of detecting and measuring a single cell Raman spectrum (SCRS). A typical SCRS provides an intrinsic biochemical "fingerprint" of a single cell. A SCRS contains rich information of the biomolecules within it, including nucleic acids, proteins, carbohydrates and lipids, which enables characterization of different cell species, physiological changes and cell phenotypes. Raman microscopy examines the scattering of laser light by the chemical bonds of different cell biomarkers. A SCRS is a sum of the spectra of all the biomolecules in one single cell, indicating a cell's phenotypic profile. Cellular phenotypes, as a consequence of gene expression, usually reflect genotypes. Thus, under identical growth conditions, different microorganism types give distinct SCRS corresponding to differences in their genotypes and can thus be identified by their Raman spectra.

In yet another embodiment, the sample, or a portion thereof is subjected to centrifugation in order to determine the presence of a microorganism type and the number of at least one microorganism type (FIG. 1, 1001-1002; FIG. 2, 2001-2002). This process sediments a heterogeneous mixture by using the centrifugal force created by a centrifuge. More dense components of the mixture migrate away from the axis of the centrifuge, while less dense components of the mixture migrate towards the axis. Centrifugation can allow fractionation of samples into cytoplasmic, membrane and extracellular portions. It can also be used to determine localization information for biological molecules of interest. Additionally, centrifugation can be used to fractionate total microbial community DNA. Different prokaryotic groups differ in their guanine-plus-cytosine (G+C) content of DNA, so density-gradient centrifugation based on G+C content is a method to differentiate organism types and the number of cells associated with each type. The technique generates a fractionated profile of the entire community DNA and indicates abundance of DNA as a function of G+C content. The total community DNA is physically separated into highly purified fractions, each representing a different G+C content that can be analyzed by additional molecular techniques such as denaturing gradient gel electrophoresis (DGGE)/amplified ribosomal DNA restriction analysis (AR-DRA) (see discussion herein) to assess total microbial community diversity and the presence/quantity of one or more microorganism types.

In another embodiment, the sample, or a portion thereof is subjected to staining in order to determine the presence of a microorganism type and the number of at least one microorganism type (FIG. 1, 1001-1002; FIG. 2, 2001-2002). Stains and dyes can be used to visualize biological tissues, cells or organelles within cells. Staining can be used in conjunction with microscopy, flow cytometry or gel electrophoresis to visualize or mark cells or biological molecules that are unique to different microorganism types. In vivo staining is the process of dyeing living tissues, whereas in vitro staining involves dyeing cells or structures that have been removed from their biological context. Examples of specific staining techniques for use with the methods described herein include, but are not limited to: gram staining to determine gram status of bacteria, endospore staining to identify the presence of endospores, Ziehl-Neelsen staining, haematoxylin and eosin staining to examine thin sections of tissue, papanicolaou staining to examine cell samples from various bodily secretions, periodic acid-Schiff staining of carbohydrates, Masson's trichome employing a three-color staining protocol to distinguish cells from the surrounding connective tissue, Romanowsky stains (or common variants that include Wright's stain, Jenner's stain, May-Grunwald stain, Leishman stain and Giemsa stain) to examine blood or bone marrow samples, silver staining to reveal proteins and DNA, Sudan staining for lipids and Conklin's staining to detect true endospores. Common biological stains include acridine orange for cell cycle determination; bismarck brown for acid mucins; carmine for glycogen; carmine alum for nuclei; COOMASSIE BLUE for proteins; Cresyl violet for the acidic components of the neuronal cytoplasm; Crystal violet for cell walls; DAPI for nuclei; eosin for cytoplasmic material, cell membranes, some extracellular structures and red blood cells; ethidium bromide for DNA; acid fuchsine for collagen, smooth muscle or mitochondria; haematoxylin for nuclei; Hoechst stains for DNA; iodine for starch; malachite green for bacteria in the Gimenez staining technique and for spores; methyl green for chromatin; methylene blue for animal cells; neutral red for Nissl substance; Nile blue for nuclei; Nile red for lipophilic entities; osmium tetroxide for lipids; rhodamine is used in fluorescence microscopy; safranin for nuclei. Stains are also used in transmission electron microscopy to enhance contrast and include phosphotungstic acid, osmium tetroxide, ruthenium tetroxide, ammonium molybdate, cadmium iodide, carbohydrazide, ferric chloride, hexamine, indium trichloride, lanthanum nitrate, lead acetate, lead citrate, lead(II) nitrate, periodic acid, phosphomolybdic acid, potassium ferricyanide, potassium ferrocyanide, ruthenium red, silver nitrate, silver proteinate, sodium chloroaurate, thallium nitrate, thiosemicarbazide, uranyl acetate, uranyl nitrate, and vanadyl sulfate.

In another embodiment, the sample, or a portion thereof is subjected to mass spectrometry (MS) in order to determine the presence of a microorganism type and the number of at least one microorganism type (FIG. 1, 1001-1002; FIG. 2, 2001-2002). MS, as discussed below, can also be used to detect the presence and expression of one or more unique markers in a sample (FIG. 1, 1003-1004; FIG. 2, 2003-2004). MS is used for example, to detect the presence and quantity of protein and/or peptide markers unique to microorganism types and therefore to provide an assessment of the number of the respective microorganism type in the sample. Quantification can be either with stable isotope labelling or label-free. De novo sequencing of peptides can also occur directly from MS/MS spectra or sequence tagging (produce a short tag that can be matched against a database). MS can also reveal post-translational modifications of proteins and identify metabolites. MS can be used in conjunction with chromatographic and other separation techniques (such as gas chromatography, liquid chromatography, capillary electrophoresis, ion mobility) to enhance mass resolution and determination.

In another embodiment, the sample, or a portion thereof is subjected to lipid analysis in order to determine the presence of a microorganism type and the number of at least one microorganism type (FIG. 1, 1001-1002; FIG. 2, 2001-2002). Fatty acids are present in a relatively constant proportion of the cell biomass, and signature fatty acids exist in microbial cells that can differentiate microorganism types within a community. In one embodiment, fatty acids are extracted by saponification followed by derivatization to give the respective fatty acid methyl esters (FAMEs), which are then analyzed by gas chromatography. The FAME profile in one embodiment is then compared to a reference FAME database to identify the fatty acids and their corresponding microbial signatures by multivariate statistical analyses.

In the aspects of the methods provided herein, the number of unique first makers in the sample, or portion thereof (e.g., sample aliquot) is measured, as well as the abundance of each of the unique first markers (FIG. 1, 1003; FIG. 2, 2003). A unique marker is a marker of a microorganism strain. It should be understood by one of ordinary skill in the art that depending on the unique marker being probed for and measured, the entire sample need not be analyzed. For example, if the unique marker is unique to bacterial strains, then the fungal portion of the sample need not be analyzed. As described above, in some embodiments, measuring the absolute abundance of one or more organism types in a sample comprises separating the sample by organism type, e.g., via flow cytometry.

Any marker that is unique to an organism strain can be employed herein. For example, markers can include, but are not limited to, small subunit ribosomal RNA genes (16S/18S rDNA), large subunit ribosomal RNA genes (23S/25S/28S rDNA), intercalary 5.8S gene, cytochrome c oxidase, beta-tubulin, elongation factor, RNA polymerase and internal transcribed spacer (ITS).

Ribosomal RNA genes (rDNA), especially the small subunit ribosomal RNA genes, i.e., 18S rRNA genes (18S rDNA) in the case of eukaryotes and 16S rRNA (16S rDNA) in the case of prokaryotes, have been the predominant target for the assessment of organism types and strains in a microbial community. However, the large subunit ribosomal RNA genes, 28S rDNAs, have been also targeted. rDNAs are suitable for taxonomic identification because: (i) they are ubiquitous in all known organisms; (ii) they possess both conserved and variable regions; (iii) there is an exponentially expanding database of their sequences available for comparison. In community analysis of samples, the conserved regions serve as annealing sites for the corresponding universal PCR and/or sequencing primers, whereas the variable regions can be used for phylogenetic differentiation. In addition, the high copy number of rDNA in the cells facilitates detection from environmental samples.

The internal transcribed spacer (ITS), located between the 18S rDNA and 28S rDNA, has also been targeted. The ITS is transcribed but spliced away before assembly of the ribosomes The ITS region is composed of two highly variable spacers, ITS1 and ITS2, and the intercalary 5.8S gene. This rDNA operon occurs in multiple copies in genomes. Because the ITS region does not code for ribosome components, it is highly variable.

In one embodiment, the unique RNA marker can be an mRNA marker, an siRNA marker or a ribosomal RNA marker.

Protein-coding functional genes can also be used herein as a unique first marker. Such markers include but are not limited to: the recombinase A gene family (bacterial RecA, archaea RadA and RadB, eukaryotic Rad51 and Rad57, phage UvsX); RNA polymerase β subunit (RpoB) gene, which is responsible for transcription initiation and elongation; chaperonins. Candidate marker genes have also been identified for bacteria plus archaea: ribosomal protein S2 (rpsB), ribosomal protein S10 (rpsJ), ribosomal protein L1 (rplA), translation elongation factor EF-2, translation initiation factor IF-2, metalloendopeptidase, ribosomal protein L22, ffh signal recognition particle protein, ribosomal protein L4/L1e (rplD), ribosomal protein L2 (rplB), ribosomal protein S9 (rps1), ribosomal protein L3 (rplC), phenylalanyl-tRNA synthetase beta subunit, ribosomal protein L14b/L23e (rplN), ribosomal protein S5, ribosomal protein S19 (rpsS), ribosomal protein S7, ribosomal protein L16/L10E (rplP), ribosomal protein S13 (rpsM), phenylalanyl-tRNA synthetase a subunit, ribosomal protein L15, ribosomal protein L25/L23, ribosomal protein L6 (rplF), ribosomal protein L11 (rplK), ribosomal protein L5 (rplE), ribosomal protein S12/S23, ribosomal protein L29, ribosomal protein S3 (rpsC), ribosomal protein S11 (rpsK), ribosomal protein L10, ribosomal protein S8, tRNA pseudouridine synthase B, ribosomal protein L18P/L5E, ribosomal protein S15P/S13e, Porphobilinogen deaminase, ribosomal protein S17, ribosomal protein L13 (rplM), phosphoribosylformylglycinamidine cyclo-ligase (rpsE), ribonuclease HII and ribosomal protein L24. Other candidate marker genes for bacteria include: transcription elongation protein NusA (nusA), rpoB DNA-directed RNA polymerase subunit beta (rpoB), GTP-binding protein EngA, rpoC DNA-directed RNA polymerase subunit beta', priA primosome assembly protein, transcription-repair coupling factor, CTP synthase (pyrG), secY preprotein translocase subunit SecY, GTP-binding protein Obg/CgtA, DNA polymerase I, rpsF 30S ribosomal protein S6, poA DNA-directed RNA polymerase subunit alpha, peptide chain release factor 1, rpll 50S ribosomal protein L9, polyribonucleotide nucleotidyltransferase, tsf elongation factor Ts (tsf), rplQ 50S ribosomal protein L17, tRNA (guanine-N(1)-)-methyltransferase (rplS), rplY probable 50S ribosomal protein L25, DNA repair protein RadA, glucose-inhibited division protein A, ribosome-binding factor A, DNA mismatch repair protein MutL, smpB SsrA-binding protein (smpB), N-acetylglucosaminyl transferase, S-adenosyl-methyltransferase MraW, UDP-N-acetylmuramoylalanine-D-glutamate ligase, rplS 50S ribosomal protein L19, rplT 50S ribosomal protein L20 (rplT), ruvA Holliday junction DNA helicase, ruvB Holliday junction DNA helicase B, serS seryl-tRNA synthetase, rplU 50S ribosomal protein L21, rpsR 30S ribosomal protein S18, DNA mismatch repair protein MutS, rpsT 30S ribosomal protein S20, DNA repair protein RecN, frr ribosome recycling factor (frr), recombination protein RecR, protein of unknown function UPF0054, miaA tRNA isopentenyltransferase, GTP-binding protein YchF, chromosomal replication initiator protein DnaA, dephospho-CoA kinase, 16S rRNA processing protein RimM, ATP-cone domain protein, 1-deoxy-D-xylulose 5-phosphate reductoisomerase, 2C-methyl-D-erythritol 2,4-cyclodiphosphate synthase, fatty acid/phospholipid synthesis protein PlsX, tRNA(Ile)-lysidine synthetase, dnaG DNA primase (dnaG), ruvC Holliday junction resolvase, rpsP 30S ribosomal protein S16, Recombinase A recA, riboflavin biosynthesis protein RibF, glycyl-tRNA synthetase beta subunit, trmU tRNA (5-methylaminomethyl-2-thiouridylate)-methyltransferase, rpml 50S ribosomal protein L35, hemE uroporphyrinogen decarboxylase, Rod shape-determining protein, rpmA 50S ribosomal protein L27 (rpmA), peptidyl-tRNA hydrolase, translation initiation factor IF-3 (infC), UDP-N-acetylmuramyl-tripeptide synthetase, rpmF 50S ribosomal protein L32, rplL 50S ribosomal protein L7/L12 (rplL), leuS leucyl-tRNA synthetase, ligA NAD-dependent DNA ligase, cell division protein FtsA, GTP-binding protein TypA, ATP-dependent Clp protease, ATP-binding subunit ClpX, DNA replication and repair protein RecF and UDP-N-acetylenolpyruvoylglucosamine reductase.

Phospholipid fatty acids (PLFAs) may also be used as unique first markers according to the methods described herein. Because PLFAs are rapidly synthesized during microbial growth, are not found in storage molecules and degrade rapidly during cell death, it provides an accurate census of the current living community. All cells contain fatty acids (FAs) that can be extracted and esterified to form fatty acid methyl esters (FAMEs). When the FAMEs are analyzed using gas chromatography-mass spectrometry, the resulting profile constitutes a 'fingerprint' of the microorganisms in the sample. The chemical compositions of membranes for organisms in the domains Bacteria and Eukarya are comprised of fatty acids linked to the glycerol by an ester-type bond (phospholipid fatty acids (PLFAs)). In contrast, the membrane lipids of Archaea are composed of long and branched hydrocarbons that are joined to glycerol by an ether-type bond (phospholipid ether lipids (PLELs)). This is one of the most widely used non-genetic criteria to distinguish the three domains. In this context, the phospholipids derived from microbial cell membranes, characterized by different acyl chains, are excellent signature molecules, because such lipid structural diversity can be linked to specific microbial taxa.

As provided herein, in order to determine whether an organism strain is active, the level of expression of one or more unique second markers, which can be the same or different as the first marker, is measured (FIG. 1, 1004; FIG. 2, 2004). Unique first unique markers are described above. The unique second marker is a marker of microorganism activity. For example, in one embodiment, the mRNA or protein expression of any of the first markers described above is considered a unique second marker for the purposes of this invention.

In one embodiment, if the level of expression of the second marker is above a threshold level (e.g., a control level) or at a threshold level, the microorganism is considered to be active (FIG. 1, 1005; FIG. 2, 2005). Activity is determined in one embodiment, if the level of expression of the second marker is altered by at least about 5%, at least about 10%, at least about 15%, at least about 20%, at least about 25%, or at least about 30%, as compared to a threshold level, which in some embodiments, is a control level.

Second unique markers are measured, in one embodiment, at the protein, RNA or metabolite level. A unique second marker is the same or different as the first unique marker.

As provided above, a number of unique first markers and unique second markers can be detected according to the methods described herein. Moreover, the detection and quantification of a unique first marker is carried out according to methods known to those of ordinary skill in the art (FIG. 1, 1003-1004, FIG. 2, 2003-2004).

Nucleic acid sequencing (e.g., gDNA, cDNA, rRNA, mRNA) in one embodiment is used to determine absolute abundance of a unique first marker and/or unique second marker. Sequencing platforms include, but are not limited to, Sanger sequencing and high-throughput sequencing methods available from Roche/454 Life Sciences, Illumina/Solexa, Pacific Biosciences, Ion Torrent and Nanopore. The sequencing can be amplicon sequencing of particular DNA or RNA sequences or whole metagenome/transcriptome shotgun sequencing.

Traditional Sanger sequencing (Sanger et al. (1977) DNA sequencing with chain-terminating inhibitors. Proc Natl. Acad. Sci. USA, 74, pp. 5463-5467, incorporated by reference herein in its entirety) relies on the selective incorporation of chain-terminating dideoxynucleotides by DNA polymerase during in vitro DNA replication and is amenable for use with the methods described herein.

In another embodiment, the sample, or a portion thereof is subjected to extraction of nucleic acids, amplification of DNA of interest (such as the rRNA gene) with suitable primers and the construction of clone libraries using sequencing vectors. Selected clones are then sequenced by Sanger sequencing and the nucleotide sequence of the DNA of interest is retrieved, allowing calculation of the number of unique microorganism strains in a sample.

454 pyrosequencing from Roche/454 Life Sciences yields long reads and can be harnessed in the methods described herein (Margulies et al. (2005) Nature, 437, pp. 376-380; U.S. Pat. Nos. 6,274,320; 6,258,568; 6,210,891, each of which is herein incorporated in its entirety for all purposes). Nucleic acid to be sequenced (e.g., amplicons or nebulized genomic/metagenomic DNA) have specific adapters affixed on either end by PCR or by ligation. The DNA with adapters is fixed to tiny beads (ideally, one bead will have one DNA fragment) that are suspended in a water-in-oil emulsion. An emulsion PCR step is then performed to make multiple copies of each DNA fragment, resulting in a set of beads in which each bead contains many cloned copies of the same DNA fragment. Each bead is then placed into a well of a fiber-optic chip that also contains enzymes necessary for the sequencing-by-synthesis reactions. The addition of bases (such as A, C, G, or T) trigger pyrophosphate release, which produces flashes of light that are recorded to infer the sequence of the DNA fragments in each well. About 1 million reads per run with reads up to 1,000 bases in length can be achieved. Paired-end sequencing can be done, which produces pairs of reads, each of which begins at one end of a given DNA fragment. A molecular barcode can be created and placed between the adapter sequence and the sequence of interest in multiplex reactions, allowing each sequence to be assigned to a sample bioinformatically.

Illumina/Solexa sequencing produces average read lengths of about 25 basepairs (bp) to about 300 bp (Bennett et al. (2005) Pharmacogenomics, 6:373-382; Lange et al. (2014). BMC Genomics 15, p. 63; Fadrosh et al. (2014) Microbiome 2, p. 6; Caporaso et al. (2012) ISME J, 6, p. 1621-1624; Bentley et al. (2008) Accurate whole human genome sequencing using reversible terminator chemistry. Nature, 456:53-59). This sequencing technology is also sequencing-by-synthesis but employs reversible dye terminators and a flow cell with a field of oligos attached. DNA fragments to be sequenced have specific adapters on either end and are washed over a flow cell filled with specific oligonucleotides that hybridize to the ends of the fragments. Each fragment is then replicated to make a cluster of identical fragments. Reversible dye-terminator nucleotides are then washed over the flow cell and given time to attach. The excess nucleotides are washed away, the flow cell is imaged, and the reversible terminators can be removed so that the process can repeat and nucleotides can continue to be added in subsequent cycles. Paired-end reads that are 300 bases in length each can be achieved. An Illumina platform can produce 4 billion fragments in a paired-end fashion with 125 bases for each read in a single run. Barcodes can also be used for sample multiplexing, but indexing primers are used.

The SOLiD (Sequencing by Oligonucleotide Ligation and Detection, Life Technologies) process is a "sequencing-by-ligation" approach, and can be used with the methods described herein for detecting the presence and abundance of a first marker and/or a second marker (FIG. 1, 1003-1004; FIG. 2, 2003-2004) (Peckham et al. SOLiD™ Sequencing and 2-Base Encoding. San Diego, Calif.: American Society of Human Genetics, 2007; Mitra et al. (2013) Analysis of the intestinal microbiota using SOLiD 16S rRNA gene sequencing and SOLiD shotgun sequencing. BMC Genomics, 14(Suppl 5): S16; Mardis (2008) Next-generation DNA sequencing methods. Annu Rev Genomics Hum Genet, 9:387-402; each incorporated by reference herein in its entirety). A library of DNA fragments is prepared from the sample to be sequenced, and are used to prepare clonal bead populations, where only one species of fragment will be present on the surface of each magnetic bead. The fragments attached to the magnetic beads will have a universal P1 adapter sequence so that the starting sequence of every fragment is both known and identical. Primers hybridize to the P1 adapter sequence within the library template. A set of four fluorescently labelled di-base probes compete for ligation to the sequencing primer. Specificity of the di-base probe is achieved by interrogating every 1st and 2nd base in each ligation reaction. Multiple cycles of ligation, detection and cleavage are performed with the number of cycles determining the eventual read length. The SOLiD platform can produce up to 3 billion reads per run with reads that are 75 bases long. Paired-end sequencing is available and can be used herein, but with the second read in the pair being only 35 bases long. Multiplexing of samples is possible through a system akin to the one used by Illumina, with a separate indexing run.

The Ion Torrent system, like 454 sequencing, is amenable for use with the methods described herein for detecting the presence and abundance of a first marker and/or a second marker (FIG. 1, 1003-1004; FIG. 2, 2003-2004). It uses a plate of microwells containing beads to which DNA fragments are attached. It differs from all of the other systems, however, in the manner in which base incorporation is detected. When a base is added to a growing DNA strand, a proton is released, which slightly alters the surrounding pH. Microdetectors sensitive to pH are associated with the wells on the plate, and they record when these changes occur. The different bases (A, C, G, T) are washed sequentially through the wells, allowing the sequence from each well to be inferred. The Ion Proton platform can produce up to 50 million reads per run that have read lengths of 200 bases. The Personal Genome Machine platform has longer reads at 400 bases. Bidirectional sequencing is available. Multiplexing is possible through the standard in-line molecular barcode sequencing.

Pacific Biosciences (PacBio) SMRT sequencing uses a single-molecule, real-time sequencing approach and in one embodiment, is used with the methods described herein for detecting the presence and abundance of a first marker and/or a second marker (FIG. 1, 1003-1004; FIG. 2, 2003-2004). The PacBio sequencing system involves no amplification step, setting it apart from the other major next-generation sequencing systems. In one embodiment, the sequencing is performed on a chip containing many zero-mode waveguide (ZMW) detectors. DNA polymerases are attached to the ZMW detectors and phospholinked dye-labeled nucleotide incorporation is imaged in real time as DNA strands are synthesized. The PacBio system yields very long read lengths (averaging around 4,600 bases) and a very high number of reads per run (about 47,000). The typical "paired-end" approach is not used with PacBio, since reads are typically long enough that fragments, through CCS, can be covered multiple times without having to sequence from each end independently. Multiplexing with PacBio does not involve an independent read, but rather follows the standard "in-line" barcoding model.

In one embodiment, where the first unique marker is the ITS genomic region, automated ribosomal intergenic spacer analysis (ARISA) is used in one embodiment to determine the number and identity of microorganism strains in a sample (FIG. 1, 1003, FIG. 2, 2003) (Ranjard et al. (2003). Environmental Microbiology 5, pp. 1111-1120, incorporated by reference in its entirety for all purposes). The ITS region has significant heterogeneity in both length and nucleotide sequence. The use of a fluorescence-labeled forward primer and an automatic DNA sequencer permits high resolution of separation and high throughput. The inclusion of an internal standard in each sample provides accuracy in sizing general fragments.

In another embodiment, fragment length polymorphism (RFLP) of PCR-amplified rDNA fragments, otherwise known as amplified ribosomal DNA restriction analysis (ARDRA), is used to characterize unique first markers and the abundance of the same in samples (FIG. 1, 1003, FIG. 2, 2003) (Massol-Deya et al. (1995). Mol. Microb. Ecol. Manual. 3.3.2, pp. 1-18, incorporated by reference in its entirety for all purposes). rDNA fragments are generated by PCR using general primers, digested with restriction enzymes, electrophoresed in agarose or acrylamide gels, and stained with ethidium bromide or silver nitrate.

One fingerprinting technique used in detecting the presence and abundance of a unique first marker is single-stranded-conformation polymorphism (SSCP) (Lee et al. (1996). Appl Environ Microbiol 62, pp. 3112-3120; Scheinert et al. (1996). J. Microbiol. Methods 26, pp. 103-117; Schwieger and Tebbe (1998). Appl. Environ. Microbiol. 64, pp. 4870-4876, each of which is incorporated by reference herein in its entirety). In this technique, DNA fragments such as PCR products obtained with primers specific for the 16S rRNA gene, are denatured and directly electrophoresed on a non-denaturing gel. Separation is based on differences in size and in the folded conformation of single-stranded DNA, which influences the electrophoretic mobility. Reannealing of DNA strands during electrophoresis can be prevented by a number of strategies, including the use of one phosphorylated primer in the PCR followed by specific digestion of the phosphorylated strands with lambda exonuclease and the use of one biotinylated primer to perform magnetic separation of one single strand after denaturation. To assess the identity of the predominant populations in a given microbial ensemble, in one embodiment, bands are excised and sequenced, or SSCP-patterns can be hybridized with specific probes. Electrophoretic conditions, such as gel matrix, temperature, and addition of glycerol to the gel, can influence the separation.

In addition to sequencing based methods, other methods for quantifying expression (e.g., gene, protein expression) of a second marker are amenable for use with the methods provided herein for determining the level of expression of one or more second markers (FIG. 1, 1004; FIG. 2, 2004). For example, quantitative RT-PCR, microarray analysis, linear amplification techniques such as nucleic acid sequence based amplification (NASBA) are all amenable for use with the methods described herein, and can be carried out according to methods known to those of ordinary skill in the art.

In another embodiment, the sample, or a portion thereof is subjected to a quantitative polymerase chain reaction (PCR) for detecting the presence and abundance of a first marker and/or a second marker (FIG. 1, 1003-1004; FIG. 2, 2003-2004). Specific microorganism strains activity is measured by reverse transcription of transcribed ribosomal and/or messenger RNA (rRNA and mRNA) into complementary DNA (cDNA), followed by PCR (RT-PCR).

In another embodiment, the sample, or a portion thereof is subjected to PCR-based fingerprinting techniques to detect the presence and abundance of a first marker and/or a second marker (FIG. 1, 1003-1004; FIG. 2, 2003-2004). PCR products can be separated by electrophoresis based on the nucleotide composition. Sequence variation among the different DNA molecules influences the melting behaviour, and therefore molecules with different sequences will stop migrating at different positions in the gel. Thus electrophoretic profiles can be defined by the position and the relative intensity of different bands or peaks and can be translated to numerical data for calculation of diversity indices. Bands can also be excised from the gel and subsequently sequenced to reveal the phylogenetic affiliation of the community members. Electrophoresis methods include, but are not limited to: denaturing gradient gel electrophoresis (DGGE), temperature gradient gel electrophoresis (TGGE), single-stranded-conformation polymorphism (SSCP), restriction fragment length polymorphism analysis (RFLP) or amplified ribosomal DNA restriction analysis (ARDRA), terminal restriction fragment length polymorphism analysis (T-RFLP), automated ribosomal intergenic spacer analysis (ARISA), randomly amplified polymorphic DNA (RAPD), DNA amplification fingerprinting (DAF) and Bb-PEG electrophoresis.

In another embodiment, the sample, or a portion thereof is subjected to a chip-based platform such as microarray or microfluidics to determine the abundance of a unique first marker and/or presence/abundance of a unique second marker (FIG. 1, 1003-1004, FIG. 2, 2003-2004). The PCR products are amplified from total DNA in the sample and directly hybridized to known molecular probes affixed to microarrays. After the fluorescently labeled PCR amplicons are hybridized to the probes, positive signals are scored by the use of confocal laser scanning microscopy. The microarray technique allows samples to be rapidly evaluated with replication, which is a significant advantage in microbial community analyses. In general, the hybridization signal intensity on microarrays is directly proportional to the abundance of the target organism. The universal high-density 16S microarray (PhyloChip) contains about 30,000 probes of 16SrRNA gene targeted to several cultured microbial species and "candidate divisions". These probes target all 121 demarcated prokaryotic orders and allow simultaneous detection of 8,741 bacterial and archaeal taxa. Another microarray in use for profiling microbial communities is the Functional Gene Array (FGA). Unlike PhyloChips, FGAs are designed primarily to detect specific metabolic groups of bacteria. Thus, FGA not only reveal the community structure, but they also shed light on the in situ community metabolic potential. FGA contain probes from genes with known biological functions, so they are useful in linking microbial community composition to ecosystem functions. An FGA termed GeoChip contains >24,000 probes from all known metabolic genes involved in various biogeochemical, ecological, and environmental processes such as ammonia oxidation, methane oxidation, and nitrogen fixation.

A protein expression assay, in one embodiment, is used with the methods described herein for determining the level of expression of one or more second markers (FIG. 1, 1004; FIG. 2, 2004). For example, in one embodiment, mass spectrometry or an immunoassay such as an enzyme-linked immunosorbant assay (ELISA) is utilized to quantify the level of expression of one or more unique second markers, wherein the one or more unique second markers is a protein.

In one embodiment, the sample, or a portion thereof is subjected to Bromodeoxyuridine (BrdU) incorporation to determine the level of a second unique marker (FIG. 1, 1004; FIG. 2, 2004). BrdU, a synthetic nucleoside analog of thymidine, can be incorporated into newly synthesized DNA of replicating cells. Antibodies specific for BRdU can then be used for detection of the base analog. Thus BrdU incorporation identifies cells that are actively replicating their DNA, a measure of activity of a microorganism according to one embodiment of the methods described herein. BrdU incorporation can be used in combination with FISH to provide the identity and activity of targeted cells.

In one embodiment, the sample, or a portion thereof is subjected to microautoradiography (MAR) combined with FISH to determine the level of a second unique marker (FIG. 1, 1004; FIG. 2, 2004). MAR-FISH is based on the incorporation of radioactive substrate into cells, detection of the active cells using autoradiography and identification of the cells using FISH. The detection and identification of active cells at single-cell resolution is performed with a microscope. MAR-FISH provides information on total cells, probe targeted cells and the percentage of cells that incorporate a given radiolabelled substance. The method provides an assessment of the in situ function of targeted microorganisms and is an effective approach to study the in vivo physiology of microorganisms. A technique developed for quantification of cell-specific substrate uptake in combination with MAR-FISH is known as quantitative MAR (QMAR).

In one embodiment, the sample, or a portion thereof is subjected to stable isotope Raman spectroscopy combined with FISH (Raman-FISH) to determine the level of a second unique marker (FIG. 1, 1004; FIG. 2, 2004). This technique combines stable isotope probing, Raman spectroscopy and FISH to link metabolic processes with particular organisms. The proportion of stable isotope incorporation by cells affects the light scatter, resulting in measurable peak shifts for labelled cellular components, including protein and mRNA components. Raman spectroscopy can be used to identify whether a cell synthesizes compounds including, but not limited to: oil (such as alkanes), lipids (such as triacylglycerols (TAG)), specific proteins (such as heme proteins, metalloproteins), cytochrome (such as P450, cytochrome c), chlorophyll, chromophores (such as pigments for light harvesting carotenoids and rhodopsins), organic polymers (such as polyhydroxyalkanoates (PHA), polyhydroxybutyrate (PHB)), hopanoids, steroids, starch, sulfide, sulfate and secondary metabolites (such as vitamin B12).

In one embodiment, the sample, or a portion thereof is subjected to DNA/RNA stable isotope probing (SIP) to determine the level of a second unique marker (FIG. 1, 1004; FIG. 2, 2004). SIP enables determination of the microbial diversity associated with specific metabolic pathways and has been generally applied to study microorganisms involved in the utilization of carbon and nitrogen compounds. The substrate of interest is labelled with stable isotopes (such as $^{13}C$ or $^{15}N$) and added to the sample. Only microorganisms able to metabolize the substrate will incorporate it into their cells. Subsequently, $^{13}C$-DNA and $^{15}N$-DNA can be isolated by density gradient centrifugation and used for metagenomic analysis. RNA-based SIP can be a responsive biomarker for use in SIP studies, since RNA itself is a reflection of cellular activity.

In one embodiment, the sample, or a portion thereof is subjected to isotope array to determine the level of a second unique marker (FIG. 1, 1004; FIG. 2, 2004). Isotope arrays allow for functional and phylogenetic screening of active microbial communities in a high-throughput fashion. The technique uses a combination of SIP for monitoring the substrate uptake profiles and microarray technology for determining the taxonomic identities of active microbial communities. Samples are incubated with a $^{14}C$-labeled substrate, which during the course of growth becomes incorporated into microbial biomass. The $^{14}C$-labeled rRNA is separated from unlabeled rRNA and then labeled with fluorochromes. Fluorescent labeled rRNA is hybridized to a phylogenetic microarray followed by scanning for radioactive and fluorescent signals. The technique thus allows simultaneous study of microbial community composition and specific substrate consumption by metabolically active microorganisms of complex microbial communities.

In one embodiment, the sample, or a portion thereof is subjected to a metabolomics assay to determine the level of a second unique marker (FIG. 1, 1004; FIG. 2, 2004). Metabolomics studies the metabolome which represents the collection of all metabolites, the end products of cellular processes, in a biological cell, tissue, organ or organism. This methodology can be used to monitor the presence of microorganisms and/or microbial mediated processes since it allows associating specific metabolite profiles with different microorganisms. Profiles of intracellular and extracellular metabolites associated with microbial activity can be obtained using techniques such as gas chromatography-mass spectrometry (GC-MS). The complex mixture of a metabolomic sample can be separated by such techniques as gas chromatography, high performance liquid chromatography and capillary electrophoresis. Detection of metabolites can be by mass spectrometry, nuclear magnetic resonance (NMR) spectroscopy, ion-mobility spectrometry, electrochemical detection (coupled to HPLC) and radiolabel (when combined with thin-layer chromatography).

According to the embodiments described herein, the presence and respective number of one or more active microorganism strains in a sample are determined (FIG. 1, 1006; FIG. 2, 2006). For example, strain identity information obtained from assaying the number and presence of first markers is analyzed to determine how many occurrences of a unique first marker are present, thereby representing a unique microorganism strain (e.g., by counting the number of sequence reads in a sequencing assay). This value can be represented in one embodiment as a percentage of total sequence reads of the first maker to give a percentage of unique microorganism strains of a particular microorganism type. In a further embodiment, this percentage is multiplied by the number of microorganism types (obtained at step 1002 or 2002, see FIG. 1 and FIG. 2) to give the absolute abundance of the one or more microorganism strains in a sample and a given volume.

The one or more microorganism strains are considered active, as described above, if the level of second unique marker expression at a threshold level, higher than a threshold value, e.g., higher than at least about 5%, at least about 10%, at least about 20% or at least about 30% over a control level.

In another aspect of the invention, a method for determining the absolute abundance of one or more microorganism strains is determined in a plurality of samples (FIG. 2, see in particular, 2007). For a microorganism strain to be classified as active, it need only be active in one of the samples. The samples can be taken over multiple time points from the same source, or can be from different environmental sources (e.g., different animals).

The absolute abundance values over samples are used in one embodiment to relate the one or more active microorganism strains, with an environmental parameter (FIG. 2, 2008). In one embodiment, the environmental parameter is the presence of a second active microorganism strain. Relating the one or more active microorganism strains to the environmental parameter, in one embodiment, is carried out by determining the co-occurrence of the strain and parameter by correlation or by network analysis.

In one embodiment, determining the co-occurrence of one or more active microorganism strains with an environmental parameter comprises a network and/or cluster analysis method to measure connectivity of strains or a strain with an environmental parameter within a network, wherein the network is a collection of two or more samples that share a common or similar environmental parameter. In another embodiment, the network and/or cluster analysis method may be applied to determining the co-occurrence of two or more active microorganism strains in a sample (FIG. 2, 2008). In another embodiment, the network analysis comprises nonparametric approaches including mutual information to establish connectivity between variables. In another embodiment, the network analysis comprises linkage analysis, modularity analysis, robustness measures, betweenness measures, connectivity measures, transitivity measures, centrality measures or a combination thereof (FIG. 2, 2009). In another embodiment, the cluster analysis method comprises building a connectivity model, subspace model, distribution model, density model, or a centroid model and/or using community detection algorithms such as the Louvain, Bron-Kerbosch, Girvan-Newman, Clauset-Newman-Moore, Pons-Latapy, and Wakita-Tsurumi algorithms (FIG. 2, 2010).

In one embodiment, the cluster analysis method is a heuristic method based on modularity optimization. In a further embodiment, the cluster analysis method is the Louvain method. See, e.g., the method described by Blondel et al. (2008). Fast unfolding of communities in large networks. Journal of Statistical Mechanics: Theory and Experiment, Volume 2008, October 2008, incorporated by reference herein in its entirety for all purposes.

In another embodiment, the network analysis comprises predictive modeling of network through link mining and prediction, collective classification, link-based clustering, relational similarity, or a combination thereof. In another embodiment, the network analysis comprises differential equation based modeling of populations. In another embodiment, the network analysis comprises Lotka-Volterra modeling.

In one embodiment, relating the one or more active microorganism strains to an environmental parameter (e.g., determining the co-occurrence) in the sample comprises creating matrices populated with linkages denoting environmental parameter and microorganism strain associations.

In one embodiment, the multiple sample data obtained at step 2007 (e.g., over two or more samples which can be collected at two or more time points where each time point corresponds to an individual sample), is compiled. In a further embodiment, the number of cells of each of the one or more microorganism strains in each sample is stored in an association matrix (which can be in some embodiments, an abundance matrix). In one embodiment, the association matrix is used to identify associations between active microorganism strains in a specific time point sample using rule mining approaches weighted with association (e.g., abundance) data. Filters are applied in one embodiment to remove insignificant rules.

In one embodiment, the absolute abundance of one or more, or two or more active microorganism strains is related to one or more environmental parameters (FIG. 2, 2008), e.g., via co-occurrence determination. Environmental parameters are chosen by the user depending on the sample (s) to be analyzed and are not restricted by the methods described herein. The environmental parameter can be a parameter of the sample itself, e.g., pH, temperature, amount of protein in the sample. Alternatively, the environmental parameter is a parameter that affects a change in the identity of a microbial community (i.e., where the "identity" of a microbial community is characterized by the type of microorganism strains and/or number of particular microorganism strains in a community), or is affected by a change in the identity of a microbial community. For example, an environmental parameter in one embodiment, is the food intake of an animal or the amount of eggs produced by poultry. In one embodiment, the environmental parameter is the presence, activity and/or abundance of a second microorganism strain in the microbial community, present in the same sample.

In some embodiments described herein, an environmental parameter is referred to as a metadata parameter.

Other examples of metadata parameters include but are not limited to genetic information from the host from which the sample was obtained (e.g., DNA mutation information), sample pH, sample temperature, expression of a particular protein or mRNA, nutrient conditions (e.g., level and/or identity of one or more nutrients) of the surrounding environment/ecosystem), susceptibility or resistance to disease, onset or progression of disease, susceptibility or resistance of the sample to toxins, efficacy of xenobiotic compounds (pharmaceutical drugs), biosynthesis of natural products, or a combination thereof.

For example, according to one embodiment, microorganism strain number changes are calculated over multiple samples according to the method of FIG. 2 (i.e., at 2001-2007). Strain number changes of one or more active strains over time is compiled (e.g., one or more strains that have initially been identified as active according to step 2006), and the directionality of change is noted (i.e., negative values denoting decreases, positive values denoting increases). The number of cells over time is represented as a network, with microorganism strains representing nodes and the abundance weighted rules representing edges. Markov chains and random walks are leveraged to determine connectivity between nodes and to define clusters. Clusters in one embodiment are filtered using metadata in order to identify clusters associated with desirable metadata (FIG. 2, 2008).

In a further embodiment, microorganism strains are ranked according to importance by integrating cell number changes over time and strains present in target clusters, with the highest changes in cell number ranking the highest.

Network and/or cluster analysis method in one embodiment, is used to measure connectivity of the one or more strains within a network, wherein the network is a collection of two or more samples that share a common or similar environmental parameter. In one embodiment, network analysis comprises linkage analysis, modularity analysis, robustness measures, betweenness measures, connectivity measures, transitivity measures, centrality measures or a combination thereof. In another embodiment, network analysis comprises predictive modeling of network through link mining and prediction, social network theory, collective classification, link-based clustering, relational similarity, or a combination thereof. In another embodiment, network analysis comprises differential equation based modeling of populations. In yet another embodiment, network analysis comprises Lotka-Volterra modeling.

Cluster analysis method comprises building a connectivity model, subspace model, distribution model, density model, or a centroid model.

Network and cluster based analysis, for example, to carry out method step 2008 of FIG. 2, can be carried out via a module. As used herein, a module can be, for example, any assembly, instructions and/or set of operatively-coupled electrical components, and can include, for example, a memory, a processor, electrical traces, optical connectors, software (executing in hardware) and/or the like.

Network Analysis

A network and/or cluster analysis method, in one embodiment, is used to measure connectivity of the one or more strains within a network, wherein the network is a collection of two or more samples that share a common or similar environmental parameter. In one embodiment, network analysis comprises linkage analysis, modularity analysis, robustness measures, betweenness measures, connectivity measures, transitivity measures, centrality measures or a combination thereof. In another embodiment, network analysis comprises predictive modeling of network through link mining and prediction, social network theory, collective classification, link-based clustering, relational similarity, or a combination thereof. In another embodiment, network analysis comprises mutual information, maximal information coefficient (MIC) calculations, or other nonparametric methods between variables to establish connectivity. In another embodiment, network analysis comprises differential equation based modeling of populations. In yet another embodiment, network analysis comprises Lotka-Volterra modeling.

The environmental parameter can be a parameter of the sample itself, e.g., pH, temperature, amount of protein in the sample. Alternatively, the environmental parameter is a parameter that affects a change in the identity of a microbial community (i.e., where the "identity" of a microbial community is characterized by the type of microorganism strains and/or number of particular microorganism strains in a community), or is affected by a change in the identity of a microbial community. For example, an environmental parameter in one embodiment, is the food intake of an animal or the amount of eggs produced. In one embodiment, the environmental parameter is the presence, activity and/or abundance of a second microorganism strain in the microbial community, present in the same sample. In some embodiments, an environmental parameter is referred to as a metadata parameter.

Other examples of metadata parameters include but are not limited to genetic information from the host from which the sample was obtained (e.g., DNA mutation information), sample pH, sample temperature, expression of a particular protein or mRNA, nutrient conditions (e.g., level and/or identity of one or more nutrients) of the surrounding environment/ecosystem), susceptibility or resistance to disease, onset or progression of disease, susceptibility or resistance of the sample to toxins, efficacy of xenobiotic compounds (pharmaceutical drugs), biosynthesis of natural products, or a combination thereof.

Poultry Pathogen Resistance and Clearance

In some aspects, the present disclosure is drawn to administering one or more microbial compositions described herein to poultry to clear the gastrointestinal tract of pathogenic microbes. In some embodiments, the present disclosure is further drawn to administering microbial compositions described herein to prevent colonization of pathogenic microbes in the gastrointestinal tract. In some embodiments, the administration of microbial compositions described herein further clear pathogens from the integument and the respiratory tract of fowl, and/or prevent colonization of pathogens on the integument and in the respiratory tract. In some embodiments, the administration of microbial compositions described herein reduce leaky gut/intestinal permeability, inflammation, and/or incidence of liver disease.

In some embodiments, the microbial compositions of the present disclosure comprise one or more microbes that are present in the gastrointestinal tract of poultry at a relative abundance of less than 15%, 14%, 13%, 12%, 11%, 10%, 9%, 8%, 7%, 6%, 5%, 4%, 3%, 2%, 1%, 0.5%, 0.1%, or 0.01%.

In some embodiments, after administration of microbial compositions of the present disclosure the one or more microbes are present in the gastrointestinal tract of the poultry at a relative abundance of at least 0.5%, 1%, 5%, 10%, 15%, 20%, 25%, 30%, 35%, 40%, 45%, 50%, 55%, 60%, 65%, 70%, 75%, 80%, 85%, 90%, or 95%.

In some embodiments the administration of microbial compositions described herein further decrease the prevalence or the likelihood of a pathogen to be found in the fowl.

In some embodiments, the administration of microbial compositions described herein further decreases the pathogen abundance in the fowl.

Pathogenic microbes of poultry include the following: *Mycoplasma gallisepticum, Mycoplasma meleagridis, Mycoplasma synoviae, Pasteurella multocida, Clostridium perfringens, Clostridium colinum, Clostridium botulinum, Salmonella typi, Salmonella typhimurium, Salmonella enterica, Salmonella pullorum, Salmonella gallinarum, Hemophilus gallinarum, Erysipelothrix insidiosa, Campylobacter jejuni, Campylobacter coli, Campylobacter lari, Listeria monocytogenes, Arcobacter butzleri, Shigella boydii, Shigella dysenteriae, Shigella flexneri, Shigella sonnei, Mycobacterium avium*, and pathogenic strains of *Escherichia coli* and *Staphylococcus aureus*. In some embodiments, the pathogenic microbes include viral pathogens. In some embodiments, the pathogenic microbes are pathogenic to both poultry and humans. In some embodiments, the pathogenic microbes are pathogenic to either poultry or humans.

In some embodiments, the administration of compositions of the present disclosure to poultry modulate the makeup of the gastrointestinal microbiome such that the administered microbes outcompete microbial pathogens present in the gastrointestinal tract. In some embodiments, the administration of compositions of the present disclosure to poultry harboring microbial pathogens outcompetes the pathogens and clears the poultry of the pathogens. In some embodiments, the administration of compositions of the present disclosure stimulate host immunity, and aids in clearance of the microbial pathogens. In some embodiments, the administration of compositions of the present disclosure introduce microbes that produce bacteriostatic and/or bactericidal components that decrease or clear the poultry of the microbial pathogens. In some embodiments, the administration of compositions of the present disclosure introduces microbes that modulate the pH, nutrient availability, minteral composition, and/or vitamin composition of the gastrointestinal tract. In some embodiments, the administration of compositions of the present disclosure introduces microbes that increase the gastrointestinal pH, resulting in the inhibition of pathogen growth. In some embodiments, the administration of compositions of the present disclosure introduces microbes that decrease the gastrointestinal pH, resulting in the inhibition of pathogen growth.

In some embodiments, challenging poultry with a microbial colonizer or microbial pathogen after administering one or more compositions of the present disclosure prevents the microbial colonizer or microbial pathogen from growing to a relative abundance of greater than 15%, 14%, 13%, 12%, 11%, 10%, 9%, 8%, 7%, 6%, 5%, 4%, 3%, 2%, 1%, 0.5%, 0.1%, or 0.01%. In further embodiments, challenging poultry with a microbial colonizer or microbial pathogen after administering one or more compositions of the present disclosure prevents the microbial colonizer or microbial pathogen from colonizing poultry In some embodiments, clearance of the microbial colonizer or microbial pathogen occurs occurs in less than 25 days, less than 24 days, less than 23 days, less than 22 days, less than 21 days, less than 20 days, less than 19 days, less than 18 days, less than 17 days, less than 16 days, less than 15 days, less than 14 days, less than 13 days, less than 12 days, less than 11 days, less than 10 days, less than 9 days, less than 8 days, less than 7 days, less than 6 days, less than 5 days, less than 4 days, less than 3 days, or less than 2 days post administration of the one or more compositions of the present disclosure.

In some embodiments, clearance of the microbial colonizer or microbial pathogen occurs within 1-30 days, 1-25 days, 1-20 day, 1-15 days, 1-10 days, 1-5 days, 5-30 days, 5-25 days, 5-20 days, 5-15 days, 5-10 days, 10-30 days, 10-25 days, 10-20 days, 10-15 days, 15-30 days, 15-25 days, 15-20 days, 20-30 days, 20-25 days, or 25-30 days post administration of the one or more compositions of the present disclosure.

Improved Traits

In some aspects, the present disclosure is drawn to administering microbial compositions described herein to poultry to improve one or more traits through the modulation of aspects of weight, musculature, meat characteristics, egg quantity, egg weight, egg volume, egg quality, egg shell density, digestive chemistry, efficiency of feed utilization and digestibility, fecal output, methane production, overall bird health, prevention of colonization of pathogenic microbes, and clearance of pathogenic microbes.

The lifespan of commercial fowl are somewhat short, 45 days in the instance of commercial broiler chickens. Short lifespans make the similarity of microbial communities of the gastrointestinal tract (GIT) between birds in the same pen low, and between pens very low. The large difference in microbial communities between the birds over time causes vastly different responds in feed efficiency (FE), final gain, mortality, and GIT disease outbreaks. The responses are then used as management metrics, which can lead to spurious decisions because of the large variance(s) exhibited. By quickly converging the microbial communities to a similar final microbial community after hatching, the variance, in response, is decreased. Furthermore, the quick transition to a more matured microbeal community contributes to fend off GIT pathogen colonization and disease outbreak. This allows for broad response observations (i.e., one feed creates higher EE over another) to be more applicable to broad populations of birds. Ultimately, the lower the variance, the greater the uniformity of the flock.

In some embodiments, the increase in egg quantity is an increase of at least 1, 2, 3, 4, 5, 6, 7, 8, 9, or 10 eggs relative to an animal not having been administered a composition of the present disclosure. In some embodiments, the increase in egg quantity is an increase of less than 2, 3, 4, 5, 6, 7, 8, 9, or 10 eggs relative to an animal not having been administered a composition of the present disclosure. In some embodiments, the increase in egg quantity is an increase of at least 10%, 20%, 30%, 40%, 50%, 60%, 70%, 80%, 90%, 100%, 110%, 120%, 130%, 140%, 150%, 160%, 170%, 180%, 190%, or 200% relative to an animal not having been administered a composition of the present disclosure.

In some embodiments, the increase in egg volume is an increase of at least 5%, 10%, 15%, 20%, 25%, 30%, 35%, 40%, 45%, 50%, 55%, 60%, 65%, 70%, 75%, 80%, 85%, 90%, 95%, or 100% relative to an animal not having been administered a composition of the present disclosure. In some embodiments, the increase in egg volume is an increase of less than 5%, 10%, 15%, 20%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the fecal output is reduced by at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure. In some embodiments, the fecal output is reduced by less than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an animal not having been administered a composition of the present disclosure.

In some embodiments, the fowl having been administered a composition of the present disclosure exhibit a weight gain of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to a fowl not having been administered a composition of the present disclosure.

In some embodiments, the fowl having been administered a composition of the present disclosure exhibit a weight gain of at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to a fowl not having been administered a composition of the present disclosure.

In some embodiments, the fowl having been administered a composition of the present disclosure exhibit a feed conversion ratio decrease of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to a fowl not having been administered a composition of the present disclosure.

In some embodiments, the fowl having been administered a composition of the present disclosure exhibit a feed conversion ratio decrease of at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to a fowl not having been administered a composition of the present disclosure.

In some embodiments, the fowl having been administered a composition of the present disclosure exhibit a decrease in the number of necrotic enteritis-causing bacteria in the gastrointestinal tract of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to a fowl not having been administered a composition of the present disclosure.

In some embodiments, the fowl having been administered a composition of the present disclosure exhibit a decrease in the number of necrotic enteritis-causing bacteria in the gastrointestinal tract of at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to a fowl not having been administered a composition of the present disclosure.

In some embodiments, the fowl having been administered a composition of the present disclosure exhibit a decrease in the number of pathogenic bacteria in the gastrointestinal tract of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to a fowl not having been administered a composition of the present disclosure.

In some embodiments, the fowl having been administered a composition of the present disclosure exhibit a decrease in the number of pathogenic bacteria in the gastrointestinal tract of at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to a fowl not having been administered a composition of the present disclosure.

In some embodiments, improving the eggs produced by poultry is desirable, wherein the eggs include triglycerides, triacylglycerides, diacylglycerides, monoacylglycerides, phospholipids, cholesterol, glycolipids, and free fatty acids. In further embodiments, free fatty acids include short chain fatty acids (i.e., C4:0, C6:0, and C8:0), medium chain fatty acids (i.e., C10:0, C10:1, C12:0, C14:0, C14:1, and C15:0), and long chain fatty acids (i.e., C16:0, C16:1, C17:0, C17:1, C18:0, C18:1, C18:2, C18:3, and C20:0).

In some embodiments, improving the quantity of vitamins in eggs produced by poultry is desirable. Vitamins found in eggs include B1, B2, B3, B5, B6, B12, choline, biotin, and folic acid.

In some embodiments, improving the quantity of minerals in eggs produced by poultry is desirable. Minerals found in eggs include phosphorous, iodine, selenium, and calcium. Trace amounts of the following may be found in eggs: barium, copper, iron, manganese, nickel, lead, selenium, strontium, vanadium, selenium, rubidium, and zinc.

In some embodiments, increasing or decreasing chicken serum levels of calcium, phosphorous, magnesium, triglycerides, cholesterol, and saccharides is desirable. The modulation of these serum components impact egg traits such as thickness, porosity, density, nutritional content, desirable taste, fat content, cholesterol content, and coloration.

In some embodiments, improving the efficiency and digestibility of animal feed is desirable. In some embodiments, increasing the degradation of lignocellulosic components from animal feed is desirable. Lignocellulosic components include lignin, cellulose, and hemicellulose.

In some embodiments, increasing the concentration of fatty acids in the gastrointestinal tract is desirable. Fatty acids include acetic acid, propionic acid, and butyric acid. In some embodiments, maintaining the pH balance in the gastrointestinal tract to prevent destruction of beneficial microbial ensembles is desirable. In some embodiments, increasing the concentration of lactic acids in the gastrointestinal tract is desirable. Lactic acid is lowers the pH of the surrounding environment, including intracellular pH which can disrupt microbial proton motive force. Lactic acid can also permeabilized the outer membrane of gram-negative bacteria such that they exhibit an increased susceptibility to antimicrobials.

In some embodiments, decreasing the amount of methane and manure produced by poultry is desirable In some embodiments, a decrease in the amount of total manure produced is desirable. In further embodiments, a decrease in the total amount of phosphorous and/or nitrogen in the total manure produced is desirable.

In some embodiments, improving the feed intake is desirable. In some embodiments, improving the efficiency of nitrogen utilization of the feed and/or dry matter ingested by poultry is desirable.

In some embodiments, the improved traits of the present disclosure are the result of the administration of the presently described microbial compositions. It is thought that the microbial compositions modulate the microbiome of poultry such that the biochemistry of one or more elements of the gastrointestinal tract is changed in such a way that the gastrointestinal liquid and solid substratum are more efficiently and more completely degraded into subcomponents and metabolites than the gastrointestinal tract of poultry not having been administered microbial compositions of the present disclosure.

In some embodiments, the increase in efficiency and the increase of degradation of the gastrointestinal substratum result in an increase in improved traits of the present disclosure.

In some embodiments, the increase of any one or more of the traits of the present disclosure is an increase of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% relative to the animal not having been administered one or more microbial compositions of the present disclosure.

In some embodiments, the increase of any one or more of the traits of the present disclosure is an increase of at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% relative to the animal not having been administered one or more microbial compositions of the present disclosure.

In some embodiments, the decrease of any one or more of the traits of the present disclosure is a decrease of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% relative to the animal not having been administered one or more microbial compositions of the present disclosure.

In some embodiments, the decrease of any one or more of the traits of the present disclosure is a decrease of at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% relative to the animal not having been administered one or more microbial compositions of the present disclosure.

Mode of Action: Gastrointestinal Health Improvement and Competitive Exclusion

Figure 14:
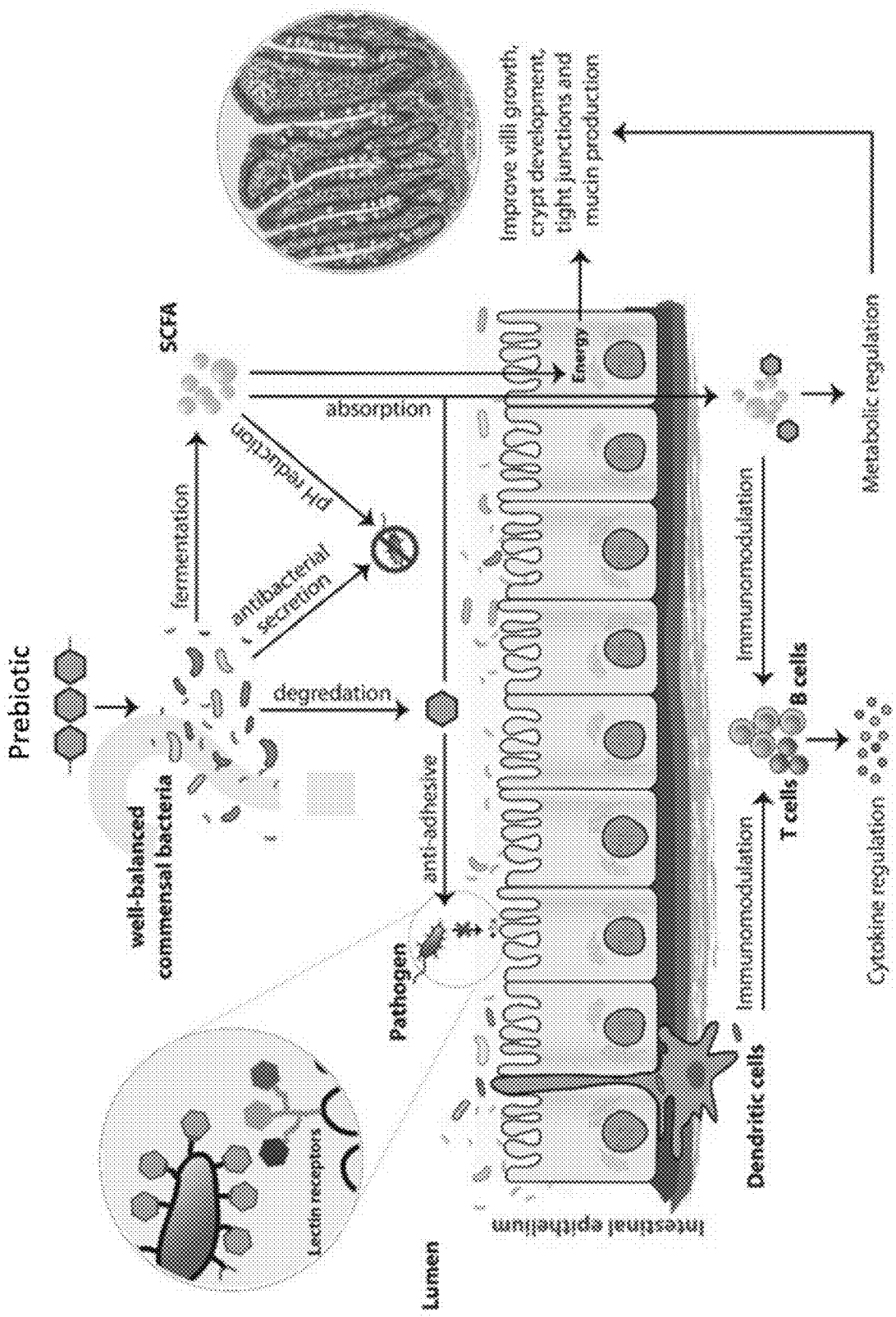
FIG. 14 depicts the complex microbial interactions occurring in the gastrointestinal tract. A well-balanced commensal microbial load is involved in maintaining multiple homeostatic systems.

The influence of the gastrointestinal microbiome on broiler health is well known (Roberts, 2015; Yeoman, 2012; Lee (presentation); Oakley, 2014)—a healthy intestinal system will improve the overall welfare and performance of birds in a commercial farm setting. Although the exact roles and mechanisms of individual species within this intricate and complicated system are still largely unknown, the overall beneficial effects of microorganisms on the host's health and performance have been studied. The current knowledge of metabolism and mechanisms of action are summarized below. See FIG. 14. (Pourabedin and Zhao. 2015. FEMS Microbiol. Lett. 362:fnv122). FIG. 14 depicts a suite of interactions that are all modulated by the composition of the gastrointestinal tract with a well-balanced population of commensal microbes with an adequate supply of prebiotic compositions. For example, the commensal bacteria are (1) producing antibacterial compounds to compete with other organisms, including pathogens, (2) producing simple fatty acids involved in metabolic regulation and energy use, (3) immunomodulating the localized immune responses in conjunction with lymphocytes and antigen presenting cells, etc.

General Nutrition and Gut Health

Increasing the Concentration of Beneficial Molecules, Including Short Chain Fatty Acids and Other Organic Acids, in the Gastrointestinal Tract of the Broiler Improves Bird Performance.

Microbial short chain fatty acid production, in particular, are absorbed and metabolized by the bird and can provide 5% to 15% of the daily requirements for bird maintenance energy (Chichlowski, 2007; Annison, 1968; Gasaway, 1976ab). Previous studies have shown that supplementation of butyrate can improve both overall weight gain and feed-conversion when administered daily to the bird, and that supplementation of any organic acid (including fumaric and lactic) can improve bird weight gain (Levy, 2015; Gilliland, 1977; Afil, 2010). Levy, et al. (2015) showed that improvements in body weight gain and feed conversion increased linearly with increasing concentrations of encapsulated butyric acid levels. Butyrate also enhances vili development (Chamba, 2014) activates the immune response, and can also have a direct bactericidal effect (Gantois, 2006).

Improving Development of the Gastrointestinal Tract, Enhancing Villi Growth, and Stimulating the Immune System.

Supplementation of butyrate and other organic acids to the diets of birds have been shown to enhance viii development and stimulate the immune system (Chamba, 2014; Adil 2010; Adil 2011).

Improving Apparent Metabolizable Energy of the Diet

Fermentation of various microbes can convert carbohydrates to various end products. Most short chain fatty acids produced by these microorganisms are absorbed and utilized by the bird (Rinttila, 2013; Annison, 1968; Gasaway, 1976ab). The synthesis of vitamins, including vitamins B and K, are also carried out by microorganisms (Cummings, 1997).

Competitive Exclusion

Bacteriocin Production

Microorganisms within the gastrointestinal tract self-regulate through the production of various antimicrobial chemicals. Bacteriocins, for example, are commonly produced by lactic acid microorganisms and can prevent the colonization of pathogens (Chen, 2007; Juven 1990). Short-chain fatty acids been shown to impact and inhibit enteric bacteria including *Salmonella typhimurium*, but do not inhibit beneficial, native microorganisms (Van der Wielen et al., 2000). Both propionic acid, butyric acid, acetate has also been shown to inhibit pathogenic bacteria (Marounek, 1999; Van der Wielen, 2000; Immerseei, 2003).

Competitive Use of Nutrients/Binding Sites

Birds are first inoculated with microorganisms shortly after birth. As the bird continues to develop, the microbiome colonizes and establishes itself, ultimately creating a stable ecosystems that houses organisms that occupy all niches and utilizes all available nutrients (Callaway, 2008). This expansive, stable community can prevent pathogens from colonizing.

Creating Environments that are not Conducive to Pathogen Growth

Microorganisms residing within the gut reduce the redox potential within the gut, creating an environment suitable for obligate anaerobes to flourish (Cummings, 1997; Chicklowki, 20017; Juven 1990). Lactate and other short chain fatty acid production lowers the pH of the gastrointestinal environment, making it more difficult for pathogens to colonize and grow (Pourabedin, 2015). Native microorganisms have also been shown to neutralize enterotoxins (M'Sadeq, 2015).

EXAMPLES

Example I. Microbial Compositions Associated with Improved Feed Efficiency in Broilers (ASC-15-1 Phase I and II)

The objective of this study was to leverage the Ascus Biosciences technology to utilize mutual information to rank the importance of microbial strains residing in the gastrointestinal tract of broilers associated with improved feed efficiency. For each sample, the presence and number (cell count) of each microorganism type was determined and integrated to yield the absolute cell count of each microorganism strain present in the samples. The active strains were identified, and all inactive strains were removed from subsequent analysis. The maximal information coefficient (MIC) was then determined for all active microorganisms as well as relevant performance metadata of each bird. Results were pooled to create a list of all relationships and their corresponding MIC scores. If the relationship scored below a given threshold, the relationship was identified as irrelevant. If the relationship was above a given threshold, the relationship was identified as relevant, and is further subjected to network analysis in order to identify the strains that best influenced desirable physiological and performance characteristics. In this example, this approach was used to identify microoganisms that improve feed efficiency/reduced feed conversion ratio.

Phase 1 comprises the utilization of 216 Cobb 500 broiler chickens over 21 study days, with actions/events performed on days 0, 14, 15, 16, 17, 18, 19, 20, and 21 (FIG. 3). Phase II comprises the utilization of 216 Ross 708 broiler chickens over 21 study days, with actions/events performed on days 0, 14, 15, 16, 17, 18, 19, 20, and 21 (FIG. 4). The Cobb 500 and Ross 708 commercial production broiler chickens were all male and were ~1 day of age upon receipt (Day 0); Cobb 500 chickens were from Siloam Springs North and Ross 708 chickens were from Siloam Springs North. Chickens were separated into two main groups, 120 were utilized at day 0 and tagged and placed into floor pens, and 96 were utilized at day 14 and were placed into individual cages.

Phase I and II utilized Test Article I, Coccidiostat (Sacox 60); Lot Number/Expiration: JSB443/August 2017, which is manufactured by Huvepharma Inc. Coccidiostat was commercially available at a concentration of 60 g/lb with an inclusion level of 50 g/ton, and was stored in a secured and temperature-monitored dry area. The method of administration was via complete feed over a duration of 21 days (Starter). Coccidiostat was administered ad libitum in complete feed.

Phase I utilized Feed Additive I, Phytase 2500 from Nutra Blend, LLC; Lot Number: 06115A07. Phytase 2500 was commercially available at a concentration of 2,500 FTU/g with an inclusion level of 0.02%, and was stored in a secured and temperature-monitored dry area. The method of administration is via complete feed over a duration of 21 days. Phytase 2500 was administered ad libitum in complete feed.

The starter basal diets were manufactured at Colorado Quality Research, Inc. (CQR) feed mill using a standard CQR formulated broiler diet representative of a commercial broiler diet (Industry Standard Average). Basal and treatment diet mixing, pelleting, and crumbling was conducted at CQR using a 500-lb capacity vertical mixer, a 4,000-lb capacity vertical mixer, or a 14,000-lb horizontal mixer and California Pellet Mill system. Approximately 342 lbs of feed was mixed per treatment. The feed was stored in 50lb capacity feed sacks and/or bulk storage bins labelled with treatment identity and further identified with a color code.

The basal feed and treatment diets were sampled in duplicate (~300 g sample size). One sample of the basal and each treatment diet was submitted to the sponsor for assay and one sample was retained by CQR until study end. All samples were labelled with the CQR project number, treatment number, sample description, and date of collection.

Experimental Design
Test Groups

Upon placement, chicks were placed into pens based on breed and dietary treatment. The study was divided into two phases, the aforementioned Phase I and Phase II. The phases took place two weeks apart. The birds were placed in floor pens by treatment from 0-14D. For each phase, the test facility was divided into 1 block of 2 pens and 48 blocks of 2 individual cages each. Treatments were assigned to the pens/cages using a complete randomized block design; pens/cages retained their treatments throughout the study. The treatments were identified by numeric codes. Birds were assigned to the cages/pens randomly according to CQR standard operating procedure B-10. Specific treatment groups were designed as depicted in Table 12

TABLE 13

Lighting programing for incandescent bird lighting

| Approximate Bird Age (Days) | Approximate Hours of Continuous Light per 24 Hour Period | Approximate Light Intensity (Foot Candles) |
|---|---|---|
| 0-6 | 23 | 1.0-1.3 |
| 7-21 | 16 | 0.2-0.3 |

Environmental conditions for the birds (i.e., 0.53 ft$^2$ in pen, temperature, lighting, feeder, and water space) was similar for all treatment groups. In order to prevent bird migration, each pen was checked to assure no openings greater than 1 inch existed for approximately 14 inches in height between pens.

Vaccinations

Birds were vaccinated for Mareks at the hatchery. Birds were vaccinated for Newcastle and infectious bronchitis by spray application on study day 0. No other vaccinations, except those in the experimental design, were administered during the study. Records of the vaccinations (vaccine source, type, lot number, and expiration date) were maintained with the study records. No vaccinations or medications other than those disclosed herein were utilized.

Water

Water was provided ad libitum throughout the study. The floor pen water was via automatic bell drinkers. The battery cage water was via one nipple waterer. Drinkers were checked twice daily and cleaned as needed to assure a clean water supply to birds at all times.

Feed

Feed was proved ad libitum throughout the study. The floor pen feed was via hanging, ~17-inch diameter tube

TABLE 12

Experimental design treatments of Phase I and II, treatment I and II.

| Treatment | Treatment Description | Strain | No. Birds/ Floor Pen | No. Floor Pens/ Treatment | No. of Birds/ Cage | No. Cages/ Treatment | No. Birds/ Treatment |
|---|---|---|---|---|---|---|---|
| Phase I | | | | | | | |
| 1 | 0.042% Salinomycin | Cobb 500 | 60 | 1 | 1 | 48 | 48 (D 14) 60 (D 0) |
| 2 | No Salinomycin | Cobb 500 | 60 | 1 | 1 | 48 | 48 (D 14) 60 (D 0) |
| Phase II | | | | | | | |
| 1 | 0.042% Salinomycin | Ross 708 | 60 | 1 | 1 | 48 | 48 (D 14) 60 (D 0) |
| 2 | No Salinomycin | Ross 708 | 60 | 1 | 1 | 48 | 48 (D 14) 60 (D 0) |

Housing

Figure 5:
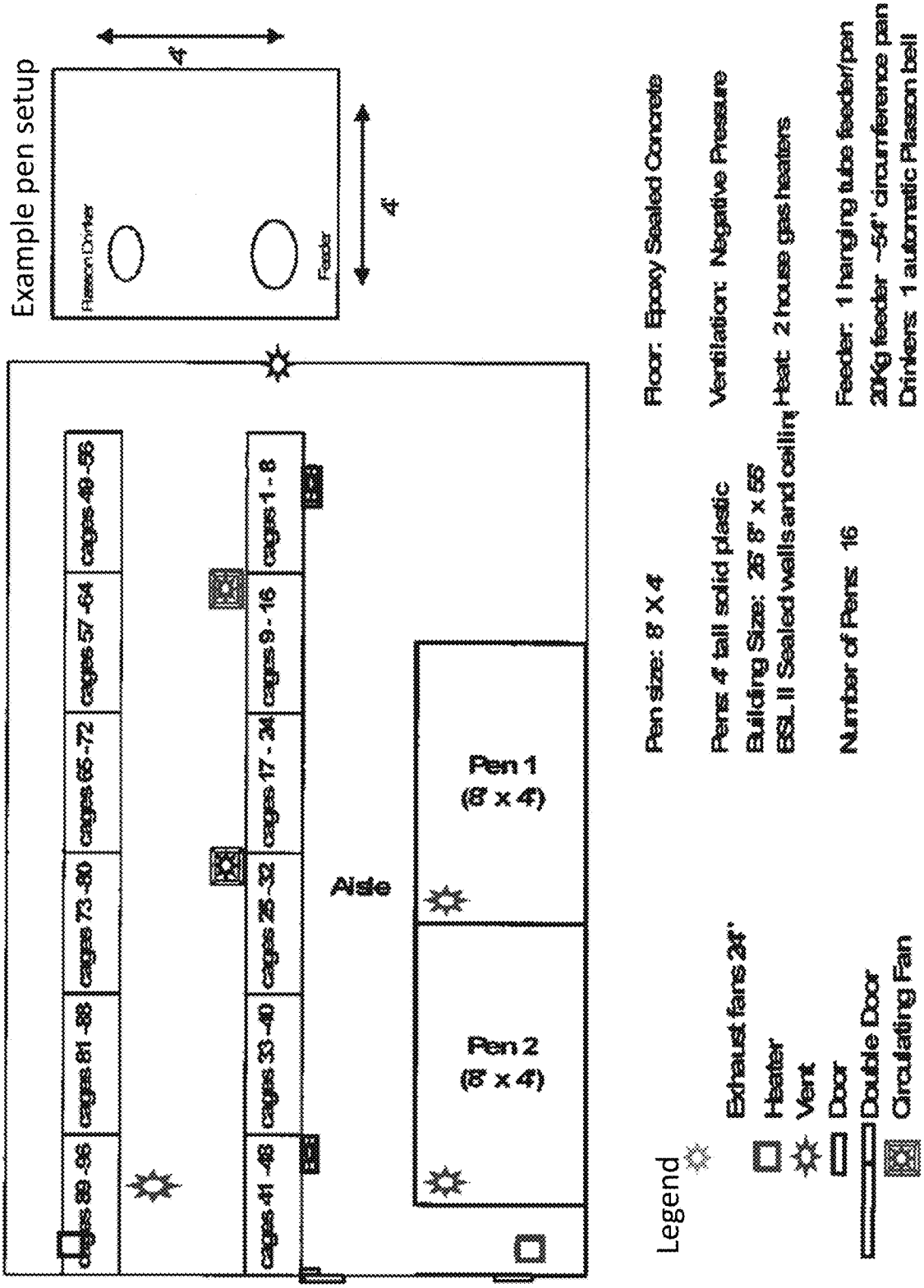
FIG. 5 is a graphical representation of an exemplary pen and cage setup for use in the phase I or II studies described in example I.
Figure 6:
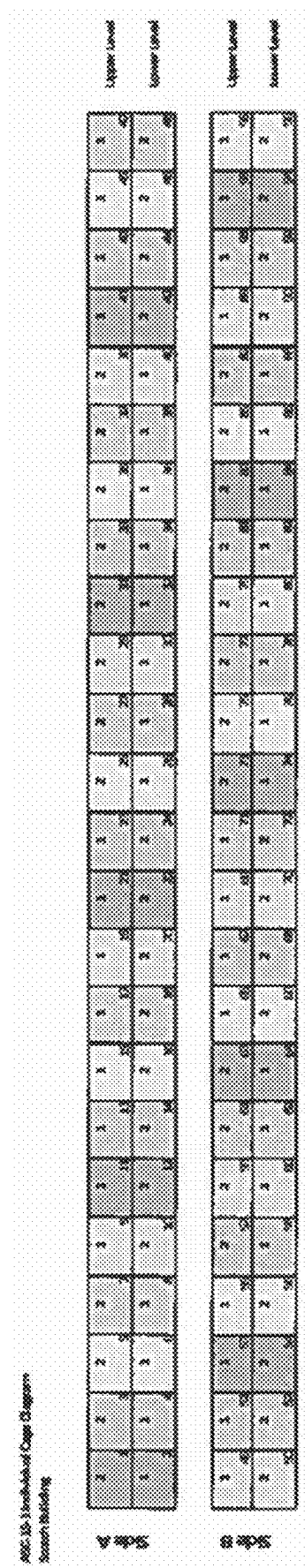
FIG. 6 is a graphical representation of an exemplary cage setup for use in the phase I or II studies described in example I.

Assignment of treatments to cages/pens were conducted using a computer program. The computer-generated assignment was as follows: Birds housed in an environmentally control facility in large concrete floor pen (size 4'×8') constructed of solid plastic (4' tall) with clean litter (See FIG. 5). At day 14, 96 birds were moved into cages within the same environmentally controlled facility. Each cage was 24"×18"×24" (See FIG. 6) Lighting was via incandescent lights and a commercial lighting program was used. Hours of continuous light for every 24 hour period was as follows in Table 13.

feeders. The cage feed was via one feeder trough, 9"×4". A chick feeder tray was placed in each floor pen for approximately the first 4 days.

Daily Observations

The test facility, pens, and birds were observed at least twice daily for general flock condition, lighting, water, feed, ventilation, and unanticipated events. The minimum-maximum temperature of the test facility was recorded once daily.

Mortality and Culls

Starting on study day 0, any bird that was found dead was removed. Birds that were unable to reach feed or water were sacrificed and necropsied. Identification of probable cause of death and necropsy findings were recorded on the pen mortality record.

Body Weight and Feed Intake

~96 birds were weighed individually each day (days 14-21). Feed remaining in each cage was weighed and recorded daily from days 14-21. The feed intake for each cage was determined for each day.

Weight Gain and Feed Conversion

Body weight gain on a cage basis and an average body weight gain on a treatment basis was determined from days 14-21. Feed conversion was calculated for each day and overall for the period of days 14-21 using the total feed consumption for the cage divided by bird weight. Average treatment feed conversion was determined for the period of days 14-21 by averaging the individual feed conversions from each cage within the treatment.

Excreta and Digesta Collection

At days 15, 18, and 21, excreta produced over a 24-hour period was collected by cage, pooled and dried to measure gross energy values with bomb calorimetry. Gross energy of the feed on day 14 was measured for gross energy to determine apparent metabolic energy (AME). On day 21, each bird was euthanized by cervical dislocation to collect the following using the described procedures (gloves were changed between each bird):

Randomly Select 25% of the Birds:

Make 2 aliquots into 1.5 ml tubes for each location: cecum, small intestine (anywhere), gizzard, and crop (including mucosal scrapings). One aliquot will contain 150 µl of stop solution (5% phenol & 95% ethanol) to submerge the sample. The second aliquot did not contain stop solution and was stored at 4° C. for shipping.

Immediately placed the contents of one cecum in a 1.5-ml tube prefilled with 150 µl stop solution.

Placed the contents of the second cecum into an empty 1.5-ml tube.

Immediately split the contents of the small intestine and placed half in 1.5-ml tube prefilled with 150 µl stop solution. Placed the other half in an empty 1.5-ml tube.

Dissected the gizzard out of the GI tract, removed the contents with forceps, split the contents and placed half in a 1.5-ml tube prefilled with 150 µl stop solution. Placed the other half in an empty 1.5-ml tube.

Dissected the crop out of the GI tract, removed the contents with forceps/scraped out mucosal lining, and placed half in a 1.5-ml tube prefilled with 150 µl stop solution. Placed the other half in an empty 1.5 ml tube.

For the Remaining Birds:

Immediately placed the contents of one cecum in a 1.5-ml tube prefilled with 150 µl stop solution.

Immediately placed the contents of the small intestine into a 1.5-ml tube prefilled with 150 µl stop solution.

Dissected the gizzard out of the GI tract, removed the contents with forceps, and placed in a 1.5-ml tube prefilled with 150 µl stop solution.

Dissected the crop out of the GI tract, removed the contents with forceps/scrape out mucosal lining, and placed in a 1.5-ml tube prefilled with 150 µl stop solution.

Store all samples at 4° C. until shipment.

Veterinary Care, Intervention, and Euthanasia

Animals that developed significant concurrent disease, which were injured and/or whose condition may have affected the outcome of the study were removed from the study and euthanized at the time that the determination was made. Six days post challenge, all birds in cages were removed and lesion scored.

Scales used in weighing of feed and feed additives were licensed and/or certified by the State of Colorado. At each use the scales were checked using standard weights according to CQR standard operating procedures.

Dispositions

Feed

An accounting was maintained of all diets. The amount mixed, used and discarded was documented. Unused feed was disposed of either by salvage sale and/or placing into a dumpster for commercial transport to a local landfill for burial. Disposition was documented in the study records.

Test Animals

An accounting was maintained for birds received for the study. Disposal of mortalities and birds sacrificed during the study and at study end was discarded to the landfill at study end. Documentation of disposition was provided with the study records. No food products derived from animals enrolled in this study entered the human food chain.

Data Collected (Phase I)

Average Bird weights (Day 14-21) (Table 14)

Figure 7:
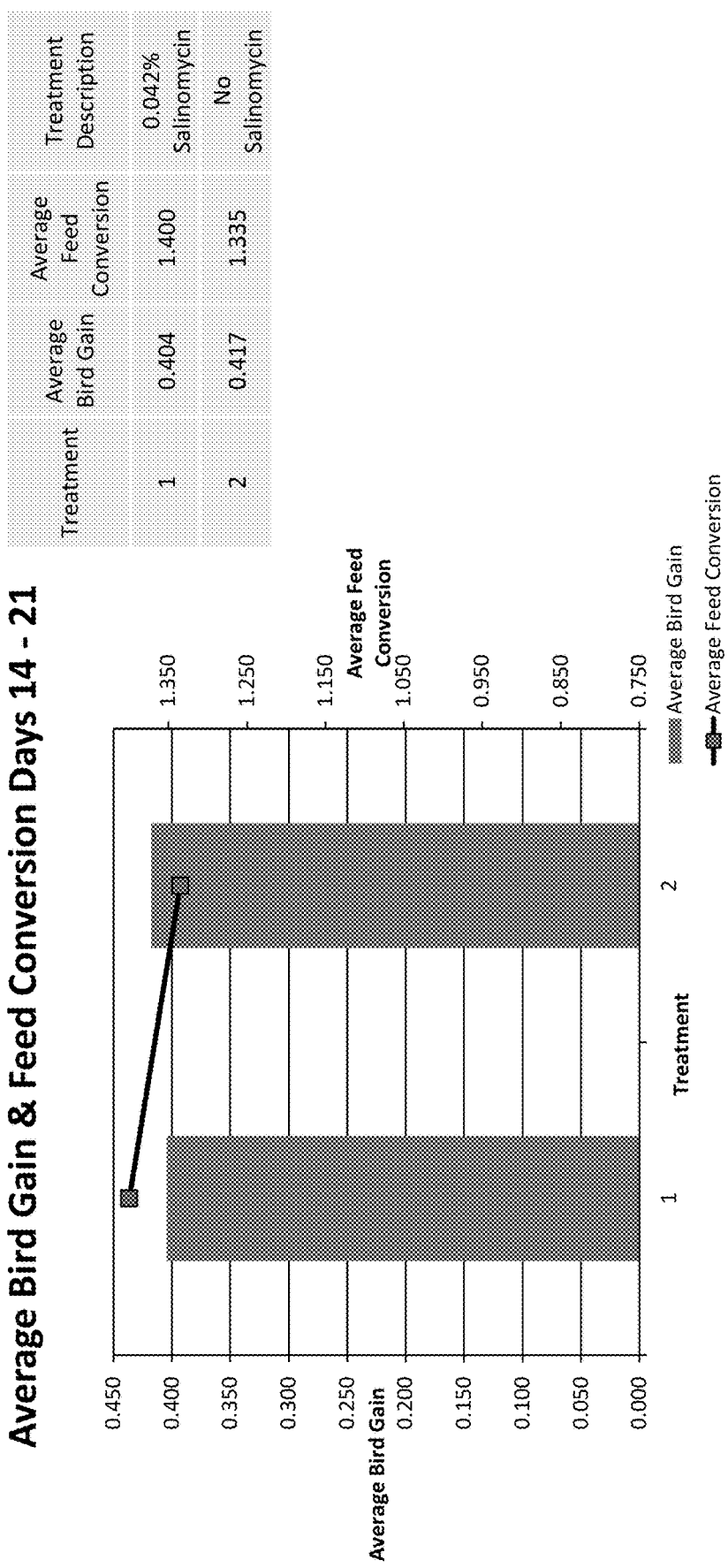
FIG. 7 is a graphical representation of the summarized data demonstrating the statistical outcomes of treatment 1 vs treatment 2 in the Phase I study described in Example I.

Daily Bird Performance Summarized by Treatment (Day 14-21) (FIG. 7)

Data Collected (Phase II)

Average Bird weights (Day 14-21) (Table 15)

Mortality and Removal Weights (Day 14-21) (Table 16)

Figure 8:
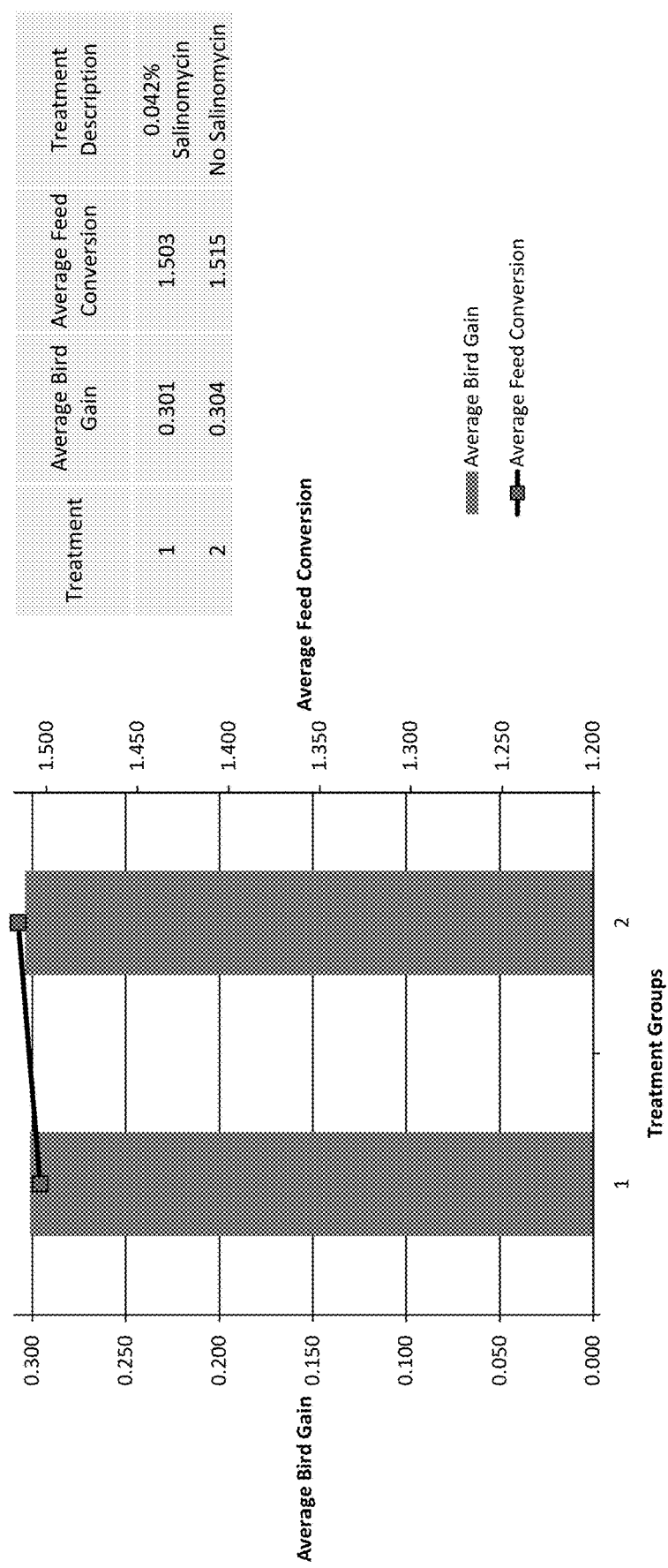
FIG. 8 is a graphical representation of the summarized data demonstrating the statistical outcomes of treatment 1 vs treatment 2 in the Phase II study described in Example I.

Daily Bird Performance Summarized by Treatment (Day 14-21) (FIG. 8)

TABLE 14

Phase 1, Cobb 500 performance

|  | D21 Wt (kg) | D14 Wt (kg) | D14-21 Gain (kg) | D14-21 Feed Consumed (kg) | D14-21 Feed Conversion |
|---|---|---|---|---|---|
| Treatment Group 1 | | | | | |
| Averages | 0.820 | 0.416 | 0.404 | 0.560 | 1.400 |
| Standard Deviations | 0.078 | 0.032 | 0.061 | 0.053 | 0.126 |
| CV's | 0.095 | 0.078 | 0.150 | 0.096 | 0.090 |
| Treatment Group 2 | | | | | |
| Averages | 0.831 | 0.414 | 0.417 | 0.554 | 1.335 |
| Standard Deviations | 0.067 | 0.033 | 0.047 | 0.046 | 0.089 |
| CV's | 0.081 | 0.079 | 0.112 | 0.082 | 0.067 |

TABLE 15

Phase II, Ross 708 performances 708

|  | D21 Wt (kg) | D14 Wt (kg) | D14-21 Gain (kg) | D14-21 Feed Consumed (kg) | D14-21 Feed Conversion |
|---|---|---|---|---|---|
| Treatment Group 1 | | | | | |
| Averages | 0.679 | 0.378 | 0.301 | 0.443 | 1.503 |
| Standard Deviations | 0.058 | 0.034 | 0.042 | 0.063 | 0.117 |
| CV's | 0.085 | 0.089 | 0.141 | 0.143 | 0.078 |
| Treatment Group 2 | | | | | |
| Averages | 0.690 | 0.384 | 0.304 | 0.447 | 1.515 |
| Standard Deviations | 0.085 | 0.033 | 0.071 | 0.075 | 0.244 |
| CV's | 0.123 | 0.086 | 0.234 | 0.168 | 0.161 |

TABLE 16

Mortality and Removal Weights for Phase II (Day 14-21)

| | | | | | Days 14-21 | | | | | | |
|---|---|---|---|---|---|---|---|---|---|---|---|
| TRT | Cage | Sex | Bird # | No. Birds Started Day 0 | Mortality | Removal-1 | Removal-2 | Cause of Death | Mortality Wt (kg) | Removed Wt (kg) | Total M & R Wt (kg) Days 14-21 | No. Birds Remaining Day 14 |
| 2 | 12 | M | 9109 | 1 | 1 | 0 | 0 | BAC-DH | 0.304 | 0.000 | 0.304 | 0 |
| 2 | 20 | M | 9105 | 1 | 1 | 0 | 0 | BAC-DH | 0.262 | 0.000 | 0.262 | 0 |
| 1 | 69 | M | 4608 | 1 | 1 | 0 | 0 | BAC-NA | 0.360 | 0.000 | 0.360 | 0 |

GI Sample Preparation and Sequencing:

After collection, the gastrointestinal (GI) samples were centrifuged at 4,000 rpm in a swing bucket centrifuge for 20 minutes at 4° C. The supernatant was decanted, and an aliquot of each gastrointestinal content sample (1-2 mg) was added to a sterile 1.7 mL tube prefilled with 0.1 mm glass beads. A second aliquot was collected and stored in an empty, sterile 1.7 mL tube for cell counting.

GI samples in empty tubes were stained and put through a flow cytometer to quantify the number of cells of each microorganism type in each sample. GI samples with glass beads were homogenized with bead beating to lyse microorganisms. DNA and RNA was extracted and purified from each sample and prepared for sequencing on an Illumina Miseq. Samples were sequenced using paired-end chemistry, with 300 base pairs sequenced on each end of the library.

Sequencing Read Processing and Data Analysis:

Sequencing reads were quality trimmed and processed to identify bacterial species present in the GI tract based on a marker gene, 16S rDNA, or ITS1 and/or ITS2. Count data sets and activity datasets were integrated with the sequencing reads to determine the absolute cell numbers of active microbial species within the gastrointestinal microbial community. Production characteristics of the broiler over time, including feed conversion, weight, mortality, and lesion scores, were linked to the distribution of active microorganisms within each sample over the course of the experiment using mutual information.

Results

One component of the Ascus Biosciences technology utilized in this application leverages mutual information to rank the importance of native microbial strains residing in the gastrointestinal tract of the animal to specific animal traits. The maximal information coefficient (MIC) scores are calculated for all microorganisms and the desired animal trait. Relationships were scored on a scale of 0 to 1, with 1 representing a strong relationship between the microbial strain and the animal trait, and 0 representing no relationship. A cut-off based on this score is used to define useful and non-useful microorganisms with respect to the improvement of specific traits.

The MICs were calculated between production characteristics, including indicators for disease such as lesion scores, and the absolute abundance of each active microorganism. Microorganisms were ranked by MIC score, and microorganisms with the highest MIC scores were selected as the most relevant target species. MIC scores of the microbes of the present disclosure are recited in Table 1. The greater the MIC score, the greater the ability of the microbe to confer an improvement in the performance and GI health of the bird.

Example II. Microbial Compositions of Broilers with Necrotic Enteritis Utilizing a *Clostridium perfringens* Challenge Model The objective of this study was to determine the difference in microbial compositions during necrotic enteritis when challenged with various levels of *Clostridium perfringens*. More specifically, the study sought to calculate MIC scores for microbes in the gastrointestinal tract of broilers challenged with the pathogen. In this instance, the MIC scores were calculated between production characteristics, including indicators for disease such as lesion scores and the absolute abundance of each active microorganism. Microbes with the highest MIC scores have the greatest ability to confer an improvement in the gut performance and gastrointestinal health of broilers.

This study utilized 160 Cobb 500 broiler chickens over 21 study days. The Cobb 500 commercial production broiler chickens were all male and were ~1 day of age upon receipt (Day 0); Cobb 500 chickens were from Siloam Springs North. Chickens were separated into four treatments with twenty birds per pen and two pens per treatment.

The study utilized a feed additive, Phytase 2500 from Nutra Blend, LLC; Lot Number: 06115A07. Phytase 2500 occurred was commercially available at a concentration of 2,500 FTU/g with an inclusion level of 0.02%, and is stored in a secured and temperature-monitored dry area. The method of administration was via feed over a duration of 21 days.

The starter basal diets were manufactured at Colorado Quality Research, Inc. (CQR) feed mill using a standard CQR formulated broiler diet representative of a commercial broiler diet (Industry Standard Average) without medication. Basal and starter diet mixing, pelleting and crumbling was conducted at CQR using a 500-lb capacity vertical mixer, a 4,000-lb capacity vertical mixer, or a 14,000-lb horizontal mixer and California Pellet Mill system. Approximately 540 lbs of feed was mixed per treatment. The feed was stored in 50 lb capacity feed sacks and/or bulk storage bins labelled with treatment identity and further identified with a color code.

The basal feed and treatment diets were sampled in duplicate (~300 g sample size). One sample of the basal and each treatment diet was submitted to the sponsor for assay and one sample was retained by CQR until study end. All samples were labelled with the CQR project number, treatment number, sample description, and date of collection.

Experimental Design

Test Groups

The test facility was divided into 2 blocks of 4 pens. Treatments were assigned to the pens/cages using a completely randomized block design. Birds were assigned to the pens randomly according to CQR standard operating procedure B-10. Specific treatment groups were designed as depicted in Table 18.

Vaccinations

Birds were vaccinated for Mareks at the hatchery. Birds were vaccinated at CQR for Newcastle and infectious bronchitis by spray application on study day 0. No other vaccinations, except those in the experimental design, were administered during the study. Records of the vaccinations (vaccine source, type, lot number, and expiration date) were maintained with the study records. No vaccinations or medications other than those disclosed herein were utilized.

Water

TABLE 18

Experimental design for treatments 1-4.

| Treatment | NE Challenge (Y/N) | Treatment Description | No. Birds/Pen | No. of Pens | No. of Birds/Treatment |
|---|---|---|---|---|---|
| 1 | N | Non-Challenged | 20 | 2 | 40 |
| 2 | Y | Challenged with half typical dose (1.25 ml/bird; 2.0-9.0X10$^8$ cfu/ml) | 20 | 2 | 40 |
| 3 | Y | Challenged with typical dose (2.5 ml/bird; 2.0-9.0 × 10$^8$ cfu/ml) | 20 | 2 | 40 |
| 4 | Y | Challenged with twice the typical dose (5 ml/bird; 2.0-9.0X10$^8$ cfu/ml) | 20 | 2 | 40 |
| | | Total | 80 | 8 | 160 |

Housing

Assignment of treatments to cages/pens were conducted using a computer program. The computer-generated assignment was as follows in Table 19

TABLE 19

Computer selection of treatments to pens.

| Block | Treatment 1 | Treatment 2 | Treatment 3 | Treatment 4 |
|---|---|---|---|---|
| B1 | 4 | 1 | 3 | 2 |
| B2 | 7 | 5 | 8 | 6 |

Figure 9:
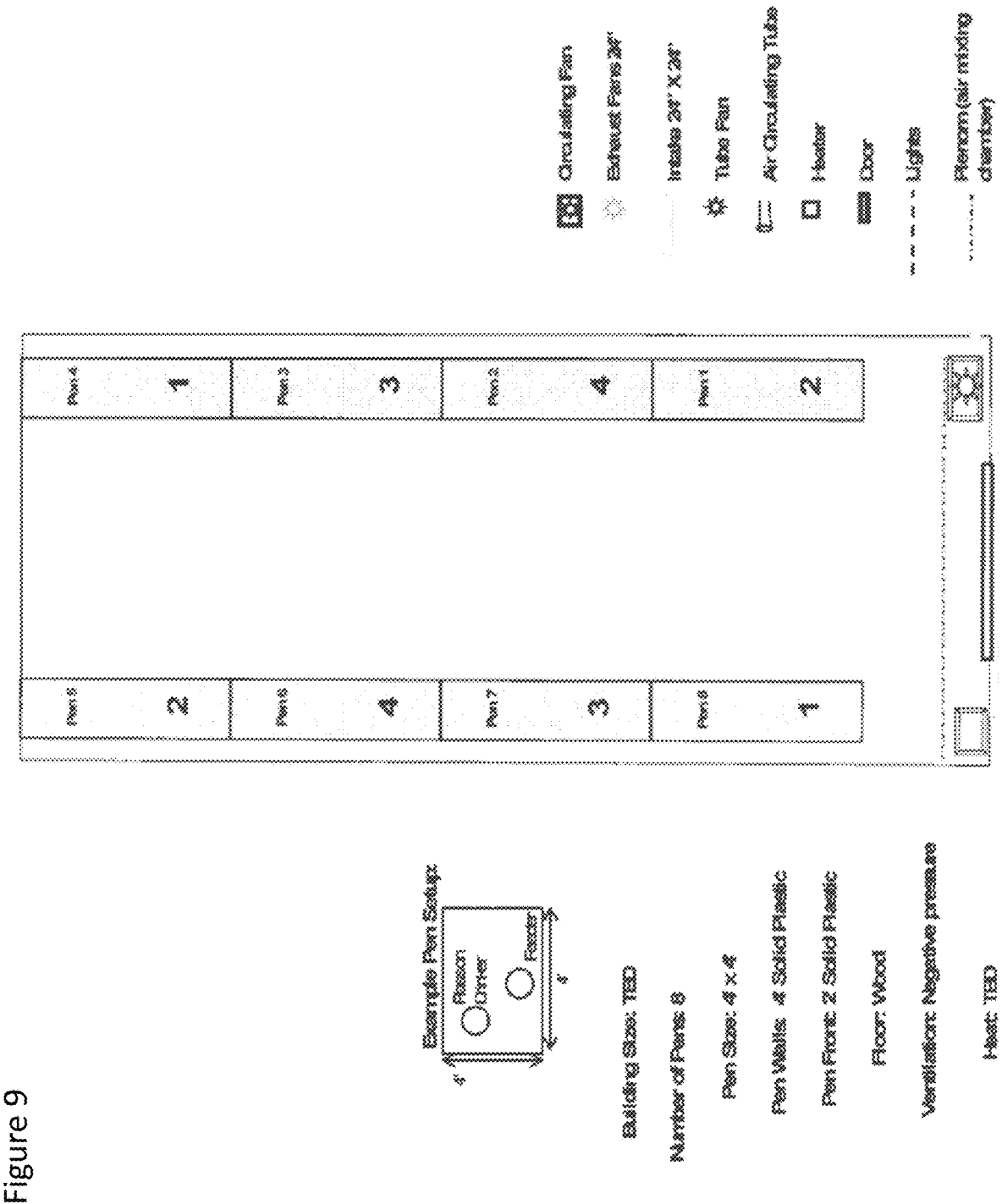
FIG. 9 is a graphical representation of an exemplary pen setup for use in the study described in Example II, wherein the birds are challenged with *Clostrium perfringens*.
Figure 11A:
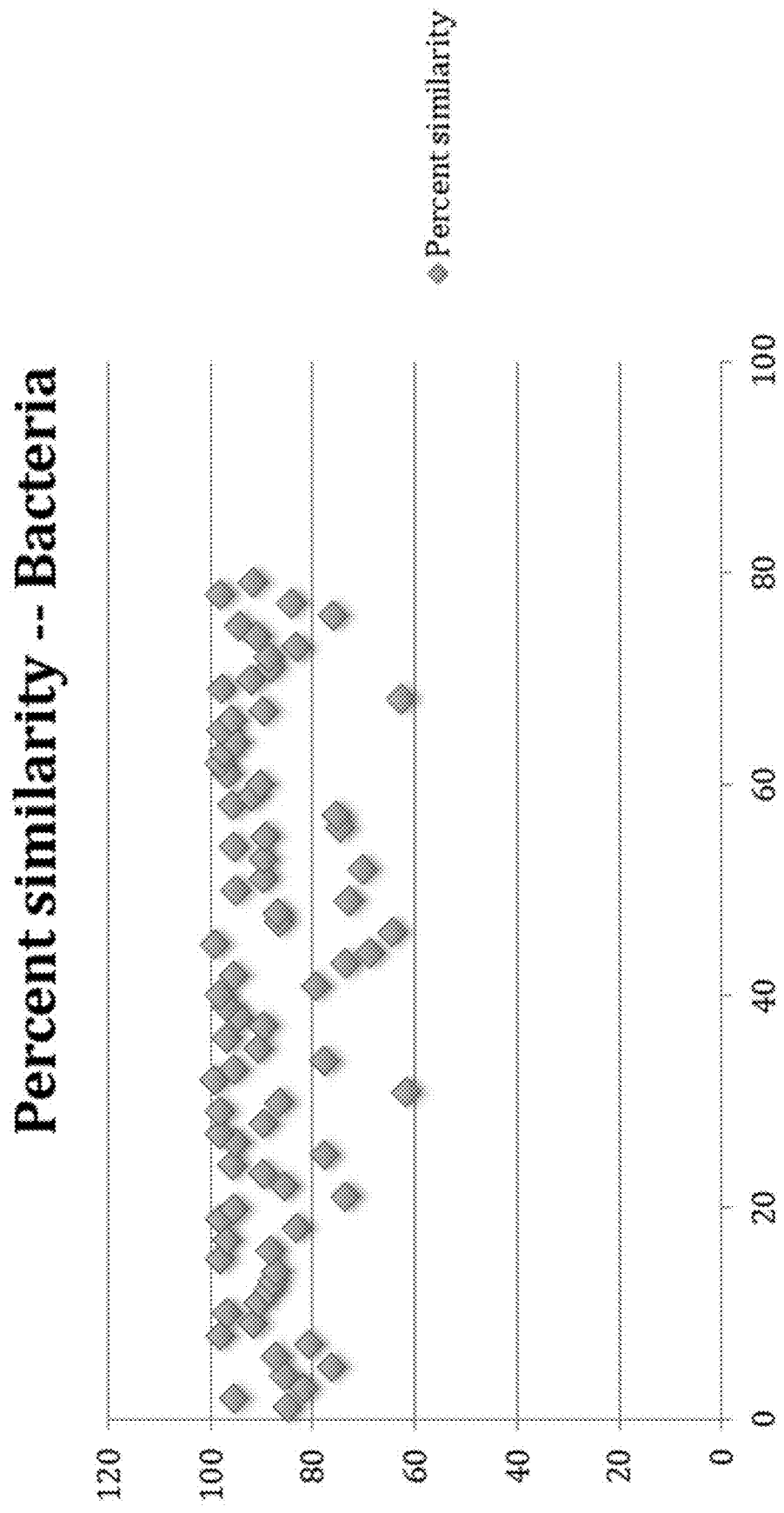
FIG. 11A and FIG. 11B depict the shared percent similarity (percent identity) among the bacteria (A) and fungi (B) of Table 1. The data points represent the greatest percent similarity pairing for each strain.
Figure 11B:
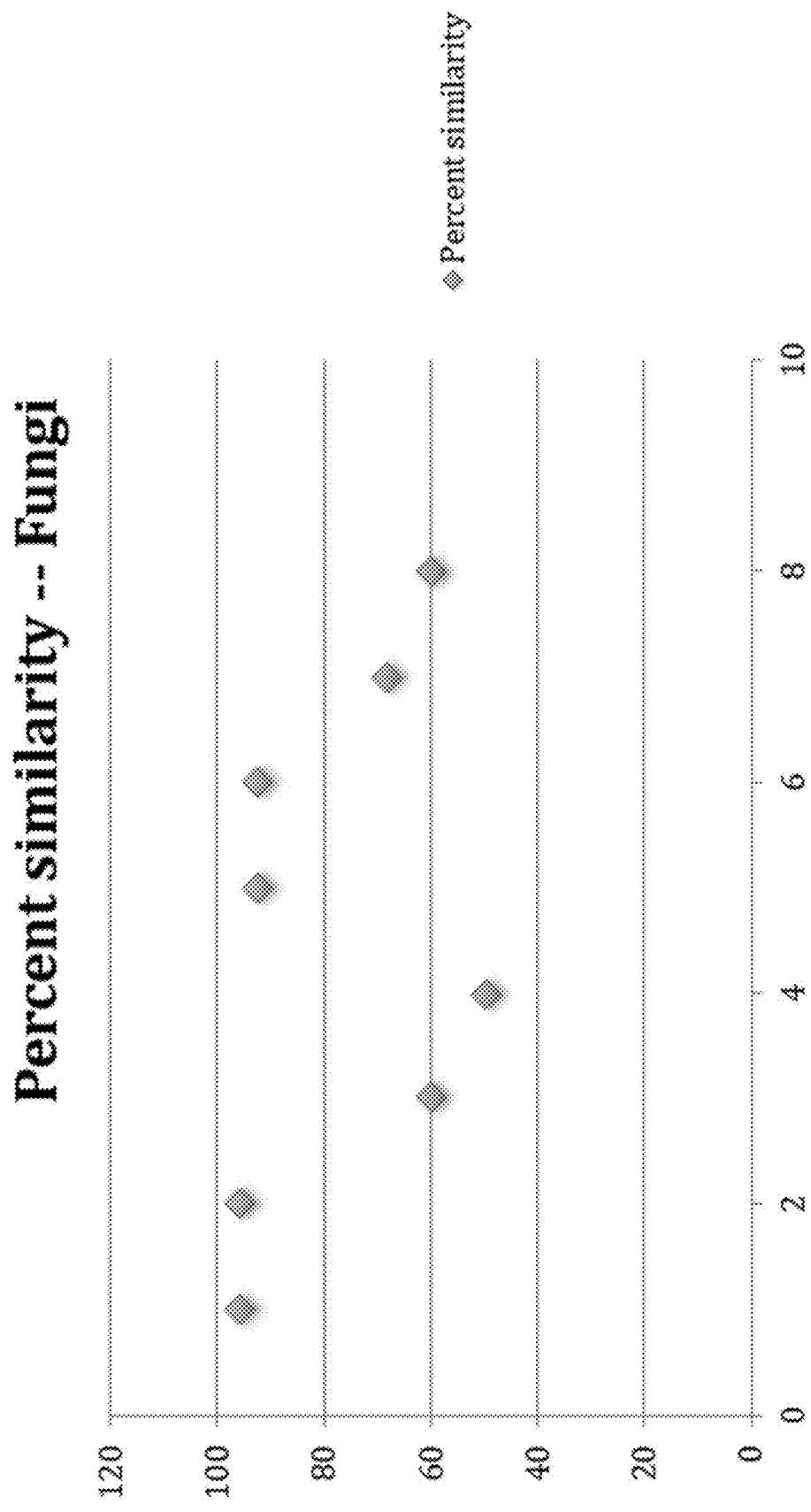

Birds were housed in an environmentally control facility in wooden floor pens (~4'×4' minus 2.25 sq. ft for feeder space) providing floor space and bird density of ~0.69 ft$^2$/bird and temperature, lighting, feeder and water space was similar for all test groups (See FIG. 9). Birds were placed in clean pens containing an appropriate depth of wood shavings to provide a comfortable environment for the chicks. Additional shavings were added to pens if they became too damp for comfortable conditions for the test birds during the study. Lighting was via incandescent lights and a commercial lighting program was used as noted in the following table.

TABLE 20

Lighting programing for incandescent bird lighting (Reproduced from Table 11 in previous example)

| Approximate Bird Age (Days) | Approximate Hours of Continuous Light per 24 Hour Period | Approximate Light Intensity (Foot Candles) |
|---|---|---|
| 0-6 | 23 | 1.0-1.3 |
| 7-21 | 16 | 0.2-0.3 |

In order to prevent bird migration and bacterial spread from pen to pen, each pen had a solid (plastic) divider for approximately 24 inches in height between pens.

Water was provided ad libitum throughout the study via one Plasson drinker per pen. Drinkers were checked twice daily and cleaned as needed to assure a clean water supply to birds at all times.

Feed

Feed was proved ad libitum throughout the study via one hanging, ~17-inch diameter tube feeder per pen. A chick feeder tray was placed in each floor pen for approximately the first 4 days. Birds were placed on their respective treatment diets upon receipt (day 0), according to the Experimental Design. Feed added and removed from pens from day 0 to study end were weighed and recorded.

Daily Observations

The test facility, pens, and birds were observed at least twice daily for general flock condition, lighting, water, feed, ventilation, and unanticipated events. If abnormal conditions or abnormal behavior was noted at any of the twice-daily observations they were noted in the study records. The minimum-maximum temperature of the test facility was recorded once daily.

Pen Cards

There were 2 cards attached to each pen. One card identifies the pen number and the second will include the treatment number.

Animal Handling

Animals were kept under ideal conditions for livability. The animals were handled in such a manner as to reduce injuries and unnecessary stress. Humane measures were strictly enforced.

Veterinary Care, Intervention, and Euthanasia

Birds that developed clinically significant concurrent disease unrelated to the test procedures were, at the discretion of the investigator or designee, removed from the study and euthanized in accordance with site standard operating procedures. In addition, moribund or injured birds may also be euthanized upon authority of a site veterinarian or a qualified technician. Any reasons for withdrawal were documented. In an animal died, or was removed and euthanized for humane reasons, it was recorded on the mortality sheet for the pen and a necropsy performed, and was filed to document the reason for removal. If euthanasia was deemed necessary, animals were euthanized via cervical dislocation.

Mortality and Culls

Starting on study day 0, any bird that was found dead was removed weighed and necropsied. Birds that are unable to reach feed or water were sacrificed and necropsied. The weight and probable cause of death and necropsy findings were recorded on the pen mortality record.

Body Weight and Feed Intake

Birds were weighed by pen and individually on approximately days 14 and 21. The feed remaining in each pen was weighed and recorded on study days 14 and 21. The feed intake during days 14-21 were calculated.

Weight Gain and Feed Conversion

Average bird weight, on a pen and individual basis, on each weigh day was summarized. The average feed conversion was calculated on study day 21 using the total feed consumption for the pen divided by the total weight of surviving birds. Adjusted feed conversion was calculated using the total feed consumption in a pen divided by the total weight of surviving birds and weight of birds that died or were removed from that pen.

Digesta Collection

On day 21, each bird was euthanized by cervical dislocation to collect the following using the described procedures, gloves were changed between each bird.

Immediately place the contents of one cecum in a 1.5-ml tube prefilled with 150 µl stop solution.

Immediately place the contents of the small intestine into a 1.5-ml tube prefilled with 150 µl stop solution.

Dissect the gizzard out of the GI tract, remove the contents with forceps, and place in a 1.5-ml tube prefilled with 150 µl stop solution.

Dissect the crop out of the GI tract, remove the contents with forceps/scrape out mucosal lining, and place in a 1.5-ml tube prefilled with 150 µl stop solution.

Store all samples at 4° C. until shipment.

Scales

Scales used in weighing of feed and feed additives were licensed and/or certified by the State of Colorado. At each use the scales were checked using standard weights according to CQR standard operating procedures.

*Clostridium perfringens* Challenge

Method of Administration

The *Clostridium perfringens* culture was obtained from Microbial Research, Inc. Administration of the *C. perfringens* (CL-15, Type A, α and β2 toxins) cultures in this study were via the feed. Feed from each pen's feeder was used to mix with the culture. Prior to placing the cultures in the pens, the treatment feed was removed from the birds for approximately 4-8 hours. For each pen of birds, a fixed amount based on study design of the broth culture at a concentration of approximately $2.0\text{-}9.0\times10^8$ cfu/ml was mixed with a fixed amount of feed (~25 g/bird) in the feeder tray and all challenged pens were treated the same. Most of the culture-feed was consumed within 1-2 hours. So that birds in all treatments are treated similar, the groups that are not challenged also had the feed removed during the same time period as the challenged groups. *Clostridium* Challenge The *C. perfringens* culture (CL-15) was grown for ~5 hours at ~37° C. in fluid thioglycollate medium containing starch. CL-15 is a field strain of *C. perfringens* from a broiler outbreak in Colorado. A fresh broth culture was prepared and used each day. For each pen of birds, a fixed amount of the overnight broth culture was mixed with a fixed amount of treatment feed in the feeder tray (see administration). The amount of feed, volume, and quantitation of culture inoculum, and number of days dosed was documented in the final report, and all pens were treated the same. Birds received the *C. perfringens* culture for one day (day 17). Quantitation was conducted by Microbial Research, Inc on the culture and results were documented in the final report. There was no target mortality for this study.

Lesion Scoring

Four days following the last *C. perfringens* culture administration, five birds were randomly selected from each pen by first bird caught, sacrificed, and intestinal lesions scored for necrotic enteritis. Lesions were scored as follows:

0=normal: No NE lesions, small intestine has normal elasticity (rolls back to normal position after being opened).

1=mild: Small intestinal wall is thin and flaccid (remains flat when opened and doesn't roll back into normal position after being opened); excess mucus covering mucus membrane.

2=moderate: Noticeable reddening and swelling of the intestinal wall; minor ulceration and necrosis of the intestinal membrane; excess mucus.

3=severe: Extensive area(s) of necrosis and ulceration of the small intestinal membrane; significant hemorrhage; layer of fibrin and necrotic debris on the mucus membrane (Turkish towel appearance).

4=dead or moribund: Bird that would likely die within 24 hours and has NE lesion score of 2 or more.

Dispositions

Excess Test Articles

An accounting was maintained of the test articles received and used for this study. Excess test articles were dispositioned or returned to the sponsor. Documentation was provided with the study records.

Feed

An accounting was maintained of all diets. The amount mixed, used and discarded was documented. Unused feed was disposed of either by salvage sale and/or placing into a dumpster for commercial transport to a local landfill for burial. Disposition was documented in the study records.

Test Animals

An accounting was maintained for birds received for the study. Disposal of mortalities and birds sacrificed during the study and at study end was discarded to the landfill at study end. Documentation of disposition was provided with the study records. No food products derived from animals enrolled in this study entered the human food chain.

Data Collected

Mortality and Removal Weights for Cobb 500 Males Spanning Days 0 to Study End (Table 21).

Average Bird Weights and Performance at Day 14 Summarized by Treatment (Table 22).

Average Bird Weights and Performance at Day 21 Summarized by Treatment (Table 23).

Pen Weights and Feed Conversion for Cobb 500 Males Days 14-21 Summarized by Treatment (Table 24).

Day 21 NE Lesion Scores for Cobb 500 Males Summarized by Treatment (Table 25).

TABLE 21

Mortality and Removal Weights for Cobb 500 Males Spanning Days 0 to Study End

Days 0-7

| Block | Trt | Pen No. | No. Birds Started Day 0 | Mortality | Added | Removal-1 | Removal-2 | Cause of Death | Mortality Wt (kg) | Added Wt (kg) | Removed Wt (kg) | Total M & R Wt (kg) Days 0-7 | No. Birds Remaining Day 7 |
|---|---|---|---|---|---|---|---|---|---|---|---|---|---|
| 1 | 2 | 1 | 20 | | | | | | | | | 0.000 | 20 |
| 1 | 4 | 2 | 20 | | | | | | | | | 0.000 | 20 |
| 1 | 3 | 3 | 20 | | | | | | | | | 0.000 | 20 |
| 1 | 1 | 4 | 20 | | | | | | | | | 0.000 | 20 |
| 2 | 2 | 5 | 20 | | | | | | | | | 0.000 | 20 |
| 2 | 4 | 6 | 20 | | | | | | | | | 0.000 | 20 |
| 2 | 1 | 7 | 20 | | | | | | | | | 0.000 | 20 |
| 2 | 3 | 8 | 20 | | | | | | | | | 0.000 | 20 |

Days 7-14

| Block | Trt | Pen No. | No. Birds Started Day 0 | Mortality | Removal-1 | Removal-2 | Cause of Death | Mortality Wt (kg) | Removed Wt (kg) | Total M & R Wt (kg) Days 7-14 | No. Birds Remaining Day 14 |
|---|---|---|---|---|---|---|---|---|---|---|---|
| 1 | 2 | 1 | 20 | | | | | | | 0.000 | 20 |
| 1 | 4 | 2 | 20 | | | | | | | 0.000 | 20 |
| 1 | 3 | 3 | 20 | 1 | | | SDS | 0.235 | | 0.235 | 19 |
| 1 | 1 | 4 | 20 | | | | | | | 0.000 | 20 |
| 2 | 2 | 5 | 20 | | | | | | | 0.000 | 20 |
| 2 | 4 | 6 | 20 | | | | | | | 0.000 | 20 |
| 2 | 1 | 7 | 20 | | | | | | | 0.000 | 20 |
| 2 | 3 | 8 | 20 | | | | | | | 0.000 | 20 |

Days 14-21

| Block | Trt | Pen No. | No. Birds Started Day 0 | Mortality | Removal-1 | Removal-2 | Cause of Death | Mortality Wt (kg) | Removed Wt (kg) | Total M & R Wt (kg) Days 14-21 | No. Birds Remaining Day 21 |
|---|---|---|---|---|---|---|---|---|---|---|---|
| 1 | 2 | 1 | 20 | 3 | | | 3NE | 1.768 | | 1.768 | 17 |
| 1 | 4 | 2 | 20 | 2 | | | 2NE | 1.156 | | 1.156 | 18 |
| 1 | 3 | 3 | 20 | 2 | | | ACT; NE | 0.912 | | 0.912 | 17 |
| 1 | 1 | 4 | 20 | | | | | | | 0.000 | 20 |
| 2 | 2 | 5 | 20 | 2 | | | 2NE | 1.231 | | 1.231 | 18 |
| 2 | 4 | 6 | 20 | 3 | | | 3NE | 1.904 | | 1.904 | 17 |
| 2 | 1 | 7 | 20 | | | | | | | 0.000 | 20 |
| 2 | 3 | 8 | 20 | 1 | | | NE | 0.672 | | 0.672 | 19 |

TABLE 22

Average Bird Weights and Performance at Day 14 Summarized by Treatment

| Block No. | Trt No. | Pen No. | No. Birds Started | Mortalities | Removed | No. Birds Weighed | Day 14 Pen Wt (kg) | Day 14 Avg Bird Wt (kg) | Feed Gain | Adjusted Feed Gain |
|---|---|---|---|---|---|---|---|---|---|---|
| 1 | 1 | 1 | 20 | 0 | 0 | 20 | 8.731 | 0.437 | 1.008 | 1.008 |
| 2 | 1 | 1 | 20 | 0 | 0 | 20 | 8.679 | 0.434 | 0.993 | 0.993 |
| Totals & Averages | | | 40 | 0 | 0 | 40 | 8.705 | 0.435 | 1.001 | 1.001 |
| Standard Deviations | | | | | | | 0.037 | 0.002 | 0.010 | 0.010 |
| CV's | | | | | | | 0.422% | 0.422% | 1.039% | 1.039% |
| 1 | 2 | 2 | 20 | 0 | 0 | 20 | 8.847 | 0.442 | 0.986 | 0.986 |
| 2 | 2 | 2 | 20 | 0 | 0 | 20 | 8.872 | 0.444 | 0.985 | 0.985 |
| Totals & Averages | | | 40 | 0 | 0 | 40 | 8.860 | 0.443 | 0.985 | 0.985 |
| Standard Deviations | | | | | | | 0.018 | 0.001 | 0.000 | 0.000 |
| CV's | | | | | | | 0.200% | 0.200% | 0.038% | 0.038% |
| 1 | 3 | 3 | 20 | 1 | 0 | 19 | 8.160 | 0.429 | 0.993 | 0.965 |
| 2 | 3 | 3 | 20 | 0 | 0 | 20 | 8.866 | 0.443 | 0.993 | 0.993 |

TABLE 22-continued

Average Bird Weights and Performance at Day 14 Summarized by Treatment

| Block No. | Trt No. | Pen No. | No. Birds Started | Mortalities | Removed | No. Birds Weighed | Day 14 Pen Wt (kg) | Day 14 Avg Bird Wt (kg) | Feed Gain | Adjusted Feed Gain |
|---|---|---|---|---|---|---|---|---|---|---|
| Totals & Averages | | | 40 | 1 | 0 | 39 | 8.513 | 0.436 | 0.993 | 0.979 |
| Standard Deviations | | | | | | | 0.499 | 0.010 | 0.000 | 0.020 |
| CV's | | | | | | | 5.864% | 2.240% | 0.006% | 2.001% |
| 1 | 4 | 4 | 20 | 0 | 0 | 20 | 8.423 | 0.421 | 0.985 | 0.985 |
| 2 | 4 | 4 | 20 | 0 | 0 | 20 | 8.553 | 0.428 | 0.996 | 0.996 |
| Totals & Averages | | | 40 | 0 | 0 | 40 | 8.488 | 0.424 | 0.991 | 0.991 |
| Standard Deviations | | | | | | | 0.092 | 0.005 | 0.008 | 0.008 |
| CV's | | | | | | | 1.083% | 1.083% | 0.767% | 0.767% |

TABLE 23

Average Bird Weights and Performance at Day 21 Summarized by Treatment

| Block No. | Trt No. | Pen No. | No. Birds Started | Mortalities | Removed | No. Birds Weighed | Day 21 Pen Wt (kg) | Day 21 Avg Bird Wt (kg) | Feed Gain | Adjusted Feed Gain |
|---|---|---|---|---|---|---|---|---|---|---|
| 1 | 1 | 1 | 20 | 0 | 0 | 20 | 16.756 | 0.838 | 1.004 | 1.004 |
| 2 | 1 | 1 | 20 | 0 | 0 | 20 | 16.967 | 0.848 | 1.010 | 1.010 |
| Totals & Averages | | | 40 | 0 | 0 | 40 | 16.862 | 0.843 | 1.007 | 1.007 |
| Standard Deviations | | | | | | | 0.149 | 0.007 | 0.005 | 0.005 |
| CV's | | | | | | | 0.885% | 0.885% | 0.448% | 0.448% |
| 1 | 2 | 2 | 20 | 3 | 0 | 17 | 14.755 | 0.868 | 1.129 | 1.008 |
| 2 | 2 | 2 | 20 | 2 | 0 | 18 | 15.102 | 0.839 | 1.157 | 1.070 |
| Totals & Averages | | | 40 | 5 | 0 | 35 | 14.929 | 0.853 | 1.143 | 1.039 |
| Standard Deviations | | | | | | | 0.245 | 0.020 | 0.020 | 0.044 |
| CV's | | | | | | | 1.644% | 2.398% | 1.754% | 4.214% |
| 1 | 3 | 3 | 20 | 2 | 0 | 17 | 14.129 | 0.831 | 1.023 | 0.961 |
| 2 | 3 | 3 | 20 | 1 | 0 | 19 | 15.024 | 0.791 | 1.126 | 1.078 |
| Totals & Averages | | | 40 | 3 | 0 | 36 | 14.577 | 0.811 | 1.075 | 1.020 |
| Standard Deviations | | | | | | | 0.633 | 0.029 | 0.073 | 0.082 |
| CV's | | | | | | | 4.342% | 3.521% | 6.761% | 8.086% |
| 1 | 4 | 4 | 20 | 2 | 0 | 18 | 14.746 | 0.819 | 1.066 | 0.989 |
| 2 | 4 | 4 | 20 | 3 | 0 | 17 | 13.895 | 0.817 | 1.186 | 1.043 |
| Totals & Averages | | | 40 | 5 | 0 | 35 | 14.321 | 0.818 | 1.126 | 1.016 |
| Standard Deviations | | | | | | | 0.602 | 0.001 | 0.085 | 0.039 |
| CV's | | | | | | | 4.202% | 0.162% | 7.535% | 3.797% |

TABLE 24

Pen Weights and Feed Conversion for Cobb 500 Males Days 14-21 Summarized by Treatment

| Block | Trt | Pen No. | No. Birds Started Day 14 | Mortality | Added | Removal-1 | Removal-2 | No. Birds Weighed D 21 | D 21 Pen Wt (kg) | D 21 Avg Bird Wt (kg) | D 14-21 Avg Bird Gain (kg) | Feed Conversion D 14-21 (kg) | Adj. Feed Conversion (kg) |
|---|---|---|---|---|---|---|---|---|---|---|---|---|---|
| 1 | 1 | 4 | 20 | 0 | 0 | 0 | 0 | 20 | 16.756 | 0.838 | 0.401 | 0.999 | 0.999 |
| 2 | 1 | 7 | 20 | 0 | 0 | 0 | 0 | 20 | 16.967 | 0.848 | 0.414 | 1.028 | 1.028 |
| Totals & Averages | | | 40 | 0 | 0 | 0 | 0 | 40 | 16.862 | 0.843 | 0.408 | 1.014 | 1.014 |
| Standard Deviations | | | | | | | | | 0.149 | 0.007 | 0.009 | 0.020 | 0.020 |
| CV's | | | | | | | | | 0.885% | 0.885% | 2.280% | 1.996% | 1.996% |
| 1 | 2 | 1 | 20 | 0 | 0 | 0 | 0 | 20 | 14.755 | 0.738 | 0.295 | 1.344 | 1.034 |
| 2 | 2 | 5 | 20 | 0 | 0 | 0 | 0 | 20 | 15.102 | 0.755 | 0.312 | 1.403 | 1.171 |
| Totals & Averages | | | 40 | 0 | 0 | 0 | 0 | 40 | 14.929 | 0.746 | 0.303 | 1.373 | 1.103 |
| Standard Deviations | | | | | | | | | 0.245 | 0.012 | 0.011 | 0.042 | 0.097 |
| CV's | | | | | | | | | 1.644% | 1.644% | 3.752% | 3.035% | 8.786% |

TABLE 24-continued

Pen Weights and Feed Conversion for Cobb 500 Males Days 14-21 Summarized by Treatment

| Block | Trt | Pen No. | No. Birds Started Day 14 | Mortality | Added | Removal-1 | Removal-2 | No. Birds Weighed D 21 | D 21 Pen Wt (kg) | D 21 Avg Bird Wt (kg) | D 14-21 Avg Bird Gain (kg) | Feed Conversion D 14-21 (kg) | Adj. Feed Conversion (kg) |
|---|---|---|---|---|---|---|---|---|---|---|---|---|---|
| 1 | 3 | 3 | 19 | 1 | 0 | 0 | 0 | 18 | 14.129 | 0.785 | 0.355 | 1.066 | 0.924 |
| 2 | 3 | 8 | 20 | 0 | 0 | 0 | 0 | 20 | 15.024 | 0.751 | 0.308 | 1.319 | 1.189 |
| Totals & Averages | | | 39 | 1 | 0 | 0 | 0 | 38 | 14.577 | 0.768 | 0.332 | 1.192 | 1.057 |
| Standard Deviations | | | | | | | | | 0.633 | 0.024 | 0.034 | 0.179 | 0.187 |
| CV's | | | | | | | | | 4.342% | 3.107% | 10.141% | 15.014% | 17.707% |
| 1 | 4 | 2 | 20 | 0 | 0 | 0 | 0 | 20 | 14.746 | 0.737 | 0.316 | 1.173 | 0.992 |
| 2 | 4 | 6 | 20 | 0 | 0 | 0 | 0 | 20 | 13.895 | 0.695 | 0.267 | 1.490 | 1.099 |
| Totals & Averages | | | 40 | 0 | 0 | 0 | 0 | 40 | 14.321 | 0.716 | 0.292 | 1.332 | 1.045 |
| Standard Deviations | | | | | | | | | 0.602 | 0.030 | 0.035 | 0.224 | 0.075 |
| CV's | | | | | | | | | 4.202% | 4.202% | 11.893% | 16.809% | 7.199% |

TABLE 25

Day 21 NE Lesion Scores for Cobb 500 Males Summarized by Treatment

| Trt | Pen No. | Bird ID | Lesion Score | Average Pen Score |
|---|---|---|---|---|
| 1 | 4 | 6943 | 1 | 0.6 |
| 1 | 4 | 6941 | 1 | |
| 1 | 4 | 6954 | 1 | |
| 1 | 4 | 6940 | 0 | |
| 1 | 4 | 6939 | 0 | |
| 1 | 7 | 2181 | 0 | 0.0 |
| 1 | 7 | 2177 | 0 | |
| 1 | 7 | 2176 | 0 | |
| 1 | 7 | 2173 | 0 | |
| 1 | 7 | 2186 | 0 | |
| Totals & Averages | | 10 | 0.3 | 0.3 |
| Standard Deviations | | | 0.5 | |
| CV's | | | 161.0% | |
| 2 | 1 | 2127 | 1 | 1.4 |
| 2 | 1 | 2118 | 1 | |
| 2 | 1 | 2113 | 1 | |
| 2 | 1 | 2114 | 2 | |
| 2 | 1 | 2117 | 2 | |
| 2 | 5 | 2154 | 1 | 2.4 |
| 2 | 5 | 2171 | 4 | |
| 2 | 5 | 2167 | 4 | |
| 2 | 5 | 2162 | 2 | |
| 2 | 5 | 2156 | 1 | |
| Totals & Averages | | 10 | 1.9 | 1.9 |
| Standard Deviations | | | 1.2 | |
| CV's | | | 63.0% | |
| 3 | 3 | 2145 | 1 | 1.40 |
| 3 | 3 | 2142 | 3 | |
| 3 | 3 | 2134 | 1 | |
| 3 | 3 | 2136 | 1 | |
| 3 | 3 | 2139 | 1 | |
| 3 | 8 | 6977 | 1 | 2.2 |
| 3 | 8 | 6980 | 1 | |
| 3 | 8 | 6989 | 4 | |
| 3 | 8 | 6978 | 1 | |
| 3 | 8 | 6994 | 4 | |
| Totals & Averages | | 10 | 1.8 | 1.8 |
| Standard Deviations | | | 1.3 | |
| CV's | | | 73.1% | |
| 4 | 2 | 6934 | 3 | 2.2 |
| 4 | 2 | 6928 | 1 | |
| 4 | 2 | 6920 | 2 | |
| 4 | 2 | 6932 | 3 | |
| 4 | 2 | 6919 | 2 | |
| 4 | 6 | 6960 | 3 | 2.2 |
| 4 | 6 | 6959 | 2 | |
| 4 | 6 | 6966 | 2 | |
| 4 | 6 | 6975 | 3 | |
| 4 | 6 | 6956 | 1 | |
| Totals & Averages | | 10 | 2.2 | 2.2 |
| Standard Deviations | | | 0.8 | |
| CV's | | | 35.9% | |

GI Sample Preparation and Sequencing:

After collection, the gastrointestinal (GI) samples were centrifuged at 4,000 rpm in a swing bucket centrifuge for 20 minutes at 4° C. The supernatant was decanted, and an aliquot of each gastrointestinal content sample (1-2 mg) was added to a sterile 1.7 mL tube prefilled with 0.1 mm glass beads. A second aliquot was collected and stored in an empty, sterile 1.7 mL tube for cell counting.

GI samples in empty tubes were stained and put through a flow cytometer to quantify the number of cells of each microorganism type in each sample. GI samples with glass beads were homogenized with bead beating to lyse microorganisms. DNA and RNA was extracted and purified from each sample and prepared for sequencing on an Illumina Miseq. Samples were sequenced using paired-end chemistry, with 300 base pairs sequenced on each end of the library.

Sequencing Read Processing and Data Analysis:

Sequencing reads were quality trimmed and processed to identify bacterial species present in the GI tract based on a marker gene, 16S rDNA, or ITS1 and/or ITS2. Count data sets and activity datasets were integrated with the sequencing reads to determine the absolute cell numbers of active microbial species within the gastrointestinal microbial community. Production characteristics of the broiler over time, including feed conversion, weight, mortality, and lesion scores, were linked to the distribution of active microorganisms within each sample over the course of the experiment using mutual information.

Results

One component of the Ascus Biosciences technology utilized in this application leverages mutual information to rank the importance of native microbial strains residing in the gastrointestinal tract of the animal to specific animal traits. The maximal information coefficient (MIC) scores are calculated for all microorganisms and the desired animal trait. Relationships were scored on a scale of 0 to 1, with 1 representing a strong relationship between the microbial strain and the animal trait, and 0 representing no relationship. A cut-off based on this score is used to define useful and non-useful microorganisms with respect to the improvement of specific traits.

The MICs were calculated between production characteristics, including indicators for disease such as lesion scores, and the absolute abundance of each active microorganism. Microorganisms were ranked by MIC score, and microorganisms with the highest MIC scores were selected as the most relevant target species. MIC scores of the microbes of the present disclosure are recited in Table 1. The greater the MIC score, the greater the ability of the microbe to confer an improvement in the performance and GI health of the bird.

Example III. Media Recipes of the Present Disclosure

Medium Preparation:

Dry reagents for each medium (recipes below) were weighed out, and combined in a flask. Liquid reagents for each medium, if applicable, are then added to the flask. DI water was added to the flask to bring the medium to its final volume (typically one liter). The medium was stirred, and then aliquoted into individual serum bottles or Hungate tubes. Serum bottles were filled with 25 mL or 50 mL of medium, and Hungate were filled with 10 mL of medium. The serum bottles/hungate tube were bubbled with 20:80 $CO_2/N_2$ for 45 minutes. The bottles were then stoppered, and autoclaved at 121° C. for 15 minutes. After autoclaving, Cysteine-HCl was added to every bottle to achieve a final concentration of 1 mM Cysteine-HCl. Any post autoclaving reagents were also added. All of the post autoclaving reagents were sterile filtered using a 0.22 um filter prior to addition.

Sample Preparation:

Samples from the gastrointestinal tract of broilers were mixed with 500 mL of 1×RAMM and homogenized by vortexing in an anaerobic chamber. The samples were then serially diluted and added to the prepared serum bottle/hungate tube. The inoculated bottles were incubated at 37° C. for a minimum of 24 hours. Additional compounds were added to the media after autoclaving when noted: (1) sterile butyric acid was added to achieve a final concentration of 10 mN, (2) glycerol was added to achieve a final concentration of 10 mM, (3) acetic acid was added to achieve a final concentration of 10 mM, (4) amin acid D solution was added to achieve a final concentration of 10 mM, and (5) arabinose and xylose solution was added to achieve a final concentration of 10 mM.

For enrichments requiring diluted media, the final media preparation was diluted 1:10 with DI water prior to autoclaving. The diluted media was aliquoted into serum bottles or hungate tubes, and then bubbled under 10:80 $CO_2/N_2$ for 45 minutes to an hour prior to autoclaving.

Media:

TABLE 26

Spirillum Medium

| Component | g/L |
|---|---|
| Bacto Peptone | 10 |
| Succinate | 1 |
| (NH4)2SO4 | 1 |
| MgSO4 × 7H20 | 1 |
| 10 mM FeCl3 × 6H2O | 0.72 mL |
| 100 mM MnSO4 × H2O | 0.12 mL |

TABLE 27

CMC Medium

| Component | g/L |
|---|---|
| Peptone | 30 |
| $K_2HPO_4$ | 5 |
| Yeast Extract | 5 |
| Glucose | 4 |
| Cellobiose | 1 |
| Maltose | 1 |
| Starch | 1 |
| L-Cysteine | 0.5 |
| Meat Extract | 15 |
| Rumen Fluid (Clarified) | 100 mL |
| Meat Peptone | 10 |
| Resazurin (1 g/L) | 1 mL |

TABLE 28

BL Medium

| Component | g/L |
|---|---|
| Meat Extract | 2.4 |
| Protease Peptone | 10 |
| Bacto peptone | 5 |
| Soya Peptone | 3 |
| Yeast Extract | 5 |
| Liver Extract | 3.2 |
| Dextrose | 10 |
| 1M $MgSO_4$ $7H_2O$ | 1.65 mL |
| 0.05M $FeSO_4$ $7H_2O$ | 0.7 mL |
| 0.25M NaCl | 0.675 mL |
| 0.05 mM $MnSO_4$ | 0.7 mL |
| TWEEN 80 | 0.53 mL |

TABLE 29

Brain Heart Infusion (BHI) Medium

| Component | g/L |
|---|---|
| Brain Heart Infusion | 18.5 |
| Dextrose | 5 |

TABLE 30

MRS Medium

| Component | g/L |
|---|---|
| Casein Digest | 10.0 |
| Meat Extract | 10.0 |
| Yeast Extract | 5.0 |
| Dextrose | 20.0 |

TABLE 30-continued

MRS Medium

| Component | g/L |
|---|---|
| TWEEN 80 | 1.0 mL |
| Sodium Acetate | 5.0 |
| Ammonium citrate | 2.0 |
| 1M MgSO$_4$ 7H$_2$O | 0.8 mL |
| 1M MnSO$_4$ H$_2$O | 0.296 mL |
| 1M K$_2$HPO$_4$ | 2.0 |

TABLE 31

M2GSC Medium

| Component | g/L |
|---|---|
| Beef Extract | 10.0 |
| Yeast Extract | 2.5 |
| NaHCO$_3$ | 4 |
| Cellobiose | 2 |
| Starch | 2 |
| Glucose | 2 |
| (NH$_4$)$_2$SO$_4$ (1M) | 5.1 mL |
| MgSO$_4$ 7H$_2$O (0.25M) | 0.575 mL |
| K$_2$HPO$_4$ (1M) | 2 mL |
| KH$_2$PO$_4$ (1M) | 2.55 mL |
| Clarified rumen fluid | 100 mL |

TABLE 32

Amino Acid D Solution-Place the components in a 100 mL bottle and sterile filer into a 50 mL conical

| Component | g/50 mL |
|---|---|
| Glutamic Acid | 0.736 g |
| Glycine | 0.375 g |
| Proline | 0.576 g |
| DI H2O | 50 mL |

TABLE 33

Arabinose + Xylose Media Addition

| Component | g/100 mL |
|---|---|
| Arabinose | 1.5013 |
| Xylose | 1.5013 |
| DI H2O | 100 mL |

Example IV. Trial 1—In Vivo Evaluation of Ascus Microbial Composition Vs. Control (Both w/Salinomycin)

Basal and Experimental Diets

The starter, grower and basal diets was manufactured using a feed mill and stored in bulk.

Final experimental diet mixing, pelleting, and crumbling was conducted using a 500-lb capacity vertical mixer, a 4000-lb capacity vertical mixer and/or a 14,000-lb horizontal mixer and a California Pellet Mill. Feed was stored in 50-lb capacity feed sacks and/or bulk storage bins labeled with treatment code. Phytase and Sacox 60 was included in all diets throughout the experiment.

The feeding schedule utilized two feeds a starter feed in crumble form and a grower feed in pellet form. The starter feed was fed from days 0 to 17, and the grower feed was fed from days 17 to 35.

Test System

| Species | Broiler Chicken |
|---|---|
| Strain | Commercial production |
| Breed/Cross | Cobb 500 |
| Supplier | Cobb Vantress, Inc |
| Sex | Males |
| Age | ~1 day of age upon receipt (day 0) |
| | ~35 days at final weights |
| Identification | Pen cards |
| Number of birds: | 800 (D0) |
| Number of treatments: | 2 |
| Number of pens/treatment: | 20 |
| Number of birds/pen: | 20 (D0) |
| Number of birds/treatment: | 400 (D0) |
| Total number of pens: | 40 |

Test Groups

Treatments were assigned to the pens using a complete randomized block design. Treatments were administered to the pens at start of study day 0. The treatments will identified by numeric codes. Specific treatment groups are as follows. There were two treatment groups, 1 and 2. Each group consisted of twenty birds per pen with a total of 20 pens. The total number of birds per treatment was 400. Treatment 1 consisted of non-challenged birds. Treatment 2 consisted of treatment with Ascusbbr_5796, Ascusbbr_38717, and Ascusbbr_331885. The Ascus microbial ensembles were administered to the birds in the treatment group via drinking water daily.

Housing and Management

Treatments were randomly assigned to each pen using Microsoft Excel random number generator by the Data Manager. Birds were assigned to the pens randomly.

Birds were housed within an environmentally controlled in concrete floor pens providing floor space & bird density of [~0.55 ft$^2$/bird (day 0); ~0.69 ft$^2$/bird (day 21 after lesion scores)], temperature, humidity, lighting, feeder and water space were similar for all test groups. Birds were placed in clean pens containing an appropriate depth of clean wood shavings to provide a comfortable environment for the chicks. Additional shavings were added to pens in order to maintain bird comfort. Lighting was via incandescent lights and a commercial lighting program was used as follows.

TABLE 34

Housing Description

| Approximate Bird Age (days) | Approximate Hours of Continuous Light per 24 hr period | ~Light Intensity (foot candles) |
|---|---|---|
| 0-4 | 24 | 1.0-1.3 |
| 5-10 | 10 | 1.0-1.3 |
| 11-18 | 12 | 0.2-0.3 |
| 19-end | 16 | 0.2-0.3 |

Environmental conditions for the birds (i.e. bird density, temperature, lighting, feeder and water space) were similar for all treatment groups. In order to prevent bird migration and bacterial spread from pen to pen, each pen will have a solid wood or plastic divider for approximately 24 inches in height between pens.

Vaccinations and Therapeutic Medication

Birds were vaccinated for Mareks at the hatchery. Upon receipt (study day 0), birds were vaccinated for Newcastle and Infectious Bronchitis and Coccivac by spray application using a spray cabinet. Documentation of vaccine manufacturer, lot number and expiration date was provided with the final report.

Water

Water was provided ad libitum throughout the study via one automatic nipple drinker (4 nipples per drinker) per pen. Drinkers were checked twice daily and cleaned as needed to assure a clean and constant water supply to the birds.

Feed

Feed was provided ad libitum throughout the study via one hanging, ~17-inch diameter tube feeder per pen. A chick feeder tray was placed in each pen for approximately the first 4 days. Birds were placed on their respective treatment diets upon receipt (day 0) according to the Experimental Design. Feed added and removed from pens from day 0 to study end was weighed and recorded.

Daily Observations

The test facility, pens and birds were observed at least twice daily for general flock condition, lighting, water, feed, ventilation and unanticipated events. If abnormal conditions or abnormal behavior is noted at any of the twice-daily observations they were documented and included with the study records. The minimum-maximum temperature of the test facility was recorded once daily.

Pen Cards

There were 2 cards attached to each pen. One card identifies the pen number and the second will include the treatment number.

Animal Handling

The animals were kept under ideal conditions for livability. The animals were handled in such a manner as to reduce injuries and unnecessary stress. Humane measures were strictly enforced.

Veterinary Care, Intervention and Euthanasia

Birds that develop clinically significant concurrent disease unrelated to the test procedures may, at the discretion of the Study Investigator, or a designee, be removed from the study and euthanized in accordance with site SOPs. In addition, moribund or injured birds may also be euthanized upon authority of a Site Veterinarian or a qualified technician. The reason for withdrawal was documented. If an animal dies, or is removed and euthanized for humane reasons, it was recorded on the mortality sheet for the pen and a necropsy performed and was filed to document the reason for removal. If euthanasia is deemed necessary animals were euthanized by cervical dislocation.

Mortality and Culls

From Day 0 to study end any bird that is found dead or is sacrificed was weighed and necropsied. The weight and probable cause of death and necropsy findings were recorded on the mortality record. If sex-slips are noted at any time during the study they were removed, weighed, necropsied to confirm sex and recorded on the pen mortality record.

Body Weights and Feed Intake

Birds were weighed by pen on approximately day 0, 17, 28 and 35. The feed remaining in each pen was weighed and recorded on study days 17, 28 and 35. The feed intake during days 0-17, 17-28, and 0-35 was calculated.

Weight Gains and Feed Conversion

Average bird weight, on a pen basis, on each weigh day was summarized. Bird weight gain by pen days 17-28 was calculated. The average feed conversion was calculated on the study days 17 and 28 (i.e. days 0-17, 17-35, and 0-35) using the total feed consumption for the pen divided by the total weight of surviving birds. Adjusted feed conversion was calculated using the total feed consumption in a pen divided by the total weight of surviving birds and weight of birds that died or were removed from that pen.

TABLE 35

Results

| Trt Group | Avg Individual Bird Wt Gain (kg) | Adj. Feed Conversion | Treatment Description |
|---|---|---|---|
| 1 | 2.304 | 1.420 | Non-Challenged with salinomycin |
| 2 | 2.399 | 1.407 | Treated with salinomycin and Ascus Composition: Ascusbbr_5796, Ascusbbr_38717, Ascusbbr_331885 |

The birds were treated with a composition of Ascus microorganisms to determine their effects on performance. Three microorganisms, Ascusbbr_5796, Ascusbbr_38717, and Ascusbbr_331885 were administered daily to the experimental birds via their drinking water over the course of the entire experiment. All birds were on a commercially relevant pelleted feed that included salinomycin.

At the end of the experiment, birds were sacrificed and weighed. Feed conversion was calculated based on the total feed consumption for the pen divided by the total weight of the surviving birds. The treatment group was found to have a slight improvement in feed conversion (1%) and individual bird weight gain (4%) as compared to the control group.

Example V. Trial 2—In Vivo Evaluation of Ascus Microbial Composition Vs. *Clostridium perfringens* Challenge Basal and Experimental Diets The starter, grower and basal diets was manufactured using a feed mill and stored in bulk.

Final experimental diet mixing, pelleting, and crumbling was conducted using a 500-lb capacity vertical mixer, a 4000-lb capacity vertical mixer and/or a 14,000-lb horizontal mixer and a California Pellet Mill. Feed was stored in 50-lb capacity feed sacks and/or bulk storage bins labeled with treatment code. Phytase was included in all diets throughout the experiment.

The feeding schedule utilized two feeds a starter feed in crumble form and a grower feed in pellet form. The starter feed was fed from days 0 to 17, and the grower feed was fed from days 17 to 35. The Ascus microbial ensembles were administered to the birds in the treatment group via drinking water daily.

Test System

| | |
|---|---|
| Species | Broiler Chicken |
| Strain | Commercial production |
| Breed/Cross | Cobb 500 |
| Supplier | TBD |
| Sex | Males |
| Age | ~1 day of age upon receipt (day 0) ~35 days at final weights |
| Identification | Pen cards |
| Number of birds: | 900 (D 0) |
| Number of treatments: | 3 |
| Number of pens/treatment: | 12 |
| Number of birds/pen: | 25 (D 0) |
| Number of birds/treatment: | 300 (D 0) |
| Total number of pens: | 36 |

Test Groups

Treatments were assigned to the pens using a complete randomized block design.

Treatments were administered to the pens at start of study day 0. The treatments will identified by numeric codes. Challenged control treatments comprise the administration of pathogens as the control. Challenged Ascus compositions comprise the administration of experimental microbes. Specific treatment groups are as follows:

TABLE 36

Test Groups

| CP Trt | Challenged | Treatment Description | No. of Birds/Pen | No. of Pens | Number of Birds/Trt |
|---|---|---|---|---|---|
| 1 | Yes | Challenged Control (non-medicated) | 25 | 12 | 300 |
| 2 | Yes | Challenged Control w/salinomycin | 25 | 12 | 300 |
| 3 | Yes | Challenged, Ascus Composition administered: Ascusbbr_4729, Ascusbbr_331885, Ascusbbr_170211 (water application) | 25 | 12 | 300 |

Housing and Management

Housing

Treatments were randomly assigned to each pen using Microsoft Excel random number generator by the Data Manager. Birds were assigned to the pens randomly. Birds were housed within an environmentally controlled in concrete floor pens providing floor space & bird density of [~0.55 ft$^2$/bird (day 0); ~0.69 ft$^2$/bird (day 21 after lesion scores)], temperature, humidity, lighting, feeder and water space were similar for all test groups. Birds were placed in clean pens containing an appropriate depth of clean wood shavings to provide a comfortable environment for the chicks. Additional shavings were added to pens in order to maintain bird comfort. Lighting was via incandescent lights and a commercial lighting program was used as follows.

TABLE 37

Lighting

| Approximate Bird Age (days) | Approximate Hours of Continuous Light per 24 hr period | ~Light Intensity (foot candles) |
|---|---|---|
| 0-4 | 24 | 1.0-1.3 |
| 5-10 | 10 | 1.0-1.3 |
| 11-18 | 12 | 0.2-0.3 |
| 19-end | 16 | 0.2-0.3 |

Environmental conditions for the birds (i.e. bird density, temperature, lighting, feeder and water space) were similar for all treatment groups. In order to prevent bird migration and bacterial spread from pen to pen, each pen will have a solid wood or plastic divider for approximately 24 inches in height between pens.

Vaccinations and Therapeutic Medication

Birds were vaccinated for Mareks at the hatchery. Upon receipt (study day 0), birds were vaccinated for Newcastle and Infectious Bronchitis and Coccivac by spray application using a spray cabinet. Documentation of vaccine manufacturer, lot number and expiration date was provided with the final report.

Water

Water was provided ad libitum throughout the study via one automatic nipple drinker (4 nipples per drinker) per pen. Drinkers were checked twice daily and cleaned as needed to assure a clean and constant water supply to the birds.

Feed

Feed was provided ad libitum throughout the study via one hanging, ~17-inch diameter tube feeder per pen. A chick feeder tray was placed in each pen for approximately the first 4 days.

Birds were placed on their respective treatment diets upon receipt (day 0) according to the Experimental Design. Feed added and removed from pens from day 0 to study end was weighed and recorded.

Daily Observations

The test facility, pens and birds were observed at least twice daily for general flock condition, lighting, water, feed, ventilation and unanticipated events. If abnormal conditions or abnormal behavior is noted at any of the twice-daily observations they were documented and included with the study records. The minimum-maximum temperature of the test facility was recorded once daily.

Pen Cards

There were 2 cards attached to each pen. One card identifies the pen number and the second will include the treatment number.

Animal Handling

The animals were kept under ideal conditions for livability. The animals were handled in such a manner as to reduce injuries and unnecessary stress. Humane measures were strictly enforced.

Veterinary Care, Intervention and Euthanasia

Birds that develop clinically significant concurrent disease unrelated to the test procedures may, at the discretion of the Study Investigator, or a designee, be removed from the study and euthanized in accordance with site SOPs. In addition, moribund or injured birds may also be euthanized upon authority of a Site Veterinarian or a qualified technician. The reason for withdrawal was documented. If an animal dies, or is removed and euthanized for humane reasons, it was recorded on the mortality sheet for the pen and a necropsy performed and was filed to document the reason for removal. If euthanasia is deemed necessary animals were euthanized by cervical dislocation.

Mortality and Culls

From Day 0 to study end any bird that is found dead or is sacrificed was weighed and necropsied. The weight and probable cause of death and necropsy findings were recorded on the mortality record. If sex-slips are noted at any time during the study they were removed, weighed, necropsied to confirm sex and recorded on the pen mortality record.

Body Weights and Feed Intake

Birds were weighed by pen on approximately day 0, 17, 28 and 35. The feed remaining in each pen was weighed and recorded on study days 17, 28 and 35. The feed intake during days 0-17, 17-28, and 0-35 was calculated.

Weight Gains and Feed Conversion

Average bird weight, on a pen basis, on each weigh day was summarized. Bird weight gain by pen days 17-28 was calculated. The average feed conversion was calculated on the study days 17 and 28 (i.e. days 0-17, 17-35, and 0-35) using the total feed consumption for the pen divided by the total weight of surviving birds. Adjusted feed conversion was calculated using the total feed consumption in a pen divided by the total weight of surviving birds and weight of birds that died or were removed from that pen.

Coccidiosis Challenge

All birds each received a 1× dose of Coccivac by spray cabinet on approximately study day 0.

Clostridium perfringens Challenge

Clostridium Challenge:

The *Clostridium perfringens* culture (CL-15) was grown ~5 hrs at ~37° C. in Fluid Thioglycollate medium containing starch. CL-15 is a field strain of *Clostridium perfringens* from a broiler outbreak in Colorado. For each pen of birds, a fixed amount of the broth culture (~2-3 ml/bird) was mixed with a fixed amount of treatment feed (~25 g/bird) in the feeder tray. The amount of feed, volume and quantitation of culture inoculum, and number of days dosed were documented in the final report and all pens were treated the same. Birds will receive the *C. perfringens* culture for one day (Study day 17). The target is 10% mortality with a minimum 5% in the challenged, non-medicated group.

Method of Administration

Administration of the *Clostridium perfringens* (CL-15, Type A, α and β2 toxins) cultures in this study was via the feed. Feed from each pen's feeder was used to mix with the culture. Prior to placing the cultures in the pens the treatment feed was removed from the birds for approximately 4-8 hours. For each pen of birds, a fixed amount (~2.5 ml/bird) of the broth culture at a concentration of approximately $2.0-9.0 \times 10^8$ cfu/ml was mixed with a fixed amount of feed (~25 g/bird) in the feeder tray and all challenged pens were treated the same. Most of the culture-feed was consumed within 1-2 hours. So that birds in all treatments are treated similar, the groups that are not challenged will also have the feed removed during the same time period as the challenged groups.

Lesion Scoring

On study day 21, 5 birds were randomly selected from each pen (by first bird caught), sacrificed and evaluated for intestinal lesions scored for necrotic enteritis. Lesions were scored as follows:

0=normal: no NE lesions, small intestine has normal elasticity (rolls back to normal position after being opened)

1=mild: small intestinal wall was thin and flaccid (remains flat when opened and doesn't roll back into normal position after being opened); excess mucus covering mucus membrane 2=moderate: noticeable reddening and swelling of the intestinal wall; minor ulceration and necrosis of the intestine membrane; excess mucus 3=severe: extensive area(s) of necrosis and ulceration of the small intestinal membrane; significant hemorrhage; layer of fibrin and necrotic debris on the mucus membrane (Turkish towel appearance)

4=dead or moribund: bird that would likely die within 24 hours and has NE lesion score of 2 or more; or birds that died due to necrotic enteritis.

TABLE 38

Results

| Trt Group | Avg Individual Bird Wt Gain (kg) | Adj. Feed Conversion | Mortality | NE-Lesion Score |
|---|---|---|---|---|
| 1 | 2.020 | 1.801 | 54.6% | 3.57 |
| 2 | 2.147 | 1.505 | 3.3% | 0.25 |
| 3 | 1.952 | 1.613 | 44.6% | 3.88 |

The birds were treated with a composition of Ascus microorganisms to determine their effects on performance and the prevention of *Clostridium perfringens* infection. Three microorganisms, Ascusbbr_4729, Ascusbbr_331885, and Ascusbbr_170211 were administered daily to the experimental birds via their drinking water over the course of the entire experiment. All birds were on a commercially relevant pelleted feed.

Birds were challenged with *C. perfringens* on day 17 of the study. On day 21, 5 birds were randomly selected, sacrificed, and lesion scored. Mortality and feed intake were measured throughout the experiment. At the end of the experiment, birds were sacrificed and weighed. Feed conversion was calculated based on the total feed consumption for the pen divided by the total weight of the surviving birds. The treatment group receiving Ascus microorganisms was found to have improved feed conversion (10.4%) and percent mortality (18.3%) when compared to the challenged control. However, lesion scores (8.6%) were higher in the Ascus microorganism group compared to to the challenged control. The salinomycin control outperformed all groups.

Example VI. Trial 3—In Vivo Evaluation of Ascus Microbial Composition Vs. *Clostridium perfringens* Challenge Basal and Experimental Diets The starter, grower and basal diets was manufactured using a feed mill and stored in bulk. Final experimental diet mixing, pelleting, and crumbling was conducted using a 500-lb capacity vertical mixer, a 4000-lb capacity vertical mixer and/or a 14,000-lb horizontal mixer and a California Pellet Mill. Feed was stored in 50-lb capacity feed sacks and/or bulk storage bins labeled with treatment code. Phytase was included in all diets throughout the experiment.

The feeding schedule utilized two feeds a starter feed in crumble form and a grower feed in pellet form. The starter feed was fed from days 0 to 17, and the grower feed was fed from days 17 to 35. The Ascus microbial ensembles were administered to the birds in the treatment group once prior to placement via spray application.

Test System

| | |
|---|---|
| Species | Broiler Chicken |
| Strain | Commercial production |
| Breed/Cross | Cobb 500 |
| Supplier | TBD |
| Sex | Males |
| Age | ~1 day of age upon receipt (day 0) |
| | ~35 days at final weights |
| Identification | Pen cards |
| Number of birds: | 1200 (D 0) |
| Number of treatments: | 4 |
| Number of pens/treatment: | 12 |
| Number of birds/pen: | 25 (D 0) |
| Number of birds/treatment: | 300 (D 0) |
| Total number of pens: | 48 |

Test Groups

Treatments were assigned to the pens using a complete randomized block design. Treatments were administered to the pens at start of study day 0. The treatments will identified by numeric codes. Challenged control treatments comprise the administration of pathogens as the control. Challenged Ascus compositions comprise the administration of experimental microbes. Specific treatment groups are as follows.

TABLE 39

Test Groups

| Cp Trt | Challenged | Treatment Description | No. of Birds/Pen | No. of Pens | Number of Birds/Trt |
|---|---|---|---|---|---|
| 1 | Yes | Challenged Control (Non-medicated) | 25 | 8 | 200 |
| 2 | Yes | Challenged Control with Salinomycin | 25 | 8 | 200 |
| 3 | Yes | Challenged, Ascus Composition administered: Ascusbbr_4729, Ascusbbr_331885, Ascusbbr_170211 (spray application) | 25 | 8 | 200 |
| 4 | Yes | Challenged, Ascus Composition administered: Ascusbbr_4729, Ascusbbr_33, Ascusbbr_127 (spray application) | 25 | 8 | 200 |

Housing and Management

Housing

Treatments were randomly assigned to each pen using Microsoft Excel random number generator by the Data Manager. Birds were assigned to the pens randomly.

Birds were housed within an environmentally controlled in concrete floor pens providing floor space & bird density of [~0.55 ft$^2$/bird (day 0); ~0.69 ft$^2$/bird (day 21 after lesion scores)], temperature, humidity, lighting, feeder and water space were similar for all test groups. Birds were placed in clean pens containing an appropriate depth of clean wood shavings to provide a comfortable environment for the chicks. Additional shavings were added to pens in order to maintain bird comfort. Lighting was via incandescent lights and a commercial lighting program was used as follows.

TABLE 40

Lighting

| Approximate Bird Age (days) | Approximate Hours of Continuous Light per 24 hr period | ~Light Intensity (foot candles) |
|---|---|---|
| 0-4 | 24 | 1.0-1.3 |
| 5-10 | 10 | 1.0-1.3 |
| 11-18 | 12 | 0.2-0.3 |
| 19-end | 16 | 0.2-0.3 |

Environmental conditions for the birds (i.e. bird density, temperature, lighting, feeder and water space) were similar for all treatment groups. In order to prevent bird migration and bacterial spread from pen to pen, each pen will have a solid wood or plastic divider for approximately 24 inches in height between pens.

Vaccinations and Therapeutic Medication

Birds were vaccinated for Mareks at the hatchery. Upon receipt (study day 0), birds were vaccinated for Newcastle and Infectious Bronchitis and Coccivac by spray application using a spray cabinet. Documentation of vaccine manufacturer, lot number and expiration date was provided with the final report.

Water

Water was provided ad libitum throughout the study via one automatic nipple drinker (4 nipples per drinker) per pen. Drinkers were checked twice daily and cleaned as needed to assure a clean and constant water supply to the birds.

Feed

Feed was provided ad libitum throughout the study via one hanging, ~17-inch diameter tube feeder per pen. A chick feeder tray was placed in each pen for approximately the first 4 days. Birds were placed on their respective treatment diets upon receipt (day 0) according to the Experimental Design. Feed added and removed from pens from day 0 to study end was weighed and recorded.

Daily Observations

The test facility, pens and birds were observed at least twice daily for general flock condition, lighting, water, feed, ventilation and unanticipated events. If abnormal conditions or abnormal behavior is noted at any of the twice-daily observations they were documented and included with the study records. The minimum-maximum temperature of the test facility was recorded once daily.

Pen Cards

There were 2 cards attached to each pen. One card identifies the pen number and the second will include the treatment number.

Animal Handling

The animals were kept under ideal conditions for livability. The animals were handled in such a manner as to reduce injuries and unnecessary stress. Humane measures were strictly enforced.

Veterinary Care, Intervention and Euthanasia

Birds that develop clinically significant concurrent disease unrelated to the test procedures may, at the discretion of the Study Investigator, or a designee, be removed from the study and euthanized in accordance with site SOPs. In addition, moribund or injured birds may also be euthanized upon authority of a Site Veterinarian or a qualified technician. The reason for withdrawal was documented. If an animal dies, or is removed and euthanized for humane reasons, it was recorded on the mortality sheet for the pen and a necropsy performed and was filed to document the reason for removal. If euthanasia is deemed necessary animals were euthanized by cervical dislocation.

Mortality and Culls

From Day 0 to study end any bird that is found dead or is sacrificed was weighed and necropsied. The weight and probable cause of death and necropsy findings were recorded on the mortality record. If sex-slips are noted at any time during the study they were removed, weighed, necropsied to confirm sex and recorded on the pen mortality record.

Body Weights and Feed Intake

Birds were weighed by pen on approximately day 0, 17, 28 and 35. The feed remaining in each pen was weighed and recorded on study days 17, 28 and 35. The feed intake during days 0-17, 17-28, and 0-35 was calculated.

Weight Gains and Feed Conversion

Average bird weight, on a pen basis, on each weigh day was summarized. Bird weight gain by pen days 17-28 was calculated. The average feed conversion was calculated on the study days 17 and 28 (i.e. days 0-17, 17-35, and 0-35) using the total feed consumption for the pen divided by the total weight of surviving birds. Adjusted feed conversion was calculated using the total feed consumption in a pen divided by the total weight of surviving birds and weight of birds that died or were removed from that pen.

Coccidiosis Challenge

All birds will each receive a 1× dose of Coccivac by spray cabinet on approximately study day 0.

*Clostridium perfringens* Challenge

*Clostridium* Challenge

The *Clostridium perfringens* culture (CL-15) was grown ~5 hrs at ~37° C. in Fluid Thioglycollate medium containing starch. CL-15 is a field strain of *Clostridium perfringens* from a broiler outbreak in Colorado. For each pen of birds, a fixed amount of the broth culture (~2-3 ml/bird) was mixed with a fixed amount of treatment feed (~25 g/bird) in the feeder tray. The amount of feed, volume and quantitation of culture inoculum, and number of days dosed were documented in the final report and all pens were treated the same. Birds will receive the *C. perfringens* culture for one day (Study day 17). The target is 10% mortality with a minimum 5% in the challenged, non-medicated group.

Method of Administration

Administration of the *Clostridium perfringens* (CL-15, Type A, α and β2 toxins) cultures in this study was via the feed. Feed from each pen's feeder was used to mix with the culture. Prior to placing the cultures in the pens the treatment feed was removed from the birds for approximately 4-8 hours. For each pen of birds, a fixed amount (~2.5 ml/bird) of the broth culture at a concentration of approximately 2.0-9.0×$10^8$ cfu/ml was mixed with a fixed amount of feed (~25 g/bird) in the feeder tray and all challenged pens were treated the same. Most of the culture-feed was consumed within 1-2 hours. So that birds in all treatments are treated similar, the groups that are not challenged will also have the feed removed during the same time period as the challenged groups.

Lesion Scoring

On study day 21, 5 birds were randomly selected from each pen (by first bird caught), sacrificed and evaluated for intestinal lesions scored for necrotic enteritis. Lesions were scored as follows:

0=normal: no NE lesions, small intestine has normal elasticity (rolls back to normal position after being opened)

1=mild: small intestinal wall was thin and flaccid (remains flat when opened and doesn't roll back into normal position after being opened); excess mucus covering mucus membrane 2=moderate: noticeable reddening and swelling of the intestinal wall; minor ulceration and necrosis of the intestine membrane; excess mucus 3=severe: extensive area(s) of necrosis and ulceration of the small intestinal membrane; significant hemorrhage; layer of fibrin and necrotic debris on the mucus membrane (Turkish towel appearance)

4=dead or moribund: bird that would likely die within 24 hours and has NE lesion score of 2 or more; or birds that died due to necrotic enteritis.

TABLE 41

| Results | | | | |
|---|---|---|---|---|
| Trt Group | Avg Individual Bird Wt Gain (kg) | Adj. Feed Conversion | Mortality | NE-Lesion Score |
| 1 | 1.912 | 1.735 | 39.5% | 3.55 |
| 2 | 2.090 | 1.712 | 5% | 1.00 |
| 3 | 1.968 | 1.724 | 27.5% | 3.4 |
| 4 | 2.006 | 1.695 | 24.8% | 2.9 |

The birds were treated with a composition of Ascus microorganisms to determine their effects on performance and the prevention of *Clostridium* perfringens infection. Two different microbial compositions were tested. The first composition consisted of Ascusbbr_4729, Ascusbbr_331885, Ascusbbr_170211, and the second consisted of Ascusbbr_4729, Ascusbbr_33, Ascusbbr_127. Microorganisms were administered once to the experimental birds via spray application prior to pen placement. All birds were on a commercially relevant pelleted feed.

Birds were challenged with *C. perfringens* on day 17 of the study. On day 21, 5 birds were randomly selected, sacrified, and lesion scored. Mortality and feed intake were measured throughout the experiment. At the end of the experiment, birds were sacrificed and weighed. Feed conversion was calculated based on the total feed consumption for the pen divided by the total weight of the surviving birds. The treatment group receiving Ascus microorganism composition 1 (treatment 3) was found to have slightly improved feed conversion (0.63%), slightly higher weight (2.93%), slightly lower lesion scores (4.23%), and lower percent mortality (30.37%) when compared to the challenged control. The treatment group receiving Ascus microorganism composition 2 (treatment 4) was found to have improved feed conversion (2.31%), higher weight (4.91%), lower lesion scores (18.31%), and lower percent mortality (37.22%) when compared to the challenged control. The salinomycin control outperformed all groups.

Example VII. Trial 4—In Vivo Evaluation of Necrotic Enteritis with Multiple Ascus Microbial Compositions Vs. *Clostridium perfringens*

Experimental Design

Experimental Ration

Rations consisted of non-medicated commercial-type broiler starter, grower, and finisher diets compounded according to NRC guidelines and contained feedstuffs commonly used in the United States. Rations were fed ad libitum from date of chick arrival as follows: Starter—DOT 0 until DOT 21, grower DOT 21 to DOT 35, and finisher DOT 35 to DOT 42 (study termination). Diets were fed as crumbles (starter feed) or pellets (grower and finisher feed).

Animal Information

One thousand eight hundred (1,800) day-of-hatch Cobb male broiler chicks were obtained. The strain was Cobb× Cobb. Birds were sexed at the hatchery. All birds were vaccinated by spray cabinet with a commercial coccidia vaccine at recommended dosage. Only healthy appearing chicks were used in this study.

Housing

Upon arrival chicks were raised in 5×10 feet floor pens (stocking density of 1.0 $feet^2$ per bird) with approximately four (4) inches of fresh pine shavings (at placement), in a solid-sided barn, with concrete floors under ambient humidity. Litter was not replaced or amended during the course of this study. Feed and water were available ad libitum throughout the trial. Each pen contained 1 (one) tube feeder and 1 (one) bell drinker (50 bird to feeder/drinker ratio). Thermostatically controlled gas heaters were the primary heat source for the barn (if needed). One (1) heat lamp per pen provided supplemental heat during brooding. Fans were used to cool birds. Birds were provided a lighting program as per the primary breeder recommendations. The pen diagram was documented and included in final report with source data.

Probiotic Administration

After coccidia vaccine administrations all chicks in Treatments 3 were coarse sprayed with 0.25 ml/chick of the Ascus probiotic and placed under bright light to allow preening. Once dry, chicks were placed in treatment appropriate pens.

TABLE 42

| | | | Treatments | | |
|---|---|---|---|---|---|
| ID | TREATMENT DESCRIPTION | COCCI-VACCINE | CLOSTRIDIUM PERFRINGENS CHALLENGE [1] | PENS/ TREATMENT | BIRDS/PEN |
| T1 | Nonmedicated Cocci Vaccine (Challenge Control) | DOT 0 | DOT 19, 20, & 21 | 12 | 50 |
| T2 | Nonmedicated Cocci Vaccine (Negative Control) | DOT 0 | NO | 12 | 50 |
| T3 | Ascus Probiotic: Ascusbbr_409, Ascusbbr_5796, Ascusbbr_1686 | DOT 0 | DOT 19, 20, & 21 | 12 | 50 |
| T4 | Ascus Probiotic: Ascusbbr_409, Ascusbbr_5796, Ascusbbr_185064 | DOT 0 | DOT 19, 20, & 21 | 12 | 50 |

[1] DOT 19, 20, & 21:*Clostridium perfringens* was added into the water at a dose of approximately $1 \times 10^8$ CFU/ml/bird.
DOT = Day of trial
*Probiotics were sprayed on chicks at 0.25 ml/chick for Treatments 3 and 4 at 1 day of age prior to placement Bird Allocation and Pen Randomization One thousand eight hundred birds were assigned to three treatment groups with twelve replicate pens per treatment and 50 birds per pen. Pen facility was divided into twelve blocks with each block containing each of the three treatment groups. Treatment groups were assigned to pens using randomized complete block. The study began when birds were placed (day-of-hatch; DOT 0), at which time birds were allocated to experimental pens. Only healthy birds were selected. On DOT 0, group body weights were recorded by pen. No birds were replaced during the course of the study.

Challenge Administration and Sample Collection and Analysis

Necrotic Enteritis Challenge

The challenge model consisted of coccidia from the DOT 0 vaccine, one coccidia seeding at DOT 14, and *Clostridium perfringens* combination.

*Clostridium perfringens* in Drinking Water

Treatment feed and water was withdrawn for a few hours prior to administration of *Clostridium perfringens*. A measured amount of *Clostridium perfringens* was added to water that was consumed within 30 minutes was used for each pen. The *Clostridium perfringens* culture was added to this water and thoroughly mixed and given to birds in each challenge pen. Once the challenge water was consumed treatment feed and water were returned to pen. *Clostridium perfringens* was added to the water on DOT 19, 20, and 21 to all bird except for Birds in Treatment Group 2.

Coccidia Challenge

Was from cycling of DOT 0 vaccination and *E. maxima* (20 ml per pen) spread around feeders and drinkers on DOT 14. (Except Treatment Group 2).

Necrotic Enteritis Lesion Scoring

On DOT 21 three (3) birds per pen were humanely euthanized, necropsied and lesion scored.

Lesion score 0=Normal

Lesion score 1=Slight mucus covering small intestine

Lesion score 2=Necrotic small intestine mucosa

Lesion score 3=Sloughed and blood small intestine mucosa and contents

Intestinal Content Sampling

On DOT 21 and 42 collected samples of the small intestines of two (2) birds per pen.

Feed Changes

Birds received treatment appropriate feed from DOT 0 to DOT 42. On DOT 21 remaining starter feed was removed, weighed, and replaced with grower feed. On DOT 35 remaining grower feed was removed, weighed, and replaced with finisher feed. On DOT 42 remaining finisher feed was removed and weighed back. All unconsumed feed was weighed and disposed of in the SPRG onsite disposal pit.

Body and Feed Weight

All birds were weighed by pen on DOT 0, 21, 35, and 42. Feed added to each pen's feeder was weighed at the beginning of each formulation period on DOT 0, 20, and 35 (starter, grower, and finisher respectively). Any additional bags of feed were weighed (and documented) for each pen (as required) during each formulation period. Feed was distributed as needed to feeders from pre-weighed bags (assigned to each pen) throughout each period. Feed remaining in feeders (and feed bags if applicable) was weighed and disposed of on DOT 21, 35, and 42. Empty pen feeder weights were recorded prior to study initiation. The trial was terminated on DOT 42.

Management

Disease Control

No concomitant drug therapy was used during the study. Disposable plastic boot were worn by all study personnel required to enter pens (e.g., collect birds for study procedures). The disposable plastic boots were removed as the person stepped out of pen to avoid tracking fecal material throughout the facility. Disposable plastic boots were properly disposed of after use.

Monitoring

All birds were monitored for general flock condition, temperature, lighting, water, feed, litter condition, and unanticipated house conditions/events. Findings were documented twice daily during the regular working hours (one observation recorded final study day). On Saturday, Sunday, and observed holidays, one (1) observation was recorded.

Mortality

Pens were checked daily for mortality. Birds were only culled to relieve suffering. Date and removal weight (kg) were recorded on all birds culled (or found dead). A gross necropsy was performed on all dead or culled birds to determine the bird sex and probable cause of death. Signs of Necrotic Enteritis or non-specific enteritis were noted.

Bird and Feed Disposition

All birds were disposed of by appropriate methods. All mortalities and remaining feeds (including mixer flushes) were buried in the Southern Poultry Research Group on site disposal pit.

Scales

Scale maintenance and standardization procedures were followed prior to use.

Source Data Control and Handling

Data were recorded in indelible ink. Entries were legible and source data sheet signed (or initialed), and dated by individual recording entry. All source data errors and/or changes were initialed, dated, and a brief explanation (or error code) written directly on form.

Data Management

Data management and statistical analysis of weight gain, feed consumption, and feed conversion, and lesion score results were performed.

TABLE 43

Results

| Trt Group | Avg Individual Bird Wt Gain (kg) | Adj. Feed Conversion | Mortality | NE-Lesion Score |
|---|---|---|---|---|
| 1 | 2.607 | 1.709 | 15.8% | 0.5 |
| 2 | 2.516 | 1.698 | 5.2% | 0 |
| 3 | 2.518 | 1.690 | 10% | 0.15 |
| 4 | 2.559 | 1.694 | 12% | 0.4 |

The birds were treated with a composition of Ascus microorganisms to determine their effects on performance and the prevention of *Clostridium perfrigens* infection. Two different microbial compositions were tested. The first composition consisted of Ascusbbr_409, Ascusbbr_5796, Ascusbbr_1686, and the second consisted of Ascusbbr_409, Ascusbbr_5796, and Ascusbbr_185064. Microorganisms were administered once to the experimental birds via spray application prior to pen placement. All birds were on a commercially relevant pelleted feed.

Birds were challenged with *C. perfringens* on day 17 of the study. On day 21, 5 birds were randomly selected, sacrificed, and lesion scored. Mortality and feed intake were measured throughout the experiment. At the end of the experiment, birds were sacrificed and weighed. Feed conversion was calculated based on the total feed consumption for the pen divided by the total weight of the surviving birds. The treatment group receiving Ascus microorganism composition 1 (treatment 3) was found to have slightly improved feed conversion (1.11%), lower lesion scores (70.0%), and lower percent mortality (36.70%) when compared to the challenged control. The treatment group receiving Ascus microorganism composition 2 (treatment 4) was found to have slightly improved feed conversion (0.88%), lower lesion scores (20.0%), and lower percent mortality (24.05%) when compared to the challenged control. Surprisingly, the challenged control exhibited the highest weight gain.

Example VIII. Comparative Analysis of MIC Scores from Published Work of Other Groups Utilizing Ascus Biosciences' technology, the performance of currently available microbial feed additive products was predicted.

Direct-fed microbial products that claim to enhance broiler performance are available on the market. A few of these products contain microorganism strains that are native chicken gastrointestinal microorganisms or are within 97% sequence similarity of native gastrointestinal microorganisms. Here, we've identified the strains that are used in these products, and calculated their platform score with respect to feed efficiency and body weight (FIG. 15 and FIG. 16). As can be seen from the curves, many of the currently available strains fall below the threshold used to define "useful" and "non-useful" strains. The one strain above the cutoff, *Enterococcus faecium*, has shown beneficial effects when fed to broiler chickens.

Other common strains used in fowl/poultry direct fed microbial products, were either not found in the gastrointestinal tract of any birds or were less than 97% similar to a strain found within the birds. Scores could not be generated for these microorganisms (Table 44).

TABLE 44

Microbes not appearing on the curve in FIG. 15 or FIG. 16.
Microbial Organism

*Bacillus subtilis* DSM 29870
*Bacillus subtilis* DSM 29871
*Bacillus subtilis* AJ276351
*Bacillus vallimortis* AB021198
*Bacillus amyloliquefaciens* DSM 29869
*Bacillus amyloliquefaciens* DSM 29872
*Bifidobacterium animalis*

*Enterococcus faecium*: 0.72083

Positive effects on overall weight gain, did not change FCR: Effects of dietary *Enterococcus faecium* on growth performance, carcass characteristics, faecal microbiota, and blood profile in broilers. doi: 10.17221/8680-VETMED Positive effects of weight gain: Effects of *Enterococcus faecium* supplementation and floor type on performance, morphology of erythrocytes and intestinal microbiota in broiler chickens. doi: 10.1080/00071668.2010.507241.

Positive effects on weight gain: Effects of *Enterococcus faecium* and dried whey on broiler performance, gut histomorphology and intestinal microbiota. DOI: 10.1080/17450390601106655

Positive effects on weight gain and intestinal development: Intestinal Structure and Function of Broiler Chickens on Diets Supplemented with a Synbiotic Containing *Enterococcus faecium* and Oligosaccharides. doi:10.3390/ijms9112205.

*Pediococcus acidilactici*: 0.17931

Did not affect body weight: Effects of dietary probiotic (*Pediococcus acidilactici*) supplementation on performance, nutrient digestibility, egg traits, egg yolk cholesterol, and fatty acid profile in laying hens. DOI: doi.org/10.3382/ps.2012-02370.

Did not affect body weight: Efficacy of Bactocell® and Toyocerin® as Probiotics on Growth Performance, Blood Parameters and Intestinal Morphometry of Turkey Poults.

No significant difference to performance: Growth performance and immune response of broiler chickens fed diets supplemented with probiotic and (or) prebiotic preparations.

Probiotic of *P. acidilactici* alone did not improve performance: Effect of Probiotic, Prebiotic, and Synbiotic on Broiler Performance.

*Lactobacillus salivarius* DSM 16351: 016462 (Weight), 0.31742 (Feed Conversion)

Does not improve body weight, slight effect on feed conversion ratio at times: Influence of probiotic administration by feed or water on growth parameters of broilers reared on medicated and nonmedicated diets. DOI: doi.org/10.3382/japr.2009-00084

*Lactobacillus reuteri*: 0.26096

Slight effect on feed conversion ratio at times: Influence of probiotic administration by feed or water on growth parameters of broilers reared on medicated and nonmedicated diets. DOI: doi.org/10.3382/japr.2009-00084.

*Bacillus amyloliquefaciens* AB255669: 0.18434

No effect on performance: Efficacy of protected sodium butyrate, a protected blend of essential oils, their combination, and *Bacillus amyloliquefaciens* spore suspension against artificially induced necrotic enteritis in broilers DOI: hypertext transfer protocol secure://doi.org/10.3382/ps.2011-01853.

Example IX. Volatile Fatty Acid and Carbon Source Assays

Volatile Fatty Acid Assay

In order to assess the ability of the strains to produce volatile fatty acids, HPLC was utilized to measure the concentrations of acetic acid, butyric acid, propionic acid, and lactic acid in spent media.

A single colony was picked from each of the desired strains (from anaerobic agar plates) and was inoculated into fresh media. At the same time, a media blank was also prepared. The cultures and the media blank were incubated at 37° C. until significant growth was visible (~5 days). The OD600 was determined for each culture, and the strain ID was confirmed with Illumina sequence. An aliquot of culture was filter sterilized into an acid washed and autoclaved glass 15 mL sample vial which was then analyzed by HPLC.

HPLC reactions were performed on a BioRad Aminex HPX-87H with the following conditions: 60° C., 0.5 mL/min mobile phase 0.00325 N H2S04, 500 psi, 35C RI detector, 45 min run time, injection volume of 5 μL. Concentrations of acetic acid, butyric acid, propionic acid, and lactic acid were quantified for the medium blanks as well as the sterile filtered culture samples. The strains were considered positive for volatile fatty acid production if the detected concentration of the individual fatty acids in the spent medium were higher than in the media blank. See Table 45.

TABLE 45

VFA production from microbes of the present disclosure.

| Strain ID | Condition/Media | lactic acid | acetic acid | propionic acid | butyric acid |
| --- | --- | --- | --- | --- | --- |
| Ascusbbr_94 | MRS | + | 0 | 0 | 0 |
| Ascusbbr_94 | MRS 10 mM_Acetic_Acid | + | − | 0 | 0 |
| Ascusbbr_91 | M2GSC Salts Butyric Acid | 0 | + | + | − |
| Ascusbbr_91 | BL Amino Acid D | + | + | 0 | 0 |
| Ascusbbr_91 | CMC Amino Acid D | 0 | + | + | 0 |
| Ascusbbr_84 | CMC Amino Acid D | 0 | + | + | 0 |
| Ascusbbr_830 | BL Amino Acid D | + | + | 0 | 0 |
| Ascusbbr_830 | CMC Amino Acid D | 0 | + | + | 0 |
| Ascusbbr_7779 | M2GSC_Arabinose Xylose | + | + | + | + |
| Ascusbbr_7363 | *Spirillium* Butyric Acid | − | 0 | 0 | + |
| Ascusbbr_7363 | M2GSC Salts Butyric Acid | 0 | + | + | − |
| Ascusbbr_72076 | 1:10 MRS | + | + | 0 | 0 |
| Ascusbbr_72076 | BL | + | + | + | 0 |
| Ascusbbr_72076 | M2GSC_Arabinose Xylose | + | + | + | + |
| Ascusbbr_72076 | BL Amino Acid D | + | + | 0 | 0 |
| Ascusbbr_6957 | BL Amino Acid D | + | + | 0 | 0 |
| Ascusbbr_6957 | CMC Amino Acid D | 0 | + | + | 0 |
| Ascusbbr_6097 | M2GSC_Arabinose Xylose | + | + | + | + |
| Ascusbbr_6097 | *Spirillium* Butyric Acid | − | 0 | 0 | + |
| Ascusbbr_6097 | BL Amino Acid D | + | + | 0 | 0 |
| Ascusbbr_6097 | CMC Amino Acid D | 0 | + | + | 0 |
| Ascusbbr_5796A | MRS | + | + | 0 | 0 |
| Ascusbbr_5796B | MRS | + | + | 0 | 0 |
| Ascusbbr_5796C | MRS | + | + | 0 | 0 |
| Ascusbbr_5796A | BL | + | + | 0 | 0 |
| Ascusbbr_5796B | BL | + | + | 0 | 0 |
| Ascusbbr_5796C | BL | + | + | + | 0 |
| Ascusbbr_5796A | 1:10 MRS | + | + | 0 | 0 |
| Ascusbbr_5796A | M2GSC_Arabinose Xylose | + | + | + | + |
| Ascusbbr_5796A | BL Amino Acid D | + | + | 0 | 0 |
| Ascusbbr_5796A | CMC Amino Acid D | 0 | + | + | 0 |
| Ascusbbr_5796A | 1:10 MRS | 0 | + | 0 | 0 |
| Ascusbbr_48584 | MRS | + | + | 0 | 0 |

TABLE 45-continued

VFA production from microbes of the present disclosure.

| Strain ID | Condition/Media | lactic acid | acetic acid | propionic acid | butyric acid |
|---|---|---|---|---|---|
| Ascusbbr_4729 | M2GSC_Arabinose Xylose | + | + | + | + |
| Ascusbbr_42760A | MRS | + | + | 0 | 0 |
| Ascusbbr_42760A | 1:10 MRS | + | + | 0 | 0 |
| Ascusbbr_42760B | 1:10 MRS | 0 | + | 0 | 0 |
| Ascusbbr_42760A | BL | + | + | + | 0 |
| Ascusbbr_42760A | M2GSC_Arabinose Xylose | + | + | + | + |
| Ascusbbr_42760A | BL Amino Acid D | + | + | 0 | 0 |
| Ascusbbr_409A | MRS | + | + | 0 | 0 |
| Ascusbbr_409B | MRS | + | + | 0 | 0 |
| Ascusbbr_409A | BL | + | + | + | 0 |
| Ascusbbr_409B | BL | + | + | + | 0 |
| Ascusbbr_409C | BL | + | + | + | 0 |
| Ascusbbr_409A | M2GSC_Arabinose Xylose | + | + | + | + |
| Ascusbbr_409A | BL Amino Acid D | + | + | 0 | 0 |
| Ascusbbr_409B | BL Amino Acid D | + | + | 0 | 0 |
| Ascusbbr_409C | BL Amino Acid D | + | + | 0 | 0 |
| Ascusbbr_409A | CMC Amino Acid D | 0 | + | + | 0 |
| Ascusbbr_409B | CMC Amino Acid D | 0 | + | + | 0 |
| Ascusbbr_409A | 1:10 MRS | 0 | + | 0 | 0 |
| Ascusbbr_38717A | MRS | + | + | 0 | 0 |
| Ascusbbr_38717B | MRS | + | + | 0 | 0 |
| Ascusbbr_38717A | BL | + | + | + | 0 |
| Ascusbbr_38717A | M2GSC_Arabinose Xylose | + | + | + | + |
| Ascusbbr_38717A | 1:10 MRS | 0 | + | 0 | 0 |
| Ascusbbr_36257 | BL Amino Acid D | + | + | 0 | 0 |
| Ascusbbr_359892 | CMC Amino Acid D | 0 | + | + | 0 |
| Ascusbbr_35 | M2GSC_Arabinose Xylose | + | + | + | + |
| Ascusbbr_339 | *Spirillium* Butyric Acid | − | 0 | 0 | + |
| Ascusbbr_339 | M2GSC Salts Butyric Acid | 0 | + | + | − |
| Ascusbbr_339 | CMC Amino Acid D | 0 | + | + | 0 |
| Ascusbbr_331885 | MRS | + | + | 0 | 0 |
| Ascusbbr_331885 | BL Amino Acid D | + | + | 0 | 0 |
| Ascusbbr_33 | MRS | + | + | + | 0 |
| Ascusbbr_33 | BL | + | + | 0 | 0 |
| Ascusbbr_33 | 1:10 MRS | 0 | + | 0 | 0 |
| Ascusbbr_32731A | MRS | − | + | 0 | 0 |
| Ascusbbr_32731A | M2GSC Salts Butyric Acid | 0 | + | + | − |
| Ascusbbr_32731A | BL Amino Acid D | + | + | 0 | 0 |
| Ascusbbr_32731A | CMC Amino Acid D | 0 | + | + | 0 |
| Ascusbbr_32731A | 1:10 MRS | + | + | 0 | 0 |
| Ascusbbr_32731B | 1:10 MRS | 0 | + | 0 | 0 |
| Ascusbbr_322104 | 1:10 MRS | 0 | + | 0 | 0 |
| Ascusbbr_313454 | M2GSC_Arabinose Xylose | + | + | + | + |
| Ascusbbr_31 | BL Amino Acid D | + | + | 0 | 0 |
| Ascusbbr_3089 | *Spirillium* Butyric Acid | − | 0 | 0 | + |
| Ascusbbr_285160 | M2GSC_Arabinose Xylose | + | + | + | + |
| Ascusbbr_285160 | BL Amino Acid D | + | + | 0 | 0 |
| Ascusbbr_285160 | 1:10 MRS | 0 | + | 0 | 0 |
| Ascusbbr_28 | *Spirillium* Butyric Acid | − | 0 | 0 | + |
| Ascusbbr_28 | M2GSC Salts Butyric Acid | 0 | + | + | − |
| Ascusbbr_28 | BL Amino Acid D | + | + | 0 | 0 |
| Ascusbbr_28 | CMC Amino Acid D | 0 | + | + | 0 |
| Ascusbbr_265A | 1:10 MRS | + | + | 0 | 0 |
| Ascusbbr_265B | 1:10 MRS | 0 | + | 0 | 0 |
| Ascusbbr_265A | BL | + | + | + | 0 |
| Ascusbbr_265A | M2GSC_Arabinose Xylose | + | + | + | + |
| Ascusbbr_25200 | BL | + | + | + | 0 |
| Ascusbbr_25200 | M2GSC_Arabinose Xylose | + | + | + | + |
| Ascusbbr_247 | M2GSC_Arabinose Xylose | + | + | + | + |

TABLE 45-continued

VFA production from microbes of the present disclosure.

| Strain ID | Condition/Media | lactic acid | acetic acid | propionic acid | butyric acid |
|---|---|---|---|---|---|
| Ascusbbr_247A | M2GSC Salts Butyric Acid | 0 | + | + | − |
| Ascusbbr_247B | M2GSC Salts Butyric Acid | 0 | + | + | − |
| Ascusbbr_247A | BL Amino Acid D | + | + | 0 | 0 |
| Ascusbbr_247A | CMC Amino Acid D | 0 | + | + | 0 |
| Ascusbbr_247B | CMC Amino Acid D | 0 | + | + | 0 |
| Ascusbbr_2158 | CMC Amino Acid D | 0 | + | + | 0 |
| Ascusbbr_21169 | MRS | + | + | 0 | 0 |
| Ascusbbr_21169 | BL | + | + | 0 | 0 |
| Ascusbbr_19 | MRS | + | 0 | 0 | 0 |
| Ascusbbr_19 | 1:10 MRS | + | + | 0 | 0 |
| Ascusbbr_185064 | MRS | − | + | + | 0 |
| Ascusbbr_185064 | BL Amino Acid D | + | + | 0 | 0 |
| Ascusbbr_1789 | *Spirillium* Butyric Acid | − | 0 | 0 | + |
| Ascusbbr_1789 | BL Amino Acid D | + | + | 0 | 0 |
| Ascusbbr_1789 | CMC Amino Acid D | 0 | + | + | 0 |
| Ascusbbr_1789 | 1:10 MRS | 0 | + | 0 | 0 |
| Ascusbbr_173 | *Spirillium* Butyric Acid | − | 0 | 0 | + |
| Ascusbbr_173 | BL Amino Acid D | + | + | 0 | 0 |
| Ascusbbr_173 | CMC Amino Acid D | 0 | + | + | 0 |
| Ascusbbr_17 | M2GSC_Arabinose Xylose | + | + | + | + |
| Ascusbbr_1686 | MRS | + | + | 0 | 0 |
| Ascusbbr_1686 | BL10 mM Acetic Acid | + | + | + | 0 |
| Ascusbbr_1686 | MRS10 mM Acetic Acid | + | − | 0 | 0 |
| Ascusbbr_1686 | M2GSC_Arabinose Xylose | + | + | + | + |
| Ascusbbr_1686 | *Spirillium* Butyric Acid | − | 0 | 0 | + |
| Ascusbbr_1686 | BL Amino Acid D | + | + | 0 | 0 |
| Ascusbbr_1686 | CMC Amino Acid D | 0 | + | + | 0 |
| Ascusbbr_1686 | 1:10 MRS | 0 | + | 0 | 0 |
| Ascusbbr_14834 | 1:10 MRS | + | + | 0 | 0 |
| Ascusbbr_14834 | BL | + | + | + | 0 |
| Ascusbbr_14834 | *Spirillium* Butyric Acid | − | 0 | 0 | + |
| Ascusbbr_14834 | M2GSC Salts Butyric Acid | 0 | + | + | − |
| Ascusbbr_14834 | BL Amino Acid D | + | + | 0 | 0 |
| Ascusbbr_14834 | CMC Amino Acid D | 0 | + | + | 0 |
| Ascusbbr_14690A | MRS | + | 0 | 0 | 0 |
| Ascusbbr_14690B | MRS | + | 0 | 0 | 0 |
| Ascusbbr_14690C | MRS | + | 0 | 0 | 0 |
| Ascusbbr_14690A | M2GSC_Arabinose Xylose | + | + | + | + |
| Ascusbbr_14690A | *Spirillium* Butyric Acid | − | 0 | 0 | + |
| Ascusbbr_14690A | BL Amino Acid D | + | + | 0 | 0 |
| Ascusbbr_14690A | 1:10 MRS | 0 | + | 0 | 0 |
| Ascusbbr_144 | BL Amino Acid D | + | + | 0 | 0 |
| Ascusbbr_1436 | MRS | + | + | 0 | 0 |
| Ascusbbr_1436A | 1:10 MRS | + | + | 0 | 0 |
| Ascusbbr_1436B | 1:10 MRS | 0 | + | 0 | 0 |
| Ascusbbr_1436A | BL | + | + | + | 0 |
| Ascusbbr_1436A | M2GSC_Arabinose Xylose | + | + | + | + |
| Ascusbbr_1436A | *Spirillium* Butyric Acid | − | 0 | 0 | + |
| Ascusbbr_1436A | M2GSC Salts Butyric Acid | 0 | + | + | − |
| Ascusbbr_1436A | BL Amino Acid D | + | + | 0 | 0 |
| Ascusbbr_1436A | CMC Amino Acid D | 0 | + | + | 0 |
| Ascusbbr_136 | *Spirillium* Butyric Acid | − | 0 | 0 | + |
| Ascusbbr_136 | M2GSC Salts Butyric Acid | 0 | + | + | − |
| Ascusbbr_13398 | CMC Amino Acid D | 0 | + | + | 0 |
| Ascusbbr_128 | M2GSC_Arabinose Xylose | + | + | + | + |
| Ascusbbr_127 | MRS | + | + | 0 | 0 |
| Ascusbbr_10593A | MRS | + | + | 0 | 0 |
| Ascusbbr_10593B | MRS | + | + | 0 | 0 |

TABLE 45-continued

VFA production from microbes of the present disclosure.

| Strain ID | Condition/Media | lactic acid | acetic acid | propionic acid | butyric acid |
|---|---|---|---|---|---|
| Ascusbbr_10593A | *Spirillium* Butyric Acid | − | 0 | 0 | + |
| Ascusbbr_10593A | M2GSC Salts Butyric Acid | 0 | + | + | − |
| Ascusbbr_10593A | BL Amino Acid D | + | + | 0 | 0 |

Soluble Carbon Source Assay

In order to assess the ability of the strains to degrade various soluble carbon sources, OD600 was used to measure growth of strains on particular carbon sources over a period of time.

A single colony from each of the desired strains (on anaerobic agar plates) was inoculated into fresh medium. Strains were inoculated into a carbon source assay anaerobically; the assay was set up in a 2 mL sterile 96well plate, with each well containing M2GSC salts, vitamins, minerals, sodium sulfide, and a single carbon source. Carbon sources included whole chicken feed, Soytone, Maltose, Raffinose, Starch, Arabinose, Sucrose, Xylose, Succinate, Cellobiose, Casamino acids, Glucose, Galactose, Manitol, Peptone, Gluconate, Malt Extract, Casein Digest, Beef Extract, and Chitosan. Cells were inoculated such that each well started at an OD600 of 0.01. The ODs were read at 600 nm with the "Synergy H4 hybrid plate reader". Strain ID was confirmed with Illumina sequencing after all wells were in stationary phase.

XTT reduction was simultaneously measured by adding 100 ul of carbon source with strain culture to a 200 ul flat bottom plate. To this aliquot 50 ul of the XTT mix (5 ml of sterile XTT with 100 ul of sterile N-methyl dibenzopyrazine methyl sulfate) was added. This culture was then incubated for 1 hour at 37° C. anaerobically in the dark. XTT reduction was determined by absorbance at 475 nm subtracted for the non-specific absorbance at 660 nm as well as the appropriate media and strain blanks. See Table 46.

TABLE 46

Carbon source growth assays with microbes of the present disclosure.

| | Whole Chicken Food | Soytone | Maltose | Raffinose | Starch | Arabinose | Sucrose | Xylose | Succinate | Cellobiose | CasAmino |
|---|---|---|---|---|---|---|---|---|---|---|---|
| Ascusbbr_94 | | | | | + | | | | | + | |
| Ascusbbr_91 | | | + | | + | | | | | + | |
| Ascusbbr_84 | | | + | | + | | | | | + | |
| Ascusbbr_830 | | | + | | + | | | | | + | |
| Ascusbbr_7779 | | | | | + | + | | + | | + | |
| Ascusbbr_7363 | | | | | + | | | | + | + | |
| Ascusbbr_72076 | | | | | + | + | | + | | + | |
| Ascusbbr_6957 | | + | | | + | | | | | + | |
| Ascusbbr_6097 | | | + | | + | + | | + | + | + | |
| Ascusbbr_5796 | + | + | + | | + | + | | + | | + | |
| Ascusbbr_48584 | | | | | | | | | | | + |
| Ascusbbr_4729 | | | | | + | + | | + | | + | |
| Ascusbbr_42760 | | | | | + | + | | + | | + | |
| Ascusbbr_409 | | + | + | | + | + | | + | | + | |
| Ascusbbr_38717 | | | | | + | + | | + | | + | + |
| Ascusbbr_36257 | | | | | | | | | | | |
| Ascusbbr_359892 | | | + | | + | | | | | + | |
| Ascusbbr_35 | | | | | + | + | | + | | + | |
| Ascusbbr_339 | | | + | | + | | | | + | + | |
| Ascusbbr_331885 | | | | | | | | | | | |
| Ascusbbr_33 | + | + | | | | | | | | | |
| Ascusbbr_32731 | | | + | | + | | | | | + | |
| Ascusbbr_322104 | | | | | | | | | | | |
| Ascusbbr_313454 | | | | | + | + | | + | | + | |
| Ascusbbr_31 | | | | | | | | | | | |
| Ascusbbr_3089 | | | | | | | | + | | | |
| Ascusbbr_285160 | | | | | + | + | | + | | + | |
| Ascusbbr_28 | | | + | | + | | | | + | + | |
| Ascusbbr_265 | | | | | + | + | | + | | + | |
| Ascusbbr_25200 | | | | | + | + | | + | | + | |
| Ascusbbr_247 | | | + | | + | + | | + | | + | |
| Ascusbbr_2158 | | | + | | + | | | | | + | |
| Ascusbbr_21169 | | | | | | | | | | | |
| Ascusbbr_19 | | | | | | | | | | | |
| Ascusbbr_185064 | + | + | | + | | + | | | | | |
| Ascusbbr_1789 | | | + | | + | | | | | + | + |
| Ascusbbr_173 | | | + | | + | | | | | + | + |
| Ascusbbr_17 | | | | | + | + | | + | | + | |
| Ascusbbr_1686 | | | + | | + | + | | + | + | + | |

TABLE 46-continued

Carbon source growth assays with microbes of the present disclosure.

| | Glucose | Galactose | Manitol | Peptone | Gluconate | Malt Extract | Casein Digest | Beef Extract | Chitosan | MRS |
|---|---|---|---|---|---|---|---|---|---|---|
| Ascusbbr_14834 | | + | | + | | | + | + | | |
| Ascusbbr_14690 | | | | + | + | | + | + | + | |
| Ascusbbr_144 | | | | | | | | | | |
| Ascusbbr_1436 | + | + | + | + | + | | + | + | + | |
| Ascusbbr_136 | | | | + | | | | + | + | |
| Ascusbbr_13398 | | + | | + | | | | | + | |
| Ascusbbr_128 | | | | + | + | | + | | + | |
| Ascusbbr_127 | | + | | | | | | | | |
| Ascusbbr_10593 | | | | + | | | | + | + | |
| Ascusbbr_94 | + | | | | | | + | + | | + |
| Ascusbbr_91 | + | | | + | | | | + | | |
| Ascusbbr_84 | + | | | + | | | | + | | |
| Ascusbbr_830 | + | | | + | | | | + | | |
| Ascusbbr_7779 | + | | | | | | | + | | |
| Ascusbbr_7363 | + | | | + | | | | + | | |
| Ascusbbr_72076 | + | | | + | | | + | + | | + |
| Ascusbbr_6957 | + | | | + | | | | + | | |
| Ascusbbr_6097 | + | | | + | | | | + | | |
| Ascusbbr_5796 | + | | | + | | + | + | + | | + |
| Ascusbbr_48584 | + | + | + | + | + | + | + | + | + | + |
| Ascusbbr_4729 | + | | | | | | | + | | |
| Ascusbbr_42760 | + | | | + | | | + | + | | + |
| Ascusbbr_409 | + | | | + | | | + | + | | + |
| Ascusbbr_38717 | + | + | + | + | + | + | + | + | | + |
| Ascusbbr_36257 | + | | | + | | | | | | |
| Ascusbbr_359892 | + | | | + | | | | + | | |
| Ascusbbr_35 | + | | | | | | | + | | |
| Ascusbbr_339 | + | | | + | | | | + | | |
| Ascusbbr_331885 | + | | | + | | | + | | | + |
| Ascusbbr_33 | + | | | | | | + | + | | + |
| Ascusbbr_32731 | + | | | + | | | + | + | | + |
| Ascusbbr_322104 | + | | | | | | + | + | | + |
| Ascusbbr_313454 | + | | | | | | | + | | |
| Ascusbbr_31 | + | | | + | | | | | | |
| Ascusbbr_3089 | | | | + | | | | | | |
| Ascusbbr_285160 | + | | | + | | | + | + | | + |
| Ascusbbr_28 | + | | | + | | | | + | | |
| Ascusbbr_265 | + | | | + | | | + | + | | + |
| Ascusbbr_25200 | + | | | + | | | | + | | |
| Ascusbbr_247 | + | | | + | | | | + | | |
| Ascusbbr_2158 | + | | | + | | | | + | | |
| Ascusbbr_21169 | | | | + | | + | | | | + |
| Ascusbbr_19 | + | | | | | | + | + | | + |
| Ascusbbr_185064 | + | | | + | | | + | + | | + |
| Ascusbbr_1789 | + | | | + | | | + | + | | + |
| Ascusbbr_173 | + | | | + | | | | + | | |
| Ascusbbr_17 | + | | | | | | | + | | |
| Ascusbbr_1686 | + | | | + | | | + | + | | + |
| Ascusbbr_14834 | + | | | + | | | + | + | | + |
| Ascusbbr_14690 | + | | | + | | | + | + | | + |
| Ascusbbr_144 | + | | | + | | | | | | |
| Ascusbbr_1436 | + | | | + | | | + | + | | + |
| Ascusbbr_136 | + | | | + | | | | + | | |
| Ascusbbr_13398 | + | | | + | | | | | | |
| Ascusbbr_128 | + | | | | | | | + | | |
| Ascusbbr_127 | | | | | | | | | | + |
| Ascusbbr_10593 | + | | | + | | | | + | | |

Insoluble Carbon Source Assay

In order to assess the ability of the strains to degrade insoluble carbon sources, visual inspection was leveraged to qualitatively determine a strain's degradation capabilities.

For pure cultures, a single colony from each of the desired strains (from anaerobic agar plates) was inoculated into anaerobic Hungate tubes containing Lowe's semi defined media with cellulose paper, starch, or grass as the sole carbon source. (Lowe et al. 1985. J. Gen. Microbiol. 131: 2225-2229). A medium blank was also prepared. Cultures were checked visually for degradation of insoluble carbon sources. See FIG. 10.

Enrichments

The same protocols as described above for the VFA assay and the soluble carbon source assay were used for enrichment assays, but instead of inoculating with a single colony, fresh gastrointestinal sample was used. Gastrointestinal sample inocula and enrichments were Illumina sequenced to determine presence or absence of target strains. Sequencing datasets were integrated with cell count data to determine if target strains grew in vitro.

Example X. Competitive Exclusion Assays (In Vitro)

In order to assess the ability of the strains to compete against pathogens in the gastrointestinal tract of the fowl, competitive exclusion against *Clostridium perfringens* or *Salmonella enterica* was measured by co-culturing strains together in a medium representative of the broiler GI tract as well as in a minimal salts medium. After substantial cell growth, each co-culture was sequenced. The relative abundance of each strain was then used to determine the efficacy of the strains at competing with or inhibiting the pathogen.

Single colonies of the strains and pathogens were inoculated into 500 μL of MRS and TSB anaerobically. The OD readings were measured the following day, and fresh MRS and TSB co-cultures were inoculated such that each strain was at a starting OD of 0.01. 300 μL of the starting inoculum was collected and sequenced to provide a relative abundance at T0, and the starting abundance of each strain was confirmed.

Strains were considered successful at competing against the pathogenic strains if the pathogen experienced a theoretical percent decrease (relative abundance as determined by sequencing*coculture OD) of at least 50% when compared to the starting inoculum. Strains were considered to have a weak competitive exclusion effect if the final OD of the co-culture was lower than the OD of the pure pathogen culture. Strains were considered negative if they were overgrown by the pathogen. See Table 47 for results. When cocultured with *Clostridium perfringens*, 15 of the 24 strains (62.5%) exhibited an inhibitory effect against *C. perfrigens*. Of the strains cocultured with *Salmonella enterica*, 4 of the 7 strains (57.14%) tested exhibited an exhibitory effect against *S. enterica*. Strains that shared similar 16S sequences (97% sequence similarity) tended to exhibit similar effects on the pathogens—this includes Ascusbbr_33A and B; Ascusbbr_409A and B; Ascusbbr_5796A, B, and C; Ascusbbr_14690A, B, and C; and Ascusbbr_38717A and B. Strains related to Ascusbbr_10593, however, did show have a few differing results. Ascusbbr_10593A and B both inhibited *S. enterica*, but Ascusbbr_10593A seemed to have a slightly stronger inhibitory effect.

TABLE 47

Strain competition data for *C. perfringens* and *S. enterica*.

|  | Clostridium perfringens | Salmonella enterica |
| --- | --- | --- |
| Ascusbbr_19 | − | NT |
| Ascusbbr_33A | − | NT |
| Ascusbbr_33B | − | NT |
| Ascusbbr_127 | − | NT |
| Ascusbbr_409A | ++ | NT |
| Ascusbbr_409B | ++ | NT |
| Ascusbbr_1436 | ++ | + |
| Ascusbbr_1686 | ++ | NT |
| Ascusbbr_5796A | ++ | NT |
| Ascusbbr_5796B | ++ | NT |
| Ascusbbr_5796C | ++ | NT |
| Ascusbbr_21169 | ++ | NT |
| Ascusbbr_38717A | ++ | NT |
| Ascusbbr_38717B | ++ | NT |
| Ascusbbr_10593A | + | ++ |
| Ascusbbr_10593B | + | + |
| Ascusbbr_14690A | − | NT |
| Ascusbbr_14690B | − | NT |
| Ascusbbr_14690C | − | − |
| Ascusbbr_32731 | − | − |
| Ascusbbr_42760 | + | ++ |

TABLE 47-continued

Strain competition data for *C. perfringens* and *S. enterica*.

|  | Clostridium perfringens | Salmonella enterica |
| --- | --- | --- |
| Ascusbbr_48584 | ++ | NT |
| Ascusbbr_185064 | − | NT |
| Ascusbbr_331885 | ++ | − |

Key
− = Strain was outcompeted by the pathogen
+ = Strain weakly inhibited the pathogen
++ = Strain inhibited the pathogen
NT = Condition not tested

NUMBERED EMBODIMENTS OF THE DISCLOSURE

1. A microbial composition comprising at least one microbial strain selected from Table 1 and/or Table 2.
2. A microbial composition comprising at least one microbial strain, wherein the at least one microbial strain comprises a 16S rRNA sequence selected from SEQ ID NOs: 1-50, or SEQ Nos:338-364; or an ITS sequence selected from SEQ ID NOs: 51-58.
3. The microbial composition of claim 2, wherein the at least one microbial strain comprises Ascusb_4729.
4. The microbial composition of claim 2, wherein the at least one microbial strain comprises Ascusb_170211.
5. The microbial composition of claim 2, wherein the at least one microbial strain comprises Ascusb_1686.
6. The microbial composition of claim 2, wherein the at least one microbial strain comprises Ascusb_33.
7. The microbial composition of claim 2, wherein the at least one microbial strain comprises Ascusb_128.
8. The microbial composition of claim 2, wherein the at least one microbial strain comprises Ascusb_4729 and Ascusb_170211.
9. The microbial composition of claim 2, wherein the at least one microbial strain comprises Ascusb_4729, Ascusb_33, and Ascusb_313454.
10. The microbial composition of any one of claims 1-9, wherein said microbial composition is encapsulated.
11. A composition comprising:
    (a) a microbial composition of any one of claims 1-10, and
    (b) an acceptable carrier.
12. The composition of claim 11, wherein the microbial composition is encapsulated.
13. The composition of claim 11, wherein the encapsulated microbial composition comprises a polymer selected from a saccharide polymer, agar polymer, agarose polymer, protein polymer, and lipid polymer.
14. The composition of claim 11, wherein the acceptable carrier is selected from the group consisting of: edible feed grade material, mineral mixture, water, glycol, molasses, and corn oil.
15. The composition of claim 11, wherein the at least two microbial strains forming the microbial consortium are present in the composition at $10^2$ to $10^{15}$ cells per gram of said composition.
16. The composition of claim 11, wherein said composition is mixed with animal feed.
17. A method of imparting at least one improved trait upon an animal, said method comprising administering the composition of claim 11 to said animal.
18. The method of claim 17, wherein said animal is a fowl.

19. The method of claim 18, wherein said fowl is a broiler chicken.

20. The method of claim 18, wherein the administration comprises injecting the composition into one or more of the crop, gizzard, cecum, small intestine, or large intestine of the animal.

21. The method of claim 17, wherein said composition is administered at least once per month.

22. The method of claim 21, wherein said composition is administered at least once per week.

23. The method of claim 22, wherein said composition is administered at least once per day.

24. The method of claim 17, wherein the administration occurs each time the animal is fed.

25. The method of claim 17, wherein the administration is a cloacal administration.

26. The method of claim 25, wherein the cloacal administration comprises inserting a suppository comprising the composition into the rectum of the animal.

27. The method of claim 17, wherein the administration is an oral administration.

28. The method of claim 27, wherein the oral administration comprises administering the composition in combination with the animal's feed, water, litter, medicine, or vaccination.

29. The method of claim 27, wherein the oral administration comprises applying the composition in a gel or viscous solution to a body part of the animal, wherein the animal ingests the composition.

30. The method of claim 17, wherein the administration comprises spraying the composition onto the animal, and wherein the animal ingests the composition.

31. The method of claim 17, wherein said at least one improved trait is selected from the group consisting of: an increase in weight; an increase in egg production; an increase of musculature; an increase of vitamins in eggs; an increase of fatty acid concentration in the gastrointestinal tract; and increase in egg volume; an improved efficiency in feed utilization and digestibility; an increase in polysaccharide and lignin degradation; an increase in fat, starch, and/or protein digestion; an increase in vitamin availability; an increase in mineral availability; an increase in amino acid availability; pH balance in the gastrointestinal tract; a reduction in methane and/or nitrous oxide emissions; a reduction in manure production; an improved efficiency of nitrogen utilization; an improved efficiency of phosphorous utilization; an increased resistance to colonization of pathogenic microbes that colonize chickens; reduced mortality, increased production of antimicrobials, increased clearance of pathogenic microbes, increased resistance to colonization of pathogenic microbes that infect chickens, increased resistance to colonization of pathogenic microbes that infect humans; wherein said increase or reduction is determined by comparing against an animal not having been administered said composition.

32. The method of claim 31, wherein said increase in weight is an increase by at least 1%.

33. The method of claim 31, wherein said reduction in manure production is a reduction by at least 1%.

34. The method of claim 31, wherein said increase in polysaccharide degradation is an increase in the degradation of lignin, cellulose and/or hemicellulose.

35. The method of claim 31, wherein said increase in fatty acid concentration is an increase in acetic acid, propionic acid, and/or butyric acid.

36. The composition of claim 11, wherein the at least one microbial strain exhibit an increased utility that is not exhibited when said at least one microbial strain occurs alone, or when said at least one microbial strain is present at naturally occurring concentrations.

37. The composition of claim 11, wherein the at leastone microbial strain exhibits a synergistic effect on imparting at least one improved trait in an animal.

38. A poultry feed supplement capable of increasing a desirable phenotypic trait in a bird, the feed supplement comprising:
 (a) a microbial consortium of any one of claims 1-9 present at a concentration that does not occur naturally in said bird, and
 (b) an acceptable carrier.

39. The poultry feed supplement of claim 38, wherein the microbial consortium is encapsulated.

40. An isolated microbial strain selected from any one of the microbial strains in Table 1 and/or Table 2.

41. An isolated microbial strain selected from the group consisting of:
 (a) Ascusb_4729 deposited as PATENT201703004
 (b) Ascusb_170211 deposited as PATENT201703002
 (c) Ascusb_1686 deposited as PTA-124016;
 (d) Ascusb_33 deposited as B-67266;
 (e) Ascusb_128 deposited as PATENT201703004;
 (f) Ascusb_127 deposited as B-67265;
 (g) Ascusb_14834 deposited as PTA-124016;
 (h) Ascusb_313454 deposited as PATENT201703003;
 (i) Ascusb_28 deposited as PTA-124039;
 (j) Ascusb_144 deposited as PTA-124039;
 (k) Ascusb_312 deposited as PATENT201703002; and
 (l) Ascusb_2158 deposited as PTA-124039

42. An isolated microbial strain comprising a polynucleotide sequence sharing at least 90% sequence identity with any one of SEQ ID NOs:1-58 and 338-364.

43. A substantially pure culture of an isolated microbial strain according to any one of claims 40 to 42.

44. A method of modulating the microbiome of a fowl, the method comprising administering the composition of claim 12.

45. The method of claim 44, wherein the administration of the composition imparts at least one improved trait upon the fowl.

46. The method of claim 45, wherein the at least one improved trait is selected from the group consisting of: an increase in weight; an increase in egg production; an increase of musculature; an increase of vitamins in eggs; an increase of fatty acid concentration in the gastrointestinal tract; and increase in egg volume; an improved efficiency in feed utilization and digestibility; an increase in polysaccharide and lignin degradation; an increase in fat, starch, and/or protein digestion; an increase in vitamin availability; an increase in mineral availability; an increase in amino acid availability; pH balance in the gastrointestinal tract; a reduction in methane and/or nitrous oxide emissions; a reduction in manure production; an improved efficiency of nitrogen utilization; an improved efficiency of phosphorous utilization; an increased resistance to colonization of pathogenic microbes that colonize chickens; reduced mortality, increased production of antimicrobials, increased clearance of pathogenic microbes, increased resistance to colonization of pathogenic microbes that infect chickens, increased resistance to colonization of pathogenic microbes that infect humans; wherein said increase or reduction is determined by comparing against an animal not having been administered said composition.

47. The method of claim 46, wherein said increase in weight is an increase by at least 1%.

48. The method of claim 46, wherein said reduction in manure production is a reduction by at least 1%.

49. The method of claim 46, wherein said increase in polysaccharide degradation is an increase in the degradation of lignin, cellulose, and/or hemicellulose.

50. The method of claim 46, wherein said increase in fat digestion, starch digestion, and/or protein digestion is an increase by at least 1%.

51. The method of claim 46, wherein said increase in fatty acid concentration is an increase in acetic acid, propionic acid, and/or butyric acid.

52. The method of claim 45, wherein the modulation of the microbiome is an increase in the proportion of the at least one microbial strain of the microbiome, wherein the increase is measured relative to a fowl that did not have the at least one microbial strain administered.

53. The method of claim 45, wherein the modulation of the microbiome is a decrease in the proportion of the microbial strains present in the microbiome prior to the administration of the composition, wherein the decrease is measured relative to the microbiome of the fowl prior to the administration of the composition.

54. A method of increasing resistance of poultry to the colonization of pathogenic microbes, the method comprising the administration of the composition of claim 11, wherein the pathogen is unable to colonize the gastrointestinal tract of the poultry.

55. The method of treating poultry for the presence of at least one pathogenic microbe, the method comprising the administration of the composition of claim 11.

56. The method of claim 55, wherein after administration of the composition the relative abundance of the at least one pathogenic microbe decreases to less than 5% relative abundance in the gastrointestinal tract.

57. The method of claim 56, wherein the relative abundance of the at least one pathogenic microbe decreases to least than 1% relative abundance in the gastrointestinal tract.

58. The method of claim 56, wherein the at least one pathogenic microbe is undetectable in the gastrointestinal tract.

59. The method of claim 58, wherein less than 10 days post administration of the composition the at least one pathogenic microbe is undetectable in the gastrointestinal tract.

60. The method of claim 58, wherein within 5-15 days post administration of the composition the at least one pathogenic microbe is undetectable in the gastrointestinal tract.

61. The method of claim 56, wherein the at least one pathogenic microbe is also undetectable in or on eggs laid by the poultry.

62. The method of any one of claims 54-61, wherein the at least one pathogenic microbe is selected from: *Mycoplasma gallisepticum, Mycoplasma meleagridis, Mycoplasma synoviae, Pasteurella multocida, Clostridium perfringens, Clostridium colinum, Clostridium botulinum, Salmonella typi, Salmonella typhimurium, Salmonella enterica, Salmonella pullorum, Salmonella gallinarum, Hemophilus gallinarum, Erysipelothrix insidiosa, Campylobacter jejuni, Campylobacter coli, Campylobacter lari, Listeria monocytogenes, Arcobacter butzleri, Mycobacterium avium*, and pathogenic strains of *Escherichia coli* and *Staphylococcus aureus*.

63. The method of claim 62, wherein the at least one pathogenic microbe is selected from *Salmonella* or *Clostridium*.

64. The composition of claim 11, wherein the microbial composition comprises bacteria and/or fungi in spore form.

65. The composition of claim 11, wherein the microbial composition comprises a dechlorinator and/or an oxygen scavenger.

In aspects, the aforementioned microbial species—that is, a purified microbial population that comprises a bacteria with a 16S nucleic acid sequence, and/or a fungi with an ITS nucleic acid sequence, which is at least about 97% identical to a nucleic acid sequence selected from the group consisting of: SEQ ID NOs: 1-387—are members of a Markush group, as the present disclosure illustrates that the members belong to a class of microbes characterized by various physical and functional attributes, which can include any of the following: a) the ability to convert a carbon source into a volatile fatty acid such as acetate, butyrate, propionate, or combinations thereof; b) the ability to degrade a soluble or insoluble carbon source; c) the ability to impart an increase in weight gain to fowl administered the microbe(s); d) the ability to modulate the microbiome of the gastrointestinal tract of fowl administered the microbe; e) the ability to be formulated into a shelf-stable composition; f) the ability to exhibit a decrease in feed conversion ratio in fowl having been administered the microbe(s); g) the ability to impart a decrease in pathogen-associated lesion formation in the gastrointestinal tract; h) the ability to impart a decrease in pathogenic microbes in the gastrointestinal tract; and/or i) possessing a MIC score of at least about 0.2 if a bacteria and possessing a MIC score of at least about 0.2 if a fungi. Thus, the members of the Markush group possess at least one property in common, which can be responsible for their function in the claimed relationship.

As used herein "shelf-stable" refers to a functional attribute and new utility acquired by the microbes formulated according to the disclosure, which enable said microbes to exist in a useful/active state outside of their natural environment in the gastrointestinal tract (i.e. a markedly different characteristic). Thus, shelf-stable is a functional attribute created by the formulations/compositions of the disclosure and denoting that the microbe formulated into a shelf-stable composition can exist outside the gastrointestinal tract and under ambient conditions for a period of time that can be determined depending upon the particular formulation utilized, but in general means that the microbes can be formulated to exist in a composition that is stable under ambient conditions for at least a few days and generally at least one week. Accordingly, a "shelf-stable fowl supplement" is a composition comprising one or more microbes of the disclosure, said microbes formulated in a composition, such that the composition is stable under ambient conditions for at least one week, meaning that the microbes comprised in the composition (e.g. whole cell, spore, or lysed cell) are able to impart one or more beneficial phenotypic properties to a fowl when administered (e.g. increased weight gain, increased eggshell density, improved gastrointestinal health, and/or modulation of the gastrointestinal microbiome).

In some embodiments, the isolated microbial strains of the present disclosure further encompass mutants thereof. In some embodiments, the present disclosure further contemplates microbial strains having all of the identifying characteristics of the presently disclosed microbial strains.

TABLE 45

Budapest Treaty Deposits of the Disclosure

| Depository | Accession Number | Date of Deposit |
|---|---|---|
| ATCC | PTA-124016 | Mar. 2, 2017 |
| ATCC | PTA-124039 | Mar. 10, 2017 |
| Bigelow | PATENT201703001 | Mar. 17, 2017 |
| Bigelow | PATENT201703002 | Mar. 24, 2017 |
| Bigelow | PATENT201703003 | Mar. 24, 2017 |
| Bigelow | PATENT201703004 | Mar. 24, 2017 |
| NRRL | B-67264 | May 16, 2016 |
| NRRL | B-67265 | May 16, 2016 |
| NRRL | B-67266 | May 16, 2016 |
| NRRL | B-67267 | May 16, 2016 |
| NRRL | B-67268 | May 16, 2016 |
| NRRL | B-67269 | May 16, 2016 |
| NRRL | B-67270 | May 16, 2016 |

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

The invention claimed is:

1. A method of inhibiting colonization of or inhibiting prevalence and/or abundance of the fowl pathogen *Clostridium perfringens* in the gastrointestinal tract of a fowl, the method comprising orally administering to the fowl an effective amount of a microbial composition comprising:
   (a) a purified population of one or more bacteria of the *Bacillus* genus having a 16S nucleic acid sequence that comprises SEQ ID NO: 13 and
   (b) a carrier suitable for fowl administration,
wherein the purified population is present in the composition in an amount effective to inhibit the colonization of, the prevalence and/or the abundance of the fowl pathogen *Clostridium perfringens* in the gastrointestinal tract of the fowl as compared to a fowl not having been administered the composition.

2. The method of claim 1, wherein the fowl is a broiler chicken.

3. The method of claim 1, wherein the administering comprises feeding the microbial composition to the fowl.

4. The method of claim 1, wherein the one or more bacteria have a MIC score of at least about 0.1.

5. The method of claim 1, wherein the microbial composition is formulated as an encapsulation, tablet, capsule, pill, feed additive, food ingredient, food preparation, food supplement, water additive, water-mixed additive, heat-stabilized additive, moisture-stabilized additive, pre-pelleted feed additive, pelleted feed additive, post-pelleting applied feed additive, consumable solution, consumable spray additive, consumable, solid, consumable gel, or bolus.

6. The method of claim 1, wherein the method improved feed conversion, increased weight gain, and lowered mortality due to *Clostridium perfringens* in the fowl as compared to a fowl not having been administered the composition.

7. The method of claim 1, wherein the method decreased incidence of *Clostridium perfringens*-associated lesion formation in the fowl as compared to a fowl not having been administered the composition.

* * * * *